United States Patent
Payne et al.

(10) Patent No.: US 9,926,312 B2
(45) Date of Patent: Mar. 27, 2018

(54) 4-AZAINDOLE DERIVATIVES

(71) Applicant: EISAI R&D MANAGEMENT CO., LTD., Tokyo (JP)

(72) Inventors: Andrew Payne, Hertfordshire (GB); Jose Luis Castro Pineiro, Hertfordshire (GB); Louise Michelle Birch, Hertfordshire (GB); Afzal Khan, Hertfordshire (GB); Alan James Braunton, Hertfordshire (GB); James Edward Kitulagoda, Hertfordshire (GB); Motohiro Soejima, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 15/025,996

(22) PCT Filed: Sep. 30, 2014

(86) PCT No.: PCT/IB2014/001978
§ 371 (c)(1),
(2) Date: Mar. 30, 2016

(87) PCT Pub. No.: WO2015/049574
PCT Pub. Date: Apr. 9, 2015

(65) Prior Publication Data
US 2016/0244445 A1 Aug. 25, 2016

(30) Foreign Application Priority Data
Oct. 1, 2013 (GB) .................................. 1317363.8

(51) Int. Cl.
*C07D 471/04* (2006.01)
*A61K 31/437* (2006.01)
*C07D 401/04* (2006.01)

(52) U.S. Cl.
CPC ......... *C07D 471/04* (2013.01); *C07D 401/04* (2013.01)

(58) Field of Classification Search
CPC ............................ C07D 471/04; A61K 31/437
USPC .......................................... 546/113; 514/300
See application file for complete search history.

(56) References Cited

U.S. PATENT DOCUMENTS

| | | | |
|---|---|---|---|
| 6,063,930 A | 5/2000 | Dinsmore et al. | |
| 2004/0186148 A1 | 9/2004 | Shankar et al. | |
| 2005/0288282 A1 | 12/2005 | Delorme et al. | |
| 2008/0009514 A1 | 1/2008 | Stoit et al. | |
| 2009/0221591 A1 | 9/2009 | Hartmann et al. | |
| 2015/0094328 A1 | 4/2015 | Payne et al. | |

FOREIGN PATENT DOCUMENTS

| | | |
|---|---|---|
| WO | WO 96/11929 | 4/1996 |
| WO | WO 03/044018 | 5/2003 |
| WO | WO 2004/031188 | 4/2004 |
| WO | WO 2004/089415 | 10/2004 |
| WO | WO 2004/089470 | 10/2004 |
| WO | WO 2004/089416 | 3/2005 |
| WO | WO 2007/084667 | 12/2007 |
| WO | WO 2008/067566 | 6/2008 |
| WO | WO 2009/023623 | 2/2009 |
| WO | WO 2009/032125 | 3/2009 |
| WO | WO 2009/094279 | 7/2009 |
| WO | WO 2009/095162 | 8/2009 |
| WO | WO 2010/002820 | 1/2010 |
| WO | WO 2010/021693 | 2/2010 |
| WO | WO 2009/121033 | 3/2010 |
| WO | WO 2009/121623 | 5/2010 |
| WO | WO 2010/059773 | 5/2010 |
| WO | WO 2010/063634 | 6/2010 |
| WO | WO 2010/033980 | 7/2010 |
| WO | WO 2010/080474 | 7/2010 |
| WO | WO 2010/096338 | 8/2010 |
| WO | WO 2010/123716 | 10/2010 |
| WO | WO 2011/019060 | 2/2011 |
| WO | WO 2011/023696 | 3/2011 |
| WO | WO 2011/025851 | 3/2011 |
| WO | WO 2011/075371 | 6/2011 |
| WO | WO 2011/078984 | 6/2011 |
| WO | WO 2011/084368 | 7/2011 |
| WO | WO 2011/084371 | 7/2011 |
| WO | WO 2011/149801 | 12/2011 |
| WO | WO 2011/159553 | 12/2011 |
| WO | WO 2011/159554 | 12/2011 |
| WO | WO 2012/003147 | 1/2012 |
| WO | WO 2012/016133 | 4/2012 |
| WO | WO 2012/047702 | 4/2012 |
| WO | WO 2012/088469 | 6/2012 |
| WO | WO 2012/112933 | 8/2012 |
| WO | WO 2012/129562 | 9/2012 |
| WO | WO 2012/154888 | 11/2012 |
| WO | WO 2012/158473 | 11/2012 |
| WO | WO 2012/158474 | 11/2012 |
| WO | WO 2012/158475 | 11/2012 |
| WO | WO 2013/063549 | 5/2013 |
| WO | WO 2013/091773 | 6/2013 |
| WO | WO 2013/106795 | 7/2013 |
| WO | WO 2015/028483 | 3/2015 |
| WO | WO 2015/028483 A1 * 3/2015 ........... C07D 471/04 |  |

OTHER PUBLICATIONS

Anagnostaras et al., "Selective cognitive dysfunction in acetylcholine $M_1$ muscarinic receptor mutant mice," Nature Neuroscience, Dec. 2002, 6:51-58.

Arendt et al., "Synergistic effects of tetrahydroaminoacridine and lithium on cholinergic function after excitotoxic basal forebrain lesions in rat," Pharmacopsychiat, Nov. 1999, 32(6):242-247.

Berge et al., "Pharmaceutical salts," J. Pharm. Sci., Jan. 1977, 66(1):1-19.

(Continued)

*Primary Examiner* — Charanjit Aulakh
(74) *Attorney, Agent, or Firm* — Fish & Richardson P.C.

(57) ABSTRACT

4-Azaindole derivatives which are modulators of muscarinic acetylcholine receptor (mAChR) M1 and which may be effective for the prevention or disease modifying or symptomatic treatment of cognitive deficits associated with neurological disorders such as Alzheimer-type dementia (AD) or dementia with Lewy bodies (DLB), and a pharmaceutical composition comprising a 4-azaindole derivative as an active ingredient.

15 Claims, No Drawings

(56) References Cited

OTHER PUBLICATIONS

Bernotas et al., "1-(2-Aminoethyl)-3-(arylsulfonyl)-1H-pyrrolopyridines are 5-HT(6) receptor ligands," Bioorg. Med. Chem. Lett., Dec. 2009, 24:6935-6938.
Buxbaum et al. ,"Cholinergic agonists and interleukin 1 regulate processing and secretion of the Alzheimer beta/A4 amyloid protein precursor," Proc. Natl. Acad. Sci. USA, Nov. 1992, 89(21):10075-10078.
Clayden J., Greeves N., Warren S., "Organic Chemistry, 2nd edition," Oxford University Press, 2012.
Conn et al., "Subtype-selective allosteric modulators of muscarinic receptors for the treatment of CNS disorders," Trends in Pharmacological Sciences, Mar. 2009, 30(3)148-155.
Ennaceur et al., "A new one-trial test for neurobiological studies of memory in rats. 1: Behavioral data," Behav. Brain Res., Nov. 1988, 31(1)47-59.
Green T.W., Wuts PG., "Protective Groups in Organic Synthesis, 3rd edition,", Wiley-Interscience, 1999.
Hagan et al., "Blockade of spatial learning by the M1 muscarinic antagonist pirenzepine," Psychopharmacology, 1987, 93:470-476.
Hagan et al., "Place navigation in rats is impaired by lesions of medial septum and diagonal band but not nucleus basalis magnocellularis," Behav. Brain Res., Jan. 1988, 27(1):9-20.
Kenakin, "'7TM receptor allostery: putting numbers to shapeshifting proteins," Trends in Pharmacological Sciences, Sep. 2009, 30(9):460-469.

Kocienski PJ, "Protecting Groups," Georg Thieme Verlag, Stuttgart New York, 1994.
Langmead et al., "Muscarinic acetylcholine receptors as CNS drug targets," Pharmacology and Therapeutics, Feb. 2008, 117(2):232-43.
Lazareno et al., "Allosteric interactions of staurosporine and other indolocarbazoles with N-[methyl-(3)H]scopolamine and acetylcholine at muscarinic receptor subtypes: identification of a second allosteric site," Molecular Pharmacology, Jul. 2000, 58(1):194-207.
Lazareno et al., "Analogs of WIN 62,577 define a second allosteric site on muscarinic receptors," Molecular Pharmacology, Dec. 2002, 62(6):1492-1505.
March J., "March's Advanced Organic Chemistry, 6th edition," Wiley-VCH, 2007.
Merkul et al., "Rapid preparation of triazolyl substituted NH-heterocyclic kinase inhibitors via one-pot Sonogashira coupling-TMS-deprotection-CuAAC sequence," Org. Bio. Chem., Jul. 2011, 14:5129-5136.
Mori et al., "Donepezil for dementia with Lewy bodies: a randomized, placebo-controlled trial," Ann. Neurol., Jul. 2012, 72(1):41-52.
USPTO Requirement for Restriction in U.S. Appl. No. 14/501,355 dated Mar. 27, 2015, 7 pages.
Whitehouse et al., "Alzheimer's disease and senile dementia: loss of neurons in the basal forebrain," Science (1982), 215:1237-1239.
Zhang et al., "'Ru(II) complexes of tetradentate ligands related to 2,9-di(pyrid-2'-yl)-1,10-phenanthroline," Inorg. Chem., Feb. 2008, 47(3):990-998.

* cited by examiner

4-AZAINDOLE DERIVATIVES

FIELD OF THE INVENTION

The present invention relates to 4-azaindole derivatives and the pharmaceutical use thereof. More particularly, the present invention relates to 4-azaindole derivatives which are modulators of muscarinic acetylcholine receptor (mAChR) M1 (mAChR M1) and may be effective for the prevention or disease modifying or symptomatic treatment of cognitive deficits associated with neurological disorders such as Alzheimer-type dementia (AD) or dementia with Lewy bodies (DLB), and to a pharmaceutical composition comprising a 4-azaindole derivative as an active ingredient.

BACKGROUND

It is believed that cholinergic hypofunction contributes to the cognitive deficits associated with Alzheimer's disease (Science, 1982, 215, 1237-1239) and acetylcholinesterase inhibitors, which inhibit acetylcholine hydrolysis, are used clinically for the treatment of cognitive impairment in Alzheimer's disease. Cholinergic deficits are also prominent in dementia with Lewy bodies (DLB) and when administered to patients with DLB the cholinesterase inhibitor donepezil has been reported to give significant improvements in behavioural measures (Ann. Neurol., 2012, 72(1), 41-52). Therefore, activation of central cholinergic neurotransmission via enhanced signalling of muscarinic receptors may be effective for the symptomatic treatment of cognitive deficits associated with neurological disorders such as AD or DLB.

Muscarinic acetylcholine receptors are G-protein coupled receptors that mediate the actions of the neurotransmitter acetylcholine. Five distinct mammalian mAChR subtypes (M1-M5) have been identified in mammals. mAChR M1 which is predominantly expressed in the cortex, hippocampus and striatum, has been found to have an important role in cognitive processing (Psychopharmacology, 1987, 93, 470-476; Behav. Brain Res. 1988, 27, 9-20; Nature Neuroscience, 2002, 6, 51-58) and, more recently, has also been implicated as having a potential role in modifying Alzheimer's disease progression (Proc. Natl. Acad. Sci. USA, 1992, 89, 10075-10078). However, other muscarinic subtypes, in addition to being expressed centrally are also expressed peripherally e.g. mAChR M2 is expressed in cardiac tissue and in smooth muscle whilst mAChR M3 is expressed in sweat and salivary glands (Pharmacology and Therapeutics, 2008, 117, 232). As a result, muscarinic activation by non-selective agonists has resulted in dose-limiting peripheral cholinergic side-effects which may be attributed to their relative lack of selectivity. Selective mAChR M1 activation may therefore prove useful in the treatment of cognitive impairment, including diseases such as Alzheimer's disease and DLB, as well as for the treatment of cognitive disorders associated with psychotic disorders such as schizophrenia, but without the peripheral cholinergic side-effects mediated predominantly through mAChR M2 and mAChR M3.

Since the orthosteric acetylcholine binding site is highly conserved across the muscarinic family, obtaining selective mAChR M1 orthosteric ligands may prove challenging. However, recent advances in the understanding of alternative binding motifs and receptor states (Trends in Pharmacological Sciences, 2009, 30, 460-469) has identified the possibility of allosteric binding sites which are distinct from the endogenous ligand site and thus potentially much less conserved across the family. mAChR M1 is known to contain one or more such allosteric sites, which may alter the affinity with which muscarinic ligands bind to the primary binding or orthosteric sites or affect downstream signalling (Molecular Pharmacology, 2000, 58, 194-207; Molecular Pharmacology, 2002, 62, 1492-1505). Positive Allosteric Modulators (PAM) of mAChR M1 are thus expected to be useful in enhancing muscarinic receptor function in a selective fashion, avoiding many of the potential side effects associated with activation of other muscarinic subtypes (Trends in Pharmacological Sciences, 2009, 30, 148-155).

mAChR M1PAM compounds have been investigated as potential therapies for cognitive impairment associated with neurological disorders such as dementia (for example dementia associated with Alzheimer's disease), mild cognitive impairment and age related cognitive decline and also for psychiatric disorders such as schizophrenia, for example as described in WO2009094279, WO2011075371, WO2012158473, WO2013063549 and WO2013091773.

Examples of other diseases that might be treatable or preventable with a compound which acts as a modulator of mAChR M1 are: Huntington's disease, amyotrophic lateral sclerosis (ALS), post-operative cognitive deficit (POCD), Parkinson's disease, Parkinson's dementia, Down's syndrome, cognitive deficits in various forms of mild cognitive impairment, cognitive deficits in various forms of dementia, dementia pugilistica, vascular and frontal lobe dementia, cognitive impairment, learning impairment, attention deficit hyperactivity disorder (ADHD), attention deficit syndrome (ADS), cognitive disorders related to drug abuse including cocaine abuse, cognitive disorders related to nicotine withdrawal, autism, dementia, dementia in Korsakoff syndrome, Korsakoff syndrome, vascular dementia, dementia related to HIV infections, HIV-1 encephalopathy, AIDS encephalopathy, AIDS dementia complex, AIDS-related dementia, major depressive disorder, major depression, depression, depression resulting from Borna virus infection, major depression resulting from Borna virus infection, bipolar manic-depressive disorder, fragile-X syndrome, autism-spectrum disorders, pain, chronic pain, acute pain, inflammatory pain, neuropathic pain, diabetic neuropathic pain (DNP), pain related to rheumatic arthritis, allodynia, hyperalgesia, nociceptive pain, cancer pain, positive or negative or cognitive symptoms of schizophrenia, sleep disorders, delusional disorder, schizoaffective disorder, schizophreniform disorder, substance-induced psychotic disorder, or delirium, sleep disturbances, synucleinopathies, alpha-synucleinopathies, neurodegeneration with Brain Iron Accumulation, Parkinson-plus syndrome, Pick's disease, progressive supranuclear palsy (PSP), frontotemporal dementia and parkinsonism linked to chromosome 17 (FTDP-17), and other neurodegenerative diseases.

SUMMARY OF THE INVENTION

An object of the present invention is to provide compounds that are modulators of mAChR M1 which may be useful as prophylactic or therapeutic agents for a neurological disorder such as Alzheimer-type dementia (AD) or dementia with Lewy bodies (DLB). In particular, an object of the present invention is to provide compounds that are positive allosteric modulators of mAChR M1.

The present invention relates to a series of 4-azaindole derivatives which may act as positive allosteric modulators of mAChR M1. Specific aspects according to the present invention are:—

[1] A compound or a pharmaceutically acceptable salt thereof, which is
N-((1S,2S)-2-hydroxycyclohexyl)-1-(4-methylbenzyl)-1H-pyrrolo[3,2-b]pyridine-3-carboxamide;
1-(3,5-difluorobenzyl)-N-((1S,2S)-2-hydroxycyclohexyl)-1H-pyrrolo[3,2-b]pyridine-3-carboxamide;

1-(2,5-difluorobenzyl)-N-((1S,2S)-2-hydroxycyclohexyl)-1H-pyrrolo[3,2-b]pyridine-3-carboxamide;
1-(3-fluorobenzyl)-N-((1S,2S)-2-hydroxycyclohexyl)-1H-pyrrolo[3,2-b]pyridine-3-carboxamide;
1-(4-fluorobenzyl)-N-((1S,2S)-2-hydroxycyclohexyl)-1H-pyrrolo[3,2-b]pyridine-3-carboxamide;
1-(4-fluoro-3-methylbenzyl)-N-((1S,2S)-2-hydroxycyclohexyl)-1H-pyrrolo[3,2-b]pyridine-3-carboxamide;
1-(2,3-difluorobenzyl)-N-((1S,2S)-2-hydroxycyclohexyl)-1H-pyrrolo[3,2-b]pyridine-3-carboxamide;
N-((1S,2S)-2-hydroxycyclohexyl)-1-(4-(trifluoromethoxy)benzyl)-1H-pyrrolo[3,2-b]pyridine-3-carboxamide;
1-(4-fluorobenzyl)-N-((1S,2S)-2-hydroxycyclohexyl)-7-methyl-1H-pyrrolo[3,2-b]pyridine-3-carboxamide;
1-(2,3-difluorobenzyl)-N-((1S,2S)-2-hydroxycyclohexyl)-7-methyl-1H-pyrrolo[3,2-b]pyridine-3-carboxamide;
N-((1S,2S)-2-hydroxycyclohexyl)-1-(4-methoxybenzyl)-7-methyl-1H-pyrrolo[3,2-b]pyridine-3-carboxamide;
1-(3-fluoro-4-methoxybenzyl)-N-((1S,2S)-2-hydroxycyclohexyl)-7-methyl-1H-pyrrolo[3,2-b]pyridine-3-carboxamide;
7-chloro-1-(4-fluorobenzyl)-N-((1S,2S)-2-hydroxycyclohexyl)-1H-pyrrolo[3,2-b]pyridine-3-carboxamide;
7-chloro-1-(2,3-difluorobenzyl)-N-((1S,2S)-2-hydroxycyclohexyl)-1H-pyrrolo[3,2-b]pyridine-3-carboxamide;
7-chloro-N-((1S,2S)-2-hydroxycyclohexyl)-1-((6-methylpyridin-2-yl)methyl)-1H-pyrrolo[3,2-b]pyridine-3-carboxamide;
7-chloro-1-((5-fluoropyridin-2-yl)methyl)-N-((1S,2S)-2-hydroxycyclohexyl)-1H-pyrrolo[3,2-b]pyridine-3-carboxamide;
1-(2-fluorobenzyl)-N-((1S,2S)-2-hydroxycyclohexyl)-1H-pyrrolo[3,2-b]pyridine-3-carboxamide;
1-(4-chlorobenzyl)-N-((1S,2S)-2-hydroxycyclohexyl)-1H-pyrrolo[3,2-b]pyridine-3-carboxamide;
1-(2,4-difluorobenzyl)-N-((1S,2S)-2-hydroxycyclohexyl)-1H-pyrrolo[3,2-b]pyridine-3-carboxamide;
1-(4-fluorobenzyl)-N-(trans-2-hydroxycycloheptyl)-1H-pyrrolo[3,2-b]pyridine-3-carboxamide;
1-(4-fluorobenzyl)-N-(piperidin-4-yl)-1H-pyrrolo[3,2-b]pyridine-3-carboxamide;
1-(4-fluorobenzyl)-N-(1-methylpiperidin-4-yl)-1H-pyrrolo[3,2-b]pyridine-3-carboxamide;
7-cyano-1-(4-fluorobenzyl)-N-((1S,2S)-2-hydroxycyclohexyl)-1H-pyrrolo[3,2-b]pyridine-3-carboxamide;
7-cyano-N-((1S,2S)-2-hydroxycyclohexyl)-1-(4-(trifluoromethyl)benzyl)-1H-pyrrolo[3,2-b]pyridine-3-carboxamide;
N-(trans-4,4-difluoro-2-hydroxycyclohexyl)-1-(4-fluorobenzyl)-1H-pyrrolo[3,2-b]pyridine-3-carboxamide;
1-(4-fluorobenzyl)-N-((1S,2S)-2-hydroxycyclohexyl)-7-methoxy-1H-pyrrolo[3,2-b]pyridine-3-carboxamide;
1-(4-(1H-pyrazol-1-yl)benzyl)-N-((1S,2S)-2-hydroxycyclohexyl)-5-methyl-1H-pyrrolo[3,2-b]pyridine-3-carboxamide;
1-(4-(1H-pyrazol-1-yl)benzyl)-5-cyano-N-((1S,2S)-2-hydroxycyclohexyl)-1H-pyrrolo[3,2-b]pyridine-3-carboxamide;
N-((1S,2S)-2-hydroxycyclohexyl)-1-(4-(1-methyl-1H-imidazol-2-yl)benzyl)-1H-pyrrolo[3,2-b]pyridine-3-carboxamide;
N-((1S,2S)-2-hydroxycyclohexyl)-1-(4-(1-methyl-1H-imidazol-4-yl)benzyl)-1H-pyrrolo[3,2-b]pyridine-3-carboxamide;
1-(2-fluoro-4-(6-methylpyridin-2-yl)benzyl)-N-((1S,2S)-2-hydroxycyclohexyl)-1H-pyrrolo[3,2-b]pyridine-3-carboxamide;
1-(2-fluoro-4-(2-methylpyridin-4-yl)benzyl)-N-((1S,2S)-2-hydroxycyclohexyl)-1H-pyrrolo[3,2-b]pyridine-3-carboxamide;
1-((4'-fluoro-[1,1'-biphenyl]-4-yl)methyl)-N-(trans-2-hydroxycyclohexyl)-1H-pyrrolo[3,2-b]pyridine-3-carboxamide;
1-(4-(1H-pyrazol-1-yl)benzyl)-N-((1S,2S)-2-hydroxycyclohexyl)-1H-pyrrolo[3,2-b]pyridine-3-carboxamide;
1-(4-(1H-pyrazol-1-yl)benzyl)-N-((1R,2R)-2-hydroxycyclohexyl)-1H-pyrrolo[3,2-b]pyridine-3-carboxamide;
1-(4-(1H-pyrazol-1-yl)benzyl)-N-cyclohexyl-1H-pyrrolo[3,2-b]pyridine-3-carboxamide;
1-(4-(1H-pyrazol-1-yl)benzyl)-N-(4,4-difluorocyclohexyl)-1H-pyrrolo[3,2-b]pyridine-3-carboxamide;
(S)-1-(4-(1H-pyrazol-1-yl)benzyl)-N-(piperidin-3-yl)-1H-pyrrolo[3,2-b]pyridine-3-carboxamide;
(S)-1-(4-(1H-pyrazol-1-yl)benzyl)-N-(1-methylpiperidin-3-yl)-1H-pyrrolo[3,2-b]pyridine-3-carboxamide;
(R)-1-(4-(1H-pyrazol-1-yl)benzyl)-N-(1-methylpiperidin-3-yl)-1H-pyrrolo[3,2-b]pyridine-3-carboxamide;
1-(4-bromobenzyl)-N-((1S,2S)-2-hydroxycyclohexyl)-1H-pyrrolo[3,2-b]pyridine-3-carboxamide;
N-((1S,2S)-2-hydroxycyclohexyl)-1-(4-(1-methyl-1H-pyrazol-4-yl)benzyl)-1H-pyrrolo[3,2-b]pyridine-3-carboxamide;
7-chloro-N-((1S,2S)-2-hydroxycyclohexyl)-1-(4-methoxybenzyl)-1H-pyrrolo[3,2-b]pyridine-3-carboxamide;
1-((6-chloropyridin-3-yl)methyl)-N-((1S,2S)-2-hydroxycyclohexyl)-7-methyl-1H-pyrrolo[3,2-b]pyridine-3-carboxamide;
1-(4-chlorobenzyl)-N-((1S,2S)-2-hydroxycyclohexyl)-7-methyl-1H-pyrrolo[3,2-b]pyridine-3-carboxamide;
7-chloro-N-((1S,2S)-2-hydroxycyclohexyl)-1-((5-methylpyridin-2-yl)methyl)-1H-pyrrolo[3,2-b]pyridine-3-carboxamide;
7-chloro-N-((1S,2S)-2-hydroxycyclohexyl)-1-((6-methylpyridin-3-yl)methyl)-1H-pyrrolo[3,2-b]pyridine-3-carboxamide;
N-((1S,2S)-2-hydroxycyclohexyl)-7-methyl-1-(4-methylbenzyl)-1H-pyrrolo[3,2-b]pyridine-3-carboxamide;
N-((1S,2S)-2-hydroxycyclohexyl)-7-methyl-1-((5-methylpyridin-2-yl)methyl)-1H-pyrrolo[3,2-b]pyridine-3-carboxamide;
1-(3-fluorobenzyl)-N-((1S,2S)-2-hydroxycyclohexyl)-7-methyl-1H-pyrrolo[3,2-b]pyridine-3-carboxamide;
N-((1S,2S)-2-hydroxycyclohexyl)-1-(4-methoxy-3-methylbenzyl)-7-methyl-1H-pyrrolo[3,2-b]pyridine-3-carboxamide;
N-((1S,2S)-2-hydroxycyclohexyl)-1-((6-methoxypyridin-3-yl)methyl)-7-methyl-1H-pyrrolo[3,2-b]pyridine-3-carboxamide;
7-chloro-N-((1S,2S)-2-hydroxycyclohexyl)-1-((6-methoxypyridin-3-yl)methyl)-1H-pyrrolo[3,2-b]pyridine-3-carboxamide;
7-chloro-N-((1S,2S)-2-hydroxycyclohexyl)-1-((2-methoxypyridin-4-yl)methyl)-1H-pyrrolo[3,2-b]pyridine-3-carboxamide;
7-chloro-1-((6-cyanopyridin-3-yl)methyl)-N-((1S,2S)-2-hydroxycyclohexyl)-1H-pyrrolo[3,2-b]pyridine-3-carboxamide;
N-((1S,2S)-2-hydroxycyclohexyl)-1-((2-methoxypyridin-4-yl)methyl)-7-methyl-1H-pyrrolo[3,2-b]pyridine-3-carboxamide;
7-chloro-N-((1S,2S)-2-hydroxycyclohexyl)-1-((1-methyl-1H-pyrazol-4-yl)methyl)-1H-pyrrolo[3,2-b]pyridine-3-carboxamide;

N-((1S,2S)-2-hydroxycyclohexyl)-7-methyl-1-((1-methyl-1H-pyrazol-4-yl)methyl)-1H-pyrrolo[3,2-b]pyridine-3-carboxamide;
7-chloro-N-((1S,2S)-2-hydroxycyclohexyl)-1-((4-methylthiazol-2-yl)methyl)-1H-pyrrolo[3,2-b]pyridine-3-carboxamide;
7-chloro-N-((1S,2S)-2-hydroxycyclohexyl)-1-((5-methylthiazol-2-yl)methyl)-1H-pyrrolo[3,2-b]pyridine-3-carboxamide;
N-((1S,2S)-2-hydroxycyclohexyl)-1-((2-methylpyridin-4-yl)methyl)-1H-pyrrolo[3,2-b]pyridine-3-carboxamide;
N-((1S,2S)-2-hydroxycyclohexyl)-1-(pyridin-4-ylmethyl)-1H-pyrrolo[3,2-b]pyridine-3-carboxamide;
7-chloro-N-((1S,2S)-2-hydroxycyclohexyl)-1-((2-methylpyridin-4-yl)methyl)-1H-pyrrolo[3,2-b]pyridine-3-carboxamide;
7-chloro-N-((1S,2S)-2-hydroxycyclohexyl)-1-(pyridin-4-ylmethyl)-1H-pyrrolo[3,2-b]pyridine-3-carboxamide;
7-chloro-N-((1S,2S)-2-hydroxycyclohexyl)-1-((4-methylpyridin-2-yl)methyl)-1H-pyrrolo[3,2-b]pyridine-3-carboxamide;
1-((5-chloropyridin-2-yl)methyl)-N-((1S,2S)-2-hydroxycyclohexyl)-7-methyl-1H-pyrrolo[3,2-b]pyridine-3-carboxamide;
1-(4-fluorobenzyl)-N-(trans-3-hydroxytetrahydro-2H-pyran-4-yl)-7-methyl-1H-pyrrolo[3,2-b]pyridine-3-carboxamide;
1-(4-methoxybenzyl)-N-(trans-3-hydroxytetrahydro-2H-pyran-4-yl)-7-methyl-1H-pyrrolo[3,2-b]pyridine-3-carboxamide;
1-(3-fluoro-4-methoxybenzyl)-N-(trans-3-hydroxytetrahydro-2H-pyran-4-yl)-7-methyl-1H-pyrrolo[3,2-b]pyridine-3-carboxamide;
N-(trans-3-hydroxytetrahydro-2H-pyran-4-yl)-1-((2-methoxypyridin-4-yl)methyl)-7-methyl-1H-pyrrolo[3,2-b]pyridine-3-carboxamide;
7-chloro-1-(3-fluorobenzyl)-N-(trans-3-hydroxytetrahydro-2H-pyran-4-yl)-1H-pyrrolo[3,2-b]pyridine-3-carboxamide;
7-chloro-1-(4-methoxybenzyl)-N-(trans-3-hydroxytetrahydro-2H-pyran-4-yl)-1H-pyrrolo[3,2-b]pyridine-3-carboxamide;
7-chloro-1-(4-fluorobenzyl)-N-((3R,4S)-3-hydroxytetrahydro-2H-pyran-4-yl)-1H-pyrrolo[3,2-b]pyridine-3-carboxamide; or
7-chloro-1-(4-fluorobenzyl)-N-((3S,4R)-3-hydroxytetrahydro-2H-pyran-4-yl)-1H-pyrrolo[3,2-b]pyridine-3-carboxamide.

[2] A compound of formula (IA), or a pharmaceutically acceptable salt thereof,

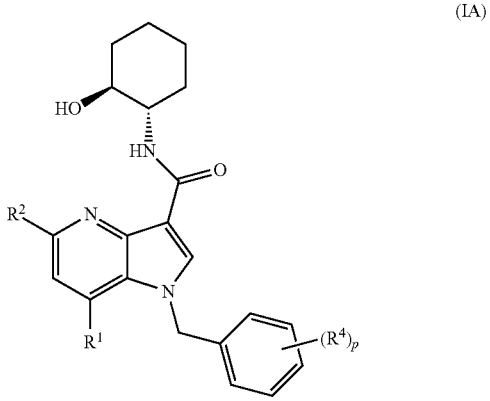

(IA)

wherein
R$^1$ is hydrogen, halogen, cyano, C$_{1-4}$alkyl or C$_{1-4}$alkoxy;
R$^2$ is hydrogen;
p is 1 or 2 and each R$^4$ is independently selected from halogen, C$_{1-4}$alkyl, C$_{1-4}$alkoxy, C$_{1-4}$haloalkyl and C$_{1-4}$haloalkoxy.

[3] A compound of formula (IB), or a pharmaceutically acceptable salt thereof,

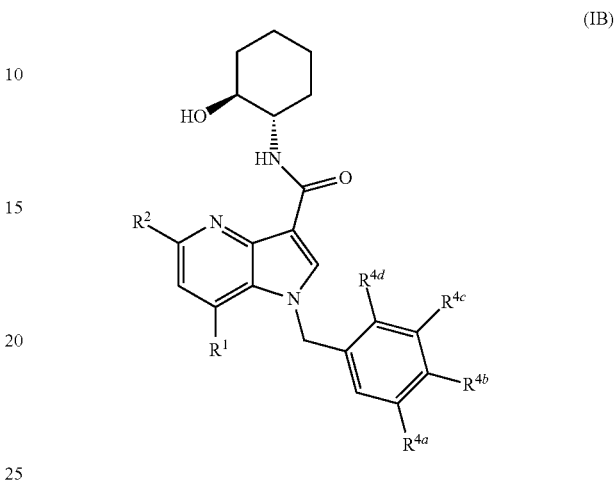

(IB)

wherein
R$^1$ is hydrogen, halogen, C$_{1-4}$alkyl or C$_{1-4}$alkoxy;
R$^2$ is hydrogen;
R$^{4a}$ is hydrogen or halogen;
R$^{4b}$ is hydrogen, halogen, C$_{1-4}$alkyl, C$_{1-4}$alkoxy, C$_{1-4}$haloalkyl or C$_{1-4}$haloalkoxy;
R$^{4c}$ is hydrogen, halogen, C$_{1-4}$alkyl, C$_{1-4}$alkoxy or C$_{1-4}$haloalkyl; and
R$^{4d}$ is hydrogen or halogen,
wherein at least one of R$^{4a}$, R$^{4b}$, R$^{4c}$ and R$^{4d}$ is other than hydrogen and no more than two of R$^{4a}$, R$^{4b}$, R$^{4c}$ and R$^{4d}$ are hydrogen.

[4] A compound according to [3] or a pharmaceutically acceptable salt thereof, which is 1-(4-fluorobenzyl)-N-((1S,2S)-2-hydroxycyclohexyl)-1H-pyrrolo[3,2-b]pyridine-3-carboxamide.

[5] A compound according to [3] or a pharmaceutically acceptable salt thereof, which is 1-(4-fluoro-3-methylbenzyl)-N-((1S,2S)-2-hydroxycyclohexyl)-1H-pyrrolo[3,2-b]pyridine-3-carboxamide.

[6] A compound according to [3] or a pharmaceutically acceptable salt thereof, which is 1-(2,3-difluorobenzyl)-N-((1S,2S)-2-hydroxycyclohexyl)-1H-pyrrolo[3,2-b]pyridine-3-carboxamide.

[7] A compound according to [3] or a pharmaceutically acceptable salt thereof, which is 1-(4-fluorobenzyl)-N-((1S,2S)-2-hydroxycyclohexyl)-7-methyl-1H-pyrrolo[3,2-b]pyridine-3-carboxamide.

[8] A compound according to [3] or a pharmaceutically acceptable salt thereof, which is 1-(2,3-difluorobenzyl)-N-((1S,2S)-2-hydroxycyclohexyl)-7-methyl-1H-pyrrolo[3,2-b]pyridine-3-carboxamide.

[9] A compound according to [3] or a pharmaceutically acceptable salt thereof, which is N-((1S,2S)-2-hydroxycyclohexyl)-1-(4-methoxybenzyl)-7-methyl-1H-pyrrolo[3,2-b]pyridine-3-carboxamide.

[10] A compound according to [3] or a pharmaceutically acceptable salt thereof, which is 1-(3-fluoro-4-methoxybenzyl)-N-((1S,2S)-2-hydroxycyclohexyl)-7-methyl-1H-pyrrolo[3,2-b]pyridine-3-carboxamide.

[11] A compound according to any one of [1] to [10] or a pharmaceutically acceptable salt thereof, for use in positive allosteric modulation of muscarinic receptor mAChR M1.
[12] A compound according to any one of [1] to [10] or a pharmaceutically acceptable salt thereof, for use as a cognitive impairment improving agent in Alzheimer-type dementia (AD).
[13] A method for symptomatic treatment of cognitive impairment in Alzheimer-type dementia (AD) involving administering to a human subject in need thereof a therapeutically effective amount of a compound according to any one of [1] to [10] or a pharmaceutically acceptable salt thereof.
[14] A compound according to any one of [1] to [10] or a pharmaceutically acceptable salt thereof, for use as a cognitive impairment improving agent in dementia with Lewy bodies (DLB).
[15] A method for symptomatic treatment of cognitive impairment in dementia with Lewy bodies (DLB) involving administering to a human subject in need thereof a therapeutically effective amount of a compound according to any one of [1] to [10] or a pharmaceutically acceptable salt thereof.
[16] A pharmaceutical composition comprising the compound according to any one of [1] to [10] or a pharmaceutically acceptable salt thereof, as an active ingredient in association with a pharmaceutically acceptable carrier.

DESCRIPTION OF THE INVENTION

The compounds of the present invention belong to a group of compounds of general formula (I), or a pharmaceutically acceptable salt thereof,

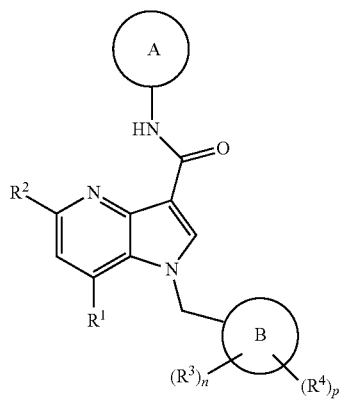

(I)

wherein
Ring A is a non-aromatic $C_{5-8}$ carbocyclic group or a non-aromatic 5 to 8-membered heterocyclic group, wherein Ring A may be optionally substituted with one or more substituents independently selected from Substituent Group α;
$R^1$ is hydrogen, halogen, cyano, hydroxyl, $C_{1-6}$alkyl, $C_{1-6}$alkoxy, $C_{1-6}$haloalkyl or $C_{1-6}$ haloalkoxy;
$R^2$ is hydrogen, halogen, cyano, hydroxyl, $C_{1-6}$alkyl, $C_{1-6}$alkoxy, $C_{1-6}$haloalkyl or $C_{1-6}$ haloalkoxy;

Ring B is phenyl or a 5 to 6-membered heteroaryl group;
n is 0 or 1;
$R^3$ is phenyl or a 5 to 6-membered heteroaryl group, which phenyl or heteroaryl group may be optionally substituted with one or more substituents independently selected from Substituent Group α;
p is 0, 1, 2, 3 or 4;
each $R^4$ independently is a group selected from Substituent Group α;
each substituent selected from Substituent Group α is independently halogen, hydroxyl, cyano, nitro, —$NR^5R^5$, $C(O)NR^5R^5$, —$C(O)OR^5$, —$C(O)R^5$, —$S(O)_2R^5$, —$NR^5S(O)_2R^5$, $S(O)_2NR^5R^5$, —$NR^5C(O)R^5$, $C_{1-6}$alkyl and $C_{1-6}$alkoxy, which $C_{1-6}$alkyl and $C_{1-6}$alkoxy are each optionally substituted by one or more substituents independently selected from halogen, hydroxyl, cyano, —$NH_2$, —$NH(C_{1-6}$alkyl) and —$N(C_{1-6}$alkyl$)_2$; and
each $R^5$ independently is hydrogen or $C_{1-6}$alkyl.

Certain compounds of formula (I) are capable of existing in stereoisomeric forms. It will be understood that the present description encompasses all geometric and structural isomers of the compounds of formula (I) and mixtures thereof including racemates. Tautomers and mixtures thereof also form an aspect of the description.

Certain compounds of formula (I) may exist in solvated, for example hydrated, as well as unsolvated forms. It is to be understood that the present description encompasses all such solvated forms of compounds of formula (I).

In an embodiment of formula (I), Ring A is a $C_{5-7}$ cycloalkyl group or a 6-membered heterocycloalkyl group, wherein Ring A is optionally substituted with one or more substituents independently selected from halogen, hydroxyl, $C_{1-4}$alkyl and $C_{1-4}$hydroxyalkyl.

In one embodiment of formula (I), Ring A is a $C_{5-7}$ cycloalkyl group optionally substituted with one or more substituents independently selected from halogen, hydroxyl, $C_{1-4}$alkyl and $C_{1-4}$hydroxyalkyl.

In one embodiment of formula (I), Ring A is selected from:—

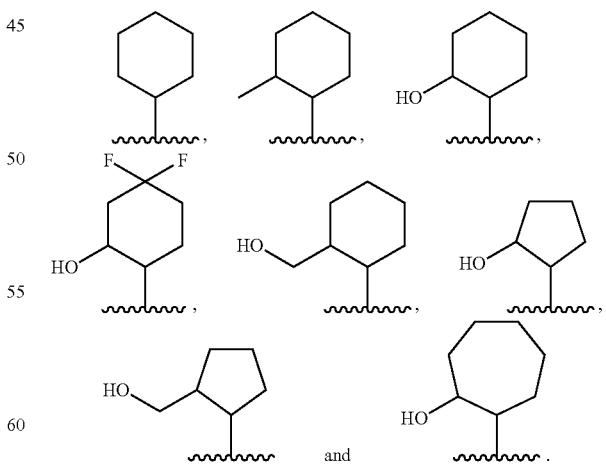

In one embodiment of formula (I), Ring A is a piperidin-4-yl or piperidin-3-yl group, optionally substituted with one or more substituents independently selected from halogen, hydroxyl, $C_{1-4}$alkyl and $C_{1-4}$hydroxyalkyl.

In an embodiment of formula (I), Ring A is selected from:—

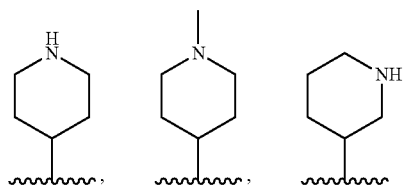

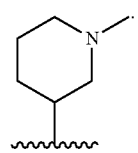

In one embodiment of formula (I), Ring A is a tetrahydropyran-4-yl or tetrahydropyran-3-yl group optionally substituted with one or more substituents independently selected from halogen, hydroxyl, $C_{1-4}$alkyl and $C_{1-4}$hydroxyalkyl. In an embodiment of formula (I), Ring A is selected from:—

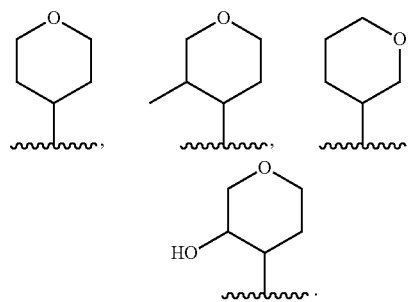

In an embodiment of formula (I), Ring A is a group of formula (II), wherein $R^a$ is hydroxyl, methyl or hydroxymethyl; and Z is $CH_2$, $CF_2$ or O

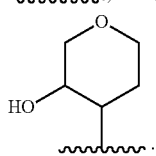

(II)

In an embodiment of formula (I), Ring A is

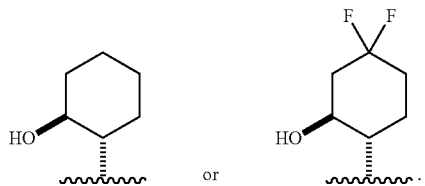 [SMILES: *[C@H]1CCCC[C@@H]1O ; *[C@H]1CCC(F)(F)C[C@@H]1O]

In an embodiment of formula (I), Ring A is

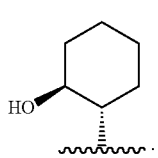

In an embodiment of formula (I), Ring A is

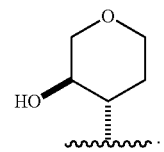

In an embodiment of formula (I), $R^1$ is hydrogen, halogen, cyano, or $C_{1-4}$alkoxy.

In an embodiment of formula (I), $R^1$ is hydrogen, chloro, cyano, methyl or methoxy.

In an embodiment of formula (I), $R^1$ is hydrogen, chloro, cyano or methyl.

In an embodiment of formula (I), $R^2$ is hydrogen, halogen, cyano, $C_{1-4}$alkyl or $C_{1-4}$alkoxy.

In an embodiment of formula (I), $R^2$ is hydrogen, cyano, methyl or methoxy.

In an embodiment of formula (I), $R^2$ is hydrogen, cyano or methyl.

In an embodiment of formula (I), n is 0.

In an embodiment of formula (I), p is 1 or 2 and each $R^4$ is independently selected from halogen, hydroxyl, cyano, —$NH_2$, —$NH(C_{1-4}alkyl)$, $N(C_{1-4}alkyl)_2$, $C_{1-4}$alkyl, $C_{1-4}$alkoxy, $C_{1-4}$haloalkyl and $C_{1-4}$ haloalkoxy.

In an embodiment of formula (I), Ring B is a phenyl, pyridin-2-yl, pyridin-3-yl, pyridin-4-yl, thiazol-2-yl, thiazol-4-yl or pyrazol-4-yl group, wherein Ring B is optionally substituted with one or two substituents independently selected from halogen, hydroxyl, cyano, —$NH_2$, —$NH(C_{1-4}alkyl)$, $N(C_{1-4}alkyl)_2$, $C_{1-4}$alkyl, $C_{1-4}$alkoxy, $C_{1-4}$haloalkyl and $C_{1-4}$haloalkoxy. In a further embodiment of formula (I), Ring B is a phenyl, pyridin-2-yl, pyridin-3-yl, pyridin-4-yl, thiazol-2-yl, thiazol-4-yl or pyrazol-4-yl group, wherein Ring B is optionally substituted with one or two substituents independently selected from fluoro, chloro, cyano, methyl, trifluoromethyl, methoxy and trifluoromethoxy.

In one embodiment of formula (I), Ring B is a phenyl group optionally substituted with one or two substituents independently selected from halogen, hydroxyl, cyano, —$NH_2$, —$NH(C_{1-4}alkyl)$, $N(C_{1-4}alkyl)_2$, $C_{1-4}$alkyl, $C_{1-4}$alkoxy, $C_{1-4}$haloalkyl and $C_{1-4}$haloalkoxy. In a further embodiment, Ring B is a phenyl group optionally substituted with one or two substituents independently selected from fluoro, chloro, bromo, methyl, methoxy, trifluoromethyl and trifluoromethoxy.

In one embodiment of formula (I), Ring B is selected from:—

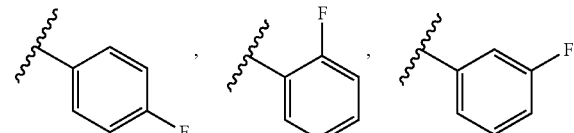

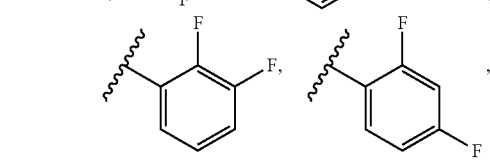

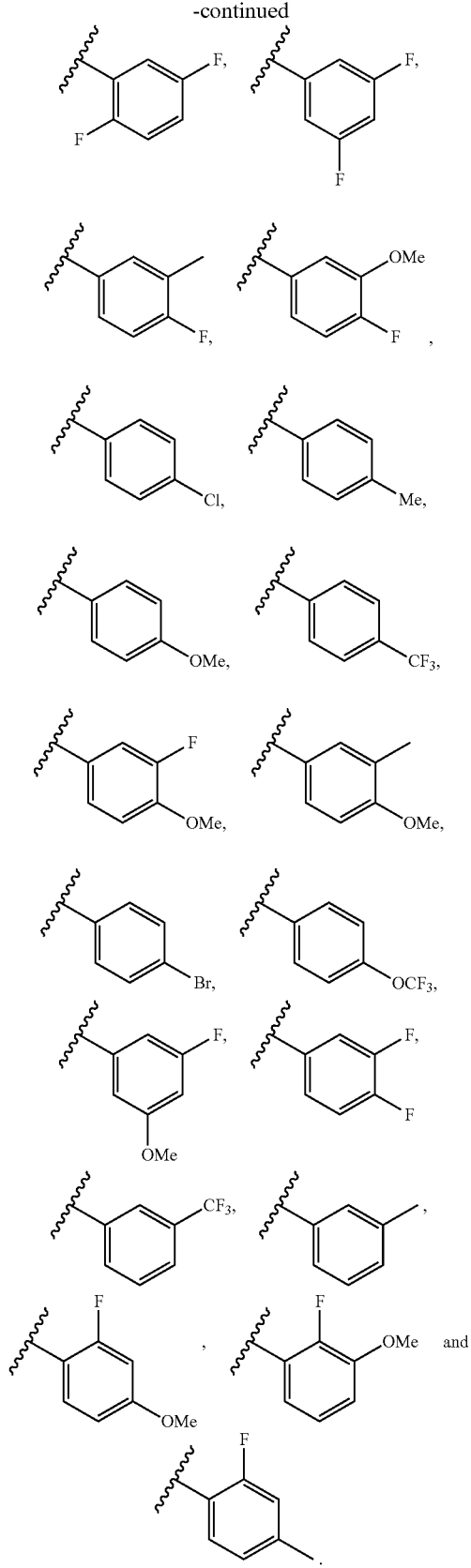

In one embodiment of formula (I), Ring B is a pyridin-2-yl, pyridin-3-yl or pyridin-4-yl group, wherein Ring R is optionally substituted with one or two substituents independently selected from halogen, hydroxyl, cyano, —NH₂, —NH(C₁₋₄alkyl), N(C₁₋₄alkyl)₂, C₁₋₄alkyl, C₁-4alkoxy, C₁₋₄haloalkyl and C₁₋₄ haloalkoxy. In a further embodiment, Ring B is a pyridin-2-yl, pyridin-3-yl or pyridin-4-yl group, wherein Ring B is optionally substituted with one or two substituents independently selected from fluoro, chloro, cyano, methyl and methoxy.

In an embodiment of formula (I), Ring B is selected from:—

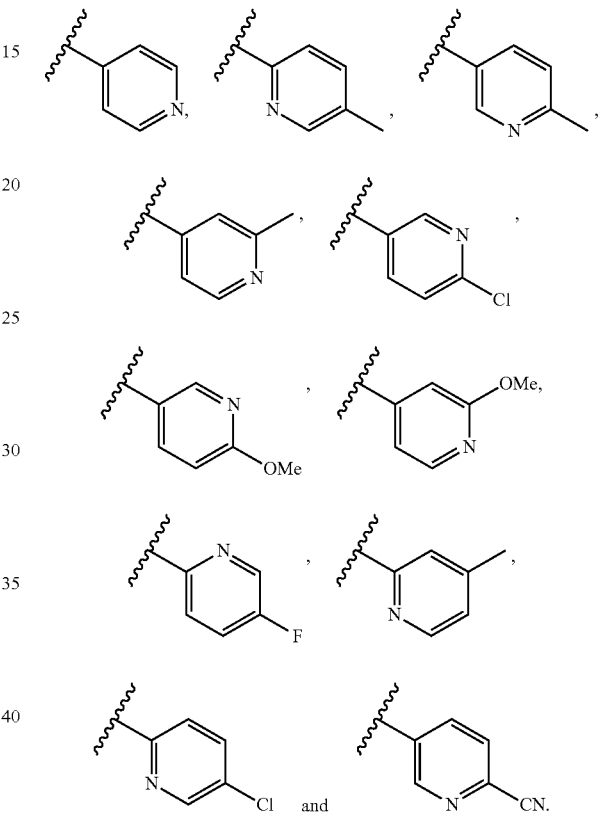

In one embodiment of formula (I), Ring B is a thiazol-2-yl, a thiazol-4-yl or a pyrazol-4-yl group, any of which may be optionally substituted with one or two substituents independently selected from halogen, hydroxyl, cyano, —NH₂, —NH(C₁₋₄alkyl), N(C₁₋₄alkyl)₂, C₁₋₄alkyl, C₁₋₄alkoxy, C₁₋₄haloalkyl and C₁₋₄ haloalkoxy.

In one embodiment of formula (I), Ring B is selected from:—

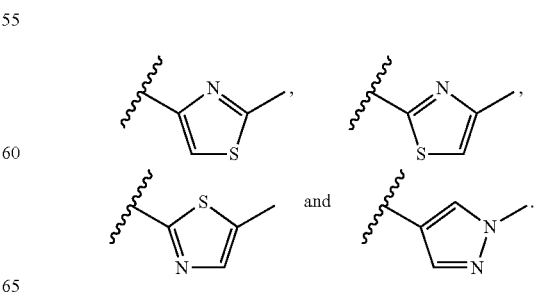

In an embodiment of formula (I), n is 1.

In an embodiment of formula (I), Ring B is a group of formula (III),

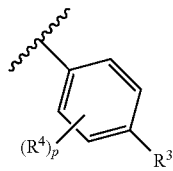

(III)

wherein $R^3$ is a phenyl, pyridin-2-yl, pyridin-4-yl, pyrazol-1-yl, pyrazol-4-yl, imidazol-2-yl or imidazol-4-yl group, wherein $R^3$ is optionally substituted with one or more substituents independently selected from halogen, hydroxyl, cyano, —$NH_2$, —$NH(C_{1-4}alkyl)$, $N(C_{1-4}alkyl)_2$, $C_{1-4}alkyl$, $C_{1-4}alkoxy$, $C_{1-4}haloalkyl$ and $C_{1-4}$ haloalkoxy; p is 0 or 1; and $R^4$ is halogen, hydroxyl, cyano, —$NH_2$, —$NH(C_{1-4}alkyl)$, $N(C_{1-4}alkyl)_2$, $C_{1-4}alkyl$, $C_{1-4}alkoxy$, $C_{1-4}haloalkyl$ or $C_{1-4}$ haloalkoxy.

In one embodiment of formula (I), Ring B is a group of formula (III) wherein $R^3$ is a phenyl group optionally substituted with one or more substituents independently selected from halogen, hydroxyl, cyano, —$NH_2$, —$NH(C_{1-4}alkyl)$, $N(C_{1-4}alkyl)_2$, $C_{1-4}alkyl$, $C_{1-4}alkoxy$, $C_{1-4}haloalkyl$ and $C_{1-4}$ haloalkoxy; p is 0 or 1; and $R^4$ is halogen hydroxyl, cyano, —$NH_2$, —$NH(C_{1-4}alkyl)$, $N(C_{1-4}alkyl)_2$, $C_{1-4}alkoxy$, $C_{1-4}haloalkyl$ or $C_{1-4}$ haloalkoxy.

In one embodiment of formula (I), Ring B is:

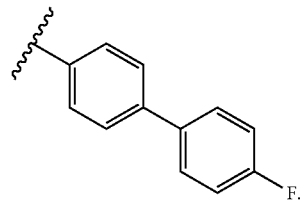 [SMILES: *c1ccc(-c2ccc(F)cc2)cc1]

In one embodiment of formula (I), Ring B is a group of formula (III) wherein $R^3$ is a pyridin-4-yl or pyridin-2-yl group optionally substituted with one or more substituents independently selected from halogen, hydroxyl, cyano, —$NH_2$, —$NH(C_{1-4}alkyl)$, $N(C_{1-4}alkyl)_2$, $C_{1-4}alkyl$, $C_{1-4}alkoxy$, $C_{1-4}haloalkyl$ and $C_{1-4}$ haloalkoxy; p is 0 or 1; and $R^4$ is halogen, hydroxyl, cyano, —$NH_2$, —$NH(C_{1-4}alkyl)$, $N(C_{1-4}alkyl)_2$, $C_{1-4}alkyl$, $C_{1-4}alkoxy$, $C_{1-4}haloalkyl$ or $C_{1-4}$ haloalkoxy.

In one embodiment of formula (I), Ring B is selected from:—

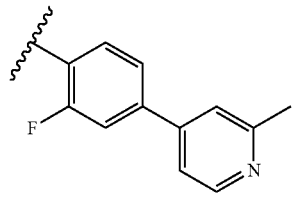

and

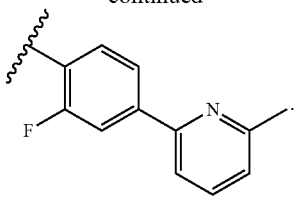

In one embodiment of formula (I), Ring B is a group of formula (III) wherein $R^3$ is a pyrazol-1-yl or pyrazol-4-yl group optionally substituted with one or more substituents independently selected from halogen, hydroxyl, cyano, —$NH_2$, —$NH(C_{1-4}alkyl)$, $N(C_{1-4}alkyl)_2$, $C_{1-4}alkoxy$, $C_{1-4}haloalkyl$ and $C_{1-4}$ haloalkoxy; p is 0 or 1; and $R^4$ is halogen, hydroxyl, cyano, —$NH_2$, —$NH(C_{1-4}alkyl)$, $N(C_{1-4}alkyl)_2$, $C_{1-4}alkyl$, $C_{1-4}alkoxy$, $C_{1-4}haloalkyl$ or $C_{1-4}$ haloalkoxy.

In one embodiment of formula (I), Ring B is selected from:—

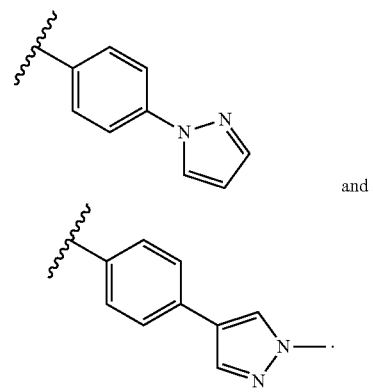

and

In one embodiment of formula (I), Ring B is a group of formula (III) wherein $R^3$ is an imidazol-2-yl or imidazol-4-yl group optionally substituted with one or more substituents independently selected from halogen, hydroxyl, cyano, —$NH_2$, —$NH(C_{1-4}alkyl)$, $N(C_{1-4}alkyl)_2$, $C_{1-4}alkyl$, $C_{1-4}alkoxy$, $C_{1-4}haloalkyl$ and $C_{1-4}$ haloalkoxy; p is 0 or 1; and $R^4$ is halogen, hydroxyl, cyano, —$NH_2$, —$NH(C_{1-4}alkyl)$, $N(C_{1-4}alkyl)_2$, $C_{1-4}alkyl$, $C_{1-4}alkoxy$, $C_{1-4}haloalkyl$ or $C_{1-4}$ haloalkoxy.

In one embodiment of formula (I), Ring B is selected from:—

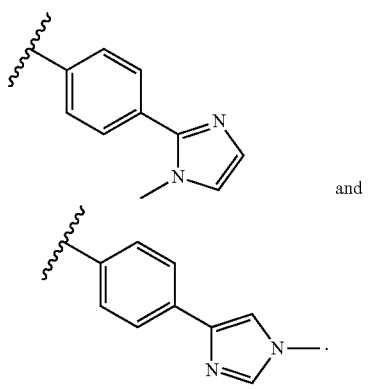

and

In one aspect, the present invention provides a compound or pharmaceutically acceptable salt which is N-((1S,2S)-2-hydroxycyclohexyl)-1-(4-methylbenzyl)-1H-pyrrolo[3,2-b]pyridine-3-carboxamide;
1-(3,5-difluorobenzyl)-N-((1S,2S)-2-hydroxycyclohexyl)-1H-pyrrolo[3,2-b]pyridine-3-carboxamide;
1-(2,5-difluorobenzyl)-N-((1S,2S)-2-hydroxycyclohexyl)-1H-pyrrolo[3,2-b]pyridine-3-carboxamide;
1-(3-fluorobenzyl)-N-((1S,2S)-2-hydroxycyclohexyl)-1H-pyrrolo[3,2-b]pyridine-3-carboxamide;
1-(4-fluorobenzyl)-N-((1S,2S)-2-hydroxycyclohexyl)-1H-pyrrolo[3,2-b]pyridine-3-carboxamide;
1-(4-fluoro-3-methylbenzyl)-N-((1S,2S)-2-hydroxycyclohexyl)-1H-pyrrolo[3,2-b]pyridine-3-carboxamide;
1-(2,3-difluorobenzyl)-N-((1S,2S)-2-hydroxycyclohexyl)-1H-pyrrolo[3,2-b]pyridine-3-carboxamide;
N-((1S,2S)-2-hydroxycyclohexyl)-1-(4-(trifluoromethoxy)benzyl)-1H-pyrrolo[3,2-b]pyridine-3-carboxamide;
1-(4-fluorobenzyl)-N-((1S,2S)-2-hydroxycyclohexyl)-7-methyl-1H-pyrrolo[3,2-b]pyridine-3-carboxamide;
1-(2,3-difluorobenzyl)-N-((1S,2S)-2-hydroxycyclohexyl)-7-methyl-1H-pyrrolo[3,2-b]pyridine-3-carboxamide;
N-((1S,2S)-2-hydroxycyclohexyl)-1-(4-methoxybenzyl)-7-methyl-1H-pyrrolo[3,2-b]pyridine-3-carboxamide;
1-(3-fluoro-4-methoxybenzyl)-N-((1S,2S)-2-hydroxycyclohexyl)-7-methyl-1H-pyrrolo[3,2-b]pyridine-3-carboxamide;
7-chloro-1-(4-fluorobenzyl)-N-((1S,2S)-2-hydroxycyclohexyl)-1H-pyrrolo[3,2-b]pyridine-3-carboxamide;
7-chloro-1-(2,3-difluorobenzyl)-N-((1S,2S)-2-hydroxycyclohexyl)-1H-pyrrolo[3,2-b]pyridine-3-carboxamide;
7-chloro-N-((1S,2S)-2-hydroxycyclohexyl)-1-((6-methylpyridin-2-yl)methyl)-1H-pyrrolo[3,2-b]pyridine-3-carboxamide;
7-chloro-1-((5-fluoropyridin-2-yl)methyl)-N-((1S,2S)-2-hydroxycyclohexyl)-1H-pyrrolo[3,2-b]pyridine-3-carboxamide;
1-(2-fluorobenzyl)-N-((1S,2S)-2-hydroxycyclohexyl)-1H-pyrrolo[3,2-b]pyridine-3-carboxamide;
1-(4-chlorobenzyl)-N-((1S,2S)-2-hydroxycyclohexyl)-1H-pyrrolo[3,2-b]pyridine-3-carboxamide;
1-(2,4-difluorobenzyl)-N-((1S,2S)-2-hydroxycyclohexyl)-1H-pyrrolo[3,2-b]pyridine-3-carboxamide;
1-(4-fluorobenzyl)-N-(trans-2-hydroxycycloheptyl)-1H-pyrrolo[3,2-b]pyridine-3-carboxamide;
1-(4-fluorobenzyl)-N-(piperidin-4-yl)-1H-pyrrolo[3,2-b]pyridine-3-carboxamide;
1-(4-fluorobenzyl)-N-(1-methylpiperidin-4-yl)-1H-pyrrolo[3,2-b]pyridine-3-carboxamide;
7-cyano-1-(4-fluorobenzyl)-N-((1S,2S)-2-hydroxycyclohexyl)-1H-pyrrolo[3,2-b]pyridine-3-carboxamide;
7-cyano-N-((1S,2S)-2-hydroxycyclohexyl)-1-(4-(trifluoromethyl)benzyl)-1H-pyrrolo[3,2-b]pyridine-3-carboxamide;
N-(trans-4,4-difluoro-2-hydroxycyclohexyl)-1-(4-fluorobenzyl)-1H-pyrrolo[3,2-b]pyridine-3-carboxamide;
1-(4-fluorobenzyl)-N-((1S,2S)-2-hydroxycyclohexyl)-7-methoxy-1H-pyrrolo[3,2-b]pyridine-3-carboxamide;
1-(4-(1H-pyrazol-1-yl)benzyl)-N-((1S,2S)-2-hydroxycyclohexyl)-5-methyl-1H-pyrrolo[3,2-b]pyridine-3-carboxamide;
1-(4-(1H-pyrazol-1-yl)benzyl)-5-cyano-N-((1S,2S)-2-hydroxycyclohexyl)-1H-pyrrolo[3,2-b]pyridine-3-carboxamide;
N-((1S,2S)-2-hydroxycyclohexyl)-1-(4-(1-methyl-1H-imidazol-2-yl)benzyl)-1H-pyrrolo[3,2-b]pyridine-3-carboxamide;
N-((1S,2S)-2-hydroxycyclohexyl)-1-(4-(1-methyl-1H-imidazol-4-yl)benzyl)-1H-pyrrolo[3,2-b]pyridine-3-carboxamide;
1-(2-fluoro-4-(6-methylpyridin-2-yl)benzyl)-N-((1S,2S)-2-hydroxycyclohexyl)-1H-pyrrolo[3,2-b]pyridine-3-carboxamide;
1-(2-fluoro-4-(2-methylpyridin-4-yl)benzyl)-N-((1S,2S)-2-hydroxycyclohexyl)-1H-pyrrolo[3,2-b]pyridine-3-carboxamide;
1-((4'-fluoro-[1,1'-biphenyl]-4-yl)methyl)-N-(trans-2-hydroxycyclohexyl)-1H-pyrrolo[3,2-b]pyridine-3-carboxamide;
1-(4-(1H-pyrazol-1-yl)benzyl)-N-((1S,2S)-2-hydroxycyclohexyl)-1H-pyrrolo[3,2-b]pyridine-3-carboxamide;
1-(4-(1H-pyrazol-1-yl)benzyl)-N-((1R,2R)-2-hydroxycyclohexyl)-1H-pyrrolo[3,2-b]pyridine-3-carboxamide;
1-(4-(1H-pyrazol-1-yl)benzyl)-N-cyclohexyl-1H-pyrrolo[3,2-b]pyridine-3-carboxamide;
1-(4-(1H-pyrazol-1-yl)benzyl)-N-(4,4-difluorocyclohexyl)-1H-pyrrolo[3,2-b]pyridine-3-carboxamide;
(S)-1-(4-(1H-pyrazol-1-yl)benzyl)-N-(piperidin-3-yl)-1H-pyrrolo[3,2-b]pyridine-3-carboxamide;
(S)-1-(4-(1H-pyrazol-1-yl)benzyl)-N-(1-methylpiperidin-3-yl)-1H-pyrrolo[3,2-b]pyridine-3-carboxamide;
(R)-1-(4-(1H-pyrazol-1-yl)benzyl)-N-(1-methylpiperidin-3-yl)-1H-pyrrolo[3,2-b]pyridine-3-carboxamide;
1-(4-bromobenzyl)-N-((1S,2S)-2-hydroxycyclohexyl)-1H-pyrrolo[3,2-b]pyridine-3-carboxamide;
N-((1S,2S)-2-hydroxycyclohexyl)-1-(4-(1-methyl-1H-pyrazol-4-yl)benzyl)-1H-pyrrolo[3,2-b]pyridine-3-carboxamide;
7-chloro-N-((1S,2S)-2-hydroxycyclohexyl)-1-(4-methoxybenzyl)-1H-pyrrolo[3,2-b]pyridine-3-carboxamide;
1-((6-chloropyridin-3-yl)methyl)-N-((1S,2S)-2-hydroxycyclohexyl)-7-methyl-1H-pyrrolo[3,2-b]pyridine-3-carboxamide;
1-(4-chlorobenzyl)-N-((1S,2S)-2-hydroxycyclohexyl)-7-methyl-1H-pyrrolo[3,2-b]pyridine-3-carboxamide;
7-chloro-N-((1S,2S)-2-hydroxycyclohexyl)-1-((5-methylpyridin-2-yl)methyl)-1H-pyrrolo[3,2-b]pyridine-3-carboxamide;
7-chloro-N-((1S,2S)-2-hydroxycyclohexyl)-1-((6-methylpyridin-3-yl)methyl)-1H-pyrrolo[3,2-b]pyridine-3-carboxamide;
N-((1S,2S)-2-hydroxycyclohexyl)-7-methyl-1-(4-methylbenzyl)-1H-pyrrolo[3,2-b]pyridine-3-carboxamide;
N-((1S,2S)-2-hydroxycyclohexyl)-7-methyl-1-((5-methylpyridin-2-yl)methyl)-1H-pyrrolo[3,2-b]pyridine-3-carboxamide;
1-(3-fluorobenzyl)-N-((1S,2S)-2-hydroxycyclohexyl)-7-methyl-1H-pyrrolo[3,2-b]pyridine-3-carboxamide;
N-((1S,2S)-2-hydroxycyclohexyl)-1-(4-methoxy-3-methylbenzyl)-7-methyl-1H-pyrrolo[3,2-b]pyridine-3-carboxamide;
N-((1S,2S)-2-hydroxycyclohexyl)-1-((6-methoxypyridin-3-yl)methyl)-7-methyl-1H-pyrrolo[3,2-b]pyridine-3-carboxamide;
7-chloro-N-((1S,2S)-2-hydroxycyclohexyl)-1-((6-methoxypyridin-3-yl)methyl)-1H-pyrrolo[3,2-b]pyridine-3-carboxamide;
7-chloro-N-((1S,2S)-2-hydroxycyclohexyl)-1-((2-methoxypyridin-4-yl)methyl)-1H-pyrrolo[3,2-b]pyridine-3-carboxamide;
7-chloro-1-((6-cyanopyridin-3-yl)methyl)-N-((1S,2S)-2-hydroxycyclohexyl)-1H-pyrrolo[3,2-b]pyridine-3-carboxamide;

N-((1S,2S)-2-hydroxycyclohexyl)-1-((2-methoxypyridin-4-yl)methyl)-7-methyl-1H-pyrrolo[3,2-b]pyridine-3-carboxamide;

7-chloro-N-((1S,2S)-2-hydroxycyclohexyl)-1-((1-methyl-1H-pyrazol-4-yl)methyl)-1H-pyrrolo[3,2-b]pyridine-3-carboxamide;

N-((1S,2S)-2-hydroxycyclohexyl)-7-methyl-1-((1-methyl-1H-pyrazol-4-yl)methyl)-1H-pyrrolo[3,2-b]pyridine-3-carboxamide;

7-chloro-N-((1S,2S)-2-hydroxycyclohexyl)-1-((4-methylthiazol-2-yl)methyl)-1H-pyrrolo[3,2-b]pyridine-3-carboxamide;

7-chloro-N-((1S,2S)-2-hydroxycyclohexyl)-1-((5-methylthiazol-2-yl)methyl)-1H-pyrrolo[3,2-b]pyridine-3-carboxamide;

N-((1S,2S)-2-hydroxycyclohexyl)-1-((2-methylpyridin-4-yl)methyl)-1H-pyrrolo[3,2-b]pyridine-3-carboxamide;

N-((1S,2S)-2-hydroxycyclohexyl)-1-(pyridin-4-ylmethyl)-1H-pyrrolo[3,2-b]pyridine-3-carboxamide;

7-chloro-N-((1S,2S)-2-hydroxycyclohexyl)-1-((2-methylpyridin-4-yl)methyl)-1H-pyrrolo[3,2-b]pyridine-3-carboxamide;

7-chloro-N-((1S,2S)-2-hydroxycyclohexyl)-1-(pyridin-4-ylmethyl)-1H-pyrrolo[3,2-b]pyridine-3-carboxamide;

7-chloro-N-((1S,2S)-2-hydroxycyclohexyl)-1-((4-methylpyridin-2-yl)methyl)-1H-pyrrolo[3,2-b]pyridine-3-carboxamide;

1-((5-chloropyridin-2-yl)methyl)-N-((1S,2S)-2-hydroxycyclohexyl)-7-methyl-1H-pyrrolo[3,2-b]pyridine-3-carboxamide;

1-(4-fluorobenzyl)-N-(trans-3-hydroxytetrahydro-2H-pyran-4-yl)-7-methyl-1H-pyrrolo[3,2-b]pyridine-3-carboxamide;

1-(4-methoxybenzyl)-N-(trans-3-hydroxytetrahydro-2H-pyran-4-yl)-7-methyl-1H-pyrrolo[3,2-b]pyridine-3-carboxamide;

1-(3-fluoro-4-methoxybenzyl)-N-(trans-3-hydroxytetrahydro-2H-pyran-4-yl)-7-methyl-1H-pyrrolo[3,2-b]pyridine-3-carboxamide;

N-(trans-3-hydroxytetrahydro-2H-pyran-4-yl)-1-((2-methoxypyridin-4-yl)methyl)-7-methyl-1H-pyrrolo[3,2-b]pyridine-3-carboxamide;

7-chloro-1-(3-fluorobenzyl)-N-(trans-3-hydroxytetrahydro-2H-pyran-4-yl)-1H-pyrrolo[3,2-b]pyridine-3-carboxamide;

7-chloro-1-(4-methoxybenzyl)-N-(trans-3-hydroxytetrahydro-2H-pyran-4-yl)-1H-pyrrolo[3,2-b]pyridine-3-carboxamide;

7-chloro-1-(4-fluorobenzyl)-N-((3R,4S)-3-hydroxytetrahydro-2H-pyran-4-yl)-1H-pyrrolo[3,2-b]pyridine-3-carboxamide;

7-chloro-1-(4-fluorobenzyl)-N-((3S,4R)-3-hydroxytetrahydro-2H-pyran-4-yl)-1H-pyrrolo[3,2-b]pyridine-3-carboxamide;

N-((1S,2S)-2-hydroxycyclohexyl)-1-(4-(trifluoromethyl)benzyl)-1H-pyrrolo[3,2-b]pyridine-3-carboxamide;

1-(4-fluoro-3-methoxybenzyl)-N-((1S,2S)-2-hydroxycyclohexyl)-1H-pyrrolo[3,2-b]pyridine-3-carboxamide;

1-(2-fluoro-4-methoxybenzyl)-N-((1S,2S)-2-hydroxycyclohexyl)-1H-pyrrolo[3,2-b]pyridine-3-carboxamide;

N-((1S,2S)-2-hydroxycyclohexyl)-1-(4-methoxybenzyl)-1H-pyrrolo[3,2-b]pyridine-3-carboxamide;

1-(3,4-difluorobenzyl)-N-((1S,2S)-2-hydroxycyclohexyl)-1H-pyrrolo[3,2-b]pyridine-3-carboxamide;

N-((1S,2S)-2-hydroxycyclohexyl)-1-(3-methylbenzyl)-1H-pyrrolo[3,2-b]pyridine-3-carboxamide;

1-(2-fluoro-4-methylbenzyl)-N-((1S,2S)-2-hydroxycyclohexyl)-1H-pyrrolo[3,2-b]pyridine-3-carboxamide;

1-(2,5-difluorobenzyl)-N-((1S,2S)-2-hydroxycyclohexyl)-7-methyl-1H-pyrrolo[3,2-b]pyridine-3-carboxamide;

7-chloro-N-((1S,2S)-2-hydroxycyclohexyl)-1-(4-(trifluoromethoxy)benzyl)-1H-pyrrolo[3,2-b]pyridine-3-carboxamide;

N-((1S,2S)-2-hydroxycyclohexyl)-7-methyl-1-(4-(trifluoromethoxy)benzyl)-1H-pyrrolo[3,2-b]pyridine-3-carboxamide;

1-(3,5-difluorobenzyl)-N-((1S,2S)-2-hydroxycyclohexyl)-7-methyl-1H-pyrrolo[3,2-b]pyridine-3-carboxamide;

1-(2-fluoro-3-methoxybenzyl)-N-((1S,2S)-2-hydroxycyclohexyl)-1H-pyrrolo[3,2-b]pyridine-3-carboxamide;

N-((1S,2S)-2-hydroxycyclohexyl)-1-(4-methoxy-3-methylbenzyl)-1H-pyrrolo[3,2-b]pyridine-3-carboxamide; or N-((1S,2S)-2-hydroxycyclohexyl)-7-methoxy-1-(4-methoxybenzyl)-1H-pyrrolo[3,2-b]pyridine-3-carboxamide.

In a further aspect, the present invention provides a compound of formula (IA), or a pharmaceutically acceptable salt thereof,

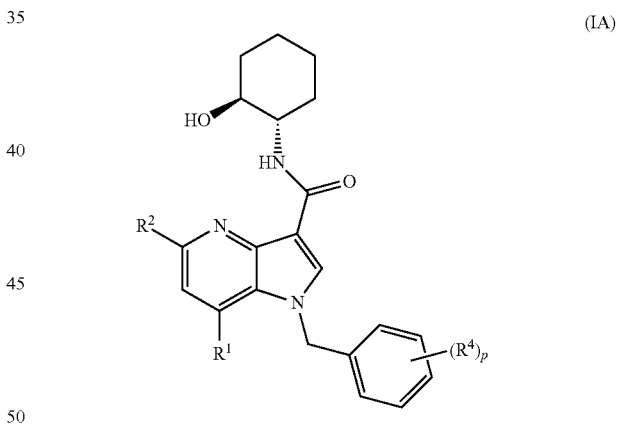

(IA)

wherein $R^1$ is hydrogen, halogen, cyano, $C_{1-4}$alkyl or $C_{1-4}$alkoxy;

$R^2$ is hydrogen;

p is 1 or 2 and each $R^4$ is independently selected from halogen, $C_{1-4}$alkyl, $C_{1-4}$ alkoxy, $C_{1-4}$haloalkyl and $C_{1-4}$ haloalkoxy.

In one embodiment, the present invention provides a compound of formula (IA), or a pharmaceutically acceptable salt thereof, wherein $R^1$ is hydrogen, chloro, methyl or methoxy; $R^2$ is hydrogen; p is 1 or 2 and each $R^4$ is independently selected from fluoro, chloro, bromo, methyl, methoxy, trifluoromethyl and trifluoromethoxy.

In a further aspect, the present invention provides a compound of formula (IB), or a pharmaceutically acceptable salt thereof,

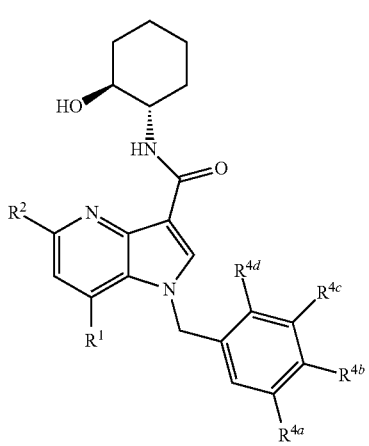

(IB)

wherein $R^1$ is hydrogen, halogen, $C_{1-4}$alkyl or $C_{1-4}$alkoxy;

$R^2$ is hydrogen;

$R^{4a}$ is hydrogen or halogen;

$R^{4b}$ is hydrogen, halogen, $C_{1-4}$alkyl, $C_{1-4}$alkoxy, $C_{1-4}$haloalkyl or $C_{1-4}$haloalkoxy;

$R^{4c}$ is hydrogen, halogen, $C_{1-4}$alkyl, $C_{1-4}$alkoxy or $C_{1-4}$haloalkyl; and $R^{4d}$ is hydrogen or halogen, wherein at least one of $R^{4a}$, $R^{4b}$, $R^{4c}$ and $R^{4d}$ is other than hydrogen and no more than two of $R^{4a}$, $R^{4b}$, $R^{4c}$ and $R^{4d}$ are hydrogen.

In one embodiment, the present invention provides a compound of formula (IB), or a pharmaceutically acceptable salt thereof, wherein $R^1$ is hydrogen, chloro, methyl or methoxy; $R^2$ is hydrogen; $R^{4a}$ is hydrogen or fluoro; $R^{4b}$ is hydrogen, fluoro, chloro, methyl, methoxy, bromo, trifluoromethyl or trifluoromethoxy; $R^{4c}$ is hydrogen, fluoro, methyl, methoxy or trifluoromethyl; and $R^{4d}$ is hydrogen or fluoro; wherein at least one of $R^{4a}$, $R^{4b}$, $R^{4c}$ and $R^{4d}$ is other than hydrogen and no more than two of $R^{4a}$, $R^{4b}$, $R^{4c}$ and $R^{4d}$ are hydrogen.

In a further aspect, the present invention provides a compound of formula (IB) or a pharmaceutically acceptable salt thereof, which is 1-(4-fluorobenzyl)-N-((1S,2S)-2-hydroxycyclohexyl)-1H-pyrrolo[3,2-b]pyridine-3-carboxamide;

1-(4-fluoro-3-methylbenzyl)-N-((1S,2S)-2-hydroxycyclohexyl)-1H-pyrrolo[3,2-b]pyridine-3-carboxamide;

1-(2,3-difluorobenzyl)-N-((1S,2S)-2-hydroxycyclohexyl)-1H-pyrrolo[3,2-b]pyridine-3-carboxamide;

1-(4-fluorobenzyl)-N-((1S,2S)-2-hydroxycyclohexyl)-7-methyl-1H-pyrrolo[3,2-b]pyridine-3-carboxamide;

1-(2,3-difluorobenzyl)-N-((1S,2S)-2-hydroxycyclohexyl)-7-methyl-1H-pyrrolo[3,2-b]pyridine-3-carboxamide;

N-((1S,2S)-2-hydroxycyclohexyl)-1-(4-methoxybenzyl)-7-methyl-1H-pyrrolo[3,2-b]pyridine-3-carboxamide; or 1-(3-fluoro-4-methoxybenzyl)-N-((1S,2S)-2-hydroxycyclohexyl)-7-methyl-1H-pyrrolo[3,2-b]pyridine-3-carboxamide.

In a further aspect, the present invention provides a compound, or a pharmaceutically acceptable salt thereof, which is

1-(4-fluorobenzyl)-N-((1S,2S)-2-hydroxycyclohexyl)-1H-pyrrolo[3,2-b]pyridine-3-carboxamide.

In a further aspect, the present invention provides a compound, or a pharmaceutically acceptable salt thereof, which is

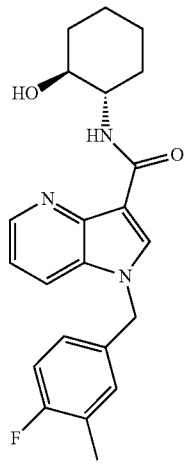 [SMILES: Cc1cc(Cn2cc(C(=O)N[C@H]3CCCC[C@@H]3O)c3ncccc32)ccc1F]

1-(4-fluoro-3-methylbenzyl)-N-((1S,2S)-2-hydroxycyclohexyl)-1H-pyrrolo[3,2-b]pyridine-3-carboxamide.

In a further aspect, the present invention provides a compound, or a pharmaceutically acceptable salt thereof, which is

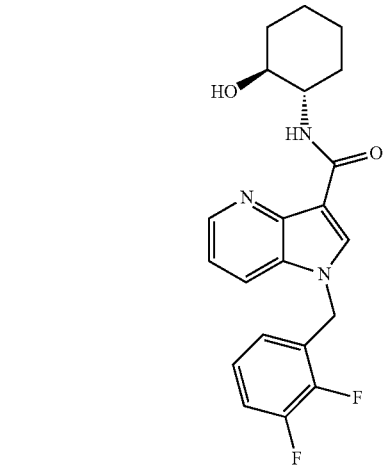 [SMILES: O=C(N[C@H]1CCCC[C@@H]1O)c1cn(Cc2cccc(F)c2F)c2cccnc12]

1-(2,3-difluorobenzyl)-N-((1S,2S)-2-hydroxycyclohexyl)-1H-pyrrolo[3,2-b]pyridine-3-carboxamide.

In a further aspect, the present invention provides a compound, or a pharmaceutically acceptable salt thereof, which is

1-(4-fluorobenzyl)-N-((1S,2S)-2-hydroxycyclohexyl)-7-methyl-1H-pyrrolo[3,2-b]pyridine-3-carboxamide.

In a further aspect, the present invention provides a compound, or a pharmaceutically acceptable salt thereof, which is

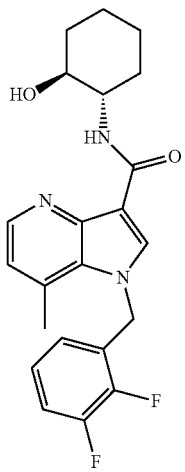 [SMILES: Cc1ccnc2c(C(=O)N[C@H]3CCCC[C@@H]3O)cn(Cc3cccc(F)c3F)c12]

1-(2,3-difluorobenzyl)-N-((1S,2S)-2-hydroxycyclohexyl)-7-methyl-1H-pyrrolo[3,2-b]pyridine-3-carboxamide.

In a further aspect, the present invention provides a compound, or a pharmaceutically acceptable salt thereof, which is

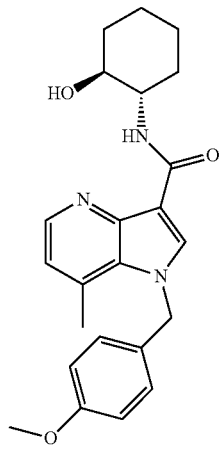 [SMILES: COc1ccc(Cn2cc(C(=O)N[C@H]3CCCC[C@@H]3O)c3nccc(C)c32)cc1]

N-((1S,2S)-2-hydroxycyclohexyl)-1-(4-methoxybenzyl)-7-methyl-1H-pyrrolo[3,2-b]pyridine-3-carboxamide.

In a further aspect, the present invention provides a compound, or a pharmaceutically acceptable salt thereof, which is

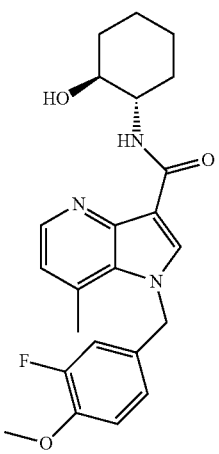 [SMILES: COc1ccc(Cn2cc(C(=O)N[C@H]3CCCC[C@@H]3O)c3nccc(C)c32)cc1F]

1-(3-fluoro-4-methoxybenzyl)-N-((1S,2S)-2-hydroxycyclohexyl)-7-methyl-1H-pyrrolo[3,2-b]pyridine-3-carboxamide.

An embodiment of formula (I) provides a compound of formula (IC), or a pharmaceutically acceptable salt thereof,

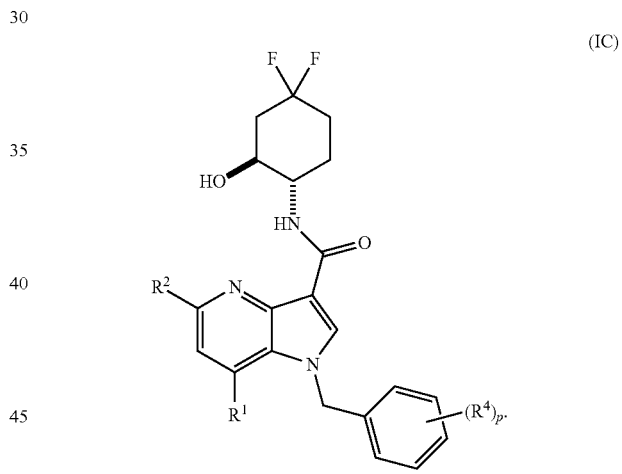

(IC)

wherein $R^1$ is hydrogen, halogen, cyano, $C_{1-4}$alkyl or $C_{1-4}$alkoxy;

$R^2$ is hydrogen;

p is 1 or 2 and each $R^4$ is independently selected from halogen, $C_{1-4}$alkyl, $C_{1-4}$alkoxy, $C_{1-4}$haloalkyl and $C_{1-4}$haloalkoxy.

In an embodiment of formula (IC), the compound or pharmaceutically acceptable salt thereof is N-((1S,2S)-4,4-difluoro-2-hydroxycyclohexyl)-1-(4-fluorobenzyl)-1H-pyrrolo[3,2-b]pyridine-3-carboxamide.

In an embodiment of formula (IC), the compound or pharmaceutically acceptable salt thereof is N-((1R,2R)-4,4-difluoro-2-hydroxycyclohexyl)-1-(4-fluorobenzyl)-1H-pyrrolo[3,2-b]pyridine-3-carboxamide.

As used herein, the term "non-aromatic $C_{5-8}$ carbocyclic group" denotes a non-aromatic ring system having 5 to 8 ring carbon atoms, including cycloalkyl rings, partially saturated rings and bridged rings. The term "cycloalkyl" denotes saturated carbocyclic rings. Examples of "cycloalkyl" rings include cyclopentyl, cyclohexyl and cycloheptyl.

As used herein, the term "non-aromatic 5-8-membered heterocyclic group" denotes a non-aromatic ring system having 5 to 8 ring atoms wherein at least one ring atom is selected from nitrogen, oxygen and sulphur, including heterocycloalkyl rings and partially saturated rings. The term "heterocycloalkyl" denotes saturated heterocyclic rings. Examples of a "5 to 8-membered non-aromatic heterocyclic group", include pyrrolidinyl, piperidinyl, piperazinyl, morpholinyl and tetrahydropyranyl groups.

As used herein, the term "heteroaryl" denotes aromatic rings having 5 to 6 ring atoms wherein at least one ring atom is selected from nitrogen, oxygen and sulphur. Examples of "heteroaryl" groups include furanyl, thienyl, pyrazolyl, imidazolyl, triazolyl, oxazolyl, isooxazolyl, thiazolyl, isothiazolyl, oxadiazolyl, pyridinyl, pyridazinyl, pyrimidinyl, pyrazinyl and triazinyl groups.

As used herein, the term "$C_{1-6}$alkyl" refers to an alkyl group having 1 to 6 carbon atoms. Examples of the group include linear and branched alkyl groups such as methyl, ethyl, n-propyl, isopropyl, n-butyl, isobutyl, t-butyl, n-pentyl, isopentyl, neopentyl, n-hexyl, 1-methylpropyl, 1,2-dimethylpropyl, 1-ethylpropyl, 1-methyl-2-ethylpropyl, 1-ethyl-2-methylpropyl, 1,1,2-trimethylpropyl, 1-methylbutyl, 2-methylbutyl, 1,1-dimethylbutyl, 2,2-dimethylbutyl, 2-ethylbutyl, 1,3-dimethylbutyl, 2-methylpentyl and 3-methylpentyl.

As used herein, the term '$C_{1-6}$ haloalkyl' denotes a $C_{1-6}$alkyl group substituted with one or more halogen atoms wherein each halogen is independently selected from fluorine, chlorine, bromine and iodine. Examples of $C_{1-6}$ haloalkyl groups include $CF_3$ (trifluoromethyl), $CHF_2$ (difluoromethyl), $CH_2F$ (monofluoromethyl), $CH_2CF_3$, $CH_2CHF_2$ and $CH_2CH_2F$.

As used herein, the term "$C_{1-6}$alkoxy" refers to a group containing an alkyl group bonded to an oxygen atom. Examples of the group include methoxy, ethoxy, n-propoxy, isopropoxy, n-butoxy, isobutoxy, sec-butoxy, t-butoxy, n-pentoxy, isopentoxy, sec-pentoxy, t-pentoxy, n-hexyloxy, isohexyloxy, 1,2-dimethylpropoxy, 2-ethylpropoxy, 1-methyl-2-ethylpropoxy, 1-ethyl-2-methylpropoxy, 1,1,2-trimethylpropoxy, 1,1-dimethylbutoxy, 2,2-dimethylbutoxy, 2-ethylbutoxy, 1,3-dimethylbutoxy, 2-methylpentoxy, 3-methylpentoxy and hexyloxy. Examples of a "$C_{1-6}$haloalkoxy" group include —$OCHF_2$ (difluoromethoxy) and —$OCF_3$ (trifluoromethoxy).

As used herein, the term '$C_{1-4}$ hydroxyalkyl' denotes a $C_{1-4}$alkyl group substituted with one to three hydroxyl groups. Examples of $C_{1-4}$ hydroxyalkyl groups include —$CH_2OH$ (hydroxymethyl).

In the context of the present specification, where it is stated that a group is optionally substituted with one or more substituents, the group may be substituted or unsubstituted. When substituted the group may for example be substituted with 1, 2 or 3 substituents.

In the present description, although crystal polymorphs of a compound of formula (I) may be present, the compound is similarly not limited thereto and may be present as a single crystal form or a mixture of single crystal forms. The compound may be an anhydride or a hydrate. Any of these forms are included in the scope of formula (I) and the present invention.

The present description also includes isotopically-labelled compounds, which are identical to the compounds of formula (I), except that one or more atoms are replaced by an atom having an atomic mass or mass number different from the atomic mass or mass number usually found in nature. Examples of isotopes that can be incorporated into compounds of the description include isotopes of hydrogen, carbon, nitrogen, oxygen, fluorine, phosphorous, chlorine, technetium and iodine, such as $^2H$, $^3H$, $^{11}C$, $^{14}C$, $^{13}N$, $^{15}O$ $^{18}F$, $^{32}P$, $^{99m}Tc$, $^{123}I$ and $^{131}I$.

Compounds of the present description and pharmaceutically acceptable derivatives (e.g. salts) of said compounds that contain the aforementioned isotopes and/or other isotopes of other atoms are within the scope of the present description Isotopically-labelled compounds of the present description for example those into which radioactive isotopes such as $^3H$ and/or $^{14}C$ are incorporated, may be useful in drug and/or substrate tissue distribution assays. $^3H$ and $^{14}C$ are considered useful due to their ease of preparation and detectability. $^{11}C$, $^{15}O$ and $^{18}F$ isotopes are considered useful in PET (positron emission tomography), and $^{99m}Tc$, $^{123}I$ and 131I isotopes are considered useful in SPECT (single photon emission computerized tomography), all useful in brain imaging. Substitution with heavier isotopes such as $^2H$ can afford certain therapeutic advantages resulting from greater metabolic stability, for example increased in vivo half-life or reduced dosage requirements and, hence, are considered useful in some circumstances. Isotopically labeled compounds of formula (I) of this description can generally be prepared by carrying out the procedures disclosed in the Schemes and/or in the Examples below, by substituting a readily available isotopically labelled reagent for a non-isotopically labelled reagent.

The 4-azaindole derivative of formula (I) according to the present description may be a pharmaceutically acceptable salt. Pharmaceutically acceptable salts include those described by Berge, Bighley and Monkhouse, J. Pharm. Sci., 1977, 66, 1-19. Specific examples of the pharmaceutically acceptable salt include inorganic acid salts (such as sulfates, nitrates, perchlorates, phosphates, carbonates, bicarbonates, hydrofluorides, hydrochlorides, hydrobromides and hydroiodides), organic carboxylates (such as acetates, oxalates, maleates, tartrates, fumarates, citrates, malonates and lactates), organic sulfonates (such as methanesulfonates, trifluoromethanesulfonates, ethanesulfonates, benzenesulfonates, toluenesulfonates and camphorsulfonates), amino acid salts (such as aspartates and glutamates), quaternary amine salts, alkali metal salts (such as sodium salts and potassium salts) and alkali earth metal salts (such as magnesium salts and calcium salts).

The compound of formula (I) according to the present description can be converted to a pharmaceutically acceptable salt by a conventional method where necessary. The salt can be prepared by a method in which methods typically used in the field of organic synthetic chemistry and the like are appropriately combined. Specific examples of the method include neutralization titration of a free solution of the compound of the present description with an acid solution.

In one embodiment, the present description provides a compound of formula (I), or a pharmaceutically acceptable salt thereof, for use in therapy.

In one embodiment, the present description provides a compound of formula (I), or a pharmaceutically acceptable salt thereof, for use in positive allosteric modulation of mAChR M1.

In one embodiment, the present description provides a compound of formula (I), or a pharmaceutically acceptable salt thereof, which has potential use for treating or preventing a neurodegenerative disease.

In one embodiment, the present description provides a compound of formula (I), or a pharmaceutically acceptable salt thereof, which has potential use for treating or preventing Alzheimer-type dementia (AD).

In one embodiment, the present description provides a compound of formula (I), or a pharmaceutically acceptable salt thereof, for use as a cognitive impairment improving agent in Alzheimer-type dementia (AD).

In one embodiment, the present description provides the use of a compound of formula (I), or a pharmaceutically acceptable salt thereof, for the manufacture of a medicament which has potential use for the treatment or prevention of Alzheimer-type dementia (AD).

In one embodiment, the present description provides the use of a compound of formula (I), or a pharmaceutically acceptable salt thereof, for the manufacture of a medicament for use as a cognitive impairment improving agent in Alzheimer-type dementia (AD).

In one embodiment, the description provides a method that has potential for use in treating or preventing Alzheimer-type dementia (AD) involving administering to a human subject in need thereof a therapeutically or prophylactically effective amount of a compound of formula (I) or a pharmaceutically acceptable salt thereof.

In one embodiment, the description provides a method for symptomatic treatment of cognitive impairment in Alzheimer-type dementia (AD) involving administering to a human subject in need thereof a therapeutically amount of a compound of formula (I) or a pharmaceutically acceptable salt thereof.

In one embodiment, the present description provides a compound of formula (I), or a pharmaceutically acceptable salt thereof, which has potential use for treating or preventing dementia with Lewy bodies (DLB).

In one embodiment, the present description provides a compound of formula (I), or a pharmaceutically acceptable salt thereof, for use as a cognitive impairment improving agent in dementia with Lewy bodies (DLB).

In one embodiment, the present description provides the use of a compound of formula (I), or a pharmaceutically acceptable salt thereof, for the manufacture of a medicament which has potential use for the treatment or prevention of dementia with Lewy bodies (DLB).

In one embodiment, the present description provides the use of a compound of formula (I), or a pharmaceutically acceptable salt thereof, for the manufacture of a medicament for use as a cognitive impairment improving agent in dementia with Lewy bodies (DLB).

In one embodiment, the present description provides a method that has potential for use in treating or preventing dementia with Lewy bodies (DLB) involving administering to a human subject in need thereof a therapeutically or prophylactically effective amount of a compound of formula (I) or a pharmaceutically acceptable salt thereof.

In one embodiment, the present description provides a method for symptomatic treatment of cognitive impairment in dementia with Lewy bodies (DLB) involving administering to a human subject in need thereof a therapeutically effective amount of a compound of formula (I) or a pharmaceutically acceptable salt thereof.

In one embodiment, the present description provides a compound of formula (I), or a pharmaceutically acceptable salt thereof, which has potential for use in treating or preventing schizophrenia, including the cognitive deficits associated with schizophrenia.

In another embodiment, the present description provides the use of a compound of formula (I), or a pharmaceutically acceptable salt thereof, for the manufacture of a medicament which has potential use for the treatment or prevention of schizophrenia, including the cognitive deficits associated with schizophrenia.

In a further embodiment, the present description provides a method that has potential use for treating or preventing schizophrenia, including the cognitive deficits associated with schizophrenia, involving administering to a human subject in need thereof a therapeutically or prophylactically effective amount of a compound of formula (I) or a pharmaceutically acceptable salt thereof.

In the context of the present specification "effective amount" means an amount sufficient to cause a benefit to the subject or at least to cause a change in the subject's condition.

A further aspect of the description provides a pharmaceutical composition comprising a compound of formula (I) as defined above, or a pharmaceutically acceptable salt thereof, as active ingredient in association with a pharmaceutically acceptable carrier. The composition may be in any suitable form, depending on the intended method of administration. It may for example be in the form of a tablet, capsule or liquid for oral administration, or of a solution or suspension for administration parenterally.

The 4-azaindole derivative or pharmaceutically acceptable salt thereof according to the present description may be formulated by a conventional method. Preferable examples of the dosage form include tablets, coated tablets such as film tablets and sugar-coated tablets, fine granules, granules, powders, capsules, syrups, troches, inhalants, suppositories, injections, ointments, eye drops, nasal drops, ear drops, cataplasms and lotions.

These solid preparations such as tablets, capsules, granules and powders can contain generally 0.01 to 100 wt %, and preferably 0.1 to 100 wt % of the 4-azaindole derivative or pharmaceutically acceptable salt thereof according to the present description as an active ingredient.

The active ingredient is formulated by blending ingredients generally used as materials for a pharmaceutical preparation and adding an excipient, a disintegrant, a binder, a lubricant, a colorant and a corrective typically used, and adding a stabilizer, an emulsifier, an absorbefacient, a surfactant, a pH adjuster, a preservative and an antioxidant where necessary, for example, using a conventional method. Examples of such ingredients include animal and vegetable oils such as soybean oil, beef tallow and synthetic glyceride; hydrocarbons such as liquid paraffin, squalane and solid paraffin; ester oils such as octyldodecyl myristate and isopropyl myristate; higher alcohols such as cetostearyl alcohol and behenyl alcohol; a silicone resin; silicone oil; surfactants such as polyoxyethylene fatty acid ester, sorbitan fatty acid ester, glycerol fatty acid ester, polyoxyethylene sorbitan fatty acid ester, polyoxyethylene hydrogenated castor oil and a polyoxyethylene-polyoxypropylene block copolymer; water-soluble polymers such as hydroxyethylcellulose, polyacrylic acid, a carboxyvinyl polymer, polyethylene glycol, polyvinylpyrrolidone and methylcellulose; lower alcohols such as ethanol and isopropanol; polyhydric alcohols such as glycerol, propylene glycol, dipropylene glycol and sorbitol; sugars such as glucose and sucrose; inorganic powders such as silicic anhydride, magnesium aluminum silicate and aluminum silicate; and purified water. Examples of the excipient used include lactose, corn starch, saccharose, glucose, mannitol, sorbitol, crystalline cellulose and silicon dioxide. Examples of the binder used include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, a polypropylene glycol-polyoxyethylene block copolymer and meglumine. Examples of the disintegrant used include starch, agar, gelatin powder, crystalline cellulose, calcium carbonate, sodium bicarbonate, calcium citrate, dextrin, pectin and carboxymethylcellulose calcium. Examples of the lubricant used include magnesium stearate, talc, polyethylene glycol, silica and hydrogenated vegetable oil. Examples of the colorant used include those permitted to be added to pharmaceuticals. Examples of the corrective used include cocoa powder, menthol, empasm, mentha oil, borneol and cinnamon powder. Obviously, the ingredients are not limited to the above additive ingredients.

For example, an oral preparation is prepared by adding the 4-azaindole derivative or pharmaceutically acceptable salt thereof according to the present description as an active ingredient, an excipient and, where necessary, a binder, a disintegrant, a lubricant, a colorant, a corrective and the like, and then forming the mixture into powder, fine granules, granules, tablets, coated tablets, capsules or the like by a conventional method. Obviously, tablets or granules may be appropriately coated, for example, sugar coated, where necessary.

For example, a syrup or an injection preparation is prepared by adding a pH adjuster, a solubilizer, an isotonizing agent and the like, and a solubilizing agent, a stabilizer and the like where necessary by a conventional method. The injection may be a previously prepared solution, or may be powder itself or powder containing a suitable additive, which is dissolved before use. The injection can contain usually 0.01 to 100 wt %, and preferably 0.1 to 100 wt % of the active ingredient. Further, a liquid preparation for oral administration such as a suspension or a syrup can contain usually 0.01 to 100 wt %, and preferably 0.1 to 100 wt % of the active ingredient.

For example, an external preparation can be prepared by any conventional method without specific limitations. As a base material, any of various materials usually used for a pharmaceutical, a quasi drug, a cosmetic or the like can be used. Examples of the base material include materials such as animal and vegetable oils, mineral oils, ester oils, waxes, higher alcohols, fatty acids, silicone oils, surfactants, phospholipids, alcohols, polyhydric alcohols, water-soluble polymers, clay minerals and purified water. A pH adjuster, an antioxidant, a chelator, a preservative and fungicide, a colorant, a flavor or the like can be added where necessary. Further, ingredients such as an ingredient having a differentiation inducing effect, a blood flow enhancer, a bactericide, an antiphlogistic, a cell activator, vitamin, amino acid, a humectant and a keratolytic agent can be blended where necessary.

The dose of the 4-azaindole derivative or pharmaceutically acceptable salt thereof according to the present description varies according to the degree of symptoms, age, sex, body weight, mode of administration, type of salt and specific type of disease, for example. Typically, the active ingredient is orally administered to an adult at about 30 μg to 10 g, preferably 100 μg to 5 g, and more preferably 100 μg to 1 g per day, or is administered to an adult by injection at about 30 μg to 1 g, preferably 100 μg to 500 mg, and more preferably 100 μg to 300 mg per day, in one or several doses, respectively.

Compounds of formula (I) may be used in combination with other therapeutic agents, for example medicaments claimed to be useful as either disease modifying or symptomatic treatments of a neurological disorder such as Alzheimer-type dementia (AD) or schizophrenia. Thus, in a further aspect, the present description provides a pharmaceutical product comprising, in combination, a first active ingredient which is a compound of formula (I) or a pharmaceutically acceptable salt thereof and at least one further active ingredient useful in treating a neurological disorder such as Alzheimer-type dementia (AD) or schizophrenia. In one embodiment of the description, the neurodegenerative neurological disorder is Alzheimer-type dementia (AD). Suitable examples of such further active ingredients may be symptomatic agents, for example M4 agonists or positive allosteric modulators (PAMs), acetylcholinesterase inhibitors (such as tetrahydroaminoacridine, donepezil hydrochloride and rivastigmine), NMDA receptor antagonists, nicotinic receptor agonists or allosteric modulators (such as α7 agonists or allosteric modulators or α4β2 agonists or allosteric modulators), PPAR agonists (such as PPARγ agonists), beta-site amyloid-β precursor protein cleavage enzyme 1 (hereinafter referred to as BACE1 or beta-secretase) inhibitors 5-HT4 receptor agonists or partial agonists, histamine H3 antagonists, 5-HT6 receptor antagonists or 5HT1A receptor ligands and, 5-HT2A antagonists, 5-HT7 antagonists, D1 agonists or PAMs, D2 antagonists, D4 agonists or PAMs, D5 agonists or PAMs, GABA-A α5 inverse agonists or negative allosteric modulators (NAMs), GABA-A α2/3 agonists or PAMs, mGluR2 inverse agonists or negative allosteric modulators, mGluR5 positive allosteric modulators, PDE 1 inhibitors, PDE 2 inhibitors, PDE 4 inhibitors, PDE 5 inhibitors, PDE 9 inhibitors, PDE 10 inhibitors, GlyT1 inhibitors, DAAO inhibitors, ASC1 inhibitors, AMPA modulators, SIRT1 activators or inhibitors, AT4 antagonists, GalR1 antagonists, GalR3 ligands, adenosine A1 antagonists, adenosine A2a antagonists, α2A antagonists or agonists, selective and unselective norepinephrine reuptake inhibitors (SNRIs), or potential disease modifying agents such as gamma secretase inhibitors or modulators, alpha secretase activators or modulators, amyloid aggregation inhibitors, amyloid antibodies, tau aggregation inhibitors or tau phosphorylation/kinase inhibitors, tau dephosphorylation/phosphatase activators, mitogen-activated protein kinase kinase 4 (MKK4/MEK4/MAP2K4) inhibitors, c-Jun N-terminal kinase (JNK) inhibitors, casein kinase inhibitors, MK2 (mitogen activated protein kinase-activated protein kinase 2) inhibitors, MARK (microtubule affinity regulating kinase) inhibitors, CDK5 (cyclin dependent kinase 5) inhibitors, GSK-3 (glycogen synthase kinase-3) inhibitors and tau-tubulin kinase-1 (TTBK1) inhibitors. Further examples of such other therapeutic agents may be calcium channel blockers, HMG-CoA (3-hydroxy-3-methylglutaryl-CoA) reductase inhibitors (statins) and lipid lowering agents, NGF (nerve growth factor) mimics, antioxidants, GPR3 ligands, plasmin activators, neprilysin (NEP) activators, IDE (insulin degrading enzyme) activators, melatonin MT1 and/or MT2 agonists, TLX/NR2E1 (tailless X receptor) ligands, GluR1 ligands, RAGE (receptor for advanced glycation end-products) antagonists, EGFR (epidermal growth factor receptor) inhibitors, FPRL-1 (formyl peptide-like receptor-1) ligands, GABA antagonists, and MICAL (molecule interacting with casL) inhibitors, e.g. oxoreductase inhibitors, CB1 antagonists/inverse agonists, non-steroidal anti-inflammatory drugs (NSAIDs), anti-inflammatory agents (for example agents that could be used to treat neuroinflammation either by enhancing or reducing neuroinflammation), amyloid precursor protein (APP) ligands, anti-amyloid vaccines and/or antibodies, agents that promote or enhance amyloid efflux and/or clearance, histone deacetylase (HDAC) inhibitors, EP2 antagonists, 11-beta HSD1 (hydroxysteroid dehydrogenase) inhibitors, liver X receptor (LXR) agonists or PAMs, lipoprotein receptor-related protein (LRP) mimics and/or ligands and/or enhancers and/or inhibitors, butyryl cholinesterase inhibitors, kynurinic acid antagonists and/or inhibitors of kynurenine aminotransferease (KAT), orphanin FQ/nociceptin (NOP)/opioid-like receptor 1 (ORL1) antagonists, excitatory amino acid transporter (EAAT) ligands (activators or inhibitors), and plasminogen activator inhibitor-1 (PAI-1) inhibitors, niacin and/or GPR109 agonists or PAMs in combination with cholesterol lowering agents and/or HMGCoA reductase inhibitors (statins), dimebolin or similar agents, antihistamines, metal binding/chelating agents, antibiotics, growth hormone secretagogues, cholesterol lowering agents, vitamin E, cholesterol absorption inhibitors, cholesterol efflux promoters and/or activators, and insulin upregulating agents.

In one embodiment, the present description provides a pharmaceutical product comprising, in combination, a first active ingredient which is a compound of formula (I) or a pharmaceutically acceptable salt thereof and at least one further active ingredient useful in treating Alzheimer-type dementia selected from:

cholinesterase inhibitors, e.g. donepezil, galantamine, rivastigamine, tetrahydroaminoacridine and pharmaceutically acceptable salts thereof, NMDA receptor antagonists, e.g. memantine and pharmaceutically acceptable salts thereof, 5-HT6 antagonists, e.g. SB-742457 and pharmaceutically acceptable salts thereof, and HMGCoA reductase inhibitors e.g. lovastatin, rosuvastatin, atorvastatin, simvastatin, fluvastatin, pitavastatin, pravastatin and pharmaceutically acceptable salts thereof.

In another embodiment, the present description provides a pharmaceutical product comprising, in combination, a first active ingredient which is a compound of formula (I) or a pharmaceutically acceptable salt thereof and at least one further active ingredient useful in treating schizophrenia selected from:—

Antipsychotic drugs e.g. chlorpromazine, thioridazine, mesoridazine, fluphenazine, perphanazine, prochlorperazine, trifluoperazine, thiothixine, haloperidol, molindone, loxapine, clozapine, olanzapine, risperidone, quetiapine, aripirazole, ziprasidone, amisulpride and pharmaceutically acceptable salts thereof, and Drugs used as mood stabilisers e.g. lithium, valproic acid, carbamazepine, lamotrigine, gabapentin, topiramate, tiagabine and pharmaceutically acceptable salts thereof, The individual components of such combinations may be administered either sequentially or simultaneously in separate or combined pharmaceutical formulations. Consequently, the pharmaceutical product may, for example be a pharmaceutical composition comprising the first and further active ingredients in admixture. Alternatively, the pharmaceutical product may for example comprise the first and further active ingredients in separate pharmaceutical preparations suitable for simultaneous, sequential or separate administration to a patient in need thereof.

The combinations referred to above may conveniently be presented for use in the form of a pharmaceutical formulation and thus pharmaceutical formulations comprising a combination as defined above together with a pharmaceutically acceptable carrier or excipient comprise a further aspect of the description.

When a compound of formula (I) or a pharmaceutically acceptable salt thereof is used in combination with a second therapeutic agent active, the dose of each compound may differ from that when the compound is used alone. Appropriate doses will be readily appreciated by those skilled in the art.

Thus, an additional aspect of the description provides a method of preparation of a pharmaceutical composition, involving admixing at least one compound of formula (I) as defined above, or a pharmaceutically acceptable salt thereof, with one or more pharmaceutically acceptable adjuvants, diluents or carriers and/or with one or more other therapeutically or prophylactically active agents.

General Methods for preparing a compound of formula (I) or a pharmaceutically acceptable salt thereof, according to the present description, are described herein below.

It will be appreciated by those skilled in the art that when preparing certain compounds of formula (I) it may be appropriate to modify the general preparation methods by alternating the sequence of reaction steps and/or incorporating additional steps to vary substituent groups on intermediate compounds. Moreover, it will also be recognised that compounds of formula (I) prepared according to the general preparation methods may subsequently be converted to other compounds of formula (I) using known chemistry. It will also be appreciated by those skilled in the art that in some instances certain functional groups such as hydroxyl, carboxyl or amino groups in starting reagents or intermediate compounds may need to be protected by protecting groups. Thus the following preparation methods may involve at certain stages the incorporation of one or more protecting groups. The protection and deprotection of functional groups is, for example, described in 'Protective Groups in Organic Synthesis, 3rd edition, T. W. Greene and P. G. M. Wuts, Wiley-Interscience (1999) and 'Protecting Groups', P. J. Kocienski, Georg Thieme Verlag (1994), hereby known as references 1 and 2. Many of the reaction schemes to make intermediates utilise chemistry that will be known to those skilled in the art and can be found in references such as 'Organic Chemistry', 2nd edition, J. Clayden, N. Greeves and S. Warren, Oxford University Press (2012) and 'March's Advanced Organic Chemistry', 6th edition, J. March, Wiley-VCH (2007), hereby known as references 3 and 4. Moreover, it will also be appreciated by those skilled in the art that preparation methods involving the reaction of a carboxyl group may in certain instances be conducted using an equivalent alkyl ester or acid chloride.

The choice of solvent used in the steps described in the general preparation methods may vary according to the specific reagents used. Unless otherwise stated the choice of solvent is not particularly limited insofar as it does not inhibit the reaction, allows the reagents to be dissolved therein to a certain extent, and is inert during the reaction.

General Preparation Method:

Scheme 1

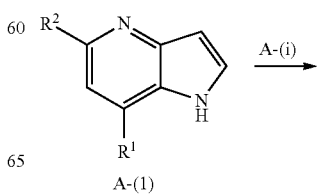

A-(1)

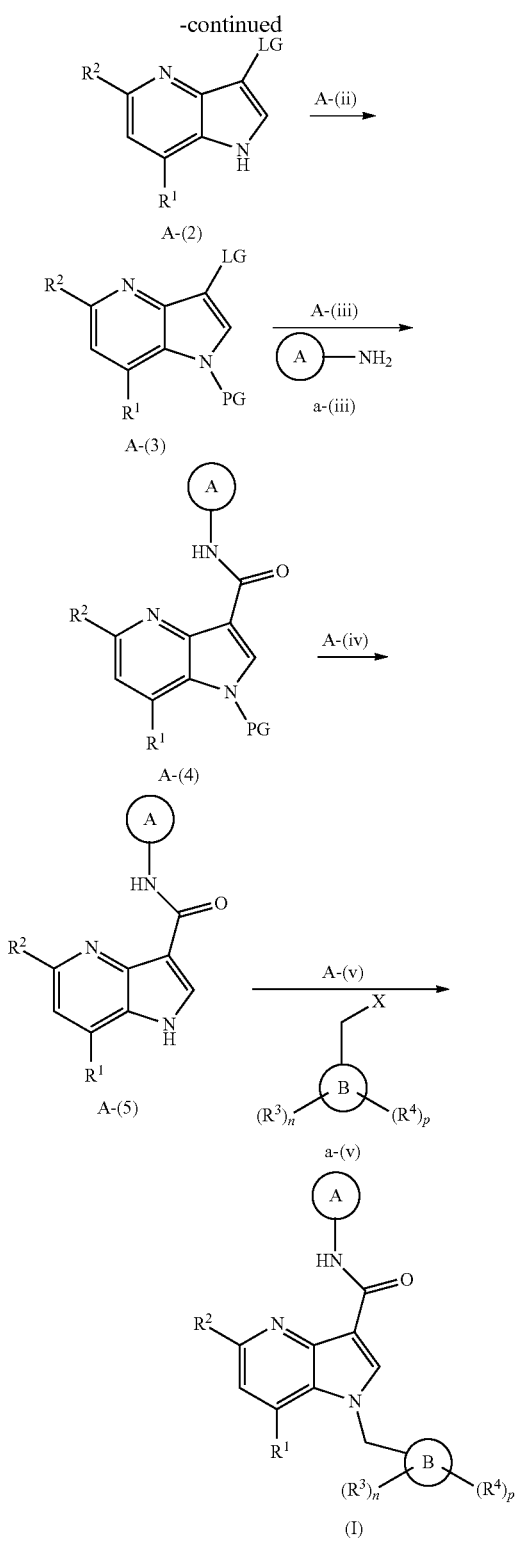

General Preparation Method A is a method for preparing a compound of formula (I) according to the present description from a compound A-(1) as a raw material through multiple steps of Step A-(i) to Step A-(v), as depicted in scheme 1. In scheme 1, RingA, RingB, $R^1$, $R^2$, $R^3$ $R^4$, n and p are as defined above in respect of compounds of formula (I). PG is a suitable protecting group for nitrogen, such as Boc, CBz or phenylsulfone for example. LG is a suitable halogen leaving group, such as F, Cl, Br, I. Compounds of formula A-(1) are either commercially available, may be prepared by literature methods or may be prepared by methods known to those skilled in the art.

Step A-(i):

This is a step of obtaining a compound A-(2) by substitution reaction of a suitable halogen into a compound A-(1). The halogen introduced is not particularly limited, insofar as it permits the desired reactivity in the derivatives produced. Typically, bromine or iodine may be introduced. Methods of introducing bromine include those described in US20080009514A1 and WO201033980A2, and methods of introducing iodine include those described in WO2011/78984 A1, Bioorg. Med. Chem. Lett. 2009, 24, 6935-6938, and Org. Bio. Chem. 2011, 14, 5129-5136. Alternatively, the reaction may be performed with iodine in the presence of a suitable base.

The solvent used in this step varies according to starting material and the reagent used. Examples of solvents include organic solvents, such as N-,N-dimethylformamide or N-,N-dimethylacetamide When a base is required the choice of base used is not particularly limited. Examples of bases include inorganic bases, for example potassium hydroxide or sodium hydroxide. The reaction time is not particularly limited and is usually 0.5 to 72 hours, typically 0.5 to 5 hours. The reaction temperature varies according to the starting material, the reagent used and the like, and is typically in the range of from 20° C. to 100° C.

Step A-(ii):

This is a step of protecting the aza-indole nitrogen in A-(2) to generate A-(3). The protection and deprotection of functional groups is, for example, described in references 1 and 2. The protecting group used in this step can be varied according to starting material, and is not particularly limited insofar as the protecting group does not interfere with reactions to which compound A-(3) and any future protected derivatives will be subjected. Specifically, when PG=Boc, the reaction can be carried out using di-tert butyl dicarbonate and a suitable base.

The solvent used in this step varies according to starting material and the reagent used. Examples of solvents include organic solvents, such as dichloromethane or tetrahydrofuran. When a base is required the choice of base is not particularly limited. Examples of bases include organic bases, such as triethylamine or DIPEA, or inorganic salts, for example sodium bicarbonate or potassium carbonate. The reaction time is not particularly limited and is usually 0.5 to 72 hours, typically 0.5 to 5 hours. The reaction temperature varies according to the starting material, the reagent used and the like, and is typically in the range of from 20° C. to 100° C.

Step A-(iii):

This step is a step of obtaining compound A-(4) by the reaction of compound A-(3) and an amine compound a-(iii) (RingA-NH$_2$) utilizing a transition metal-mediated coupling reaction in the presence of carbon monoxide and a suitable base.

Those skilled in the art will appreciate that this transformation can be accomplished by a range of conditions. For example compound A-(3) can be transformed to A-(4) using a transition metal catalyst, for example a palladium catalyst such as palladium (II) acetate and Xantphos™ in a 1:2 ratio. Alternatively, a wide variety of other related transition metal catalysts may also be suitable for this transformation, for example tetrakis(triphenylphosphine)palladium (0), [1,1'-bis(diphenylphosphino)ferrocene]palladium (II) dichloride, bis(triphenylphosphino) palladium (II) dichloride. The amount of the organometallic catalyst used is about 0.001 to 0.5 equivalent with respect to the raw material. Those skilled in the art will understand that many such catalysts are known and that many of such catalysts are capable of effecting this transformation and that the substrate A-(3) or the coupling partner may dictate which catalyst can or cannot be used.

The aforementioned transition metal mediated coupling reactions require an amine compound a-(iii) to act as the coupling partner. Such amines are not particularly limited. The amount of the coupling partner used is not particularly limited and is usually 1 to 5 equivalents with respect to the compound A-(3). Amine compounds a-(iii) are either commercially available, may be prepared by literature methods or may be prepared by methods known to those skilled in the art.

In addition to the aforementioned catalyst and reaction partner, these transition-metal mediated reactions require a solvent and often a base or salt is required to be present. The solvent used in this reaction is not particularly limited insofar as it does not inhibit the reaction. Examples of the solvent include benzene, toluene, N,N-dimethylformamide, tetrahydrofuran, 1,2-dimethoxyethane, 1,4-dioxane, and the like and mixtures thereof. Such a base or salt is not particularly limited. Examples of the base or salt include bases or salts such as sodium carbonate, potassium carbonate, barium hydroxide, cesium carbonate, potassium phosphate, cesium fluoride, potassium fluoride and solutions thereof, and organic bases, such as triethylamine, N,N-diisopropylethylamine.

The reaction can be carried out in an atmosphere of carbon monoxide with pressure typically ranging from 20 to 100 p.s.i.

The reaction may be conducted at various temperatures, for example from room temperature to solvent reflux temperature. The reaction time is not particularly limited and is usually 0.5 to 48 hours, typically 0.5 to 24 hours.

Step A-(iv):

This is a step of obtaining compound A-(5) from compound A-(4) by removal of the protecting group.

Suitable conditions to convert A-(4) to A-(5) include those described in references 1 and 2. For example, a) when PG=Boc, A-(4) may be converted to A-(5) by treating with an acid e.g. TFA or HCl in ether or dioxane; b) when PG=Cbz, A-(4) may be converted to A-(5) by hydrogenation in the presence of a palladium catalyst in a suitable solvent; and c) when PG=Teoc, A-(4) may be converted to A-(5) by treatment with fluoride in a suitable solvent.

Step A-(v):

This is a step of obtaining a compound (I) by substitution reaction of an alkyl halide of formula a-(v) to the compound A-(5) in the presence of a suitable base. In the compound of formula a-(v), X may for example be Cl or Br.

The reaction in this step can be performed under many conditions known to those skilled in the art, such as those reported in WO2004/31188 A1, WO2010/80474 A1, WO2012/88469 A1 or WO2009/32125 A1, for example.

Alkyl halides of formula a-(v) are either commercially available, may be prepared by literature methods or may be prepared by methods known to those skilled in the art.

The solvent used in this step varies according to starting material and the reagent used. Examples of solvents include organic solvents, such as tetrahydrofuran mixed with water or N-,N-dimethylformamide in the absence of water. The base used is not particularly limited insofar as it does not react with the alkyl halide. Examples of bases include inorganic bases, for example cesium carbonate or potassium hydroxide. The reaction time is not particularly limited and is usually 0.5 to 72 hours, typically 0.5 to 5 hours. The reaction temperature varies according to the starting material, the reagent used and the like, and is typically in the range of from 20° C. to 100° C.

The present invention will be described more specifically below with reference to the following illustrative Examples. However, the present invention is not limited thereto. The abbreviations used in Examples are conventional abbreviations known to a person skilled in the art. Some abbreviations are listed below:

DCM—Dichloromethane

TEA—Triethylamine

EtOAc—Ethyl Acetate

BOP—(Benzotriazol-1-yloxy)tris(dimethylamino)phosphonium hexafluorophosphate

DMF—N-, N-dimethylformamide

HOBt—Hydroxybenzotriazole

THF—Tetrahydrofuran $Pd(PPh_3)_4$—Palladium-tetrakis(triphenylphosphine)

rt—room temperature

TFA—Trifluoroacetic acid mCPBA—meta-chloro perbenzoic acid

DBU—1,8-Diazabicyclo[5.4.0]undec-7-ene

MeCN—Acetonitrile dppf—1,1'-Bis(diphenylphosphino)ferrocene $Pd(OAc)_2$—Palladium (II) Acetate XantPhos—4,5-Bis(diphenylphosphino)-9,9-dimethylxanthene DMSO—dimethylsulfoxide AIBN—2,2'-Azobis(2-methylpropionitrile)

HATU—1-[Bis(dimethylamino)methylene]-1H-1,2,3-triazolo[4,5-b]pyridinium 3-oxid hexafluorophosphate DMAP—4-dimethylamino pyridine $CDCl_3$—deutero-chloroform prep.—preparatory $CD_3OD$—deutero-methanol MeOH—Methanol LC-MS—Liquid Chromatography-Mass Spectrometry NMR—Nuclear Magnetic Resonance TBAF—tetra-n-butylammonium fluoride $^1$H NMR spectra were recorded on a Bruker AV 400, a Bruker Avance III 400 spectrometer operating at a (reported) frequency of 400 MHz, a Bruker Avance III 600 series operating at a (reported) frequency of 600 MHz, or Varian MERCURYplus 400 operating at a (reported) frequency of 400 MHz. Chemical shifts in proton nuclear magnetic resonance spectra are recorded in δ units (ppm) relative to tetramethylsilane and coupling constants (J) are recorded in Hertz (Hz). Chemical shift and coupling constants were analyzed using ACD/Spectrus Processor (Fujitsu) Patterns are designated as s: singlet, d: doublet, t: triplet, br: broad, m: multiplet. Chemical names were generated from chemical structures using ChemBioDraw Ultra 11.0 and 12.0 or E-notebook version 12 (PerkinElmer)

Intermediate Compounds

Intermediate 4: Synthesis of N-((1S,2S)-2-Hydroxycyclohexyl)-1H-pyrrolo[3,2-b]pyridine-3-carboxamide

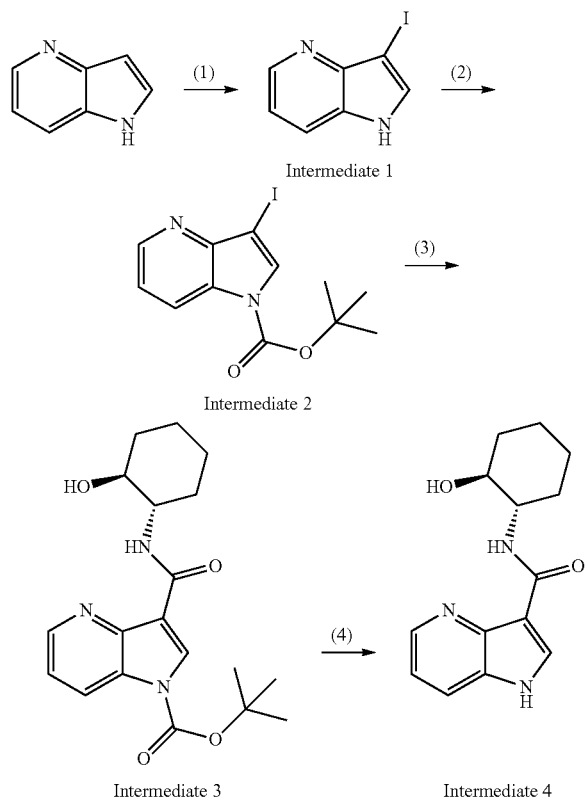

(1) Intermediate 1:
3-Iodo-1H-pyrrolo[3,2-b]pyridine

To a mixture of 1H-pyrrolo[3,2-b]pyridine (Purchased from Combi Blocks Inc.), (5 g) and DMF (100 mL) stirred under nitrogen at room temperature was added potassium hydroxide (9.02 g) followed by iodine (12.89 g) and the resulting mixture was stirred at room temperature for 1 h 5 min., then poured onto a mixture of $Na_2S_2O_5.5H_2O$ (4.25 g), water (635 mL), and 28-30% ammonium hydroxide (43 mL). The resultant mixture was cooled in an ice bath for 20 min, and the precipitate thus produced was filtered and washed with ice water then dried under vacuum to give the title compound (9.18 g).
LCMS: m/z 245.39 [M+H]$^+$.
$^1$H NMR (400 MHz, DMSO-d$_6$) ppm 7.17 (dd, J=8.1, 4.5 Hz, 1H) 7.72-7.87 (m, 2H) 8.38 (d, J=4.4 Hz, 1H) 11.74 (br. s., 1H)

(2) Intermediate 2: tert-Butyl 3-iodo-1H-pyrrolo[3,2-b]pyridine-1-carboxylate

To a mixture of 3-iodo-1H-pyrrolo[3,2-b]pyridine (Intermediate 1), (6 g), 4-Dimethylaminopyridine (0.390 g) and DCM (60.0 mL) stirred under nitrogen at room temperature was added dropwise a solution of di-t-butyldicarbonate (8.05 g) in DCM (60 mL) and the reaction was stirred overnight at rt, then concentrated under vacuum. The residue was purified by column chromatography (normal phase, 100 g, Biotage SNAP cartridge KP-Sil, 50 mL per min, gradient 0% to 30% EtOAc in n-hexane) to give the desired compound (8.21 g).
LCMS: m/z 345.45 [M+H]$^+$.
$^1$H NMR (400 MHz, CDCl$_3$) ppm 1.69 (s, 9H) 7.31 (dd, J=8.3, 4.8 Hz, 1H) 7.99 (s, 1H) 8.33-8.45 (m, 1H) 8.64 (dd, J=4.7, 1.2 Hz, 1H)

(3) Intermediate 3: tert-Butyl 3-(((1S,2S)-2-hydroxycyclohexyl)carbamoyl)-1H-pyrrolo[3,2-b]pyridine-1-carboxylate tert-Butyl 3-iodo-1H-pyrrolo[3,2-b]pyridine-1-carboxylate (Intermediate 2), (8 g), (1S,2S)-2-aminocyclohexanol hydrochloride (Purchased from Greenchempharm Inc.), (5.29 g), palladium (II) acetate (0.157 g), XantPhos (0.807 g), toluene (210 mL) and TEA (9.72 mL) were placed in a 500 mL three necked flask with a CO balloon and condenser attached. The reaction mixture was purged with CO then heated to 80° C. over a weekend. The reaction was cooled to rt and poured onto EtOAc, the remaining solid in the reaction flask was sonicated with a small amount of THF and the slurry added to the EtOAc organic phases. The combined organic phases were washed with water (2×) then brine and the combined aqueous phases extracted with EtOAc (1×). The combined organic extracts were dried (MgSO$_4$), filtered and evaporated under vacuum to give the desired compound (8.72 g), which was taken on crude.
LCMS: m/z 360.60 [M+H]$^+$.

(4) Intermediate 4: N-((1S,2S)-2-Hydroxycyclohexyl)-1H-pyrrolo[3,2-b]pyridine-3-carboxamide To a solution of tert-butyl 3-(((1S,2S)-2-hydroxycyclohexyl)carbamoyl)-1H-pyrrolo[3,2-b]pyridine-1-carboxylate (Intermediate 3), (8.35 g) in DCM (100 mL) stirred at rt under nitrogen was added TFA (50 mL) and the reaction was stirred at rt for 1.5 h. The reaction was concentrated under vacuum and the residue was purified by column chromatography (normal phase, 375 g, Biotage SNAP cartridge KP-NH, 100 mL per min, gradient 0% to 100% EtOAc in n-hexane, then 0-20% MeOH in EtOAc) to give the desired compound (5.64 g).
LCMS: m/z 260.51 [M+H]$^+$.
$^1$H NMR (400 MHz, DMSO-d$_6$) ppm 1.18-1.41 (m, 4H) 1.51-1.72 (m, 2H) 1.88 (d, J=9.1 Hz, 1H) 2.04 (d, J=9.4 Hz, 1H) 3.24-3.48 (m, 1H) 3.65-3.80 (m, 1H) 4.79 (br. s., 1H) 7.24 (dd, J=8.1, 4.7 Hz, 1H) 7.91 (d, J=8.2 Hz, 1H) 8.15 (s, 1H) 8.46 (d, J=4.5 Hz, 1H) 8.81 (d, J=7.5 Hz, 1H).

Intermediate 13: Synthesis of N-((1S,2S)-2-Hydroxycyclohexyl)-7-methyl-1H-pyrrolo[3,2-b]pyridine-3-carboxamide (1) Intermediate 5: 1H-Pyrrolo[3,2-b]pyridine 4-oxide To a mixture of 1H-pyrrolo[3,2-b]pyridine (25 g) in DCM (885 mL) stirred at rt under nitrogen was added a suspension of m-chloroperbenzoic acid (54.8 g) in DCM (885 mL). The reaction was stirred at rt overnight, at which point LC-MS indicated completion. The crude reaction was filtered and the residue was stirred as a slurry in Et$_2$O (1 L) for 30 min, then filtered. The residue was again stirred as a slurry in 1

L Et$_2$O and filtered. The residue was dried under vacuum to give the title compound, (27.9 g) which still contained traces of m-chlorobenzoic acid, but was used without further purification.

LCMS: m/z 135.43 [M+H]$^+$.

$^1$H NMR (400 MHz, CD$_3$OD) ppm 6.87 (d, J=3.2 Hz, 1H) 7.23-7.32 (m, 1H) 7.69 (s, 1H) 7.77 (d, J=8.3 Hz, 1H) 8.21 (d, J=6.4 Hz, 1H).

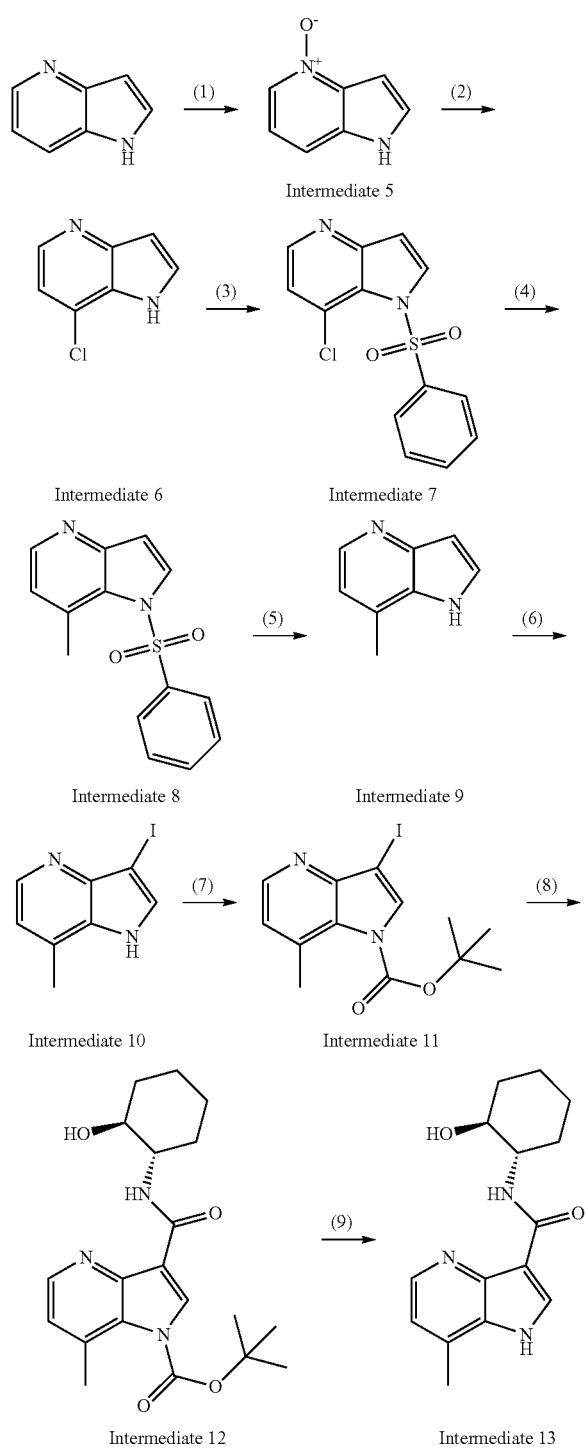

(2) Intermediate 6: 7-Chloro-1H-pyrrolo[3,2-b]pyridine

To a mixture of 1H-pyrrolo[3,2-b]pyridine 4-oxide (Intermediate 5), (27.9 g) stirred at rt under nitrogen was added phosphorus oxychloride (85 mL) and the resulting mixture was heated under nitrogen at 80° C. overnight to give a dark solution, at which point LC-MS indicated completion. The reaction was cooled to rt and added slowly to ice-cold 5N NaOH (300 mL) with vigorous stirring. Water (50 mL) was added and the resultant emulsion was filtered and washed with water to give a solid which was dried under suction then high vacuum and the crude material was taken on as such.

LCMS: m/z 153.36 [M+H]$^+$.

(3) Intermediate 7: 7-Chloro-1-(phenylsulfonyl)-1H-pyrrolo[3,2-b]pyridine

To a mixture of 7-chloro-1H-pyrrolo[3,2-b]pyridine (Intermediate 6), (31.7 g) in DCM (1.23 L) stirred under nitrogen at rt was added benzenesulfonyl chloride (39.8 mL), tetrabutylammonium hydrogen sulfate (9.18 g) and 50% aq. NaOH (33.2 mL) and the reaction was stirred at rt overnight, at which point LC-MS indicated formation of the desired product. Sat. aq. NaHCO$_3$, (500 mL) was added, the layers were separated and the aqueous phase was extracted 2× with DCM, dried (MgSO$_4$), filtered and evaporated under vacuum. The residue was purified by column chromatography (normal phase, 100 g, Biotage SNAP cartridge KP-Sil, 50 mL per min, gradient 0% to 80% EtOAc in n-hexane) to give the desired product (14.6 g).

LCMS: m/z 293.42 [M+H]$^+$.

$^1$H NMR (400 MHz, CDCl$_3$) ppm 6.82 (d, J=3.9 Hz, 1H) 7.24-7.29 (m, 1H) 7.50 (t, J=7.8 Hz, 2H) 7.55-7.67 (m, 1H) 7.81 (d, J=3.7 Hz, 1H) 7.84-7.92 (m, 2H) 8.23 (d, J=8.8 Hz, 1H).

(4) Intermediate 8: 7-Methyl-1-(phenylsulfonyl)-1H-pyrrolo[3,2-b]pyridine

A mixture of 7-chloro-1-(phenylsulfonyl)-1H-pyrrolo[3,2-b]pyridine (Intermediate 7), (16.6 g) and Pd(PPh$_3$)$_4$ (5 g) were de-aerated by placing under high vacuum then purging with nitrogen (3×). To these solids was added THF (251 mL) then a 2M THF solution of methylzinc(II) chloride (56.7 mL). This mixture was heated to 90° C. for 2 h, at which point LC-MS indicated full conversion to product. The reaction was cooled to rt and solvents were removed under reduced pressure. The residue was slurried in 500 mL diethyl ether for 30 min, and the supernatant was removed and concentrated to reveal. The process was repeated 3× and supernatants were combined. The residue was partitioned between water (500 mL) and DCM (500 mL), layers were separated and the aqueous layer was extracted 3× with DCM. Combined organic phases were washed with NaHCO$_3$ and brine. The combined ether supernatants were dissolved in DCM, washed with water, NaHCO$_3$ and brine. Organic phases were combined with those from the DCM extractions and the resultant product was taken on as such without further purification.

LCMS: m/z 273.53 [M+H+]$^+$.

(5) Intermediate 9: 7-Methyl-1H-pyrrolo[3,2-b]pyridine

To a solution of 7-methyl-1-(phenylsulfonyl)-1H-pyrrolo[3,2-b]pyridine (Intermediate 8), (15.44 g) in ethanol (1059 mL) stirred at rt was added 10% aq. NaOH (100 mL) and the reaction was heated at 70° C. for 2 h, at which point LC-MS indicated disappearance of SM. The reaction was cooled to rt, reduced in vacuo, poured onto brine, extracted with EtOAc (3×), and evaporated under vacuum. The residue was purified by column chromatography (normal phase, 50 g, Biotage SNAP cartridge KP-Sil, 50 mL per min, gradient 0% to 100% EtOAc in n-hexane) to yield the desired product (3.75 g).

LCMS: m/z 133.45 [M+1-1]$^+$.

$^1$H NMR (400 MHz, CDCl$_3$) ppm 2.55 (s, 3H) 6.74-6.79 (m, 1H) 6.96 (d, J=4.9 Hz, 1H) 7.45 (t, J=2.7 Hz, 1H) 8.38 (d, J=4.7 Hz, 1H) 8.77 (br. s., 1H).

(6) Intermediate 10: 3-Iodo-7-methyl-1H-pyrrolo[3,2-b]pyridine

To a solution of 7-methyl-1H-pyrrolo[3,2-b]pyridine (Intermediate 9), (3.65 g) in THF (219 mL) stirred at rt under nitrogen was added N-iodosuccinimide (6.83 g) and the reaction was stirred at rt under nitrogen overnight, at which point LC-MS indicated completion. The reaction was then reduced in vacuo, dissolved in MeOH and loaded onto a 20 g SCX-2 cartridge, washing with 5CV MeOH. The product was eluted by washing with 5CV 2M NH$_3$/MeOH and the ammonia-containing fractions were combined and reduced in vacuo to yield the desired compound. The MeOH fractions were combined and reduced in vacuo, dissolved in MeOH and loaded onto a fresh 20 g SCX-2 cartridge, washing with 5CV MeOH, then eluted with 5CV 2M NH$_3$/MeOH. The ammonia-containing fractions were combined with those from the first SCX-2 cartridge and reduced in vacuo to yield the desired compound (5.756 g).

LCMS: m/z 259.41 [M+H]$^+$.

$^1$H NMR (400 MHz, CD$_3$OD) ppm 2.58 (s, 3H) 7.07 (d, J=4.9 Hz, 1H) 7.65 (s, 1H) 8.25 (d, J=4.7 Hz, 1H).

(7) Intermediate 11: tert-Butyl 3-iodo-7-methyl-1H-pyrrolo[3,2-b]pyridine-1-carboxylate To a mixture of 3-iodo-7-methyl-1H-pyrrolo[3,2-b]pyridine (Intermediate 10), (1.355 g) and 4-dimethylaminopyridine (83 mg) in DCM (12.84 mL) stirred at rt under nitrogen was added a solution of di-t-butyldicarbonate (1.719 g) in DCM (5 mL) dropwise and the reaction was stirred overnight, at which point LC-MS indicated completion. The reaction was reduced in vacuo and the residue was purified by column chromatography (normal phase, 10 g, Biotage SNAP cartridge KP-Sil, 12 mL per min, gradient 0% to 20% EtOAc in n-hexane) to yield the desired compound (1.706 g).

LCMS: m/z 359.46 [M+H]$^+$.

$^1$H NMR (400 MHz, CDCl$_3$) ppm 1.67 (s, 9H) 2.73 (s, 3H) 7.10 (d, J=4.8 Hz, 1H) 7.95 (s, 1H) 8.49 (d, J=4.8 Hz, 1H).

(8) Intermediate 12: tert-Butyl 3-(((1S,2S)-2-hydroxycyclohexyl)carbamoyl)-7-methyl-1H-pyrrolo[3,2-b]pyridine-1-carboxylate (1S,2S)-2-Aminocyclohexanol hydrochloride (1.096 g), XantPhos (251 mg), tert-butyl 3-iodo-7-methyl-1H-pyrrolo[3,2-b]pyridine-1-carboxylate (Intermediate 11), (2.588 g), palladium (II) acetate (49 mg) toluene (46.2 mL) and TEA (3.02 mL) were placed in a sealed microwave vial with a CO balloon attached. The microwave tube was purged with CO then heated to 80° C. overnight at which point LC-MS indicated completion. The reaction was then cooled to rt and filtered through celite, washing with EtOAc. The residue at the bottom of the flask was then sonicated in EtOAc and filtered through the same celite pad. The filtrate was reduced in vacuo. The residue was dissolved in MeOH (5 mL) and loaded onto an SCX-2 cartridge, washing with 5 CV MeOH, then eluting with 5 CV 2M NH3/MeOH. The NH$_3$-containing fractions were combined and reduced in vacuo. The residue was purified by column chromatography (normal phase, 25 g, Biotage SNAP cartridge KP-Sil, 25 mL per min, gradient 0% to 100% EtOAc in hexane followed by 0% to 100% EtOAc in hexane). To yield the desired product (2.147 g).

LCMS: m/z 374.62 [M+H]$^+$.

$^1$H NMR (400 MHz, CDCl$_3$) ppm 1.24-1.57 (m, 4H) 1.67 (s, 9H) 1.79 (d, J=10.2 Hz, 2H) 2.14 (d, J=11.4 Hz, 2H) 2.76 (s, 3H) 3.60 (d, J=4.3 Hz, 1H) 3.89 (br. S., 1H) 7.13 (d, J=4.8 Hz, 1H) 8.40 (d, J=5.0 Hz, 1H) 8.57 (br. s., 1H) 9.43 (d, J=6.2 Hz, 1H)

(9) Intermediate 13: N-((1S,2S)-2-Hydroxycyclohexyl)-7-methyl-1H-pyrrolo[3,2-b]pyridine-3-carboxamide To a solution of tert-butyl 3-(((1S,2S)-2-hydroxycyclohexyl)carbamoyl)-7-methyl-1H-pyrrolo[3,2-b]pyridine-1-carboxylate (Intermediate 12), (2.147 g) in 1,4-dioxane (5 mL) stirred under nitrogen at rt was added 4M HCl/Dioxane (10 mL) and the reaction was stirred at rt for 2 h. The reaction was incomplete by LC-MS, so an additional 20 mL 4M HCl/Dioxane was added and the reaction was stirred at rt overnight. Incomplete by LC-MS, so a further 20 mL 4M HCl/Dioxane was added and the reaction was stirred at rt for 8 h, at which point LC-MS indicated completion. The reaction was then reduced in vacuo, dissolved in MeOH (5 mL) and loaded onto an SCX-2 cartridge, washing with 5CV MeOH. The product was then eluted with 2M NH3/MeOH, and the NH3-containing fractions were combined and reduced in vacuo to yield the desired compound (1.493 g) which was taken on as such without further purification.

LCMS: m/z 274.56 [M+H]$^+$.

$^1$H NMR (400 MHz, CDCl$_3$) ppm 1.24-1.61 (m, 4H) 1.78 (d, J=7.9 Hz, 2H) 2.06-2.26 (m, 2H) 2.52 (s, 3H) 3.63 (td, J=9.9, 4.4 Hz, 1H) 3.86-4.01 (m, 1H) 6.84 (d, J=4.9 Hz, 1H) 8.03 (br. s., 1H) 8.23 (d, J=4.9 Hz, 1H) 9.24 (d, J=6.9 Hz, 1H) 11.00 (br. s., 1H)

Intermediate 17: Synthesis of 7-Chloro-N-((1S,2S)-2-hydroxycyclohexyl)-1H-pyrrolo[3,2-b]pyridine-3-carboxamide

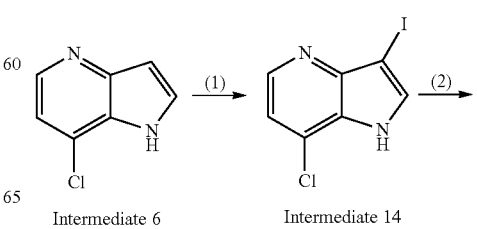

Intermediate 6      Intermediate 14

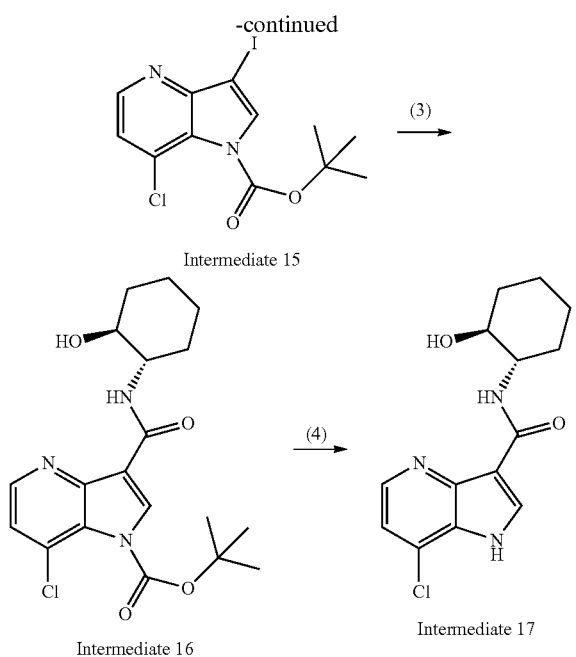

Intermediate 15

Intermediate 16

Intermediate 17

(1) Intermediate 14: 7-Chloro-3-iodo-1H-pyrrolo[3,2-b]pyridine

To a mixture of 7-chloro-1H-pyrrolo[3,2-b]pyridine (Intermediate 6), (3 g) and DMF (46.4 mL) was added KOH (4.19 g) and $I_2$ (5.49 g) and left to stir at rt for 1 h. The reaction mixture was then added to a solution of sodium bisulfite (2.5 g), water (370 mL) and 28-30% $NH_4OH$ (25 mL) cooled in an ice-bath. A precipitate formed which was collected by filtration to give the desired compound (4.99 g).

LCMS: m/z 279.32 [M+H]$^+$.

$^1$H NMR (400 MHz, DMSO-$d_6$) ppm 7.36 (d, J=5.0 Hz, 1H) 7.93 (s, 1H) 8.35 (d, J=5.0 Hz, 1H) 12.32 (br. s., 1H)

(2) Intermediate 15: tert-Butyl 7-chloro-3-iodo-1H-pyrrolo[3,2-b]pyridine-1-carboxylate To a mixture of 7-chloro-3-iodo-1H-pyrrolo[3,2-b]pyridine (Intermediate 14), (4.99 g) and DMAP (285 mg) in DCM (43.4 mL), was added dropwise a solution of di-tert-butyl dicarbonate (5.87 g) in DCM (10 mL) and the reaction mixture left to stir at rt for 4 h 20 min. The reaction mixture was evaporated under vacuum and then loaded onto a column in DCM (normal phase, 100 g, Biotage SNAP cartridge KP-Sil, 53 mL/min, gradient 0-5% EtOAc in n-hexane) to give the desired compound (6.04 g).

LCMS: m/z 379.37 [M+H]$^+$.

$^1$H NMR (400 MHz, CDCl$_3$) ppm 1.68 (s, 9H) 7.35 (d, J=5.1 Hz, 1H) 7.99 (s, 1H) 8.51 (d, J=5.1 Hz, 1H)

(3) Intermediate 16: tert-Butyl 7-chloro-3-(((1S,2S)-2-hydroxycyclohexyl)carbamoyl)-1H-pyrrolo[3,2-b]pyridine-1-carboxylate tert-Butyl 7-chloro-3-iodo-1H-pyrrolo[3,2-b]pyridine-1-carboxylate (Intermediate 15), (6.04 g), Pd(OAc)$_2$ (107 mg), (1S,2S)-2-aminocyclohexanol hydrochloride (3.63 g), Xant-Phos (554 mg), toluene (144 mL) and TEA (6.67 mL) was added to a two-neck round-bottomed flask fitted with a reflux condenser. This was purged with CO and stirred at 80° C. overnight under a CO balloon. The reaction mixture was allowed to cool to rt and then diluted with EtOAc and transferred to a separatory funnel. The remaining solid in the microwave tube was dissolved in THF by sonication and added to the EtOAc layer. The organic layer was washed with water (2×) and brine. The combined aqueous layers were extracted with EtOAc and the combined organic layers dried over MgSO$_4$, filtered and evaporated under vacuum to give a solid (8.48 g) which was taken on crude without further purification.

LCMS: m/z 394.57 [M+H]$^+$.

(4) Intermediate 17: 7-Chloro-N-((1S,2S)-2-hydroxycyclohexyl)-1H-pyrrolo[3,2-b]pyridine-3-carboxamide To a solution of tert-butyl 7-chloro-3-(((1S,2S)-2-hydroxycyclohexyl)carbamoyl)-1H-pyrrolo[3,2-b]pyridine-1-carboxylate (Intermediate 16), (1.03 g) in DCM (5.47 mL) was added TFA (10.92 mL) dropwise and left to stir at rt for 1 h. The solvent was evaporated under vacuum and then left under high vacuum for 15 min to give an oil. This was dissolved in DCM and purified using column chromatography (normal phase, 55 g, Biotage SNAP cartridge KP-NH, 25 mL/min, gradient 0-100% EtOAc in n-hexane, then 0-20% MeOH in EtOAc) to give the desired compound (529 mg)

LCMS: m/z 294.53 [M+H]$^+$.

$^1$H NMR (400 MHz, CDCl$_3$) ppm 0.85-2.70 (m, 8H) 3.64 (td, J=10.1, 4.5 Hz, 1H) 3.83-4.09 (m, 1H) 4.68 (br. s, 1H) 7.11 (d, J=5.0 Hz, 1H) 8.15 (br. s., 1H) 8.27 (d, J=5.0 Hz, 1H) 8.93 (d, J=7.1 Hz, 1H) 10.15 (br. s., 1H)

Intermediate 18: Synthesis of 1-(4-Fluorobenzyl)-3-iodo-1H-pyrrolo[3,2-b]pyridine

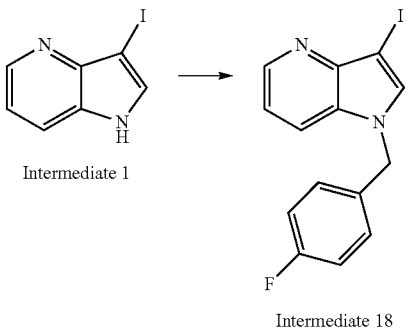 [SMILES: Ic1c[nH]c2cccnc12 ; Fc1ccc(Cn2cc(I)c3ncccc32)cc1]

Intermediate 1

Intermediate 18

To an ice-cold solution of 3-iodo-1H-pyrrolo[3,2-b]pyridine (Intermediate 1), (500 mg) in N,N-dimethylacetamide (5 mL) stirred at rt under nitrogen was added sodium hydride (98 mg) portionwise and the reaction was stirred for 10 min. 1-(Bromomethyl)-4-fluorobenzene (0.26 mL) in DMA (5 mL) was added dropwise and the reaction was stirred at rt overnight, at which point LC-MS indicated presence of the desired product. The reaction was diluted with EtOAc, washed with water (2×), brine (2×), dried (MgSO$_4$), filtered and evaporated under vacuum. The residue was purified by column chromatography (normal phase, 25 g, Biotage SNAP cartridge KP-Sil, 25 mL per min, gradient 0% to 50% EtOAc in n-hexane) to yield the desired product (649 mg).

LCMS: m/z 353.39 [M+H]$^+$.

¹H NMR (400 MHz, CDCl₃) ppm 5.31 (s, 2H) 6.98-7.20 (m, 5H) 7.45 (s, 1H) 7.54 (d, J=8.2 Hz, 1H) 8.59 (d, J=4.5 Hz, 1H)

Intermediate 21: Synthesis of tert-Butyl 4-(1-(4-fluorobenzyl)-1H-pyrrolo[3,2-b]pyridine-3-carboxamido)piperidine-1-carboxylate

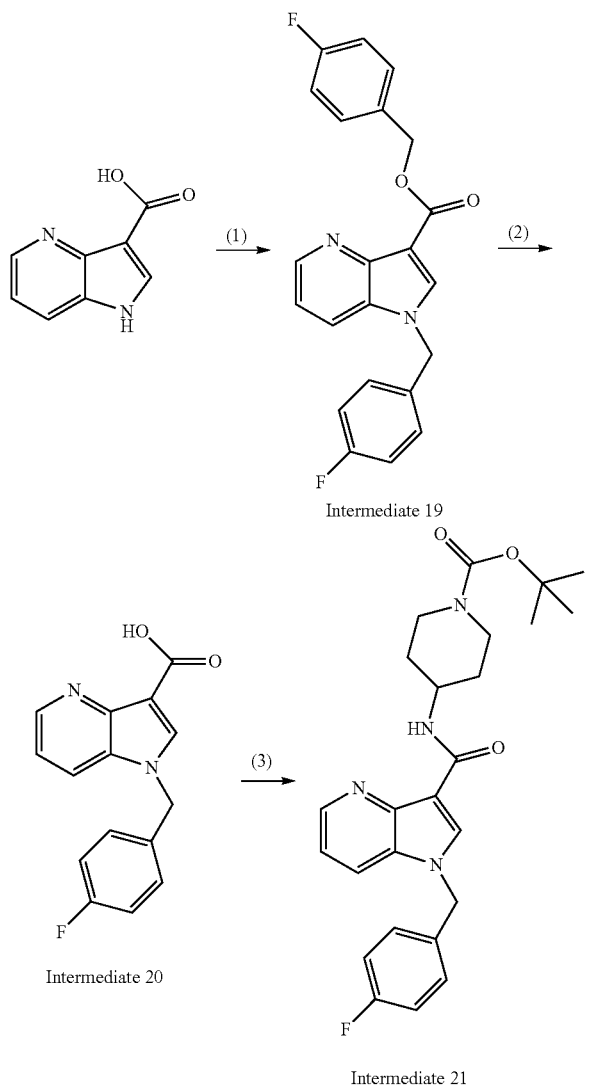

Intermediate 19

Intermediate 20

Intermediate 21

(1) Intermediate 19: 4-Fluorobenzyl 1-(4-fluorobenzyl)-1H-pyrrolo[3,2-b]pyridine-3-carboxylate To a solution of 1H-pyrrolo[3,2-b]pyridine-3-carboxylic acid (purchased from Ontario Chemicals Inc.), (771 mg) in DMF (100 mL) stirred at rt under nitrogen was added K₂CO₃ (1314 mg) and the reaction was stirred at rt for 5 min. 1-(Bromomethyl)-4-fluorobenzene (1.13 mL) was then added in one portion and the reaction was stirred at rt overnight, at which point LC-MS indicated presence of mainly the desired product. The reaction was then diluted with water (35 mL) and stirred for 10 min and then filtered. The residue was collected and dried azeotropically to yield the crude product (1.314 g), which was taken on as such without further purification.

LCMS: m/z 379.54 [M+H]⁺.

(2) Intermediate 20: 1-(4-Fluorobenzyl)-1H-pyrrolo[3,2-b]pyridine-3-carboxylic acid To a solution of 4-fluorobenzyl 1-(4-fluorobenzyl)-1H-pyrrolo[3,2-b]pyridine-3-carboxylate (Intermediate 19), (1.314 g) in THF (14.42 mL) and water (4.12 mL) was added lithium hydroxide monohydrate (0.097 mL) and the reaction was heated to reflux and stirred for 4 h and then cooled to rt and stirred overnight, at which point LC-MS indicated disappearance of SM and presence of the desired product. The reaction was then neutralised by dropwise addition of 2M HCl, then dried azeotropically. The residue (939 mg) was taken on as such without further purification.

LCMS: m/z 271.51 [M+H]⁺.

(3) Intermediate 21: tert-Butyl 4-(1-(4-fluorobenzyl)-1H-pyrrolo[3,2-b]pyridine-3-carboxamido)piperidine-1-carboxylate To a solution of 1-(4-fluorobenzyl)-1H-pyrrolo[3,2-b]pyridine-3-carboxylic acid (Intermediate 20), (110 mg) in DMF (2.1 mL) stirred at rt under nitrogen was added HATU (248 mg) and TEA (0.11 mL). This mixture was left to stir for 15 minutes and tert-butyl 4-aminopiperidine-1-carboxylate (82 mg) was introduced. The reaction was left to stir overnight at room temperature, at which point LC-MS indicated completion. The reaction mixture was transferred to a separating flask and EtOAc and water were added. The phases were separated and the aqueous phase was extracted twice more with EtOAc. The organic phases were combined, washed with brine and the solvent was removed in vacuo. The residue was purified by column chromatography (normal phase, 25 g, Biotage SNAP cartridge KP-Sil, 25 mL per min, gradient 0% to 100% EtOAc in hexane, followed by 0-15% MeOH/EtOAc) to give an impure product (184 mg), which was taken on as such without further purification.

LCMS: m/z 453.66 [M+H]⁺.

Intermediate 27: Synthesis of 7-Cyano-N-((1S,2S)-2-hydroxycyclohexyl)-1H-pyrrolo[3,2-b]pyridine-3-carboxamide

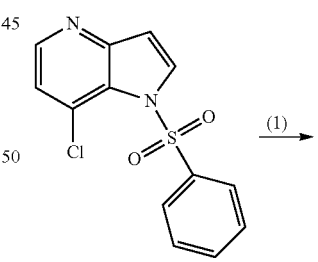

Intermediate 7

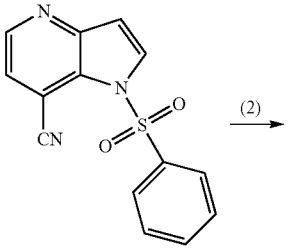

Intermediate 22

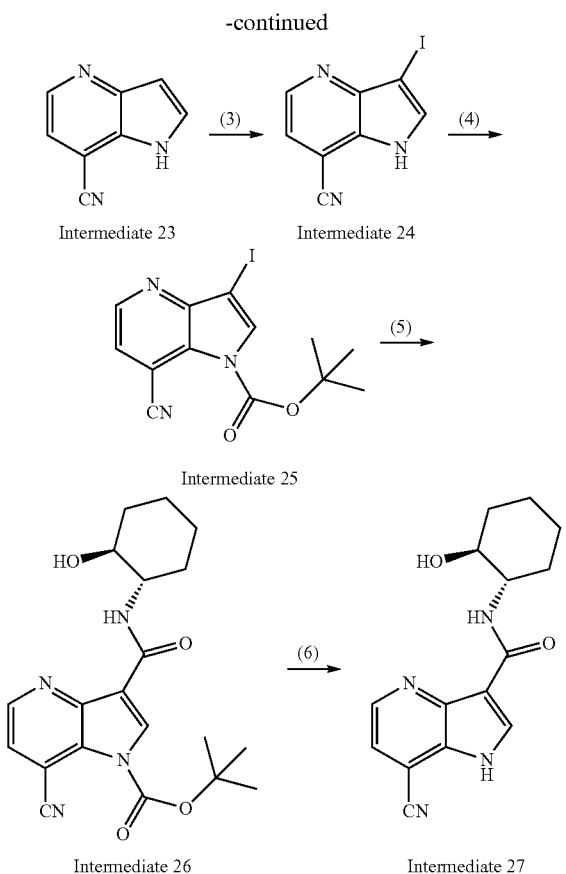

Intermediate 23
Intermediate 24
Intermediate 25
Intermediate 26
Intermediate 27

(1) Intermediate 22: 1-(Phenylsulfonyl)-1H-pyrrolo[3,2-b]pyridine-7-carbonitrile A mixture of 7-chloro-1-(phenylsulfonyl)-1H-pyrrolo[3,2-b]pyridine (Intermediate 7), (1.0 g), Pd(PPh$_3$)$_4$ (0.50 g), zinc cyanide (0.50 g) and DMF (10 mL) was purged with nitrogen then microwaved at 130° C. for 0.5 h. The reaction mixture was then diluted with EtOAc, washed with water the insoluble solid filtered and the layers separate. The organic phase was washed with more water (2×), brine, dried (MgSO$_4$), filtered and evaporate under vacuum and the residue was purified by column chromatography (normal phase, gradient 0% to 50% EtOAc in n-hexane) followed by prep. LCMS to give the pure desired compound (0.88 g).

LCMS: m/z 284.43 [M+H]$^+$.

$^1$H NMR (400 MHz, CDCl$_3$) ppm 7.01 (d, J=3.8 Hz, 1H) 7.45-7.67 (m, 4H) 8.04 (d, J=7.7 Hz, 2H) 8.14 (d, J=3.8 Hz, 1H) 8.55-8.66 (m, 1H).

(2) Intermediate 23: 1H-pyrrolo[3,2-b]pyridine-7-carbonitrile

A mixture of 1-(phenylsulfonyl)-1H-pyrrolo[3,2-b]pyridine-7-carbonitrile (Intermediate 22), (6.00 g), EtOH (400 mL) and 10% aq. NaOH (9 mL) was heated at 80° C. for 0.5 h. The reaction mixture was cooled, evaporated to dryness and the solid dissolved in EtOAc, washed with brine (2×) and the brine extracts washed with EtOAc (3×), the combined organic phases dried (MgSO$_4$), filter and evaporate under vacuum. The resulting solid was suspended in DCM, filtered and washed with more DCM to give the desired compound (2.02 g). The DCM washes were evaporated and the residue was purified by column chromatography (normal phase, 50 g silica, gradient 0% to 50% EtOAc in n-hexane) to give more of the desired compound (197 mg).

LCMS: m/z 144.40 [M+H]+.

$^1$H NMR (400 MHz, DMSO-d6) ppm 6.77 (d, J=1.7 Hz, 1H) 7.57 (d, J=4.8 Hz, 1H) 7.86 (t, J=2.8 Hz, 1H) 8.50 (d, J=4.8 Hz, 1H) 12.36 (br. s., 1H).

(3) Intermediate 24: 3-Iodo-1H-pyrrolo[3,2-b]pyridine-7-carbonitrile

To a mixture of 1H-pyrrolo[3,2-b]pyridine-7-carbonitrile (Intermediate 23), (2.20 g) and DMF (36.3 mL) was added KOH (3.28 g) followed by iodine (4.29 g) then the reaction mixture stirred at rt for 1 h 15 min. It was then diluted with EtOAc (300 mL), washed with water (3×80 mL) then brine (2×80 mL). To the combined aqueous phase was added EtOAc which caused a precipitate to form which was filtered, washed with water then EtOAc to give the desired compound (1.42 g). The combined aqueous phases were extracted with EtOAc (3×) then the combined organic extracts dried (MgSO$_4$), filtered and evaporated under vacuum to give more of the desired compound (2.49 g).

LCMS: m/z 270.37 [M+H]$^+$.

$^1$H NMR (400 MHz, DMSO-d6) ppm 7.68 (d, J=4.9 Hz, 1H) 8.07 (s, 1H) 8.56 (d, J=4.8 Hz, 1H) 12.83 (br. s., 1H)

(4) Intermediate 25: tert-Butyl 7-cyano-3-iodo-1H-pyrrolo[3,2-b]pyridine-1-carboxylate To a mixture of 3-iodo-1H-pyrrolo[3,2-b]pyridine-7-carbonitrile (Intermediate 24), (3.91 g) and N,N-dimethylpyridin-4-amine (0.23 g) in DCM (35 mL), was added dropwise a solution of di-tert-butyl dicarbonate (4.76 g) in DCM (35 mL) over 2 min, and the reaction mixture left to stir at r.t. for 1 h. The solvent was evaporated and the residue was purified by column chromatography (normal phase, 100 g silica, gradient 0% to 40% EtOAc in n-hexane) to give the desired compound (4.92 g).

LCMS: m/z 370.39 [M+H]$^+$.

$^1$H NMR (400 MHz, CDCl$_3$) ppm 1.73 (s, 9H) 7.63 (d, J=4.9 Hz, 1H) 8.08 (s, 1H) 8.74 (d, J=4.9 Hz, 1H).

(5) Intermediate 26: tert-Butyl 7-cyano-3-(((1S,2S)-2-hydroxycyclohexyl)carbamoyl)-1H-pyrrolo[3,2-b]pyridine-1-carboxylate tert-Butyl 7-cyano-3-iodo-1H-pyrrolo[3,2-b]pyridine-1-carboxylate (Intermediate 25), (4.92 g), palladium (II) acetate (90 mg), (1S,2S)-2-aminocyclohexanol hydrochloride (3.03 g), XantPhos (0.46 g) toluene (121 mL) and TEA (5.57 mL) were added to a one necked round bottom flask. This was purged with CO and stirred at 80° C. for 5 hr under CO. The reaction mixture was diluted with EtOAc and transferred to a separatory funnel. Remaining solid in the microwave tube was dissolved in THF by sonication and added to the separatory funnel. The combined organic layers were washed with water (2×) then brine. The combined aqueous layers were extracted with EtOAc (2×) and the combined organic extracts dried over MgSO$_4$, filtered and evaporated in vacuo to the crude desired compound which was taken on as such without further purification.

LCMS: m/z 385.65 [M+H]+, m/z 285.56 [M+H-Boc]$^+$.

(6) Intermediate 27: 7-Cyano-N-((1S,2S)-2-hydroxycyclohexyl)-1H-pyrrolo[3,2-b]pyridine-3-carboxamide A mixture of tert-butyl 7-cyano-3-(((1S,2S)-2-hydroxycyclohexyl)carbamoyl)-1H-pyrrolo[3,2-b]pyridine-1-carboxylate (Intermediate 26), (5.12 g), DCM (57.3 mL) and TFA (28.6 mL) were stirred for 1 h. The solvent was evaporated and the residue purified by column chromatography (normal phase, 110 g amino silica, gradient 0% to 100% EtOAc in n-hexane then gradient 0% to 20% MeOH in EtOAc) followed by another purification by column chromatography (normal phase, 110 g amino silica, gradient 0% to 100% EtOAc in n-hexane then gradient 0% to 20% MeOH in EtOAc) to give the pure desired compound (2.66 g). The mixed fractions were evaporated and purified again by column chromatography (normal phase, 55 g amino silica, gradient 0% to 100% EtOAc in n-hexane then gradient 0% to 20% MeOH in EtOAc) to give more of the pure desired compound (649 mg).

LCMS: m/z 285.52 [M+H]$^+$.

$^1$H NMR (400 MHz, DMSO-d6) ppm 1.15-1.37 (m, 4H) 1.57-1.72 (m, 2H) 1.84-1.92 (m, 1H) 1.98-2.08 (m, 1H) 3.37-3.45 (m, 1H) 3.67-3.76 (m, 1H) 7.75 (d, J=4.9 Hz, 1H) 8.32 (d, J=2.7 Hz, 1H) 8.52-8.60 (m, 1H) 8.66 (d, J=4.8 Hz, 1H) 13.04 (br. s., 1H).

Intermediate 33: Synthesis of trans-2-Amino-5,5-difluorocyclohexanol

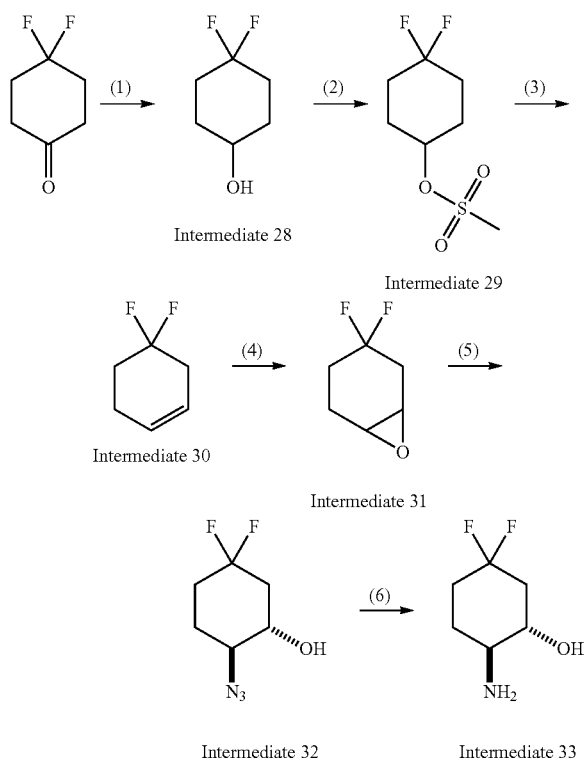

(1) Intermediate 28: 4,4-Difluorocyclohexanol

To a stirred solution of lithium aluminium hydride (46.6 mL, 4M in diethyl ether) at 0° C. was added a solution of 4,4-difluorocyclohexanone (Purchased from Manchester Organics), (25 g) in diethyl ether (250 mL) dropwise. After addition, the reaction mixture was allowed to warm to rt and stirred for 30 minutes. To the reaction mixture was added water (7 mL) dropwise, followed by 15% aqueous sodium hydroxide (7 mL), followed by water (21 mL). The resulting solid was filtered off and washed with diethyl ether. The filtrate was dried (MgSO$_4$), filtered and evaporated to afford the title compound (28.38 g).

$^1$H NMR (600 MHz, CDCl$_3$) ppm 1.69-1.78 (m, 2H) 1.80-1.93 (m, 4H) 2.08-2.17 (m, 2H) 3.73 (q, J=7.0 Hz, 1H) 3.93 (m, 1H)

(2) Intermediate 29: 4,4-Difluorocyclohexyl methanesulfonate

To a solution of 4,4-difluorocyclohexanol (Intermediate 28), (28.38 g) in anhydrous DCM (200 mL) and TEA (34.6 mL) under nitrogen at 0° C. was added methanesulfonyl chloride (17.87 ml) dropwise and the resulting mixture was allowed to warm to rt. After 1.5 hours, TEA (14.51 ml) was added and stirring continued for 1 hour. Further TEA (14.51 mL) and methanesulfonyl chloride (8.12 mL) was added and stirring continued for 30 minutes. The mixture was quenched with an aqueous solution of saturated ammonium chloride and stirred for 5 minutes and the layers separated. The organic layer was washed with aqueous ammonium chloride solution, dried (MgSO$_4$), filtered and evaporated. The residue was purified by column chromatography (normal phase, Biotage SNAP cartridge KP-Sil, gradient 0% to 60% diethyl ether in pentane) to afford the title compound (46.21 g).

$^1$H NMR (400 MHz, CDCl$_3$) ppm 1.87-2.22 (m, 8H) 3.05 (s, 3H) 4.92 (d, J=2.3 Hz, 1H)

(3) Intermediate 30: 4,4-Difluorocyclohex-1-ene

DBU (39.0 mL) was added to 4,4-difluorocyclohexyl methanesulfonate (Intermediate 29), (36.95 g) and the mixture heated to 100° C. for 1.5 hours with stirring. The title compound was isolated by distillation (11.28 g), boiling point 96° C. at 760 mmHg.

$^1$H NMR (400 MHz, CDCl$_3$) ppm 2.01 (tt, J=13.9, 6.7 Hz, 2H) 2.21-2.39 (m, 2H) 2.52 (t, J=14.5 Hz, 2H) 5.48-5.65 (m, 1H) 5.67-5.82 (m, 1H)

(4) Intermediate 31: 3,3-Difluoro-7-oxabicyclo[4.1.0]heptane

To a solution of 4,4-difluorocyclohex-1-ene (Intermediate 30), (11.25 g) in DCM (120 mL) at 0° C., was added mCPBA (42.7 g) portionwise. After addition, the reaction mixture was allowed to warm to rt and stirred overnight. An aqueous saturated solution of sodium sulphite was added and the resulting solid was collected by filtration. The filtrate was partitioned between DCM and water, and the aqueous layer re-extracted with DCM. The combined organic layer was washed with aqueous saturated sodium bicarbonate (2×), dried (MgSO$_4$), filtered and evaporated to afford the title compound (16.87 g).

$^1$H NMR (600 MHz, CDCl$_3$) ppm 1.79-1.92 (m, 2H) 2.03-2.12 (m, 1H) 2.22-2.46 (m, 3H) 3.18-3.22 (m, 1H) 3.24 (m, 1H)

(5) Intermediate 32: trans-2-Azido-5,5-difluorocyclohexanol

To a suspension of (R,R)—N,N-Bis(3,5-di-tert-butylsalicylidene)-1,2-cyclohexanediaminochromium(III) chloride (1.204 g) in diethyl ether (30 mL) was added 3,3-difluoro-7-oxabicyclo[4.1.0]heptane (Intermediate 31), (12.77 g) and the reaction mixture stirred for 15 minutes. Trimethylsilyl azide (13.27 mL) was added to the reaction mixture and the resulting solution was stirred at rt overnight. The mixture was evaporated and the residue applied onto a normal phase, Biotage SNAP KP-Sil cartridge. Elution with 40% ether in hexane gave an oil which was dissolved in methanol (30 mL) and treated with (+/−)-10-Camphorsulfonic acid (1.106 g). The mixture was stirred at rt for 30 minutes and then evaporated. The residue was purified by column chromatography (normal phase, Biotage SNAP cartridge KP-Sil, gradient 0% to 30% diethyl ether in n-hexane) to afford the title compound (4.40 g).

$^1$H NMR (600 MHz, CDCl$_3$) ppm 1.61-1.71 (m, 1H) 1.76-1.93 (m, 2H) 2.08 (m, 1H) 2.13-2.23 (m, 1H) 2.32 (br. s., 1H) 2.42-2.53 (m, 1H) 3.30-3.41 (m, 1H) 3.69-3.74 (m, 1H)

(6) Intermediate 33:
trans-2-Amino-5,5-difluorocyclohexanol

To a solution of trans-2-azido-5,5-difluorocyclohexanol (Intermediate 32), (4.35 g) in methanol (50 mL), was added 10% wet palladium on carbon (500 mg) and stirred under an atmosphere of hydrogen overnight. The residue was filtered through a pad of celite, washed with methanol and evaporated. The residue was dissolved in methanol and filtered through another pad of celite, a PTFE filter, then evaporated and purified by SCX-2 cartridge to afford the title compound (3.37 g).

$^1$H NMR (600 MHz, CDCl$_3$) ppm 1.36-1.50 (m, 1H) 1.67-2.17 (m, 7H) 2.41-2.60 (m, 2H) 3.36-3.46 (m, 1H)

Intermediate 37: Synthesis of
cis-2-Amino-5,5-difluorocyclohexanol

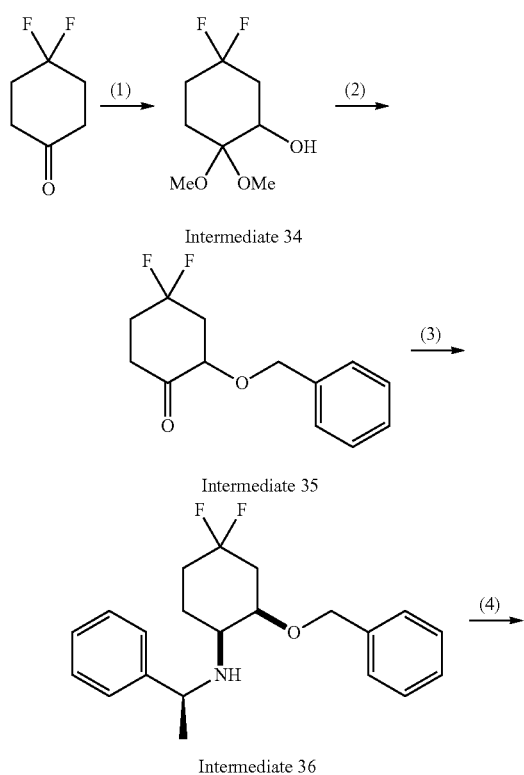

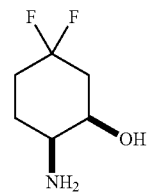

Intermediate 37

(1) Intermediate 34:
5,5-Difluoro-2,2-dimethoxycyclohexanol

To a solution of 4,4-difluorocyclohexanone (purchased from Manchester Organics), (7.0 g) in methanol (70 mL) was added potassium hydroxide (7.03 g). The mixture was cooled to 0° C. then a solution of iodine (14.6 g) in methanol (140 mL) was added over 60 minutes. The reaction mixture was returned to room temperature and stirred for a further 18 hours. It was then concentrated under vacuum, re-suspended in DCM (100 mL) and passed through a filter. Activated carbon (3 g) was added to the filtrate. The resulting suspension was stirred at room temperature for 60 minutes then filtered through a pad of celite. The filtrate was concentrated under vacuum to approximately 10 ml then purified by column chromatography (normal phase, 100 g, Biotage SNAP cartridge KP-Sil, 50 mL per min, gradient 0% to 10% methanol in DCM) to give the desired compound (5.28 g).

$^1$H NMR (400 MHz, CDCl$_3$) ppm 1.78-2.27 (m, 6H) 3.29 (s, 3H) 3.31 (s, 3H) 3.99 (br. s, 1H).

(2) Intermediate 35:
2-(Benzyloxy)-4,4-difluorocyclohexanone

To a solution of 5,5-difluoro-2,2-dimethoxycyclohexanol (Intermediate 34), (1.6 g) in DMF (30 mL) at 0° C. under an atmosphere of nitrogen was added sodium hydride (391 mg, 60 wt %) in a portionwise manner. The mixture was stirred at 0° C. for 30 minutes. Benzyl bromide (1.67 g) was added, the reaction mixture allowed to return to room temperature and stirring continued for 19 hours. The reaction mixture was diluted with water and extracted into EtOAc (2×). The combined organic extracts were washed with water (3×) then brine (1×), dried (Na$_2$SO$_4$), filtered and evaporated under vacuum. The residue was purified by column chromatography (normal phase, 100 g, Biotage SNAP cartridge KP-Sil, 50 mL per min, gradient 0% to 20% EtOAc in hexane) to give the desired compound (2.65 g).

$^1$H NMR (400 MHz, CDCl$_3$) ppm 2.25 (m, 2H) 2.43 (m, 1H) 2.58 (m, 2H) 2.75 (m 1H) 4.15 (dd, J=11.7, 6.6 Hz, 1H) 4.52 (d, J=11.7 Hz, 1H) 4.86 (d, J=11.7 Hz, 1H) 7.33 (m, 1H) 7.38 (m, 4H).

(3) Intermediate 36: cic-2-(Benzyloxy)-4,4-difluoro-N—((S)-1-phenylethyl)cyclohexanamine To a solution of 2-(benzyloxy)-4,4-difluorocyclohexanone (Intermediate 35), (2.0 g) in 1,2-dichloroethane (75 mL) under an atmosphere of nitrogen was added (S)-1-phenylethanamine (1.11 g) followed by acetic acid (0.48 mL) and sodium triacetoxyborohydride (2.65 g). The reaction mixture was stirred at room temperature for two hours. It was then quenched with saturated sodium bicarbonate solution, diluted with water and extracted into EtOAc (2×). The combined organic extracts were washed with water (3×)

then brine (1×), dried (Na$_2$SO$_4$), filtered and evaporated under vacuum. The residue was purified by column chromatography (normal phase, 100 g, Biotage SNAP cartridge KP-Sil, 50 mL per min, gradient 0% to 20% EtOAc in hexane) to isolate the desired compound, a single enantiomer of cis relative stereochemistry but unknown absolute configuration, (1.68 g)

LCMS: m/z 346.59 [M+H]$^+$.

$^1$H NMR (400 MHz, CDCl$_3$) ppm 1.33 (d, J=6.3 Hz, 3H) 1.38 (br. s, 1H), 1.57 (m, 2H), 1.68 (br. s, 1H), 2.03 (m, 2H) 2.36 (m, 1H) 2.98 (br. s, 1H), 3.69 (q, J=6.6 Hz, 1H) 3.73 (m, 1H) 4.54 (d, J=11.8 Hz, 1H) 4.65 (d, J=11.8 Hz, 1H) 7.34 (m, 10H).

(4) Intermediate 37: cis-2-Amino-5,5-difluorocyclohexanol

To a solution of cis-2-(benzyloxy)-4,4-difluoro-N—((S)-1-phenylethyl)cyclohexanamine (Intermediate 36), (1.68 g) in methanol (50 mL) was added Pearlman's catalyst (342 mg, 20 wt %, 50% H$_2$O). The mixture was purged sequentially with nitrogen and vacuum then stirred under an atmosphere of hydrogen at room temperature. Additional catalyst was added after 6 hours (172 mg) and 18 hours (342 mg) with appropriate purges of nitrogen and vacuum before re-introduction of the hydrogen atmosphere. After 24 hours the reaction mixture was passed through a pad of celite and evaporated under vacuum. The residue was redissolved in methanol. Pearlman's catalyst (342 mg) was added and the mixture purged with nitrogen and vacuum before re-applying the hydrogen atmosphere. After 20 hours the reaction mixture was passed through a pad of celite and evaporated under vacuum. The residue was washed with DCM then dried in air to give the desired compound, a single enantiomer of cis relative stereochemistry but unknown absolute configuration, (383 mg).

$^1$H NMR (400 MHz, DMSO-d$_6$) ppm 1.75 (m, 1H) 1.92 (m, 2H) 2.11 (m, 3H) 4.01 (br. s, 1H) 5.71 (d, J=3.7 Hz, 1H) 7.99 (br. s, 3H).

Intermediate 45: Synthesis of N-((1S,2S)-2-hydroxycyclohexyl)-7-methoxy-1H-pyrrolo[3,2-b]pyridine-3-carboxamide

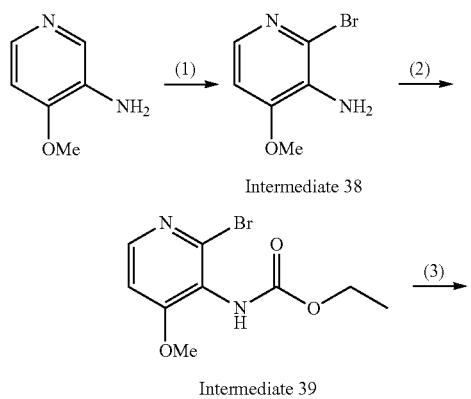

Intermediate 38

Intermediate 39

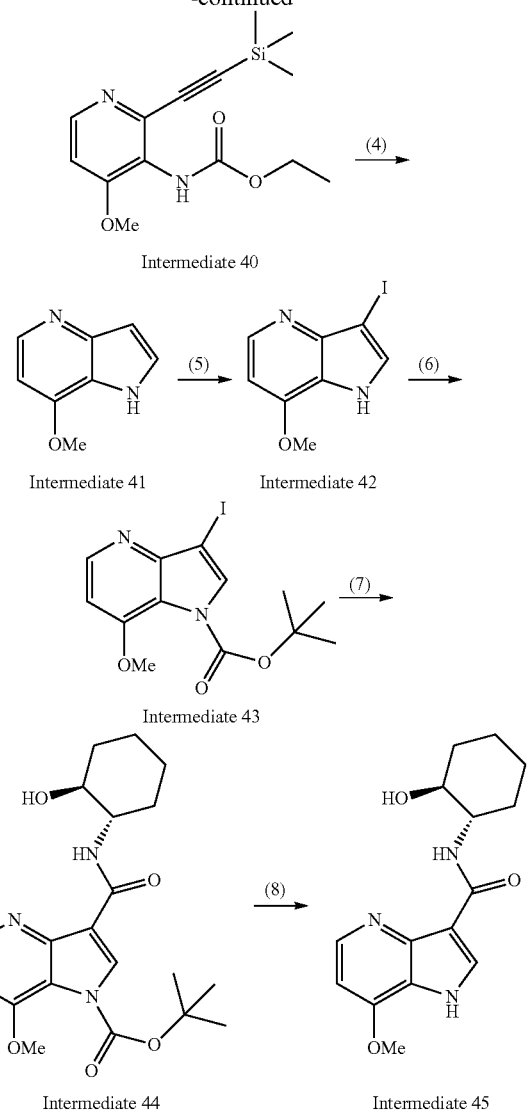

Intermediate 40

Intermediate 41    Intermediate 42

Intermediate 43

Intermediate 44    Intermediate 45

(1) Intermediate 38: 2-Bromo-4-methoxypyridin-3-amine

To a solution of 4-methoxypyridin-3-amine (purchased from Ark Pharm Inc.), (3 g) in concentrated HCl (22.17 mL) was added bromine (1.49 mL) dropwise over a 30 s period and the mixture stirred at rt for 1 h and then at 55° C. over the weekend. The reaction mixture was allowed to cool to rt and then poured into ice (250 g). Concentrated NH$_4$OH was added until the pH of the solution was basic (pH 9). The resulting solution was then partitioned between H$_2$O and EtOAc and the two layers separated. The aqueous layer was extracted with EtOAc (2×) and the combined organic layers washed with water and brine, dried (MgSO$_4$), filtered and evaporated under vacuum to give a solid which was dissolved in DCM and purified by column chromatography (normal phase, 100 g, Biotage SNAP cartridge KP-Sil, 50 mL/min, gradient 0-20% EtOAc in n-hexane) to give the desired product (2.74 g).

LCMS: m/z 203.37 [M+H]$^+$.

$^1$H NMR (400 MHz, CDCl$_3$) ppm 3.93 (s, 3H) 3.95-4.60 (br. s., 2H) 6.69 (d, J=5.4 Hz, 1H) 7.76 (d, J=5.3 Hz, 1H)

(2) Intermediate 39: Ethyl (2-bromo-4-methoxypyridin-3-yl)carbamate

To an ice-cold solution of 2-bromo-4-methoxypyridin-3-amine (Intermediate 38), (2.74 g) in pyridine (102 mL) was added ethyl chloroformate (1.91 mL) dropwise and then stirred at rt for 45 min. The reaction mixture was cooled in an ice-bath and more ethyl chloroformate (9 mL) added and the mixture left to stir overnight at rt. The reaction mixture was diluted with EtOAc and washed with sat. aq. NaHCO$_3$. The aqueous layer was extracted with EtOAc and the combined organic layers washed with brine, dried over MgSO$_4$, filtered and evaporated under vacuum to give a solid. Product was observed in the aqueous layer by LC-MS, so this was re-extracted with EtOAc (3×) and evaporated under vacuum to give a solid which was combined with the previous solid, dissolved in DCM and purified by column chromatography (normal phase, 50 g, Biotage SNAP cartridge KP-Sil, 50 mL/min, gradient 10-70% EtOAc in n-hexane) to give the desired product (2.35 g).

LCMS: m/z 275.43 [M+H]$^+$.

$^1$H NMR (400. MHz, CDCl$_3$) ppm 1.32 (t, J=7.1 Hz, 3H) 3.93 (s, 3H) 4.24 (q, J=7.1 Hz, 2H) 6.06 (br. s., 1H) 6.86 (d, J=5.6 Hz, 1H) 8.19 (d, J=5.6 Hz, 1H)

(3) Intermediate 40: Ethyl (4-methoxy-2-((trimethylsilyl)ethynyl)pyridin-3-yl)carbamate To a round bottomed flask equipped with a condenser, was added ethyl (2-bromo-4-methoxypyridin-3-yl)carbamate (Intermediate 39), (2.6 g), TEA (2.60 mL), bis(triphenylphosphine)palladium (II) chloride (332 mg), CuI (144 mg) and TMS-acetylene (1.84 g) in dry THF (48.2 mL) and heated at 60° C. under N$_2$ over the weekend. The mixture was evaporated under vacuum to give a solid which was dissolved in DCM and purified by column chromatography (normal phase, 50 g, Biotage SNAP cartridge KP-Sil, 50 mL/min, gradient 0-40% EtOAc in n-hexane) to give the desired product (2.16 g).

LCMS: m/z 293.55 [M+H]$^+$.

$^1$H NMR (400 MHz, CDCl$_3$) ppm 0.28 (s, 9H) 1.32 (t, J=7.0 Hz, 3H) 3.92 (s, 3H) 4.24 (q, J=7.1 Hz, 2H) 6.18 (br. s., 1H) 6.84 (d, J=5.5 Hz, 1H) 8.34 (d, J=5.5 Hz, 1H)

(4) Intermediate 41: 7-Methoxy-1H-pyrrolo[3,2-b]pyridine

TBAF (8.25 mL) (1 M in THF) was added to a solution of ethyl (4-methoxy-2-((trimethylsilyl)ethynyl)pyridin-3-yl)carbamate (Intermediate 40), (2.01 g) in THF (9.63 mL) and refluxed at 70° C. under N$_2$ for 4 h 45 min. The reaction mixture was allowed to cool to rt and then diluted with EtOAc (200 mL) and washed with water (40 mL) and brine (40 mL). The aqueous layers were extracted with EtOAc (2×40 mL) and the combined organic layers dried over MgSO$_4$, filtered and evaporated under vacuum to give an oil which was dissolved in EtOAc and purified by column chromatography (normal phase, 50 g, Biotage SNAP cartridge KP-Sil, 50 mL/min, 80% EtOAc in hexane, then 0-5% MeOH in EtOAc) to give the desired product (579 mg).

LCMS: m/z 149.45 [M+H]$^+$.

$^1$H NMR (400 MHz, CD$_3$OD) ppm 4.05 (s, 3H) 6.55 (br. s., 1H) 6.77 (br. s., 1H) 7.43 (d, J=2.5 Hz, 1H) 7.89-8.61 (m, 1H)

(5) Intermediate 42: 3-Iodo-7-methoxy-1H-pyrrolo[3,2-b]pyridine

To a mixture of 7-methoxy-1H-pyrrolo[3,2-b]pyridine (Intermediate 41), (102 mg) and DMF (3 mL) was added KOH (147 mg) and I$_2$ (192 mg) and left to stir at rt for 90 min. The crude product was diluted with MeOH and purified using an SCX-2 cartridge (washed sequentially with MeOH, H$_2$O, MeOH and product eluted using 2 M methanolic ammonia). The solution was evaporated under vacuum to give the desired product (178 mg).

LCMS: m/z 275.37 [M+H]$^+$.

$^1$H NMR (400 MHz, CD$_3$OD) ppm 4.07 (s, 3H) 6.85 (d, J=5.6 Hz, 1H) 7.53 (s, 1H) 8.27 (d, J=5.5 Hz, 1H)

(6) Intermediate 43: tert-Butyl 3-iodo-7-methoxy-1H-pyrrolo[3,2-b]pyridine-1-carboxylate To a suspension of 3-iodo-7-methoxy-1H-pyrrolo[3,2-b]pyridine (Intermediate 42), (1.01 g) and DMAP (58.7 mg) in DCM (8.9 mL), was added dropwise a solution of di-tert-butyl dicarbonate (1.21 g) in DCM (2 mL) over 30 s, and the reaction mixture left to stir at rt overnight. The reaction mixture was evaporated under vacuum and then loaded onto a column in DCM (normal phase, 25 g, Biotage SNAP cartridge KP-Sil, 25 mL/min, gradient 0-30% EtOAc in n-hexane) to give the desired product (1.18 g).

LCMS: m/z 375.44 [M+H]$^+$.

$^1$H NMR (400 MHz, CDCl$_3$) ppm 1.65 (s, 9H) 4.02 (s, 3H) 6.82 (d, J=5.5 Hz, 1H) 7.93 (s, 1H) 8.51 (d, J=5.6 Hz, 1H)

(7) Intermediate 44: tert-Butyl 3-(((1S,2S)-2-hydroxycyclohexyl)carbamoyl)-7-methoxy-1H-pyrrolo[3,2-b]pyridine-1-carboxylate tert-Butyl 3-iodo-7-methoxy-1H-pyrrolo[3,2-b]pyridine-1-carboxylate (Intermediate 43), (924 mg), Pd(OAc)$_2$ (33 mg), (1S,2S)-2-aminocyclohexanol hydrochloride (562 mg), XantPhos (169 mg), toluene (22 mL) and TEA (1.03 mL) were added to a round bottomed flask. This was purged with CO and stirred at 80° C. overnight under CO. The reaction mixture was diluted with EtOAc (250 mL) and washed with water (2×70 mL) and brine (70 mL). The combined aqueous layers were extracted with EtOAc (70 mL) and the combined organic layers dried over MgSO$_4$, filtered and evaporated under vacuum to give a solid (1.22 g) which was taken on as such without further purification.

LCMS: m/z 390.65 [M+H]$^+$.

(8) Intermediate 45: N-((1S,2S)-2-hydroxycyclohexyl)-7-methoxy-1H-pyrrolo[3,2-b]pyridine-3-carboxamide To a solution of tert-butyl 3-(((1S,2S)-2-hydroxycyclohexyl)carbamoyl)-7-methoxy-1H-pyrrolo[3,2-b]pyridine-1-carboxylate (Intermediate 44), (312 mg) in DCM (2 mL) was added TFA (3.3 mL) dropwise and left to stir at rt for 1 h 15 min. The solvent was evaporated under vacuum to give an oil which was dissolved in DCM and purified using column chromatography (normal phase, 28 g, Biotage SNAP cartridge KP-NH, 25 mL/min, gradient 0-5% MeOH in EtOAc) to give the desired product (157 mg).

LCMS: m/z 290.56 [M+H]$^+$.

$^1$H NMR (400 MHz, CDCl$_3$) ppm 1.05-2.23 (m, 8H) 3.58 (td, J=9.9, 4.5 Hz, 1H) 3.82-3.97 (m, 1H) 4.02 (s, 3H) 6.63 (d, J=5.5 Hz, 1H) 8.01 (s, 1H) 8.32 (d, J=5.5 Hz, 1H) 9.11 (d, J=6.6 Hz, 1H)

Intermediate 49: Synthesis of N-((1S,2S)-2-hydroxycyclohexyl)-5-methoxy-1H-pyrrolo[3,2-b]pyridine-3-carboxamide

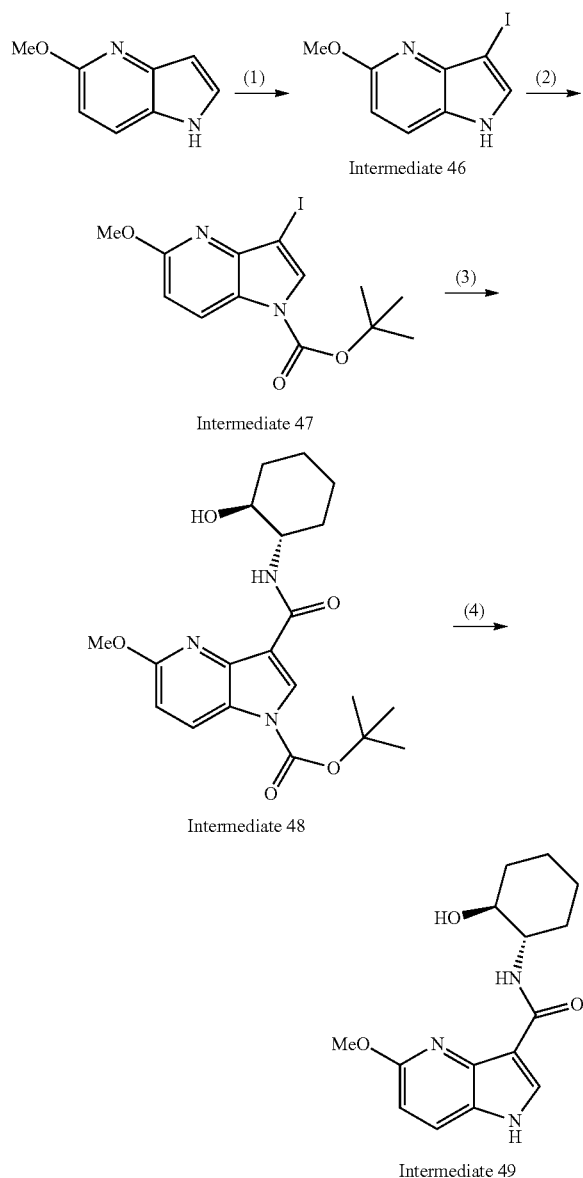 [SMILES: COc1ccc2[nH]ccc2n1 ; COc1ccc2[nH]cc(I)c2n1 ; COc1ccc2c(n1)c(I)cn2C(=O)OC(C)(C)C ; COc1ccc2c(n1)c(C(=O)N[C@H]1CCCC[C@@H]1O)cn2C(=O)OC(C)(C)C ; COc1ccc2[nH]cc(C(=O)N[C@H]3CCCC[C@@H]3O)c2n1]

(1) Intermediate 46: 3-Iodo-5-methoxy-1H-pyrrolo[3,2-b]pyridine

To a mixture of 5-methoxy-1H-pyrrolo[3,2-b]pyridine (Purchased from Combi blocks Inc.), (500 mg) and DMF (8 mL) was added KOH (719 mg) followed by iodine (942 mg) then the mixture stirred for 2 h. It was diluted with EtOAc, washed with water (3×), brine (2×), dried (MgSO$_4$), filtered and evaporated under vacuum to give the crude product (925 mg), which was used in the next step without further purification.

LCMS: m/z 275.66 [M+H]$^+$.

(2) Intermediate 47: tert-Butyl 3-iodo-5-methoxy-1H-pyrrolo[3,2-b]pyridine-1-carboxylate To a mixture of 3-iodo-5-methoxy-1H-pyrrolo[3,2-b]pyridine (Intermediate 46), (925 mg), 4-dimethylaminopyridine (54 mg) and DCM (7.2 mL) was added dropwise a solution of di-t-butyldicarbonate (1.1 g) in DCM (4 mL) and the reaction mixture stirred for 1 h 15 min. The solvent was then evaporated and the residue was purified by column chromatography (normal phase, 28 g amino silica, 50 g silica, Biotage SNAP cartridge KP-Sil, gradient 0% to 10% EtOAc in n-hexane) to give the desired compound (970 mg).

LCMS: m/z 375.41[M+H]$^+$.

$^1$H NMR (400 MHz, CDCl$_3$) ppm 1.65-1.71 (m, 9H) 4.07 (s, 3H) 6.74 (d, J=8.93 Hz, 1H) 7.86 (s, 1H) 8.18-8.31 (m, 1H).

(3) Intermediate 48: tert-Butyl 3-(((1S,2S)-2-hydroxycyclohexyl)carbamoyl)-5-methoxy-1H-pyrrolo[3,2-b]pyridine-1-carboxylate tert-Butyl 3-iodo-5-methoxy-1H-pyrrolo[3,2-b]pyridine-1-carboxylate (Intermediate 47), (950 mg), (1S,2S)-2-aminocyclohexanol hydrochloride (577 mg), palladium (II) acetate (17.10 mg), XantPhos (88 mg), toluene (23 mL) and TEA (1.2 mL) were placed in a 25 mL microwave tube with a balloon of CO. The reaction mixture was purged with CO then heated to 80° C. for 2 h 15 min (CO was bubbled through reaction mixture when it first reached 80° C.). The reaction mixture was cooled, poured onto EtOAc and the remaining solid in the reaction flask was added to the EtOAc organic phases by dissolving in water and the organic phases washed with water (2×) then brine. The combined organic extracts were dried (MgSO$_4$), filter and evaporate under vacuum to give the crude desired compound (989 mg), which was used crude.

LCMS: m/z 390.64 [M+H]$^+$.

(4) Intermediate 49: N-((1S,2S)-2-hydroxycyclohexyl)-5-methoxy-1H-pyrrolo[3,2-b]pyridine-3-carboxamide A mixture of tert-butyl 3-(((1S,2S)-2-hydroxycyclohexyl)carbamoyl)-5-methoxy-1H-pyrrolo[3,2-b]pyridine-1-carboxylate (Intermediate 48), (989 mg), DCM (11 mL) and TFA (5.6 mL) was stirred for 1 h. The solvent was evaporated and the residue purified by column chromatography (normal phase, 55 g amino silica, Biotage SNAP cartridge KP-Sil, gradient 0% to 100% EtOAc in n-hexane followed by gradient 0%-15% EtOAc in MeOH) to give the desired compound (500 mg).

LCMS: m/z 299.55 [M+H]$^+$.

1H NMR (400 MHz, DMSO-d$_6$) ppm 1.08-1.40 (m, 4H) 1.56-1.71 (m, 2H) 1.90 (d, J=10.0 Hz, 1H) 2.13 (d, J=12.4 Hz, 1H) 3.40 (br. s., 1H) 3.61-3.72 (m, 1H) 3.94 (s, 3H) 4.84 (d, J=4.0 Hz, 1H) 6.68 (d, J=8.8 Hz, 1H) 7.83 (d, J=8.8 Hz, 1H) 7.96 (s, 1H) 8.67 (d, J=6.9 Hz, 1H).

Intermediate 53: Synthesis of 5-Chloro-N-((1S,2S)-2-hydroxycyclohexyl)-1H-pyrrolo[3,2-b]pyridine-3-carboxamide

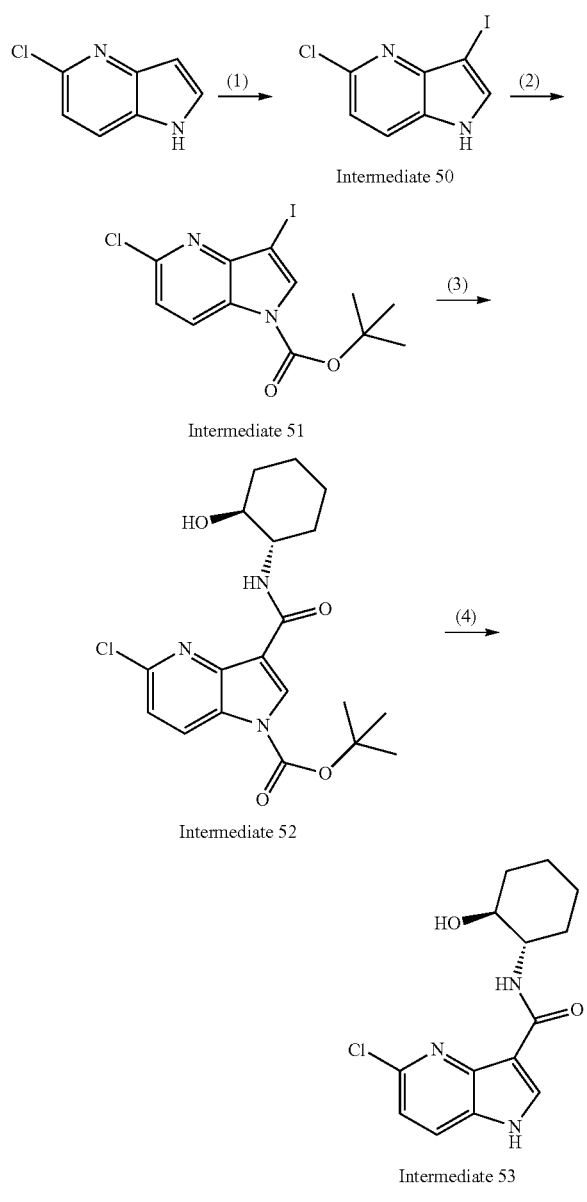 [SMILES: Clc1ccc2[nH]ccc2n1 ; Clc1ccc2[nH]cc(I)c2n1 ; CC(C)(C)OC(=O)n1cc(I)c2nc(Cl)ccc21 ; CC(C)(C)OC(=O)n1cc(C(=O)N[C@H]2CCCC[C@@H]2O)c2nc(Cl)ccc21 ; O=C(N[C@H]1CCCC[C@@H]1O)c1c[nH]c2ccc(Cl)nc12]

(1) Intermediate 50: 5-Chloro-3-iodo-1H-pyrrolo[3,2-b]pyridine

To a mixture of 5-chloro-1H-pyrrolo[3,2-b]pyridine (Purchased from Ark Pharm Inc.), (500 mg) and DMF (7.7 mL) was added KOH (699 mg) followed by iodine (915 mg) then the reaction mixture stirred for 1 h. It was then diluted with EtOAc, washed with water (3×), brine (2×), dried (MgSO$_4$), filtered and evaporated under vacuum to give the crude desired compound (1.1 g), which was used in the next step without further purification.

LCMS: m/z 279.37[M+H]$^+$.

(2) Intermediate 51: tert-Butyl 5-chloro-3-iodo-1H-pyrrolo[3,2-b]pyridine-1-carboxylate To a mixture of 5-chloro-3-iodo-1H-pyrrolo[3,2-b]pyridine (Intermediate 50), (910 mg), 4-dimethylaminopyridine (52 mg) and DCM (7.0 mL) was added dropwise a solution of di-t-butyldicarbonate (1.07 g) in DCM (2 mL) and the reaction mixture stirred for two days. The solvent was evaporated and the residue purified by column chromatography (normal phase, 50 g silica, Biotage SNAP cartridge KP-Sil, gradient 0% to 10% EtOAc in n-hexane) to give the desired compound (1.18 g).

LCMS: m/z 379.35[M+H]$^+$.

$^1$H NMR (400 MHz, CDCl$_3$) ppm 1.69 (s, 9H) 7.31 (d, J=8.6 Hz, 1H) 7.98 (s, 1H) 8.28-8.39 (m, 1H).

(3) Intermediate 52: tert-Butyl 5-chloro-3-(((1S,2S)-2-hydroxycyclohexyl)carbamoyl)-1H-pyrrolo[3,2-b]pyridine-1-carboxylate tert-Butyl 5-chloro-3-iodo-1H-pyrrolo[3,2-b]pyridine-1-carboxylate (Intermediate 51), (600 mg), (1S,2S)-2-aminocyclohexanol hydrochloride (360 mg), palladium (II) acetate (10.7 mg), XantPhos (55 mg), toluene (14.4 mL) and TEA (0.72 mL) were placed in a 25 mL microwave tube with a balloon of CO. The reaction mixture was purged with CO then heated to 80° C. for 2 h (CO was bubbled through reaction mixture when it first reached 80° C.). The reaction mixture was cooled and poured onto EtOAc and the remaining solid in the reaction flask was added to the EtOAc organic phases by dissolving in water and the organic phases washed with water (2×) then brine and the combined organic extracts dried (MgSO$_4$), filtered and evaporated under vacuum. The crude desired compound was taken on as such.

LCMS: m/z 394.58 [M+H]$^+$.

(4) Intermediate 53: 5-Chloro-N-((1S,2S)-2-hydroxycyclohexyl)-1H-pyrrolo[3,2-b]pyridine-3-carboxamide To a solution of tert-butyl 5-chloro-3-(((1S,2S)-2-hydroxycyclohexyl)carbamoyl)-1H-pyrrolo[3,2-b]pyridine-1-carboxylate (Intermediate 52), (624 mg) in DCM (7 mL) was added TFA (3.5 mL) and the reaction mixture stirred for 2 h. The solvent was evaporated and the residue purified by column chromatography (normal phase, 28 g amino silica, Biotage SNAP cartridge KP-Sil, gradient 0% to 100% EtOAc in n-hexane then gradient 0% to 20% MeOH in EtOAc) to give the desired compound (292 mg).

LCMS: m/z 294.52[M+H]$^+$.

$^1$H NMR (400 MHz, DMSO-d$_6$) ppm 1.06-1.43 (m, 4H) 1.64 (d, J=5.4 Hz, 2H) 1.79-1.92 (m, 1H) 1.99-2.09 (m, 1H) 3.42 (br. s., 1H) 3.67-3.80 (m, 1H) 4.80 (br. s., 1H) 7.29 (d, J=8.6 Hz, 1H) 7.97 (d, J=8.4 Hz, 1H) 8.21 (s, 1H) 8.28 (d, J=7.6 Hz, 1H).

Intermediate 58: Synthesis of 1-(4-(1H-Pyrazol-1-yl)benzyl)-3-bromo-5-methyl-1H-pyrrolo[3,2-b]pyridine

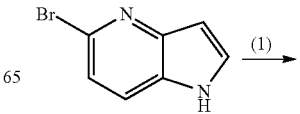

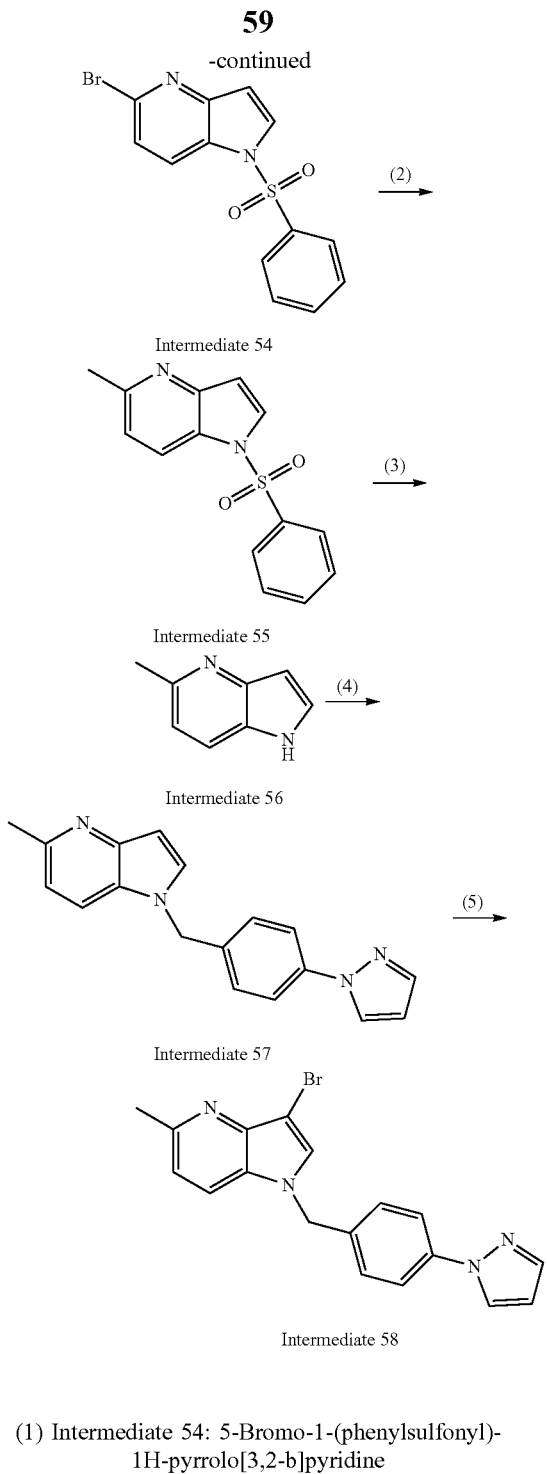

Intermediate 54

Intermediate 55

Intermediate 56

Intermediate 57

Intermediate 58

(1) Intermediate 54: 5-Bromo-1-(phenylsulfonyl)-1H-pyrrolo[3,2-b]pyridine

A mixture of 5-bromo-1H-pyrrolo[3,2-b]pyridine (Purchased from Bepharm Ltd.), (1.00 g), DCM (30.0 mL), benzenesulfonyl chloride (0.97 mL), tetrabutylammonium hydrogen sulfate (220 mg) and 50% aq. sodium hydroxide (0.96 mL) was stirred for 1 h to give a suspension. Saturated aq. NaHCO$_3$ was added, the layers separated and the aqueous phase was extracted with more DCM (2×), the combined organic extracts were dried (MgSO$_4$), filtered and evaporated under vacuum. Adding methanol (~30 mL) caused the product to precipitate. The suspension was cooled in an ice-bath and the ice-cold suspension was filtered and the solid washed with ice-cold methanol to give the desired compound (1.12 g). The mother liquor was evaporated and the residue purified by column chromatography (normal phase, 28 g amino silica, Biotage SNAP cartridge KP-Sil, gradient 0% to 100% EtOAc in n-hexane) to give more of the desired compound (600 mg).

LCMS: m/z 339.37 [M+H]$^+$.

$^1$H NMR (400 MHz, CDCl$_3$) ppm 6.84 (dd, J=3.7, 0.7 Hz, 1H) 7.41 (d, J=8.7 Hz, 1H) 7.47-7.54 (m, 2H) 7.59-7.65 (m, 1H) 7.80 (d, J=3.8 Hz, 1H) 7.85-7.91 (m, 2H) 8.15 (dd, J=8.7, 0.7 Hz, 1H).

(2) Intermediate 55: 5-Bromo-1-(phenylsulfonyl)-1H-pyrrolo[3,2-b]pyridine

A mixture of 5-bromo-1-(phenylsulfonyl)-1H-pyrrolo[3,2-b]pyridine (Intermediate 54), (1.71 g) and Pd(PPh$_3$)$_4$ (586 mg) was de-aerated by placing under high vacuum then purging with nitrogen (3×). To these solids was added THF (36 mL) then a 2M THF solution of methylzinc chloride (5.07 mL) and the reaction mixture heated to 90° C. for 1 h. It was then cooled, quenched with sat. aq. NH$_4$Cl, extracted with EtOAc (3×), the combined organic extracts dried (MgSO$_4$), filtered and evaporated under vacuum. The residue was purified by column chromatography (normal phase, 50 g silica, Biotage SNAP cartridge KP-Sil, gradient 0% to 80% EtOAc in n-hexane) to give the impure desired compound (1.60 g) which was taken on as such.

LCMS: m/z 274.46 [M+H]$^+$.

(3) Intermediate 56: 5-Methyl-1H-pyrrolo[3,2-b]pyridine

A mixture of 5-methyl-1-(phenylsulfonyl)-1H-pyrrolo[3,2-b]pyridine (Intermediate 55), (1.38 g), ethanol (96 mL) and 10% aq. sodium hydroxide (47 mL) was heated at 90° C. for 1 h. It was then cooled, poured onto brine, extracted with EtOAc (3×), the combined organic extracts dried (MgSO$_4$) and the combined organic phases filtered and evaporated under vacuum. The residue was purified by column chromatography (normal phase, 25 g silica, Biotage SNAP cartridge KP-Sil, gradient 0% to 100% EtOAc in n-hexane) to give the impure desired compound (356 mg) which was taken on as such.

LCMS: m/z 133.41 [M+H]$^+$.

$^1$H NMR (400 MHz, CDCl$_3$) ppm 2.63 (s, 3H) 6.61 (dd, J=3.2, 0.9 Hz, 1H) 6.97 (d, J=8.3 Hz, H) 7.39 (d, J=3.3 Hz, 1H) 7.62 (dd, J=8.3, 0.6 Hz, 1H)

(4) Intermediate 57: 1-(4-(1H-Pyrazol-1-yl)benzyl)-5-methyl-1H-pyrrolo[3,2-b]pyridine To an ice-cold suspension of 5-methyl-1H-pyrrolo[3,2-b]pyridine (Intermediate 56), (350 mg) in N,N-dimethylacetamide (6.5 mL) was added sodium hydride (127 mg) in one portion then the reaction mixture stirred for 20 min. 1-(4-(Bromomethyl)phenyl)-1H-pyrazole (Purchased from Butt Park Ltd.), (691 mg) in DMA (0.8 mL) was added dropwise followed by stirring at rt for 30 min. The reaction mixture was diluted with EtOAc, washed with water (2×), brine, dried (MgSO$_4$), filtered and evaporated under vacuum then left under high vacuum. The residue was purified by column chromatography (normal phase, 25 g silica, Biotage SNAP cartridge KP-Sil, gradient 0% to 100% EtOAc in n-hexane) to give the desired compound (734 mg).

LCMS: m/z 289.53 [M+H]⁺.

¹H NMR (600 MHz, CDCl₃) ppm 2.72 (s, 3H) 5.37 (s, 2H) 6.48 (t, J=2.0 Hz, 1H) 6.78 (br. s., 1H) 7.00 (d, J=8.5 Hz, 1H) 7.20 (d, J=8.5 Hz, 2H) 7.39 (d, J=2.6 Hz, 1H) 7.50 (d, J=8.2 Hz, 1H) 7.67 (d, J=8.5 Hz, 2H) 7.73 (d, J=1.5 Hz, 1H) 7.90 (d, J=2.6 Hz, 1H).

(5) Intermediate 58: 1-(4-(1H-Pyrazol-1-yl)benzyl)-3-bromo-5-methyl-1H-pyrrolo[3,2-b]pyridine A mixture of 1-(4-(1H-pyrazol-1-yl)benzyl)-5-methyl-1H-pyrrolo[3,2-b]pyridine (Intermediate 57), (200 mg), DCM (9 mL) and pyridine (0.084 mL) was cooled to −78° C. and a solution of bromine (0.036 mL) in DCM (4 mL) was added dropwise. After 20 min the reaction mixture was poured onto a mixture of sat. aq. NaHCO₃ (9 mL) and Na₂S₂O₃ (9 mL) and stirred for 1 h. The layers were separated, the aqueous phase extracted with DCM (2×), the combined organic extracts dried (MgSO₄), filtered and evaporated under vacuum. The residue was purified by column chromatography (normal phase, 25 g silica, Biotage SNAP cartridge KP-Sil, gradient 0% to 50% EtOAc in n-hexane) to give the desired compound (203 mg).

LCMS: m/z 367.46, 369.45 [M+H]⁺.

¹H NMR (400 MHz, CDCl₃) ppm 2.75 (s, 3H) 5.33 (s, 2H) 6.46-6.50 (m, 1H) 7.04 (d, J=8.4 Hz, 1H) 7.21 (d, J=8.7 Hz, 2H) 7.40 (s, 1H) 7.50 (d, J=8.4 Hz, 1H) 7.65-7.70 (m, 2H) 7.73 (d, J=1.6 Hz, 1H) 7.90 (d, J=2.3 Hz, 1H).

Intermediate 63: Synthesis of 5-Cyano-N-((1S,2S)-2-hydroxycyclohexyl)-1H-pyrrolo[3,2-b]pyridine-3-carboxamide

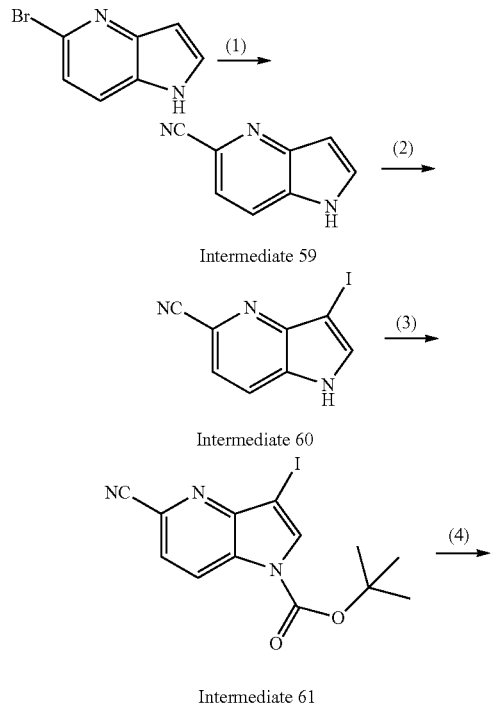

Intermediate 59

Intermediate 60

Intermediate 61

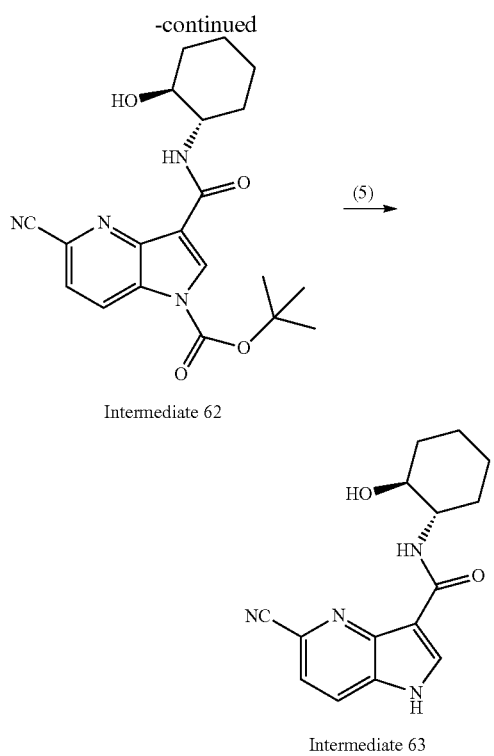

Intermediate 62

Intermediate 63

(1) Intermediate 59: 1H-pyrrolo[3,2-b]pyridine-5-carbonitrile

A mixture of 5-bromo-1H-pyrrolo[3,2-b]pyridine (500 mg), Pd(PPh₃)₄ (176 mg), zinc cyanide (179 mg) and DMF (5.1 mL) were stirred at 80° C. overnight. More zinc cyanide (90 mg) and Pd(PPh₃)₄ (90 mg) were added and the stirring continued at 80° C. for 5 h. The reaction mixture was cooled, diluted with EtOAc, water was added and the insoluble precipitate filtered, washed with water and EtOAc. The layers were separated and the organic layers washed with water (2×), brine, dried (MgSO₄), filtered and evaporated under vacuum. The residue was purified by column chromatography (normal phase, 50 g silica, Biotage SNAP cartridge KP-Sil, gradient 0% to 100% EtOAc in n-hexane) to give the desired compound (280 mg).

LCMS: m/z 144.66 [M+H]⁺.

¹H NMR (400 MHz, DMSO-d6) ppm 6.71 (dd, J=3.3, 0.9 Hz, 1H) 7.66 (d, J=8.4 Hz, 1H) 7.92 (d, J=3.3 Hz, 1H) 7.98 (dd, J=8.4, 0.8 Hz, 1H) 11.87 (br. s., 1H).

(2) Intermediate 60: 3-Iodo-1H-pyrrolo[3,2-b]pyridine-5-carbonitrile

To a solution of 1H-pyrrolo[3,2-b]pyridine-5-carbonitrile (Intermediate 59), (280 mg) and DMF (4.6 mL) was added potassium hydroxide (417 mg) followed by iodine (596 mg) then the reaction mixture stirred at rt for 60 min. A mixture of NaHSO₃ (Na₂S₂O₅) (195 mg), water (29 mL) and 28-30% ammonium hydroxide (2 mL) was added to the reaction mixture, which was then cooled in an ice-bath. The precipitate was filtered, washed with ice-cold water and dried under high vacuum to give the desired compound (292 mg). The aqueous phase was extracted with EtOAc (3×), the combined organic extracts washed with brine (3×), dried (MgSO₄), filtered and evaporated under vacuum to give more of the desired compound (101 mg).
LCMS: m/z 270.38 [M+H]⁺.

(3) Intermediate 61: tert-Butyl 5-cyano-3-iodo-1H-pyrrolo[3,2-b]pyridine-1-carboxylate To a suspension of 3-iodo-1H-pyrrolo[3,2-b]pyridine-5-carbonitrile (Intermediate 60), (393 mg) and 4-dimethylaminopyridine (23.2 mg) stirred at rt in DCM (3.6 mL) was added dropwise a solution of di-t-butyldicarbonate (478 mg) in DCM (30 mL) then the reaction mixture stirred for 30 min. The solvent was evaporated and the residue purified by column chromatography (normal phase, 25 g silica, Biotage SNAP cartridge KP-Sil, gradient 0% to 50% EtOAc in n-hexane) to give the desired compound (490 mg).
LCMS: m/z 370.3 [M+H]⁺.

(4) Intermediate 62: tert-Butyl 5-cyano-3-(((1S,2S)-2-hydroxycyclohexyl)carbamoyl)-1H-pyrrolo[3,2-b]pyridine-1-carboxylate tert-Butyl 5-cyano-3-iodo-1H-pyrrolo[3,2-b]pyridine-1-carboxylate (Intermediate 61), (490 mg), palladium (II) acetate (8.9 mg), XantPhos (46.1 mg), (1S,2S)-2-aminocyclohexanol hydrochloride (302 mg), toluene (12.0 mL) and TEA (0.56 mL) were placed in a microwave tube with a CO balloon. The microwave tube was purged with CO then heated to 80° C. overnight. The reaction mixture was diluted with EtOAc and the remaining solid in the reaction flask was dissolved/suspended in a small amount of THF (~2 mL) by sonication then added to the EtOAc organic phases then the combined organic phases washed with water (2×) then brine, dried (MgSO₄), filtered and evaporated under vacuum to give the crude product, which was used as such for Boc removal.
LCMS: m/z 385.58 [M+H]⁺ and m/z 285.52 [M+H-Boc]⁺.

(5) Intermediate 63: 5-Cyano-N-((1S,2S)-2-hydroxycyclohexyl)-1H-pyrrolo[3,2-b]pyridine-3-carboxamide A mixture of tert-butyl 5-cyano-3-(((1S,2S)-2-hydroxycyclohexyl)carbamoyl)-1H-pyrrolo[3,2-b]pyridine-1-carboxylate (Intermediate 62), (510 mg), DCM (5.2 mL) and TFA (2.6 mL) were stirred at rt for 1.5 h. The solvent was evaporated and the residue was purified by column chromatography (normal phase, 28 g amino silica, Biotage SNAP cartridge KP-Sil, gradient 0% to 100% EtOAc in n-hexane) to give the desired compound (323 mg).
LCMS: m/z 285.56 [M+H]⁺.
¹H NMR (400 MHz, DMSO-d6) ppm 1.32 (d, J=6.5 Hz, 4H) 1.53-1.72 (m, 2H) 1.88 (br. s., 1H) 2.05 (d, J=9.3 Hz, 1H) 3.44 (br. s., 1H) 3.73 (d, J=8.2 Hz, 1H) 7.80 (d, J=8.3 Hz, 1H) 8.10 (d, J=8.4 Hz, 1H) 8.29 (d, J=7.5 Hz, 1H) 8.42 (s, 1H).

Intermediate 66: Synthesis of 1-(2-Fluoro-4-(6-methylpyridin-2-yl)benzyl)-3-iodo-1H-pyrrolo[3,2-b]pyridine

(1) Intermediate 64: 2-Fluoro-4-(6-methylpyridin-2-yl)benzaldehyde

Two separate reaction vessels, each containing a mixture of K₂CO₃ (823 mg), 2-bromo-6-methylpyridine (614 mg) in toluene (5 mL) and water (2.5 mL) were purged with nitrogen. To each vessel was added Pd(dppf)Cl₂.CH₂Cl₂ (242 mg) followed by (3-fluoro-4-formylphenyl)boronic acid (500 mg), the mixtures were further purged with nitrogen, before being heated at 90° C. for 2 h. Once cooled, the two reaction mixtures were combined, water was added and the reaction mixture extracted with EtOAc (3×). The organic phases were combined, dried (Na₂SO₄), filtered and evaporated under vacuum. The crude product was purified by column chromatography (silica), eluting with 4:96 EtOAc/hexanes to afford the title compound (470 mg).
¹H NMR (400 MHz, DMSO-d₆) ppm 2.57 (s, 3H), 7.34 (d, J=7.6 Hz, 1H), 7.82-7.89 (m, 1H), 7.90-8.01 (m, 2H), 8.05-8.19 (m, 2H), 10.26 (s, 1H)

(2) Intermediate 65: 2-(4-(Bromomethyl)-3-fluorophenyl)-6-methylpyridine hydrobromide Sodium borohydride (123 mg) was added to a solution of 2-fluoro-4-(6-methylpyridin-2-yl)benzaldehyde (Intermediate 64), (470 mg) in methanol (10 mL) at 0° C. The reaction mixture was stirred for 2 hours at a temperature between 10° C.-20° C. The reaction mixture was concentrated under vacuum before being diluted with water (15 mL). The product was extracted with EtOAc (30 mL). The organic phase was dried (Na₂SO₄), filtered, and evaporated under vacuum to afford (2-fluoro-4-(6-methylpyridin-2-yl)phenyl)methanol (450 mg) of sufficient purity to be used in the next step as such.
LCMS: m/z 218.09 [M+H]⁺.
(2-fluoro-4-(6-methylpyridin-2-yl)phenyl)methanol (450 mg) was dissolved in 48% aq. hydrogen bromide solution (9 mL) and heated at 80-90° C. for 2 h. The reaction mixture was concentrated under vacuum with residual solvent removed by sequential azeotrope vacuum evaporation with CH$_2$Cl$_2$ (1×) then toluene (2×). The title compound, isolated as a hydrogen bromide salt, was further dried under vacuum to yield the desired compound (620 mg) which was taken on as such.

LCMS: m/z 281.98 [M+H]$^+$ (3) Intermediate 66: 1-(2-Fluoro-4-(6-methylpyridin-2-yl)benzyl)-3-iodo-1H-pyrrolo[3,2-b]pyridine To a mixture of 3-iodo-1H-pyrrolo[3,2-b]pyridine (Intermediate 1), (350 mg) and potassium carbonate (791 mg) in DMF (8 mL) stirred at 0° C. under nitrogen was added 2-(4-(bromomethyl)-3-fluorophenyl)-6-methylpyridine hydrobromide (Intermediate 65), (620 mg). The reaction mixture was allowed to warm to rt and was stirred overnight. Water (50 mL) was added to the reaction mixture and the reaction mixture was extracted with EtOAc (100 mL). The organic phase was washed with brine (75 mL), dried (Na$_2$SO$_4$), filtered and evaporated under vacuum. The crude product was purified by column chromatography (silica) eluting with 28:72 EtOAc:hexanes to afford the title compound (580 mg) which was taken on as such.

LCMS: m/z 444.11 [M+H]$^+$.

Intermediate 69: 1-(2-Fluoro-4-(2-methylpyridin-4-yl)benzyl)-3-iodo-1H-pyrrolo[3,2-b]pyridine

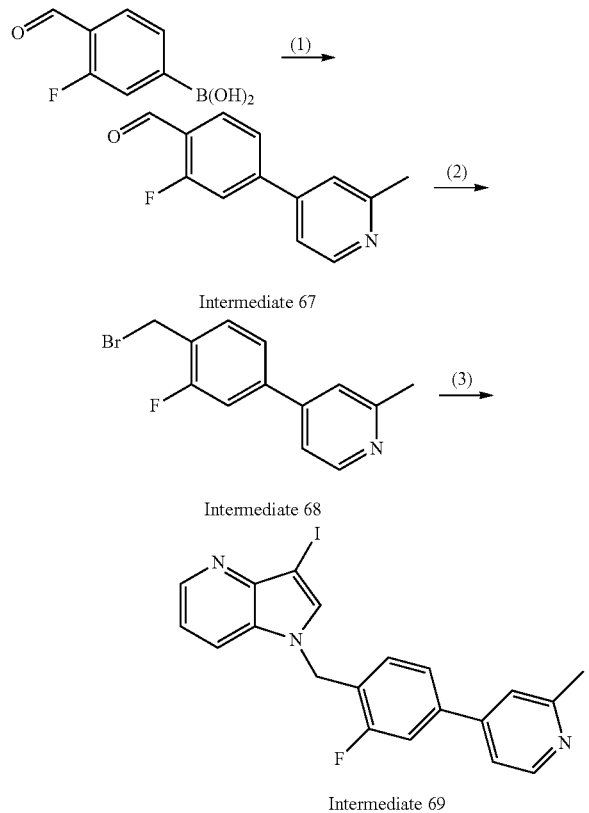

Intermediate 67

Intermediate 68

Intermediate 69

(1) Intermediate 67: 2-Fluoro-4-(2-methylpyridin-4-yl)benzaldehyde

Into two separate reaction vessels, each containing a mixture of K$_2$CO$_3$ (823 mg), 4-bromo-2-methylpyridine (614 mg) in toluene (5 mL) and water (2.5 mL) were purged with nitrogen. To each vessel was added Pd(dppf)Cl$_2$·CH$_2$Cl$_2$ (242 mg) followed by (3-fluoro-4-formylphenyl)boronic acid (500 mg), the mixtures were further purged with nitrogen, before being heated at 90° C. for 2 h. Once cooled, the two reaction mixtures were combined, water was added and the reaction mixture extracted with EtOAc (3×). The organic phases were combined, dried (Na$_2$SO$_4$), filtered and evaporated under vacuum. The crude product was purified by column chromatography (silica), eluting with 3:7 EtOAc/hexanes to afford the title compound (700 mg).

LCMS: m/z 216.09 [M+H]$^+$.

$^1$H NMR (400 MHz, DMSO-d$_6$) ppm 2.55 (s, 3H), 7.63 (dd, J=5.5, 1.8 Hz, 1H), 7.73 (d, J=1.2 Hz, 1H), 7.82-7.88 (m, 1H), 7.91 (dd, J=12.2, 1.5 Hz, 1H), 7.94-8.00 (m, 1H), 8.57 (d, J=5.2 Hz, 1H), 10.26 (s, 1H)

(2) Intermediate 68: 4-(4-(Bromomethyl)-3-fluorophenyl)-2-methylpyridine hydrobromide Sodium borohydride (0.184 g) was added to a solution of 2-fluoro-4-(2-methylpyridin-4-yl)benzaldehyde (Intermediate 67), (700 mg) in methanol (15 mL). The reaction mixture was stirred for 2 hours at a temperature between 0-5° C. The reaction mixture was concentrated under vacuum before being diluted with water (25 mL). The product was extracted with EtOAc (35 mL). The organic phase was dried (Na$_2$SO$_4$), filtered, and evaporated under vacuum to afford (2-fluoro-4-(2-methylpyridin-4-yl)phenyl)methanol (700 mg) of sufficient purity to be used in the next step.

LCMS: m/z 218.19 [M+H]$^+$.

(2-fluoro-4-(2-methylpyridin-4-yl)phenyl)methanol (700 mg) was dissolved in 48% aq. hydrogen bromide solution (14 mL) and heated at 90° C. for 2 h. The reaction mixture was concentrated under vacuum with residual solvent removed by sequential azeotrope vacuum evaporation with CH$_2$Cl$_2$ (1×) then toluene (2×). The title compound, isolated as a hydrogen bromide salt, was further dried under vacuum and taken on as such.

LCMS: m/z 282.18 [M+H]$^+$.

(3) Intermediate 69: 1-(2-Fluoro-4-(2-methylpyridin-4-yl)benzyl)-3-iodo-1H-pyrrolo[3,2-b]pyridine To a mixture of 3-iodo-1H-pyrrolo[3,2-b]pyridine (Intermediate 1), (300 mg) and potassium carbonate (678 mg) in DMF (5 mL) stirred at 0° C. under nitrogen was added 4-(4-(bromomethyl)-3-fluorophenyl)-2-methylpyridine hydrobromide (Intermediate 68), (531 mg). The reaction mixture was allowed to warm to rt and was stirred overnight. Water (35 mL) was added to the reaction mixture and the reaction mixture was extracted with EtOAc (2×35 mL). The organic phases were combined, washed with brine (40 mL), dried (Na$_2$SO$_4$), filtered and evaporated under vacuum. The crude product was purified by column chromatography (silica) eluting with 80:20 EtOAc:hexanes to afford the title compound (480 mg).

LCMS: m/z 444.16 [M+H]$^+$.

Intermediate 72: Synthesis of 1-((4'-Fluoro-[1,1'-biphenyl]-4-yl)methyl)-3-iodo-1H-pyrrolo[3,2-b]pyridine

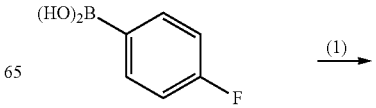

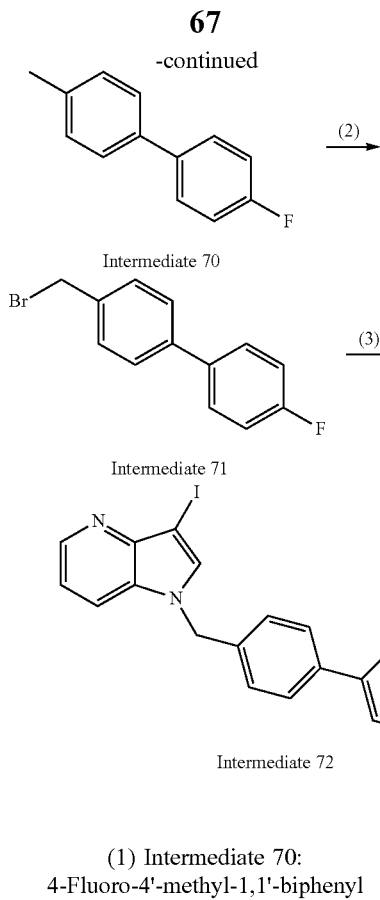

Intermediate 70

Intermediate 71

Intermediate 72

(1) Intermediate 70:
4-Fluoro-4'-methyl-1,1'-biphenyl

A solution of (4-fluorophenyl)boronic acid (2.5 g) in toluene (15 mL) was purged with nitrogen. To which, was added Pd(PPh$_3$)$_4$ (4.12 g) and the mixture purged further before the addition of 1-bromo-4-methylbenzene (3.67 g) followed by the addition of sodium carbonate (5.68 g) in water (10 mL). The mixture was further purged before being heated at 85° C. for 2 h. Once cooled, water was added and the reaction mixture extracted with EtOAc (2×). The organic phases were combined, dried, filtered and evaporated under vacuum. The crude product was purified by column chromatography (silica), eluting with 1:19 EtOAc/hexanes to afford the title compound (1.8 g) which was taken on as such.

(2) Intermediate 71:
4-Fluoro-4'-methyl-1,1'-biphenyl

N-Bromosuccinimide (2 g) was added to a solution of 4-fluoro-4'-methyl-1,1'-biphenyl (Intermediate 70), (1.8 g) in CHCl$_3$ (90 mL) followed by the addition of AIBN (300 mg). The reaction mixture was heated under reflux overnight. Once cooled, water was added and the crude product extracted with CHCl$_3$. The organic phase was dried, filtered and evaporated under vacuum. The crude product was purified by column chromatography (silica), eluting with 1:99 EtOAc/hexanes to afford the title compound (850 mg).
$^1$H NMR (400 MHz, CDCl$_3$) ppm 4.56 (s, 2H), 7.10-7.18 (m, 2H), 7.45-7.50 (m, 2H), 7.50-7.59 (m, 4H).

(3) Intermediate 72: 1-((4'-Fluoro-[1,1'-biphenyl]-4-yl)methyl)-3-iodo-1H-pyrrolo[3,2-b]pyridine Sodium hydride (140 mg, 60% dispersion in mineral oil) was added to a solution of 3-iodo-1H-pyrrolo[3,2-b]pyridine (Intermediate 1), (700 mg) in dimethyl acetamide (7 mL) at 0° C. The RM was allowed to warm to rt and was stirred for 30 min. To which, was added 4-fluoro-4'-methyl-1,1'-biphenyl (Intermediate 71), (840 mg) and the reaction mixture stirred for a further 1 h. The reaction was quenched with water (20 mL) and extracted with EtOAc (3×20 mL). The organic phases were combined, dried (Na$_2$SO$_4$), filtered, and evaporated under vacuum. The crude product was purified by column chromatography (silica), eluting with 20:80 EtOAc/hexanes to afford the title compound (700 mg).
LCMS: m/z 429.04 [M+H]$^+$.
$^1$H NMR (400 MHz, DMSO-d$_6$) ppm 5.51 (s, 2H), 7.21 (dd, J=8.2, 4.6 Hz, 1H), 7.23-7.30 (m, 2H), 7.35 (d, J=8.2 Hz, 2H), 7.54-7.62 (m, 2H), 7.62-7.69 (m, 2H), 8.00 (dd, J=8.2, 1.2 Hz, 1H), 8.09 (s, 1H), 8.40 (dd, J=4.4, 1.4 Hz, 1H)

Intermediate 73: Synthesis of N-((1R,2R)-2-hydroxycyclohexyl)-1H-pyrrolo[3,2-b]pyridine-3-carboxamide

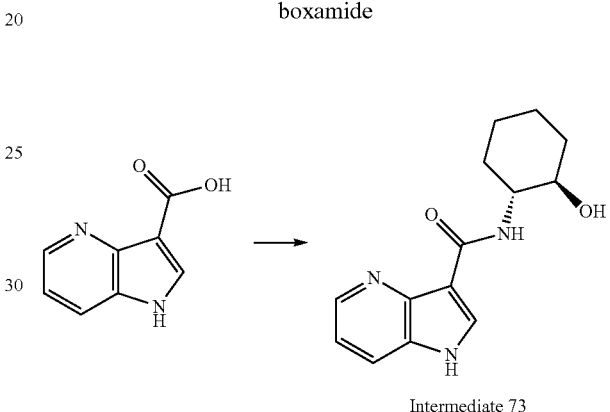

Intermediate 73

A mixture of 1H-pyrrolo[3,2-b]pyridine-3-carboxylic acid (200 mg), triethylamine (0.688 mL), BOP (818 mg), HATU (563 mg) and DMF (4.8 mL) were stirred for 15 min. (1R,2R)-2-aminocyclohexanol hydrochloride (281 mg) was added and the reaction mixture left to stir overnight. The reaction mixture was purified by preparative LCMS to give the desired compound (133 mg).
LCMS: m/z 260.1 [M+H]$^+$
$^1$H NMR (400 MHz, CDCl$_3$) ppm 1.15-1.57 (m, 6H) 1.75 (d, J=9.5 Hz, 2H) 2.03-2.14 (m, 2H) 3.53 (td, J=9.8, 4.3 Hz, 1H) 3.79-3.91 (m, 1H) 7.13 (dd, J=8.3, 4.6 Hz, 1H) 7.72 (dd, J=8.2, 1.3 Hz, 1H) 8.04 (s, 1H) 8.41 (dd, J=4.8, 1.3 Hz, 1H) 9.12 (d, J=6.8 Hz, 1H)

Intermediate 74; tert-Butyl 3-((trans-3-hydroxytetrahydro-2H-pyran-4-yl)carbamoyl)-7-methyl-1H-pyrrolo[3,2-b]pyridine-1-carboxylate

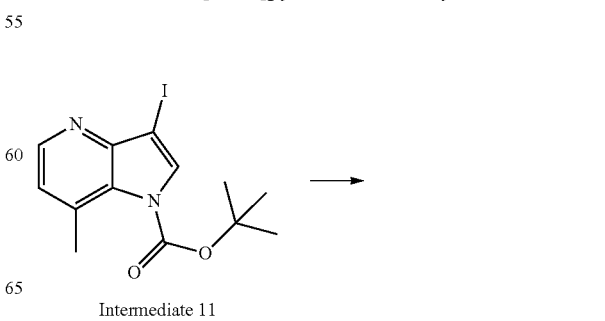

Intermediate 11

-continued

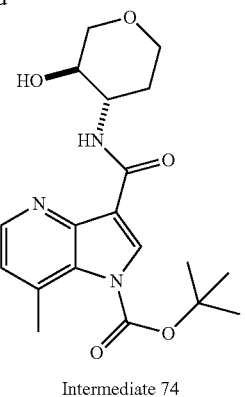

Intermediate 74 tert-Butyl 3-iodo-7-methyl-1H-pyrrolo[3,2-b]pyridine-1-carboxylate (Intermediate 11), (750 mg), trans-4-aminotetrahydro-2H-pyran-3-ol (CAS no. 215940-92-4), (245 mg), palladium (II) acetate (114 mg), XantPhos (73 mg), toluene (13.4 mL) and TEA (0.88 mL) were combined. The reaction mixture was purged with CO then heated to 80° C. over a weekend. The reaction was cooled to rt and poured onto EtOAc, the remaining solid in the reaction flask was sonicated with a small amount of THF and the slurry added to the EtOAc organic phases. The combined organic phases were washed with water (2×) then brine and the combined aqueous phases extracted with EtOAc (1×). The combined organic extracts were dried (MgSO$_4$), filtered and evaporated under vacuum to give the desired compound (786 mg), which was taken on crude.

LCMS: m/z 274.5 [M+H-BOC]$^+$.

Intermediate 75: Synthesis of tert-Butyl 7-chloro-3-((trans-3-hydroxytetrahydro-2H-pyran-4-yl)carbamoyl)-1H-pyrrolo[3,2-b]pyridine-1-carboxylate

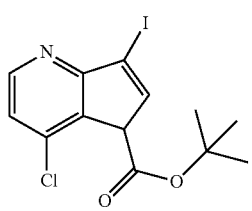

Intermediate 15

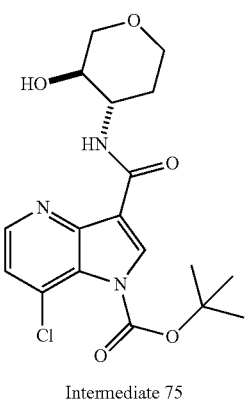

Intermediate 75 tert-Butyl 7-chloro-3-iodo-1H-pyrrolo[3,2-b]pyridine-1-carboxylate (Intermediate 15), (820 mg), trans-4-aminotetrahydro-2H-pyran-3-ol (381 mg), palladium (II) acetate (14.6 mg), XantPhos (75 mg), toluene (19.6 mL) and TEA (0.91 mL) were combined. The reaction mixture was purged with CO then heated to 80° C. over a weekend. The reaction was cooled to rt and poured onto EtOAc, the remaining solid in the reaction flask was sonicated with a small amount of THF and the slurry added to the EtOAc organic phases. The combined organic phases were washed with water (2×) then brine and the combined aqueous phases extracted with EtOAc (1×). The combined organic extracts were dried (MgSO$_4$), filtered and evaporated under vacuum to give the desired compound (540 mg), which was taken on crude.

LCMS: m/z 294.4 [M+H-BOC]$^+$.

Intermediate 76: Synthesis of tert-Butyl 3-((trans-3-hydroxytetrahydro-2H-pyran-4-yl)carbamoyl)-1H-pyrrolo[3,2-b]pyridine-1-carboxylate

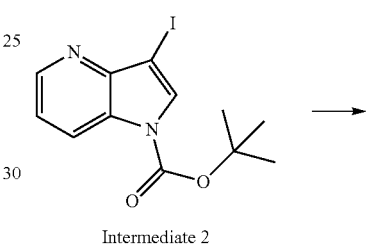

Intermediate 2

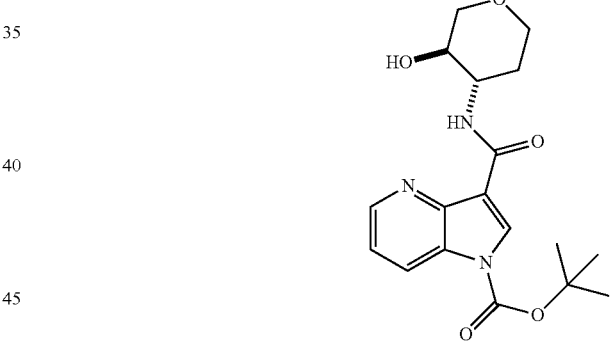

Intermediate 76

A mixture of tert-butyl 3-iodo-1H-pyrrolo[3,2-b]pyridine-1-carboxylate (Intermediate 2), (5.00 g), trans-4-aminotetrahydro-2H-pyran-3-ol hydrochloride (1.86 g), Pd(OAc)$_2$ (82 mg), XantPhos (420 mg) and TEA (5.06 mL) in toluene (50 mL) was purged with CO then heated to 80° C. overnight. The reaction was cooled to rt and poured onto EtOAc, the remaining solid in the reaction flask was sonicated with a small amount of THF and the slurry added to the EtOAc organic phases. The combined organic phases were washed with water (2×) then brine and the combined aqueous phases extracted with EtOAc (1×). The combined organic extracts were dried (MgSO$_4$), filtered and evaporated under vacuum to give the desired compound (9.36 g), which was taken on crude.

LCMS: m/z 260.5 [M+H-BOC]$^+$.

Intermediate 78: Synthesis of 7-chloro-N-((3R,4S)-3-hydroxytetrahydro-2H-pyran-4-yl)-1H-pyrrolo[3,2-b]pyridine-3-carboxamide

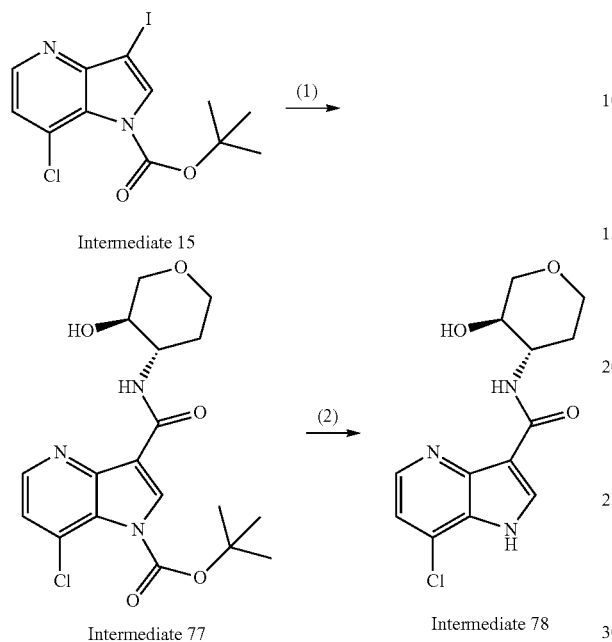

Intermediate 15

Intermediate 77

Intermediate 78

(1) Intermediate 77: tert-Butyl 7-chloro-3-(((3R,4S)-3-hydroxytetrahydro-2H-pyran-4-yl)carbamoyl)-1H-pyrrolo[3,2-b]pyridine-1-carboxylate tert-Butyl 7-chloro-3-iodo-1H-pyrrolo[3,2-b]pyridine-1-carboxylate (Intermediate 15), (200 mg), Pd(OAc)$_2$ (3.6 mg), (3R,4S)-4-aminotetrahydropyran-3-ol hydrochloride (Purchased from NetChem, Inc.), (81 mg), XantPhos (18.3 mg), toluene (6 mL) and TEA (0.22 mL) was added to a three-neck round-bottomed flask fitted with a reflux condenser. This was purged with CO and stirred at 80° C. overnight under a CO balloon. The reaction mixture was allowed to cool to rt and then diluted with EtOAc and filtered through celite and concentrated in vacuo. The residue was purified by column chromatography to afford the desired compound (104 mg).

LCMS: m/z 396.13 [M+H]$^+$.

$^1$H NMR (400 MHz, CDCl$_3$) ppm 1.67 (s, 9H) 1.87-2.10 (m, 2H) 3.60 (td, J=11.3, 2.8 Hz, 1H) 3.70 (s, 1H) 3.85-4.07 (m, 3H) 4.40 (td, J=5.4, 2.9 Hz, 1H) 7.32-7.37 (m, 1H) 8.45 (d, J=5.1 Hz, 1H) 8.50 (s, 1H) 9.42 (d, J=8.0 Hz, 1H)

(2) Intermediate 78: 7-chloro-N-((3R,4S)-3-hydroxytetrahydro-2H-pyran-4-yl)-1H-pyrrolo[3,2-b]pyridine-3-carboxamide To a solution of tert-butyl 7-chloro-3-(((3R,4S)-3-hydroxytetrahydro-2H-pyran-4-yl)carbamoyl)-1H-pyrrolo[3,2-b]pyridine-1-carboxylate (Intermediate 77), (100 mg) in MeOH (2 mL) was added HCl (4M solution in 1,4-dioxane), (10 mL) at rt and stirred for 2 d. The reaction mixture was concentrated in vacuo to afford P1 as a colorless solid without purification (74 mg).

LCMS: m/z 296.08 [M+H]$^+$.

$^1$H NMR (400 MHz, DMSO-d6) ppm 1.58 (dd, J=12.9, 3.71 Hz, 1H) 1.83-2.02 (m, 1H) 3.34-3.57 (m, 2H) 3.62-3.85 (m, 3H) 4.06-4.18 (m, 1H) 7.52-7.67 (m, 1H) 8.46 (d, J=5.5 Hz, 1H) 8.51-8.68 (m, 1H) 8.77 (d, J=7.8 Hz, 1H) 13.11 (br. s., 1H)

Intermediate 80: Synthesis of 7-chloro-N-((3S,4R)-3-hydroxytetrahydro-2H-pyran-4-yl)-1H-pyrrolo[3,2-b]pyridine-3-carboxamide

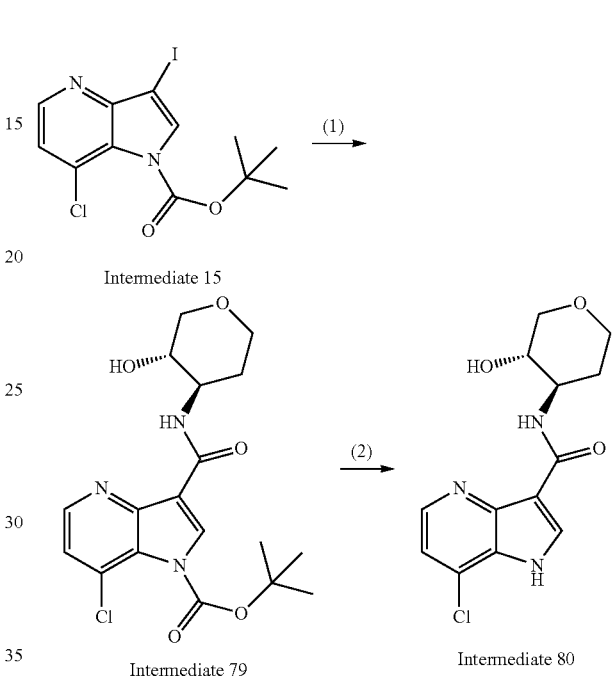

Intermediate 15

Intermediate 79

Intermediate 80

(1) Intermediate 79: tert-Butyl 7-chloro-3-(((3S,4R)-3-hydroxytetrahydro-2H-pyran-4-yl)carbamoyl)-1H-pyrrolo[3,2-b]pyridine-1-carboxylate tert-Butyl 7-chloro-3-iodo-1H-pyrrolo[3,2-b]pyridine-1-carboxylate (Intermediate 15), (200 mg), Pd(OAc)$_2$ (3.6 mg), (3S,4R)-4-aminotetrahydropyran-3-ol hydrochloride (Purchased from NetChem, Inc.), (81 mg), XantPhos (18.3 mg), toluene (6 mL) and TEA (0.22 mL) was added to a three-neck round-bottomed flask fitted with a reflux condenser. This was purged with CO and stirred at 80° C. overnight under a CO balloon. The reaction mixture was allowed to cool to rt and then diluted with EtOAc and filtered through celite and concentrated in vacuo. The residue was purified by column chromatography to afford the desired compound (113 mg).

LCMS: m/z 396.13 [M+H]P.

$^1$H NMR (400 MHz, CDCl$_3$) ppm 1.67 (s, 9H) 1.89-2.09 (m, 2H) 3.60 (td, J=11.3, 2.9 Hz, 1H) 3.68 (d, J=10.7 Hz, 1H) 3.89-4.05 (m, 3H) 4.39 (dddd, J=10.7, 8.0, 5.0, 2.8 Hz, 1H) 7.34 (d, J=5.1 Hz, 1H) 8.45 (d, J=5.3 Hz, 1H) 8.50 (s, 1H) 9.42 (d, J=8.0 Hz, 1H)

(2) Intermediate 80: 7-chloro-N-((3S,4R)-3-hydroxytetrahydro-2H-pyran-4-yl)-1H-pyrrolo[3,2-b]pyridine-3-carboxamide To a solution of tert-butyl 7-chloro-3-(((3S,4R)-3-hydroxytetrahydro-2H-pyran-4-yl)carbamoyl)-1H-pyrrolo[3, 2-b]pyridine-1-carboxylate (Intermediate 79), (100 mg) in MeOH (2 mL) was added HCl (4M solution in 1,4-dioxane), (10 mL) at rt and stirred for 2 d. The reaction mixture was concentrated in vacuo to afford P1 as a colorless solid without purification (74 mg).

LCMS: m/z 296.08 [M+H]$^+$.

$^1$H NMR (400 MHz, DMSO-d6) ppm 1.58 (d, J=11.3 Hz, 1H) 1.81-2.03 (m, 1H) 3.33-3.57 (m, 2H) 3.60-3.89 (m, 3H) 4.12 (br. s., 1H) 7.57 (br. s., 1H) 8.45 (d, J=3.5 Hz, 1H) 8.45-8.67 (m, 1H) 8.67-8.87 (m, 1H) 13.07 (br. s., 1H)

Compound Examples 1-105

Example 1: N-((1S,2S)-2-hydroxycyclohexyl)-1-(4-methylbenzyl)-1H-pyrrolo[3,2-b]pyridine-3-carboxamide To a mixture of N-((1S,2S)-2-hydroxycyclohexyl)-1H-pyrrolo[3,2-b]pyridine-3-carboxamide (Intermediate 4), (100 mg), 1-(chloromethyl)-4-methylbenzene (60 mg) and cesium carbonate (289 mg) was added DMF (4 mL) and left to stir at rt for 90 min. The crude product was purified by prep. LC-MS to give the desired compound (88 mg).

LCMS: m/z 364.65 [M+H]$^+$.

$^1$H NMR (400 MHz, CDCl$_3$) ppm 1.20-1.88 (m, 6H) 2.10-2.21 (m, 2H) 2.34 (s, 3H) 3.57 (td, J=9.9, 4.5 Hz, 1H) 3.80-4.02 (m, 1H) 4.54 (br. s., 1H) 5.30 (s, 2H) 6.99-7.10 (m, 2H) 7.10-7.22 (m, 3H) 7.50-7.72 (m, 1H) 8.09 (s, 1H) 8.39-8.59 (m, 1H) 9.05 (d, J=6.1 Hz, 1H)

Example 2: 1-(3,5-Difluorobenzyl)-N-((1S,2S)-2-hydroxycyclohexyl)-1H-pyrrolo[3,2-b]pyridine-3-carboxamide To a mixture of N-((1S,2S)-2-hydroxycyclohexyl)-1H-pyrrolo[3,2-b]pyridine-3-carboxamide (Intermediate 4), (80 mg), 1-(bromomethyl)-3,5-difluorobenzene (77 mg) and cesium carbonate (231 mg) was added DMF (3 mL) and left to stir at rt over the weekend. The crude product was diluted with MeOH and purified using an SCX-2 cartridge (washed sequentially with MeOH, H$_2$O, MeOH and product eluted using 2 M methanolic ammonia). The solution was evaporated under vacuum to give a solid which was dissolved in DCM and purified using column chromatography (normal phase, 25 g, Biotage SNAP cartridge KP-Sil, 25 mL/min, gradient 0-100% EtOAc in n-hexane) to give the desired compound (70 mg)

LCMS: m/z 386.59 [M+H]$^+$.

$^1$H NMR (400 MHz, CDCl$_3$) ppm 1.15-1.67 (m, 4H) 1.72-1.91 (m, 2H) 2.07-2.23 (m, 2H) 3.59 (td, J=9.9, 4.5 Hz, 1H) 3.92 (dddd, J=11.5, 9.4, 7.0, 4.4 Hz, 1H) 5.34 (s, 2H) 6.57-6.69 (m, 2H) 6.77 (tt, J=8.8, 2.3 Hz, 1H) 7.21 (dd, J=8.3, 4.8 Hz, 1H) 7.50-7.69 (m, 1H) 8.13 (s, 1H) 8.54 (dd, J=4.8, 1.2 Hz, 1H) 9.04 (d, J=6.6 Hz, 1H)

Example 3: 1-(2,5-Difluorobenzyl)-N-((1S,2S)-2-hydroxycyclohexyl)-1H-pyrrolo[3,2-b]pyridine-3-carboxamide To a mixture of N-((1S,2S)-2-hydroxycyclohexyl)-1H-pyrrolo[3,2-b]pyridine-3-carboxamide (Intermediate 4), (80 mg), 2-(bromomethyl)-1,4-difluorobenzene (77 mg) and cesium carbonate (231 mg) was added DMF (3 mL) and left to stir at rt over the weekend. The crude product was purified by prep. LC-MS to give the desired compound (68 mg).

LCMS: m/z 386.59 [M+H]$^+$.

$^1$H NMR (400 MHz, CDCl$_3$) ppm 1.10-1.64 (m, 4H) 1.67-1.90 (m, 2H) 2.14 (d, J=11.6 Hz, 2H) 3.57 (td, J=9.8, 4.5 Hz, 1H) 3.81-4.00 (m, 1H) 5.36 (s, 2H) 6.57-6.77 (m, 1H) 6.88-7.05 (m, 1H) 7.05-7.14 (m, 1H) 7.22 (dd, J=8.3, 4.7 Hz, 1H) 7.69 (d, J=8.3 Hz, 1H) 8.11 (s, 1H) 8.53 (d, J=4.4 Hz, 1H) 9.04 (d, J=6.2 Hz, 1H)

Example 4: 1-(3-Fluorobenzyl)-N-((1S,2S)-2-hydroxycyclohexyl)-1H-pyrrolo[3,2-b]pyridine-3-carboxamide To a mixture of N-((1S,2S)-2-hydroxycyclohexyl)-1H-pyrrolo[3,2-b]pyridine-3-carboxamide (Intermediate 4), (80 mg), 1-(bromomethyl)-3-fluorobenzene (70 mg) and cesium carbonate (231 mg) was added DMF (3.2 mL) and left to stir at rt for 90 min. The crude product was diluted with MeOH and purified using a SCX-2 cartridge (washed sequentially with MeOH, H$_2$O, MeOH and product eluted using 2 M methanolic ammonia). The solution was evaporated under vacuum to give a solid which was further purified by prep. LC-MS (1×3 mL injection) to give the desired compound (62 mg).

LCMS: m/z 368.60 [M+H]$^+$.

$^1$H NMR (400 MHz, CDCl$_3$) ppm 1.04-1.72 (m, 4H) 1.79 (m, 2H) 2.14 (d, J=9.8 Hz, 2H) 3.58 (td, J=9.9, 4.3 Hz, 1H) 3.81-4.02 (m, 1H) 4.12-4.79 (br. s., 1H) 5.35 (s, 2H) 6.84 (d, J=9.1 Hz, 1H) 6.93 (d, J=7.6 Hz, 1H) 6.97-7.10 (m, 1H) 7.19 (dd, J=8.2, 4.8 Hz, 1H) 7.28-7.41 (m, 1H) 7.60 (d, J=8.2 Hz, 1H) 8.12 (s, 1H) 8.52 (d, J=4.7 Hz, 1H) 9.05 (d, J=6.1 Hz, 1H)

Example 5: 1-(4-Fluorobenzyl)-N-((1S,2S)-2-hydroxycyclohexyl)-1H-pyrrolo[3,2-b]pyridine-3-carboxamide To a mixture of N-((1S,2S)-2-hydroxycyclohexyl)-1H-pyrrolo[3,2-b]pyridine-3-carboxamide (Intermediate 4), (3 g) and cesium carbonate (8.67 g) in DMF (82 mL) stirred at rt under nitrogen was added 1-(bromomethyl)-4-fluorobenzene (2.406 g) in DMF (5 mL) and the reaction mixture stirred for 6.5 h then left to stand overnight without stirring. The reaction was then diluted with EtOAc, washed with water (3×), brine, dried (MgSO$_4$), filtered and evaporated under vacuum. The residue was purified by column chromatography (normal phase, 100 g, Biotage SNAP cartridge KP-Sil, 50 mL per min, gradient 0% to 100% EtOAc in n-hexane, followed by 0-10% MeOH in EtOAc). The eluted products were combined and purified by column chromatography (normal phase, 110 g, Biotage SNAP cartridge KP-NH, 50 mL per min, gradient 0% to 100% EtOAc in n-hexane) to give the title compound (2.80 g).

LCMS: m/z 368.59 [M+H]$^+$.

$^1$H NMR (600 MHz, DMSO-d$_6$) ppm 1.21-1.39 (m, 4H) 1.59-1.70 (m, 2H) 1.89 (d, J=10.0 Hz, 1H) 2.00-2.08 (m, 1H) 3.42 (tt, J=8.7, 4.4 Hz, 1H) 3.69-3.78 (m, 1H) 4.78 (d, J=5.0 Hz, 1H) 5.52 (s, 2H) 7.14-7.19 (m, 2H) 7.27 (dd, J=8.2, 4.7 Hz, 1H) 7.38 (dd, J=8.5, 5.6 Hz, 2H) 8.08 (dd, J=8.4, 1.0 Hz, 1H) 8.40 (s, 1H) 8.49 (dd, J=4.7, 0.9 Hz, 1H) 8.75 (d, J=7.6 Hz, 1H).

Example 6: 1-(4-Fluoro-3-methylbenzyl)-N-((1S,2S)-2-hydroxycyclohexyl)-1H-pyrrolo[3,2-b]pyridine-3-carboxamide To a mixture of N-((1S,2S)-2-hydroxycyclohexyl)-1H-pyrrolo[3,2-b]pyridine-3-carboxamide (Intermediate 4), (100 mg), 4-(bromomethyl)-1-fluoro-2-methylbenzene (86 mg) and cesium carbonate (289 mg) was added DMF (4 mL) and left to stir at rt for 90 min. The crude product was diluted with MeOH and purified using an SCX-2 cartridge (washed sequentially with MeOH, H₂O, MeOH and product eluted using 2 M methanolic ammonia). The solution was evaporated under vacuum to give the desired compound (150 mg).

LCMS: m/z 382.64 [M+H]⁺.

¹H NMR (400 MHz, CDCl₃) ppm 1.12-1.90 (m, 6H) 2.07-2.19 (m, 2H) 2.23 (d, J=1.5 Hz, 3H) 3.57 (td, J=9.9, 4.5 Hz, 1H) 3.78-4.03 (m, 1H) 4.49 (br. s., 1H) 5.27 (s, 2H) 6.86-7.07 (m, 3H) 7.18 (dd, J=8.3, 4.8 Hz, 1H) 7.52-7.73 (m, 1H) 8.08 (s, 1H) 8.50 (dd, J=4.7, 1.0 Hz, 1H) 9.04 (d, J=6.0 Hz, 1H)

Example 7: N-((1S,2S)-2-hydroxycyclohexyl)-1-((2-methylthiazol-4-yl)methyl)-1H-pyrrolo[3,2-b]pyridine-3-carboxamide To a mixture of N-((1S,2S)-2-hydroxycyclohexyl)-1H-pyrrolo[3,2-b]pyridine-3-carboxamide (Intermediate 4), (100 mg), 4-(chloromethyl)-2-methylthiazole (68 mg) and cesium carbonate (289 mg) was added DMF (4 mL) and left to stir at rt for 3 h. The crude product was diluted with MeOH and purified using an SCX-2 cartridge (washing sequentially with MeOH, H₂O, MeOH and product eluted using 2 M methanolic ammonia). The solution was evaporated under vacuum to give a solid which was further purified by prep. LC-MS to give the desired compound (87 mg).

LCMS: m/z 371.59 [M+H]⁺.

¹H NMR (400 MHz, CDCl₃) ppm 1.05-1.94 (m, 6H) 2.11-2.25 (m, 2H) 2.70 (s, 3H) 3.57 (td, J=9.8, 4.5 Hz, 1H) 3.82-4.00 (m, 1H) 4.14-4.88 (br. s., 1H) 5.41 (s, 2H) 6.80 (s, 1H) 7.21 (dd, J=8.3, 4.7 Hz, 1H) 7.77 (d, J=8.2 Hz, 1H) 8.13 (s, 1H) 8.51 (d, J=4.7 Hz, 1H) 9.05 (d, J=6.1 Hz, 1H)

Example 8: 1-(2,3-Difluorobenzyl)-N-((1S,2S)-2-hydroxycyclohexyl)-1H-pyrrolo[3,2-b]pyridine-3-carboxamide To a mixture of N-((1S,2S)-2-hydroxycyclohexyl)-1H-pyrrolo[3,2-b]pyridine-3-carboxamide (Intermediate 4), (100 mg), 1-(bromomethyl)-2,3-difluorobenzene (96 mg) and cesium carbonate (289 mg) was added DMF (4 mL) and left to stir at rt for 90 min. The crude product was diluted with MeOH and purified using an SCX-2 cartridge (washed sequentially with MeOH, H₂O, MeOH and product eluted using 2 M methanolic ammonia). The solution was evaporated under vacuum to give the desired compound (130 mg).

LCMS: m/z 386.58 [M+H]⁺.

¹H NMR (400 MHz, CDCl₃) ppm 1.19-2.18 (m, 8H) 3.57 (td, J=10.0, 4.3 Hz, 1H) 3.74-4.01 (m, 1H) 4.03-4.91 (br. s., 1H) 5.42 (s, 2H) 6.79 (t, J=6.7 Hz, 1H) 6.93-7.09 (m, 1H) 7.10-7.20 (m, 1H) 7.23 (dd, J=8.3, 4.8 Hz, 1H) 7.72 (d, J=8.3 Hz, 1H) 8.14 (s, 1H) 8.53 (d, J=4.7 Hz, 1H) 9.04 (d, J=6.4 Hz, 1H)

Example 9: N-((1S,2S)-2-Hydroxycyclohexyl)-1-(4-(trifluoromethoxy)benzyl)-1H-pyrrolo[3,2-b]pyridine-3-carboxamide To a mixture of N-((1S,2S)-2-hydroxycyclohexyl)-1H-pyrrolo[3,2-b]pyridine-3-carboxamide (Intermediate 4), (120 mg), 1-(bromomethyl)-4-(trifluoromethoxy)benzene (130 mg) and cesium carbonate (347 mg) was added DMF (4.8 mL) and left to stir at rt overnight. The crude product was purified by prep. LC-MS to give the desired compound (126 mg).

LCMS: m/z 434.59 [M+H]⁺.

¹H NMR (400 MHz, CDCl₃) ppm 0.88-1.97 (m, 6H) 2.14 (d, J=10.1 Hz, 2H) 3.58 (td, J=9.8, 4.4 Hz, 1H) 3.77-4.01 (m, 1H) 5.37 (s, 2H) 6.92-7.25 (m, 5H) 7.62 (d, J=8.2 Hz, 1H) 8.12 (s, 1H) 8.53 (d, J=4.8 Hz, 1H) 9.04 (d, J=6.2 Hz, 1H)

¹⁹F NMR (377 MHz, CDCl₃) ppm −57.93 (s, 3F))

Example 10: 1-(4-Fluorobenzyl)-N-((1S,2S)-2-hydroxycyclohexyl)-7-methyl-1H-pyrrolo[3,2-b]pyridine-3-carboxamide To a solution of N-((1S,2S)-2-hydroxycyclohexyl)-7-methyl-1H-pyrrolo[3,2-b]pyridine-3-carboxamide (Intermediate 13), (700 mg) in DMF (25 mL) stirred under nitrogen at rt was added Cs₂CO₃ (1919 mg) followed by 1-(bromomethyl)-4-fluorobenzene (0.319 mL) the reaction was stirred at rt under nitrogen overnight, at which point LC-MS indicated completion. The reaction was filtered and the filtrate was reduced in vacuo, then purified by column chromatography (normal phase, 10 g, Biotage SNAP cartridge KP-Sil, 12 mL per min, gradient 20% to 100% EtOAc in n-hexane, then 0-15% MeOH in EtOAc) to give the desired product (0.370 g).

LCMS: m/z 382.60 [M+H]⁺.

¹H NMR (400 MHz, CDCl₃) ppm 0.96-1.97 (m, 6H) 1.98-2.17 (m, 2H) 2.51 (s, 3H) 3.57 (td, J=9.9, 4.5 Hz, 1H) 3.80-4.08 (m, 1H) 4.47 (br. s., 1H) 5.53 (s, 2H) 6.84-6.96 (m, 3H) 6.96-7.09 (m, 2H) 8.02 (s, 1H) 8.34 (d, J=4.8 Hz, 1H) 9.26 (d, J=6.1 Hz, 1H)

Example 11: 1-(2,3-Difluorobenzyl)-N-((1S,2S)-2-hydroxycyclohexyl)-7-methyl-1H-pyrrolo[3,2-b]pyridine-3-carboxamide To a solution of N-((1S,2S)-2-hydroxycyclohexyl)-7-methyl-1H-pyrrolo[3,2-b]pyridine-3-carboxamide (Intermediate 13), (150 mg) in DMF (5.5 mL) stirred under nitrogen at rt was added Cs₂CO₃ (411 mg) followed by 1-(bromomethyl)-2,3-difluorobenzene (0.070 mL). The reaction was stirred at rt under nitrogen overnight, at which point LC-MS indicated completion. The reaction was filtered and the filtrate was reduced in vacuo, then purified by column chromatography (normal phase, 10 g, Biotage SNAP cartridge KP-Sil, 12 mL per min, gradient 50% to 100% EtOAc in n-hexane, then 0-15% MeOH in EtOAc) to give the desired product (102 mg).

LCMS: m/z 400.61 [M+H]⁺.

¹H NMR (400 MHz, CDCl₃) ppm 1.19-1.61 (m, 4H) 1.70-1.84 (m, 2H) 2.07-2.17 (m, 2H) 2.50 (s, 3H) 3.56 (td, J=9.8, 4.5 Hz, 1H) 3.79-3.94 (m, 1H) 4.56 (br. s., 1H) 5.58 (s, 2H) 6.28 (t, J=6.9 Hz, 1H) 6.86-6.99 (m, 2H) 7.11 (q, J=8.4 Hz, 1H) 7.99 (s, 1H) 8.33 (d, J=4.7 Hz, 1H) 9.24 (d, J=6.4 Hz, 1H).

Example 12: N-((1S,2S)-2-Hydroxycyclohexyl)-1-(4-methoxybenzyl)-7-methyl-1H-pyrrolo[3,2-b]pyridine-3-carboxamide To a solution of N-((1S,2S)-2-hydroxycyclohexyl)-7-methyl-1H-pyrrolo[3,2-b]pyridine-3-carboxamide (Intermediate 13), (150 mg) in DMF (5 mL) stirred under nitrogen at rt was added Cs₂CO₃ (411 mg) followed by 1-(bromomethyl)-4-methoxybenzene (110 mg). The reaction was stirred at rt under nitrogen overnight, at which point LC-MS indicated completion. The reaction was filtered and the filtrate was reduced in vacuo, then purified by column chromatography (normal phase, 10 g, Biotage SNAP cartridge KP-Sil, 12 mL per min, gradient 20% to 100% EtOAc in n-hexane, followed by 0-15% MeOH in EtOAc) to yield the desired compound (103 mg).

LCMS: m/z 394.65 [M+H]$^+$.

$^1$H NMR (400 MHz, CDCl$_3$) ppm 1.21-1.62 (m, 4H) 1.77 (br. S., 2H) 2.13 (d, J=12.4, 2 H) 2.53 (s, 3H) 3.56 (td, J=9.8, 4.5 Hz, 1H) 3.76 (s, 3H) 3.82-3.94 (m, 1H) 4.68 (br. s., 1H) 5.46 (s, 2H) 6.77-6.92 (m, 5H) 7.95-8.03 (m, 1H) 8.31 (d, J=4.7 Hz, 1H) 9.27 (d, J=6.4 Hz, 1H)

Example 13: 1-(3-Fluoro-4-methoxybenzyl)-N-((1S,2S)-2-hydroxycyclohexyl)-7-methyl-1H-pyrrolo[3,2-b]pyridine-3-carboxamide To a solution of N-((1S,2S)-2-hydroxycyclohexyl)-7-methyl-1H-pyrrolo[3,2-b]pyridine-3-carboxamide (Intermediate 13), (110 mg) in DMF (3.6 mL) stirred under nitrogen at rt was added Cs$_2$CO$_3$ (302 mg) followed by 4-(bromomethyl)-2-fluoro-1-methoxybenzene (88 mg). The reaction was stirred at rt under nitrogen overnight, at which point LC-MS indicated completion. The reaction was filtered and the filtrate was reduced in vacuo, then purified by column chromatography (normal phase, 10 g, Biotage SNAP cartridge KP-Sil, 12 mL per min, gradient 50% to 100% EtOAc in n-hexane, then 0-15% MeOH in EtOAc) to give the desired product, (102 mg).

LCMS: m/z 412.63 [M+H]$^+$.

$^1$H NMR (400 MHz, CDCl$_3$) ppm 1.22-1.84 (m, 6H) 2.15 (d, J=10.8 Hz, 2H) 2.57 (s, 3H) 3.64 (br. s., 1H) 3.80-3.95 (m, 1H) 3.87 (s, 3H) 5.51 (s, 2H) 6.64 (d, J=8.2 Hz, 1H) 6.73 (d, J=11.7 Hz, 1H) 6.83-7.02 (m, 2H) 8.30-8.46 (m, 1H) 9.27 (d, J=6.4 Hz, 1H)

Example 14: 7-Chloro-1-(4-fluorobenzyl)-N-((1S,2S)-2-hydroxycyclohexyl)-1H-pyrrolo[3,2-b]pyridine-3-carboxamide To a mixture of 7-chloro-N-((1S,2S)-2-hydroxycyclohexyl)-1H-pyrrolo[3,2-b]pyridine-3-carboxamide (Intermediate 17), (140 mg), 1-(bromomethyl)-4-fluorobenzene (108 mg) and cesium carbonate (357 mg) was added DMF (4.9 mL) and left to stir at rt for 1 h 1.0 min. The crude product was purified by prep. LC-MS (1×3 mL injection) to give the desired compound (111 mg).

LCMS: m/z 402.56 [M+H]$^+$.

$^1$H NMR (400 MHz, CDCl$_3$) ppm 1.05-2.60 (m, 8H) 3.56 (td, J=9.9, 4.3 Hz, 1H) 3.76-4.07 (m, 1H) 5.50-5.91 (m, 2H) 6.89-7.13 (m, 4H) 7.19 (d, J=5.0 Hz, 1H) 8.09 (s, 1H) 8.36 (d, J=5.1 Hz, 1H) 9.04 (d, J=6.1 Hz, 1H)

Example 15: 7-Chloro-1-(2,3-difluorobenzyl)-N-((1S,2S)-2-hydroxycyclohexyl)-1H-pyrrolo[3,2-b]pyridine-3-carboxamide To a mixture of 7-chloro-N-((1S,2S)-2-hydroxycyclohexyl)-1H-pyrrolo[3,2-b]pyridine-3-carboxamide (Intermediate 17), (220 mg), 1-(bromomethyl)-2,3-difluorobenzene (171 mg) and cesium carbonate (561 mg) was added DMF (3 mL) and left to stir at rt for 3 h. The crude product was purified by prep. LC-MS then azeotroped with DCM to remove the residual AcOH to give the title compound (121 mg).

LCMS: m/z 420.56 [M+H]$^+$.

$^1$H NMR (400 MHz, CDCl$_3$) ppm 1.09-1.62 (m, 4H) 1.80 (d, J=9.3 Hz, 2H) 2.10-2.22 (m, 2H) 3.56 (td, J=9.9, 4.5 Hz, 1H) 3.76-4.01 (m, 1H) 5.62-5.95 (m, 2H) 6.50 (t, J=6.8 Hz, 1H) 6.92-7.05 (m, 1H) 7.15 (q, J=8.6 Hz, 1H) 7.20 (d, J=5.0 Hz, 1H) 8.10 (s, 1H) 8.38 (d, J=5.0 Hz, 1H) 9.03 (d, J=6.0 Hz, 1H)

Example 16: 7-Chloro-N-((1S,2S)-2-hydroxycyclohexyl)-1-((6-methylpyridin-2-yl)methyl)-1H-pyrrolo[3,2-b]pyridine-3-carboxamide To a mixture of 7-chloro-N-((1S,2S)-2-hydroxycyclohexyl)-1H-pyrrolo[3,2-b]pyridine-3-carboxamide (Intermediate 17), (200 mg), 2-(bromomethyl)-6-methylpyridine (139 mg) and cesium carbonate (510 mg) was added DMF (3 mL) and left to stir at rt overnight. The crude product was diluted with EtOAc (150 mL) and washed with water (2×40 mL) and brine (40 mL), dried over MgSO$_4$, filtered and evaporated under vacuum to give a solid which was purified by column chromatography (normal phase, 25 g, Biotage SNAP cartridge KP-Sil, 25 mL/min, gradient 20-100% EtOAc in n-hexane) to give the desired compound (143 mg).

LCMS: m/z 399.61 [M+H]$^+$.

$^1$H NMR (400 MHz, CDCl$_3$) ppm 1.10-1.94 (m, 6H) 2.14 (d, J=11.5 Hz, 2H) 2.58 (s, 3H) 3.57 (td, J=9.9, 4.5 Hz, 1H) 3.82-4.01 (m, 1H) 4.30 (br. s., 1H) 5.67-5.94 (m, 2H) 6.49 (d, J=7.7 Hz, 1H) 7.08 (d, J=7.7 Hz, 1H) 7.18 (d, J=5.1 Hz, 1H) 7.49 (t, J=7.8 Hz, 1H) 8.14 (s, 1H) 8.36 (d, J=5.1 Hz, 1H) 9.05 (d, J=6.5 Hz, 1H)

Example 17: 7-Chloro-1-((5-fluoropyridin-2-yl)methyl)-N-((1S,2S)-2-hydroxycyclohexyl)-1H-pyrrolo[3,2-b]pyridine-3-carboxamide To a mixture of 5-fluoro-2-hydroxymethylpyridine (purchased from Ark Pharm Inc.), (250 mg) in anhydrous DCM (8.4 mL) stirred at rt under nitrogen, was added thionyl chloride (0.29 mL). The reaction was stirred at rt overnight, at which point LC-MS indicated presence of the product. The reaction was then concentrated in vacuo and re-dissolved in DCM (10 mL) and concentrated in vacuo again to give 2-(chloromethyl)-5-fluoropyridine hydrochloride (102 mg), which was added to a mixture of 7-chloro-N-((1S,2S)-2-hydroxycyclohexyl)-1H-pyrrolo[3,2-b]pyridine-3-carboxamide (Intermediate 17), (150 mg), and cesium carbonate (383 mg) in DMF (3 mL) and left to stir at rt over the weekend. The crude product was purified by prep. LC-MS to give the desired compound (129 mg).

LCMS: m/z 403.56 [M+H]$^+$.

$^1$H NMR (400 MHz, CDCl$_3$) ppm 1.22-1.62 (m, 4H) 1.80 (d, J=9.5 Hz, 2H) 2.07-2.18 (m, 2H) 3.57 (td, J=9.9, 4.4 Hz, 1H) 3.84-3.99 (m, 1H) 5.69-5.95 (m, 2H) 6.86 (dd, J=8.6, 4.0 Hz, 1H) 7.19 (d, J=5.1 Hz, 1H) 7.34 (td, J=8.3, 2.8 Hz, 1H) 8.19 (br. s., 1H) 8.37 (d, J=5.1 Hz, 1H) 8.43 (d, J=2.7 Hz, 1H) 9.04 (d, J=6.2 Hz, 1H)

$^{19}$F NMR (377 MHz, CDCl$_3$) ppm −127.69 (s, 1F)

Example 18: 1-(4-Fluorobenzyl)-N-(trans-2-(hydroxymethyl)cyclohexyl)-1H-pyrrolo[3,2-b]pyridine-3-carboxamide 1-(4-Fluorobenzyl)-3-iodo-1H-pyrrolo[3,2-b]pyridine (Intermediate 18), (150 mg), palladium (II) acetate (2.9 mg), XantPhos (14.8 mg), (trans-2-aminocyclohexyl)methanol (83 mg), toluene (2.7 mL) and TEA (0.18 mL) were placed in a microwave tube fitted with a CO balloon. The microwave tube was purged with CO then heated to 80° C.

overnight at which point LC-MS indicated completion. The reaction was then filtered through celite, washing with EtOAc. The residue at the bottom of the flask was sonicated in EtOAc and filtered through the same celite pad. The filtrate was reduced in vacuo. The residue was dissolved in MeOH (5 mL) and loaded onto an SCX-2 cartridge, washing with 5 CV MeOH, then eluting with 5 CV 2M NH3/MeOH. The basic fractions were combined and reduced in vacuo. The residue was purified by column chromatography (normal phase, 25 g, Biotage SNAP cartridge KP-Sil, 25 mL per min, gradient 0% to 100% EtOAc in hexane followed by 0% to 10% MeOH in EtOAc) to yield the desired compound as a racemic mixture of trans isomers (46 mg).

LCMS: m/z 382.58 $[M+H]^+$.

$^1$H NMR (400 MHz, CDCl$_3$) ppm 1.17-1.49 (m, 3H) 1.51-1.90 (m, 5H) 2.01-2.16 (m, 1H) 3.35 (d, J=7.2 Hz, 1H) 3.81 (dd, J=11.9, 1.8 Hz, 1H) 3.92-4.05 (m, 1H) 4.41 (br. s., 1H) 5.24-5.36 (m, 2H) 6.97-7.21 (m, 5H) 7.61 (d, J=8.2 Hz, 1H) 8.07 (s, 1H) 8.45-8.54 (m, 1H) 8.88 (d, J=8.4 Hz, 1H)

Example 19: 1-(4-Fluorobenzyl)-N-(trans-3-methyltetrahydro-2H-pyran-4-yl)-1H-pyrrolo[3,2-b]pyridine-3-carboxamide 1-(4-Fluorobenzyl)-3-iodo-1H-pyrrolo[3,2-b]pyridine (Intermediate 18), (50 mg), palladium (II) acetate (1.0 mg), XantPhos (4.9 mg), trans-3-methyltetrahydro-2H-pyran-4-amine hydrochloride (WO 2010/063634 A1), (25.8 mg), toluene (0.9 mL) and TEA (0.06 mL) were placed in a microwave tube fitted with a CO balloon. The microwave tube was purged with CO then heated to 80° C. overnight at which point LC-MS indicated completion. The reaction was then filtered through celite, washing with EtOAc. The residue at the bottom of the flask was sonicated in EtOAc and filtered through the same celite pad. The filtrate was reduced in vacuo. The residue was dissolved in MeOH (5 mL) and loaded onto an SCX-2 cartridge, washing with 5 CV MeOH, then eluting with 5 CV 2M NH3/MeOH. The basic fractions were combined and reduced in vacuo. The residue was purified by column chromatography (normal phase, 25 g, Biotage SNAP cartridge KP-Sil, 25 mL per min, gradient 0% to 100% EtOAc in hexane followed by 0% to 10% MeOH in EtOAc) to yield the desired compound as a racemic mixture of trans isomers (9 mg).

LCMS: m/z 368.55 $[M+H]^+$.

$^1$H NMR (400 MHz, CDCl$_3$) ppm 0.97 (d, J=6.6 Hz, 3H) 1.66-1.95 (m, 2H) 2.01-2.14 (m, 1H) 3.20 (t, J=11.1 Hz, 1H) 3.58 (td, J=11.9, 2.1 Hz, 1H) 3.90-4.10 (m, 3H) 5.32 (s, 2H) 6.98-7.07 (m, 2H) 7.09-7.21 (m, 3H) 7.60 (dd, J=8.3, 1.0 Hz, 1H) 8.09 (s, 1H) 8.52 (dd, J=4.7, 1.1 Hz, 1H) 8.88 (d, J=8.4 Hz, 1H)

Example 20: 1-(4-Fluorobenzyl)-N-(trans-2-methylcyclohexyl)-1H-pyrrolo[3,2-b]pyridine-3-carboxamide 1-(4-Fluorobenzyl)-3-iodo-1H-pyrrolo[3,2-b]pyridine (Intermediate 18), (150 mg), palladium (II) acetate (2.9 mg), XantPhos (14.8 mg), trans-2-methylcyclohexanamine, (purchased from J&W PharmLab.), (48.2 mg), toluene (2.7 mL) and TEA (0.18 mL) were placed in a microwave tube fitted with a CO balloon. The microwave tube was purged with CO then heated to 80° C. overnight at which point LC-MS indicated completion. The reaction was then filtered through celite, washing with EtOAc. The residue at the bottom of the flask was sonicated in EtOAc and filtered through the same celite pad. The filtrate was reduced in vacuo. The residue was dissolved in MeOH (5 mL) and loaded onto an SCX-2 cartridge, washing with 5 CV MeOH, then eluting with 5 CV 2M NH3/MeOH. The basic fractions were combined and reduced in vacuo. The residue was purified by column chromatography (normal phase, 25 g, Biotage SNAP cartridge KP-Sil, 25 mL per min, gradient 0% to 100% EtOAc in hexane followed by 0% to 10% MeOH in EtOAc) to yield the desired compound as a racemic mixture of trans isomers (52 mg).

LCMS: m/z 366.60 $[M+H]^+$.

$^1$H NMR (400 MHz, CDCl$_3$) ppm 1.03 (d, J=6.5 Hz, 3H) 1.11-1.62 (m, 5H) 1.64-1.86 (m, 3H) 2.07-2.16 (m, 1H) 3.70-3.83 (m, 1H) 5.29 (s, 2H) 6.94-7.17 (m, 5H) 7.57 (d, J=8.2 Hz, 1H) 8.06 (s, 1H) 8.49 (d, J=4.5 Hz, 1H) 8.76 (d, J=8.7 Hz, 1H).

Example 21: 1-(4-Fluorobenzyl)-N-(1-(hydroxymethyl)cyclopentyl)-1H-pyrrolo[3,2-b]pyridine-3-carboxamide (1-Aminocyclopentyl)methanol (49.1 mg), 1-(4-fluorobenzyl)-3-iodo-1H-pyrrolo[3,2-b]pyridine (Intermediate 18), (150 mg), palladium (II) acetate (2.9 mg), XantPhos (14.8 mg) toluene (2.7 mL) and TEA (0.18 mL) were placed in a microwave tube fitted with a CO balloon. The microwave tube was purged with CO then heated to 80° C. overnight at which point LC-MS indicated completion. The reaction was then filtered through celite, washing with EtOAc. The residue at the bottom of the flask was sonicated in EtOAc and filtered through the same celite pad. The filtrate was reduced in vacuo. The residue was dissolved in MeOH (5 mL) and loaded onto an SCX-2 cartridge, washing with 5 CV MeOH, then eluting with 5 CV 2M NH3/MeOH. The basic fractions were combined and reduced in vacuo. The residue was purified by column chromatography (normal phase, 25 g, Biotage SNAP cartridge KP-Sil, 25 mL per min, gradient 0% to 100% EtOAc in hexane followed by 0% to 10% MeOH in EtOAc) to yield the desired compound (5 mg).

LCMS: m/z 368.57 $[M+H]^+$.

$^1$H NMR (400 MHz, CDCl$_3$) ppm 1.66-2.10 (m, 8H) 3.80 (s, 2H) 5.32 (s, 2H) 5.68-5.99 (m, 1H) 6.99-7.22 (m, 5H) 7.61 (d, J=8.3 Hz, 1H) 8.05 (s, 1H) 8.52 (d, J=4.7 Hz, 1H) 9.32 (br. s., 1. H)

Example 22: 1-(2-Fluorobenzyl)-N-((1S,2S)-2-hydroxycyclohexyl)-1H-pyrrolo[3,2-b]pyridine-3-carboxamide A mixture of palladium (II) acetate (3.0 mg) in toluene (2.6 mL) was purged with nitrogen. To this mixture was added XantPhos (8.0 mg) followed by Na$_2$CO$_3$ (238 mg) and (1S,2S)-2-aminocyclohexanol (127 mg) and the reaction was purged with nitrogen. 1-(2-fluorobenzyl)-3-iodo-1H-pyrrolo[3,2-b]pyridine (made by alkylation of Intermediate 1, using a method analogous to that described in Intermediate 18), (260 mg) was then added and the reaction was purged with CO gas for 5 min at rt and then stirred under CO at 85° C. overnight, at which point TLC indicated disappearance of SM. The reaction was cooled to rt, diluted with EtOAc and filtered through celite. The filtrate was diluted with water and extracted 2× with EtOAc. Combined organic layers were dried over Na$_2$SO$_4$, filtered and reduced in vacuo. The residue was purified by column chromatography, eluting with 80-90% EtOAc/Hexane) to give an impure product, which was triturated with 4:1 pentane:Et$_2$O to give the desired compound (75 mg).

LCMS: m/z 368.24 [M+H]$^+$.

$^1$H NMR (400 MHz, DMSO-d$_6$) ppm 1.25-1.49 (m, 4H) 1.59-1.72 (m, 2H) 1.83-1.93 (m, 1H) 1.98-2.08 (m, 1H) 3.38-3.47 (m, 1H) 3.67-3.77 (m, 1H) 4.80 (d, J=5.2 Hz, 1H) 5.61 (s, 2H) 7.12-7.42 (m, 5H) 8.07 (dd, J=8.4, 1.2 Hz, 1H) 8.29 (s, 1H) 8.50 (dd, J=4.8, 1.2 Hz, 1H) 8.75 (d, J=7.6 Hz, 1H)

Example 23: 1-(4-Chlorobenzyl)-N-((1S,2S)-2-hydroxycyclohexyl)-1H-pyrrolo[3,2-b]pyridine-3-carboxamide A mixture of palladium (II) acetate (3.0 mg) in toluene (3 mL) was purged under nitrogen. To this mixture was added XantPhos (8.0 mg), followed by Na$_2$CO$_3$ (240 mg) and (1S,2S)-2-aminocyclohexanol (130 mg). 1-(4-chlorobenzyl)-3-iodo-1H-pyrrolo[3,2-b]pyridine (made by alkylation of Intermediate 1, using a method analogous to that described in Intermediate 18), (280 mg) was then added and the reaction was purged with CO gas and stirred under CO at 85° C. overnight, at which point TLC indicated disappearance of SM. The reaction was cooled to rt, diluted with water and extracted 2× with EtOAc. Combined organic layers were reduced in vacuo and the residue was purified by column chromatography, eluting with 80% EtOAc/Hexane) to give an impure product, which was triturated with pentane, followed by trituration with 4:1 pentane:Et$_2$O to give the desired compound (50 mg).

LCMS: m/z 384.25 [M+H]$^+$.

$^1$H NMR (400 MHz, DMSO-d$_6$) ppm 1.12-1.40 (m, 4H) 1.57-1.72 (m, 2H) 1.82-2.10 (m, 2H) 3.39-3.49 (m, 1H) 3.67-3.79 (m, 1H) 4.80 (d, J=5.2 Hz, 1H) 5.54 (s, 2H) 7.27 (dd, J=8.4, 4.8 Hz, 1H) 7.31 (d, J=8.4 Hz, 2H) 7.40 (dd, J=6.4, 2.0 Hz, 2H) 8.05 (dd, J=8.4, 1.2 Hz, 1H) 8.41 (s, 1H) 8.49 (dd, J=4.4, 1.2 Hz, 1H) 8.74 (d, J=8.0 Hz, 1H).

Example 24: 1-(2,4-Difluorobenzyl)-N-((1S,2S)-2-hydroxycyclohexyl)-1H-pyrrolo[3,2-b]pyridine-3-carboxamide A mixture of palladium (II) acetate (2 mg) in toluene (3 mL) was purged under nitrogen. To this mixture was added XantPhos (7 mg), followed by Na$_2$CO$_3$ (198 mg) and (1S,2S)-2-aminocyclohexanol (107 mg). 1-(2,4-difluorobenzyl)-3-iodo-1H-pyrrolo[3,2-b]pyridine (made by alkylation of Intermediate 1, using a method analogous to that described in Intermediate 18), (0.23 g) was then added and the reaction was purged with CO gas and stirred under CO at 85° C. overnight, at which point TLC indicated disappearance of SM. The reaction was cooled to rt, diluted with water and extracted 2× with EtOAc. Combined organic layers were reduced in vacuo and the residue was purified by column chromatography, eluting with 80% EtOAc/Hexane) to give the desired compound (80 mg).

LCMS: m/z 386.17 [M+H]$^+$.

$^1$H NMR (400 MHz, CDCl$_3$) ppm 1.27-1.85 (m, 6H) 2.08-2.19 (m, 2H) 3.53-3.65 (m, 1H) 3.85-3.97 (m, 1H) 4.51 (br. S., 1H) 5.37 (s, 2H) 6.82-6.97 (m, 2H) 7.07 (dd, J=14.4, 8.4 Hz, 1H) 7.24 (dd, J=8.4, 4.8 Hz, 1H) 7.75 (d, J=8.8 Hz, 1H) 8.17 (br. s., 1H) 8.53 (dd, J=4.8, 1.2 Hz, 1H) 9.05 (d, J=6.4 Hz, 1H)

Example 25: N-((1S,2S)-2-Hydroxycyclohexyl)-1-((6-methylpyridin-3-yl)methyl)-1H-pyrrolo[3,2-b]pyridine-3-carboxamide To a mixture of palladium (II) acetate (4.0 mg) in toluene (3 mL) was added XantPhos (10.0 mg) followed by Na$_2$CO$_3$ (273 mg), (1S,2S)-2-aminocyclohexanol (196 mg) and 3-iodo-1-((6-methylpyridin-3-yl)methyl)-1H-pyrrolo[3,2-b]pyridine (made by alkylation of Intermediate 1, using a method analogous to that described in Intermediate 18), (300 mg) was purged with Argon and then with CO gas for 5 min. The mixture was then stirred under CO at 85° C. overnight, at which point TLC indicated formation of product. The reaction was cooled to rt and reduced in vacuo. The residue was purified by column chromatography, eluting with 57% EtOAc/Hexane) to give an impure product, which was purified by preparative HPLC to give the desired product (50 mg).

LCMS: m/z 365.08 [M+H]$^+$.

$^1$H NMR (400 MHz, DMSO-d$_6$) ppm 1.29 (d, J=8.2 Hz, 4H) 1.62 (d, J=11.3 Hz, 2H) 1.86 (br. s., 1H) 2.01 (d, J=9.8 Hz, 1H) 2.40 (s, 3H) 3.36-3.43 (m, 1H) 3.70 (br. s., 1H) 4.79 (d, J=5.2 Hz, 1H) 5.51 (s, 2H) 7.19 (d, J=7.9 Hz, 1H) 7.27 (dd, J=8.4, 4.7 Hz, 1H) 7.57 (dd, J=7.9, 2.4 Hz, 1H) 8.12 (dd, J=8.6, 1.2 Hz, 1H) 8.42 (s, 1H) 8.48 (d, J=4.7 Hz, 1H) 8.52 (s, 1H) 8.73 (d, J=7.9 Hz, 1H).

Example 26: N-((1S,2S)-2-Hydroxycyclohexyl)-1-((5-methylpyridin-2-yl)methyl)-1H-pyrrolo[3,2-b]pyridine-3-carboxamide To a mixture of Palladium (II) acetate (5.0 mg) in toluene (4 mL) was added XantPhos (12.0 mg) followed by Na$_2$CO$_3$ (337 mg), (1S,2S)-2-aminocyclohexanol (241 mg) and 3-iodo-1-((5-methylpyridin-2-yl)methyl)-1H-pyrrolo[3,2-b]pyridine (made by alkylation of Intermediate 1, using a method analogous to that described in Intermediate 18), (370 mg) was purged with Argon and then with CO gas for 5 min. The mixture was then stirred under CO at 85° C. overnight, at which point TLC indicated formation of product. The reaction was cooled to rt and reduced in vacuo. The residue was purified by column chromatography, eluting with 60% EtOAc/Hexane) to give an impure product, which was purified by preparative HPLC to give the desired product (25 mg).

LCMS: m/z 365.08 [M+H]$^+$.

$^1$H NMR (400 MHz, DMSO-d$_6$) ppm 1.29 (d, J=8.2 Hz, 4H) 1.65 (s, 2H) 1.87 (br. s., 1H) 2.03 (d, J=10.4 Hz, 1H) 2.23 (s, 3H) 3.40 (d, J=4.9 Hz, 1H) 3.72 (d, J=7.9 Hz, 1H) 4.80 (d, J=5.2 Hz, 1H) 5.57 (s, 2H) 7.16 (d, J=7.9 Hz, 1H) 7.24 (dd, J=8.4, 4.7 Hz, 1H) 7.57 (dd, J=7.8, 2.0 Hz, 1H) 8.00 (dd, J=8.4, 1.4 Hz, 1H) 8.33 (s, 2H) 8.47 (dd, J=4.7, 1.4 Hz, 1H) 8.74 (d, J=7.6 Hz, 1H)

Example 27: 1-(4-Fluorobenzyl)-N-(trans-2-hydroxycyclopentyl)-1H-pyrrolo[3,2-b]pyridine-3-carboxamide To a solution of 1-(4-fluorobenzyl)-1H-pyrrolo[3,2-b]pyridine-3-carboxylic acid (Intermediate 20), (110 mg) in DMF (2.1 mL) stirred at rt under nitrogen was added HATU (248 mg) and TEA (0.11 mL). This mixture was left to stir for 15 minutes and then trans-2-aminocyclopentanol hydrochloride (56.0 mg) was introduced. The reaction was left to stir overnight at room temperature, at which point LC-MS indicated completion. The reaction mixture was transferred to a separating flask and EtOAc and water were added. The phases were separated and the aqueous phase was extracted twice more with ethyl acetate. The organic phases were combined, washed with brine and the solvent was removed in vacuo. The residue was purified by column chromatography (normal phase, 25 g, Biotage SNAP cartridge KP-Sil, 25 mL per min, gradient 0% to 100% EtOAc in hexane, followed by 0-15% MeOH/EtOAc) to give the desired product as a racemic mixture of trans isomers (65 mg).

LCMS: m/z 354.57 [M+H]+.

$^1$H NMR (400 MHz, CDCl$_3$) ppm 1.64-1.91 (m, 4H) 1.97-2.15 (m, 1H) 2.17-2.35 (m, 1H) 4.05-4.22 (m, 2H) 5.29 (s, 2H) 6.93-7.22 (m, 5H) 7.59 (d, J=8.3 Hz, 1H) 8.09 (s, 1H) 8.48 (d, J=4.7 Hz, 1H) 9.11 (d, J=3.1 Hz, 1H)

Example 28: 1-(4-Fluorobenzyl)-N-(trans-2-hydroxycycloheptyl)-1H-pyrrolo[3,2-b]pyridine-3-carboxamide To a solution of 1-(4-fluorobenzyl)-1H-pyrrolo[3,2-b]pyridine-3-carboxylic acid (Intermediate 20), (110 mg) in DMF (2.1 mL) stirred at rt under nitrogen was added HATU (248 mg) and TEA (0.11 mL). This mixture was left to stir for 15 minutes and then trans-2-aminocycloheptanol (52.6 mg) was introduced. The reaction was left to stir overnight at room temperature, at which point LC-MS indicated completion. The reaction mixture was transferred to a separating flask and EtOAc and water were added. The phases were separated and the aqueous phase was extracted twice more with EtOAc. The organic phases were combined and washed with brine. Solvent was removed in vacuo. The residue was purified by column chromatography (normal phase, 25 g, Biotage SNAP cartridge KP-Sil, 25 mL per min, gradient 0% to 100% EtOAc in hexane, followed by 0-15% MeOH/EtOAc) to give the desired product as a racemic mixture of trans isomers (77 mg).

LCMS: m/z 382.60 [M+H]+.

$^1$H NMR (400 MHz, CDCl$_3$) ppm 1.41-2.02 (m, 10H) 3.77-3.92 (m, 1H) 4.07 (qd, J=7.4, 3.6 Hz, 1H) 5.22-5.36 (m, 2H) 6.94-7.21 (m, 5H) 7.60 (d, J=8.3 Hz, 1H) 8.06 (s, 1H) 8.50 (d, J=4.7 Hz, 1H) 9.18 (d, J=6.1 Hz, 1H).

Example 29: 1-(4-Fluorobenzyl)-N-(tetrahydro-2H-pyran-4-yl)-1H-pyrrolo[3,2-b]pyridine-3-carboxamide To a solution of 1-(4-fluorobenzyl)-1H-pyrrolo[3,2-b]pyridine-3-carboxylic acid (Intermediate 20), (119 mg) in DMF (2.3 mL) stirred at it under nitrogen was added HATU (268 mg) and TEA (0.12 mL). This mixture was left to stir for 15 minutes and then tetrahydro-2H-pyran-4-amine (40 mg) was introduced. The reaction was left to stir overnight at room temperature, at which point LC-MS indicated completion. The reaction mixture was transferred to a separating flask and EtOAc and water were added. The phases were separated and the aqueous phase was extracted twice more with EtOAc. The organic phases were combined, washed with brine and the solvent was removed in vacuo. The residue was purified by column chromatography (normal phase, 25 g, Biotage SNAP cartridge KP-Sil, 25 mL per min, gradient 0% to 100% EtOAc in hexane, followed by 0-15% MeOH/EtOAc) to give impure product, which was purified a second time by column chromatography (normal phase, 25 g, Biotage SNAP cartridge KP-Sil, 25 mL per min, gradient 0% to 100% EtOAc in hexane, followed by 0-15% MeOH/EtOAc) to give the desired product (5 mg).

LCMS: m/z 354.46 [M+H]+.

$^1$H NMR (400 MHz, CDCl$_3$) ppm 1.67-1.84 (m, 2H) 2.07 (d, J=11.3 Hz, 2H) 3.62 (t, J=10.4 Hz, 2H) 3.98-4.09 (m, 2H) 4.23-4.39 (m, 1H) 5.32 (s, 2H) 6.96-7.09 (m, 2H) 7.09-7.22 (m, 3H) 7.60 (d, J=8.3 Hz, 1H) 8.09 (s, 1H) 8.52 (d, J=4.7 Hz, 1H) 8.98 (d, J=7.3 Hz, 1H).

Example 30: 1-(4-Fluorobenzyl)-N-(piperidin-4-yl)-1H-pyrrolo[3,2-b]pyridine-3-carboxamide To a solution of crude tert-butyl 4-(1-(4-fluorobenzyl)-1H-pyrrolo[3,2-b]pyridine-3-carboxamido)piperidine-1-carboxylate (Intermediate 21), (184 mg) in DCM (5 mL) stirred at rt under nitrogen was added TFA (5 mL) and the reaction was stirred at rt under nitrogen overnight, at which point LC-MS indicated disappearance of SM. The reaction was then reduced in vacuo and taken up into MeOH (1 mL) and loaded onto a 2 g SCX-2 cartridge, washing with 20 ml MeOH, followed by 20 ml 2M NH3/MeOH. The ammonia-containing fraction were collected and reduced in vacuo to yield the desired product (43 mg)

LCMS: m/z 353.58 [M+H]+.

$^1$H NMR (400 MHz, CDCl$_3$) ppm 1.53-1.71 (m, 2H) 2.03-2.16 (m, 2H) 2.43 (br. s., 1H) 2.75-2.89 (m, 2H) 3.12-3.24 (m, 2H) 4.13-4.30 (m, 1H) 5.31 (s, 2H) 6.96-7.06 (m, 2H) 7.08-7.21 (m, 3H) 7.58 (d, J=8.2 Hz, 1H) 8.07 (s, 1H) 8.50 (d, J=4.7 Hz, 1H) 8.97 (d, J=7.7 Hz, 1H)

Example 31: 1-(4-Fluorobenzyl)-N-(1-methylpiperidin-4-yl)-1H-pyrrolo[3,2-b]pyridine-3-carboxamide To a stirred suspension of 1-(4-fluorobenzyl)-N-(piperidin-4-yl)-1H-pyrrolo[3,2-b]pyridine-3-carboxamide (Example 30), (53 mg) in DCM (1.2 mL) at it was added TEA (0.028 mL) and formaldehyde (0.023 mL) followed by sodium tri-acetoxyborohydride (115 mg). The resultant reaction mixture was stirred at rt overnight, at which point LC-MS showed product formation. The reaction mixture was diluted with DCM and was washed with saturated NaHCO$_3$. The aqueous layer was re-extracted with DCM and the combined organic layers were further washed with saturated NaHCO$_3$, dried over Na$_2$SO$_4$, filtered and concentrated to dryness to give the desired product (37 mg)

LCMS: m/z 367.59 [M+H]+.

$^1$H NMR (400 MHz, CDCl$_3$) ppm 1.68-1.84 (m, 2H) 2.01-2.15 (m, 2H) 2.18-2.38 (m, 5H) 2.82 (d, J=11.4 Hz, 2H) 4.04-4.19 (m, 1H) 5.30 (s, 2H) 6.95-7.07 (m, 2H) 7.06-7.19 (m, 3H) 7.58 (d, J=8.3 Hz, 1H) 8.06 (s, 1H) 8.50 (d, J=4.7 Hz, 1H) 8.95 (d, J=7.0 Hz, 1H)

Example 32: 7-Cyano-1-(4-fluorobenzyl)-N-((1S,2S)-2-hydroxycyclohexyl)-1H-pyrrolo[3,2-b]pyridine-3-carboxamide To a mixture of 7-cyano-N-((1S,2S)-2-hydroxycyclohexyl)-1H-pyrrolo[3,2-b]pyridine-3-carboxamide (Intermediate 27), (300 mg), 1-(bromomethyl)-4-fluorobenzene (219 mg) and cesium carbonate (791 mg) was added DMF (5 mL) and left to stir at rt for 1 h. The crude product was purified by prep. LC-MS to give the desired compound (57 mg).

LCMS: m/z 393.59 [M+H]+.

$^1$H NMR (400 MHz, CDCl$_3$) ppm 1.01-1.64 (m, 4H) 1.80 (d, J=11.0 Hz, 2H) 1.93-2.36 (m, 2H) 3.54 (td, J=9.9, 4.3 Hz, 1H) 3.73-4.21 (m, 2H) 5.59-5.77 (m, 2H) 7.06 (t, J=8.5 Hz, 2H) 7.19 (dd, J=8.3, 5.3 Hz, 2H) 7.45 (d, J=4.8 Hz, 1H) 8.20 (s, 1H) 8.61 (d, J=4.9 Hz, 1H) 8.76 (d, J=6.4 Hz, 1H)

Example 33: 7-Cyano-N-((1S,2S)-2-hydroxycyclohexyl)-1-(4-(trifluoromethyl)benzyl)-1H-pyrrolo[3,2-b]pyridine-3-carboxamide To a mixture of 7-cyano-N-((1S,2S)-2-hydroxycyclohexyl)-1H-pyrrolo[3,2-b]pyridine-3-carboxamide (Intermediate 27), (170 mg), cesium carbonate (448 mg), DMF (3 mL) was added 1-(chloromethyl)-4-(trifluoromethyl)benzene (128 mg). After stirring overnight the solid was filtered and the product purified by prep. LCMS to give the pure desired compound (92 mg).

LCMS: m/z 393.64 [M+H]+.

$^1$H NMR (600 MHz, DMSO-d$_6$): ppm 1.21-1.37 (m, 4H) 1.63 (br. s., 1H) 1.69 (br. s., 1H) 1.90 (br. s., 1H) 2.08 (br. s., 1H) 3.37-3.51 (m, 1H) 3.70-3.80 (m, 1H) 4.79 (d, J=5.6 Hz, 1H) 5.92 (s, 2H) 7.29 (d, J=7.9 Hz, 2H) 7.73 (d, J=8.2 Hz, 2H) 7.77 (d, J=5.0 Hz, 1H) 8.60 (d, J=7.6 Hz, 1H) 8.66 (s, 1H) 8.71 (d, J=4.7 Hz, 1H)

Example 34 and 35

N-(trans-4,4-Difluoro-2-hydroxycyclohexyl)-1-(4-fluorobenzyl)-1H-pyrrolo[3,2-b]pyridine-3-carboxamide A mixture of 1-(4-fluorobenzyl)-3-iodo-1H-pyrrolo[3,2-b]pyridine (Intermediate 18), (150 mg), trans-2-amino-5,5-difluorocyclohexanol (Intermediate 33), (97 mg) palladium (II) acetate (2.9 mg), XantPhos (14.8 mg) and TEA (0.119 mL) in toluene (5 mL) was sealed in a reaction vial. This was purged with carbon monoxide and heated to 80° C. overnight. The reaction mixture was filtered through a pad of celite washing with EtOAc. The filtrate was evaporated and purified by chromatography (normal phase, Biotage SNAP cartridge KP-Sil, gradient 20% to 100% EtOAc in n-hexane, 10% Methanol in EtOAc). Chiral chromatographic separation (×4) using preparative IE column (i.d. 20 mm; length 250 mm) and 95% DCM, 5% EtOH (v/v) as eluent, injection volume: 1500 microL, flow rate: 18.0 mL/min, oven temperature: 30 C, afforded the first major eluting peak (retention time: 7.42 min) N-(trans-4,4-difluoro-2-hydroxycyclohexyl)-1-(4-fluorobenzyl)-1H-pyrrolo[3,2-b]pyridine-3-carboxamide enantiomer 1, a single enantiomer of trans relative stereochemistry but unknown absolute configuration, (Example 34) (82 mg).

LCMS: m/z 404.56 [M+H]+.

$^1$H NMR (600 MHz, DMSO-d$_6$) ppm 1.39-1.49 (m, 1H) 1.89-2.15 (m, 4H) 2.27-2.36 (m, 1H) 3.60-3.68 (m, 1H) 3.86-3.92 (m, 1H) 5.22 (d, 0.7=5.6 Hz, 1H) 5.52 (s, 2H) 7.13-7.19 (m, 2H) 7.27 (dd, J=8.2, 4.7 Hz, 1H) 7.34-7.40 (m, 2H) 8.08 (dd, J=8.4, 1.3 Hz, 1H) 8.41 (s, 1H) 8.49 (dd, J=4.7, 1.2 Hz, 1H) 8.74 (d, 0.7=7.3 Hz, 1H) The second minor eluting peak (retention time: 10.86 min) afforded N-(trans-4,4-difluoro-2-hydroxycyclohexyl)-1-(4-fluorobenzyl)-1H-pyrrolo[3,2-b]pyridine-3-carboxamide enantiomer 2, a single enantiomer of trans relative stereochemistry but unknown absolute configuration, (Example 35) (27 mg).

LCMS: m/z 404.19 [M+H]+.

$^1$H NMR (600 MHz, DMSO-d$_6$) ppm 1.39-1.49 (m, 1H) 1.89-2.15 (m, 4H) 2.27-2.36 (m, 1H) 3.60-3.68 (m, 1H) 3.86-3.92 (m, 1H) 5.22 (d, J=5.6 Hz, 1H) 5.52 (s, 2H) 7.13-7.19 (m, 2H) 7.27 (dd, J=8.2, 4.7 Hz, 1H) 7.34-7.40 (m, 2H) 8.08 (dd, J=8.4, 1.3 Hz, 1H) 8.41 (s, 1H) 8.49 (dd, J=4.7, 1.2 Hz, 1H) 8.74 (d, J=7.3 Hz, 1H)

Example 36: N-(cis-4,4-Difluoro-2-hydroxycyclohexyl)-1-(4-fluorobenzyl)-1H-pyrrolo[3,2-b]pyridine-3-carboxamide A mixture of 1-(4-fluorobenzyl)-3-iodo-1H-pyrrolo[3,2-b]pyridine (Intermediate 18), (100 mg), cis-2-amino-5,5-difluorocyclohexanol (Intermediate 37), (64.4 mg), palladium (II) acetate (1.9 mg), XantPhos (9.9 mg), TEA (0.08 mL) and toluene (2 mL) was sealed in a reaction vial. This was then exposed to an atmosphere of carbon monoxide and heated to 80° C. After two hours additional cis-2-amino-5,5-difluorocyclohexanol (42.6 mg), palladium (II) acetate (1.9 mg), XantPhos (9.9 mg) and TEA (0.04 mL) were added. Heating was continued at 80° C. under an atmosphere of carbon monoxide for 18 hours. The reaction mixture was cooled to room temperature, diluted with EtOAc, filtered through a pad of celite and evaporated under vacuum. The residue was purified by column chromatography (reverse phase, gradient 5% to 95% MeCN in water, 0.1% acetic acid buffer in both solvents). The desired fractions were combined, concentrated under vacuum to 50% volume, diluted with saturated sodium bicarbonate solution and extracted into EtOAc (2×). The combined organic extracts were washed with brine (1×), dried (Na$_2$SO$_4$), filtered and evaporated under vacuum to give the desired compound, a single enantiomer of cis relative stereochemistry but unknown absolute configuration (36.8 mg).

LCMS: m/z 404.56 [M+H]+.

$^1$H NMR (400 MHz, DMSO-d$_6$) ppm 1.62-1.75 (m, 1H) 1.91-2.05 (m, 3H) 2.05-2.34 (m, 2H) 3.96 (br. s., 1H) 4.19 (br. s., 1H) 5.24 (d, J=3.9 Hz, 1H) 5.51 (s, 2H) 7.13-7.20 (m, 2H) 7.26 (dd, J=8.3, 4.7 Hz, 1H) 7.37 (dd, J=8.4, 5.5 Hz, 2H) 8.08 (d, J=8.3 Hz, 1H) 8.41 (s, 1H) 8.48 (d, J=5.1 Hz, 1H) 8.98 (d, J=7.8 Hz, 1H)

Example 37: 1-(4-Fluorobenzyl)-N-((1S,2S)-2-hydroxycyclohexyl)-7-methoxy-M-pyrrolo[3,2-b]pyridine-3-carboxamide To a mixture of N-((1S,2S)-2-hydroxycyclohexyl)-7-methoxy-1H-pyrrolo[3,2-b]pyridine-3-carboxamide (Intermediate 45), (140 mg), 1-(bromomethyl)-4-fluorobenzene (91 mg) and cesium carbonate (363 mg) was added DMF (3 mL) and left to stir at rt for 22 h. The crude product was purified by prep. LC-MS to give the desired compound (113 mg).

LCMS: m/z 398.64 [M+H]+.

$^1$H NMR (400 MHz, CDCl$_3$) ppm 0.89-1.92 (m, 6H) 1.97-2.17 (m, 2H) 3.56 (br. s., 1H) 3.77-3.92 (m, 1H) 3.97 (s, 3H) 4.20-4.89 (br. s., 1H) 5.53 (s, 2H) 6.66 (d, J=5.4 Hz, 1H) 6.87-7.06 (m, 2H) 7.07-7.18 (m, 2H) 7.94 (br. s., 1H) 8.35 (d, J=5.4 Hz, 1H) 9.15 (d, J=5.9 Hz, 1H)

$^{19}$F NMR (377 MHz, CDCl$_3$) ppm −114.10 (br. s.)

Example 38: 1-(4-Fluorobenzyl)-N-((1S,2S)-2-hydroxycyclohexyl)-5-methoxy-1H-pyrrolo[3,2-b]pyridine-3-carboxamide A mixture of N-((1S,2S)-2-hydroxycyclohexyl)-5-methoxy-1H-pyrrolo[3,2-b]pyridine-3-carboxamide (Intermediate 49), (130 mg), 1-(bromomethyl)-4-fluorobenzene (93 mg) and cesium carbonate (337 mg) in DMF (3 mL) were stirred at rt for 3 days. The solid was filtered and the product purified by prep. LCMS to give the desired compound (107 mg).

LCMS: m/z 398.59 [M+H]+.

$^1$H NMR (400 MHz, CDCl$_3$) ppm 1.23-1.54 (m, 4H) 1.79 (d, J=9.2 Hz, 2H) 2.16 (br. s., 2H) 3.54 (td, J=9.9, 4.4 Hz, 1H) 3.65 (br. S., 1H) 3.80-3.92 (m, 1H) 4.01 (s, 3H) 5.29 (s, 2H) 6.66 (d, J=8.8 Hz, 1H) 6.96-7.09 (m, 2H) 7.09-7.17 (m, 2H) 7.51 (d, J=8.9 Hz, 1H) 8.10 (s, 1H) 9.00 (br. s., 1H)

Example 39: 5-Chloro-1-(4-fluorobenzyl)-N-((1S,2S)-2-hydroxycyclohexyl)-1H-pyrrolo[3,2-b]pyridine-3-carboxamide A mixture of 5-chloro-N-((1S,2S)-2-hydroxycyclohexyl)-1H-pyrrolo[3,2-b]pyridine-3-carboxamide (Intermediate 53), (120 mg), 1-(bromomethyl)-4-fluorobenzene (85 mg) and cesium carbonate (306 mg) in DMF (3 mL) was stirred at rt overnight. The unwanted solid was filtered and the filtrate purified by prep. LCMS to give the desired product (90 mg).

LCMS: m/z 402.53 [M+H]$^+$.

$^1$H NMR (600 MHz, CDCl$_3$) ppm 1.24-1.62 (m, 4H) 1.77-1.87 (m, 2H) 2.13-2.20 (m, 2H) 3.60 (td, J=10.0, 4.4 Hz, 1H) 3.87-3.98 (m, 1H) 5.33 (s, 2H) 7.04-7.09 (m, 2H) 7.13-7.21 (m, 3H) 7.57 (d, J=8.8 Hz, 1H) 8.25 (br. s., 1H) 8.73 (br. s., 1H)

Example 40: 1-(4-(1H-Pyrazol-1-yl)benzyl-N-((1S, 2S)-2-hydroxycyclohexyl)-5-methyl-1H-pyrrolo[3,2-b]pyridine-3-carboxamide 1-(4-(1H-pyrazol-1-yl)benzyl)-3-bromo-5-methyl-1H-pyrrolo[3,2-b]pyridine (Intermediate 58) (150 mg), palladium (II) acetate (2.8 mg), XantPhos (14.2 mg), trans-(1S, 2S)-2-aminocyclohexanol hydrochloride (93 mg), toluene (2.6 mL) and TEA (0.17 mL) were placed in a microwave tube with a CO balloon. The microwave tube was purged with CO then heated to 80° C. overnight to give a dark reaction mixture with a solid precipitate. Palladium (II) acetate (2.8 mg) and XantPhos (14.2 mg) were added and the reaction was stirred overnight at 80° C. under CO. The solvent was transferred to a round bottom flask then the solid remaining in the microwave tube was dissolved in THF (~1 mL) with sonication and transferred to the round bottom flask and the solvents evaporated. To the resulting solid was added DMF (3 mL) and the suspension sonicated and filtered to remove the small amount of insoluble solid remaining. Preparative LCMS followed by column chromatography (normal phase, 10 g silica, Biotage SNAP cartridge KP-Sil, gradient 0% to 10% EtOAc in n-hexane) gave the desired compound (90 mg).

LCMS: m/z 430.65 [M+H]$^+$.

$^1$H NMR (400 MHz, CDCl$_3$) ppm 1.21-1.62 (m, 4H) 1.79 (d, J=9.5 Hz, 2H) 2.07-2.24 (m, 2H) 2.72 (br. s., 3H) 3.65 (br. s., 1H) 3.79-3.94 (m, 1H) 5.33-5.45 (m, 2H) 6.48 (t, J=2.1 Hz, 1H) 7.07 (d, J=7.8 Hz, 1H) 7.18-7.33 (m, 2H) 7.65-7.77 (m, 2H) 7.90 (d, J=2.1 Hz, 1H) 9.32 (br. s., 1H)

Example 41: 1-(4-(1H-Pyrazol-1-yl)benzyl)-5-cyano-N-((1S,2S)-2-hydroxycyclohexyl)-1H-pyrrolo[3,2-b]pyridine-3-carboxamide 5-Cyano-N-((1S,2S)-2-hydroxycyclohexyl)-1H-pyrrolo[3,2-b]pyridine-3-carboxamide (Intermediate 63), (120 mg), 1-(4-(bromomethyl)phenyl)-1H-pyrazole (110 mg) and cesium carbonate (316 mg) in DMF (3 mL) were stirred at rt for 7.5 h. The solid was filtered and the product purified by preparative LCMS to give the desired compound (62 mg).

LCMS: m/z 441.57 [M+H]$^+$.

$^1$H NMR (400 MHz, CDCl$_3$) ppm 1.22-1.61 (m, 4H) 1.70-1.86 (m, 2H) 2.13 (d, J=11.5 Hz, 2H) 3.55 (td, J=9.7, 4.3 Hz, 1H) 3.82-3.96 (m, 1H) 5.43 (s, 2H) 6.48 (s, 1H) 7.26-7.32 (m, 2H) 7.57 (d, J=8.4 Hz, 1H) 7.66-7.76 (m, 4H) 7.91 (d, J=2.5 Hz, 1H) 8.38 (s, 1H)

Example 42: N-((1S,2S)-2-Hydroxycyclohexyl)-1-(4-(1-methyl-1H-imidazol-2-yl)benzyl)-1H-pyrrolo[3,2-b]pyridine-3-carboxamide In a microwave vial, a mixture of 1-(4-bromobenzyl)-N-((1S,2S)-2-hydroxycyclohexyl)-1H-pyrrolo[3,2-b]pyridine-3-carboxamide (Example 56), (200 mg), 1-methyl-2-(tributylstannyl)-1H-imidazole (Inorg. Chem. 2008, 47, 990-998), (520 mg) in 1,4-dioxane (1.3 mL) was purged with nitrogen. Pd(PPh$_3$)$_4$ (54.0 mg) was added, the mixture was degassed further before the vial was sealed and heated to 140° C. in the microwave for 2 h. Saturated aqueous sodium bicarbonate solution was added and the crude product was extracted with EtOAc (3×). The organic phases were combined, washed with brine, dried (MgSO$_4$), filtered and evaporated under vacuum. The residue was purified by column chromatography (normal phase, 11 g, Biotage SNAP cartridge KP-NH, 14 mL per min, gradient 0% to 100% EtOAc in n-hexane, followed by 0-10% MeOH in EtOAc). The product was further purified by preparatory LC-MS to afford the title compound (94 mg).

LCMS: m/z 430.66, [M+H]$^+$.

$^1$H NMR (400 MHz, CDCl$_3$) ppm 1.20-1.45 (m, 3H), 1.45-1.60 (m, 1H), 1.76 (br. s., 2H), 2.11 (d, J=12.5 Hz, 2H), 3.54 (td, J=9.9, 4.6 Hz, 1H), 3.69 (s, 3H), 3.79-3.96 (m, 1H), 5.34 (s, 2H), 6.94 (s, 1H), 7.08 (d, J=0.7 Hz, 1H), 7.13 (dd, J=8.3, 4.8 Hz, 1H), 7.18 (d, J=8.2 Hz, 2H), 7.57 (d, J=8.2 Hz, 2H), 7.60 (d, J=0.9 Hz, 1H), 8.08 (s, 1H), 8.36-8.56 (m, 1H), 9.03 (d, J=6.6 Hz, 1H)

Example 43: N-((1S,2S)-2-Hydroxycyclohexyl)-1-(4-(1-methyl-1H-imidazol-4-yl)benzyl)-1H-pyrrolo[3,2-b]pyridine-3-carboxamide In a microwave vial, a mixture of 1-(4-bromobenzyl)-N-((1S,2S)-2-hydroxycyclohexyl)-1H-pyrrolo[3,2-b]pyridine-3-carboxamide (Example 56), (300 mg), 1-methyl-4-(tributylstannyl)-1H-imidazole (364 mg) in 1,4-dioxane (1.8 mL) was purged with nitrogen. Pd(PPh$_3$)$_4$ (81.0 mg) was added, the mixture was degassed further before the vial was sealed and heated to 140° C. in the microwave for 1 h. Saturated aqueous sodium bicarbonate solution was added and the crude product was extracted with EtOAc (3×). The organic phases were combined, washed with brine, dried (MgSO$_4$), filtered and evaporated under vacuum. The residue was purified by column chromatography (normal phase, 28 g, Biotage SNAP cartridge KP-NH, 25 mL per min, gradient 0% to 100% EtOAc in n-hexane, followed by 0-20% MeOH in EtOAc). The product was further purified by solid phase extraction (SCX-2 g cartridge), eluting components first with methanol, followed by eluting product with 2 M methanolic ammonia. The product was further purified by preparatory LC-MS to give the title compound (159 mg).

LCMS: m/z 430.64, [M+H]$^+$.

$^1$H NMR (400 MHz, CDCl$_3$) ppm 1.14-1.45 (m, 3H), 1.45-1.60 (m, 1H), 1.75 (d, J=3.1 Hz, 2H), 2.02-2.18 (m, 2H), 3.54 (td, J=9.8, 4.4 Hz, 1H), 3.66 (s, 3H), 3.79-3.96 (m, 1 H), 5.26 (s, 2H), 6.98-7.20 (m, 4H), 7.42 (s, 1H), 7.57 (d, J=8.3 Hz, 1H), 7.67 (d, J=7.9 Hz, 2H), 8.05 (s, 1H), 8.44 (d, J=4.6 Hz, 1H), 9.02 (d, J=6.6 Hz, 1H)

Example 44: 1-(2-Fluoro-4-(6-methylpyridin-2-yl)benzyl)-N-((1S,2S)-2-hydroxycyclohexyl)-1H-pyrrolo[3,2-b]pyridine-3-carboxamide Into a sealable tube, was added sodium carbonate (277 mg), XantPhos (15 mg), Pd(OAc)$_2$ (5.8 mg) and toluene (10 mL). The reaction mixture was purged with nitrogen before adding (1S,2S)-2-aminocyclohexanol (225 mg), and purged again before the addition of 1-(2-fluoro-4-(6-methylpyridin-2-yl)benzyl)-3-iodo-1H-pyrrolo[3,2-b]pyridine (Intermediate 66), (580 mg). The reaction mixture was purged further with nitrogen, then purged with carbon monoxide, before heating the reaction mixture at 70° C. overnight. Once cooled, the reaction mixture was evaporated under vacuum and the crude product was purified by column chromatography, eluting with 2:98 MeOH:CH₂Cl₂ to afford the product which was further purified by preparatory HPLC to yield the title compound (0.06 g).

LCMS: m/z 459.31 [M+H]⁺
¹H NMR (400 MHz, DMSO-d₆) ppm 1.16-1.36 (m, 4H) 1.53-1.72 (m, 2H) 1.87 (br. s., 1H) 2.03 (d, J=11.0 Hz, 1H), 2.51 (s, 3H) 3.42 (br. s., 1H) 3.72 (d, J=8.2 Hz, 1H) 4.80 (d, J=4.3 Hz, 1H) 5.66 (s, 2H) 7.19-7.38 (m, 3H) 7.76 (d, J=4.3 Hz, 2H) 7.82-7.95 (m, 2H) 8.08 (d, J=8.2 Hz, 1H) 8.33 (s, 1H) 8.50 (d, J=4.6 Hz, 1H) 8.75 (d, J=7.6 Hz, 1H)

Example 45: 1-(2-Fluoro-4-(2-methylpyridin-4-yl)benzyl)-N-((1S,2S)-2-hydroxycyclohexyl)-1H-pyrrolo[3,2-b]pyridine-3-carboxamide Into a sealable tube, was added sodium carbonate (220 mg), XantPhos (12 mg), Pd(OAc)₂ (4.8 mg) and toluene (8 mL). The reaction mixture was purged with nitrogen before adding (1S,2S)-2-aminocyclohexanol (186 mg), and purged again before the addition 1-(2-fluoro-4-(2-methylpyridin-4-yl)benzyl)-3-iodo-1H-pyrrolo[3,2-b]pyridine (Intermediate 69), (480 mg). The reaction mixture was purged further with nitrogen, then purged with carbon monoxide, before heating the reaction mixture at 70° C. overnight. Once cooled, the reaction mixture was evaporated under vacuum and the crude product was purified by column chromatography, eluting with 2:98 MeOH:CH₂Cl₂ to afford the title compound (100 mg).

LCMS: m/z 459.31 [M+H]⁺.
¹H NMR (400 MHz, CDCl₃) ppm 1.17-1.70 (m, 4H) 1.79 (br. s., 2H) 2.13 (d, J=11.3 Hz, 2H) 2.63 (s, 3H) 3.45-3.63 (m, 1H) 3.80-4.01 (m, 1H) 4.48 (br. s., 1H) 5.43 (s, 2H) 7.13 (t, J=7.8 Hz, 1 II) 7.19-7.26 (m, 2H) 7.30-7.41 (m, 3H) 7.75 (d, J=8.2 Hz, 1H) 8.14 (s, 1H) 8.54 (dd, J=15.9, 4.9 Hz, 2H) 9.05 (d, J=6.7 Hz, 1H)

Example 46: 1-((4'-Fluoro-[1,1'-biphenyl]-4-yl)methyl)-N-(trans-2-hydroxycyclohexyl)-1H-pyrrolo[3,2-b]pyridine-3-carboxamide A mixture of Pd(OAc)₂ (3 mg) in toluene (3 mL) was purged with nitrogen. To which, was sequentially added XantPhos (8 mg), sodium carbonate (220 mg), trans-2-aminocyclohexanol (120 mg) and 1-((4'-fluoro-[1,1'-biphenyl]-4-yl)methyl)-3-iodo-1H-pyrrolo[3,2-b]pyridine (Intermediate 72), (300 mg). The reaction mixture was purged with carbon monoxide gas for 10 min before heating the reaction at 85° C. overnight. Once cooled, the reaction mixture was evaporated under vacuum and the residue purified by column chromatography (silica), eluting with 20:80 EtOAc/hexanes to afford the title compound as a racemic mixture of trans isomers (50 mg).

LCMS: m/z 444.44 [M+H]⁺
¹H NMR (400 MHz, DMSO-d₆) ppm 1.16-1.41 (m, 4H) 1.61 (br. s., 2H) 1.87 (br. s., 1H) 1.97-2.10 (m, 1H) 3.27-3.47 (m, 1H) 3.72 (d, J=8.5 Hz, 1H) 4.80 (br. S., 1H) 5.57 (s, 2H) 7.21-7.32 (m, 3H) 7.37 (d, J=8.2 Hz, 2H) 7.60 (d, J=8.2 Hz, 2H) 7.65 (dd, J=8.7, 5.6 Hz, 2H) 8.12 (d, J=8.2 Hz, 1H) 8.43 (s, 1H) 8.49 (d, J=4.9 Hz, 1H) 8.74 (d, J=7.6 Hz, 1H)

Example 47: 1-(4-(1H-Pyrazol-1-yl)benzyl)-N-((1S,2S)-2-hydroxycyclohexyl)-1H-pyrrolo[3,2-b]pyridine-3-carboxamide To a solution of N-((1S,2S)-2-hydroxycyclohexyl)-1H-pyrrolo[3,2-b]pyridine-3-carboxamide (Intermediate 4), (145 mg), potassium hydroxide (72.2 mg) and potassium iodide (121 mg) in THF (2 mL) and water (2 mL) was added 1-(4-(bromomethyl)phenyl)-1H-pyrazole (172 mg) and the resulting solution stirred at 75° C. for 1 h 40 min. The reaction mixture was cooled, brine added and extracted with EtOAc (3×), the combined organic extracts dried (MgSO₄), filtered and evaporated under vacuum. Preparative LCMS of the residue gave the desired compound (50 mg).

LCMS: m/z 416.67 [M+H]⁺.
¹H NMR (400 MHz, CDCl₃) ppm 1.22-1.64 (m, 4H) 1.79 (dd, J=6.5, 2.3 Hz, 2H) 2.10-2.20 (m, 2H) 3.59 (td, J=9.9, 4.4 Hz, 1H) 3.84-3.98 (m, 1H) 5.39 (s, 2H) 6.48 (t, J=2.1 Hz, 1H) 7.14-7.30 (m, 3H) 7.59-7.75 (m, 4H) 7.90 (d, J=2.6 Hz, 1H) 8.19 (br. s., 1H) 8.49-8.55 (m, 1H) 9.06 (d, J=6.6 Hz, 1H)

Example 48: 1-(4-(1H-Pyrazol-1-yl)benzyl)-N-((1R,2R)-2-hydroxycyclohexyl)-1H-pyrrolo[3,2-b]pyridine-3-carboxamide To a mixture of N-((1R,2R)-2-hydroxycyclohexyl)-1H-pyrrolo[3,2-b]pyridine-3-carboxamide (Intermediate 73, (133 mg), KOH (66 mg) and KI (111 mg) in THF (1.75 mL) and water (1.75 mL) was added 1-(4-(bromomethyl)phenyl)-1H-pyrazole (158 mg) and the resulting solution stirred at 75° C. overnight. The solution was allowed to cool to rt before adding brine, and then extracted with EtOAc (3×). The organic extracts were combined and then dried (MgSO₄), filtered and evaporated under vacuum. The residue was purified by prep.

LC-MS to give the desired compound (81 mg).
LCMS: m/z 416.63 [M+H]⁺.
¹H NMR (600 MHz, CDCl₃) ppm 1.25-1.51 (m, 3H) 1.57 (qd, J=12.4, 3.7 Hz, 1H) 1.76-1.86 (m, 2H) 2.16 (d, J=12.0 Hz, 2H) 3.60 (td, J=10.0, 4.4 Hz, 1H) 3.88-3.97 (m, 1H) 5.40 (s, 2H) 6.49 (t, J=2.1 Hz, 1H) 7.19 (dd, J=8.2, 4.7 Hz, 1H) 7.26 (d, J=8.5 Hz, 2H) 7.64 (d, J=8.2 Hz, 1H) 7.69 (d, J=8.5 Hz, 2H) 7.74 (d, J=1.5 Hz, 1H) 7.92 (d, J=2.4 Hz, 1H) 8.18 (br. s., 1H) 8.48-8.57 (m, 1H) 9.06 (d, J=6.8 Hz, 1H)

Example 49: 1-(4-(1H-Pyrazol-1-yl)benzyl)-N-(tetrahydro-2H-pyran-3-yl)-1H-pyrrolo[3,2-b]pyridine-3-carboxamide A mixture of 1-(4-(1H-pyrazol-1-yl)benzyl)-3-iodo-1H-pyrrolo[3,2-b]pyridine (made by alkylation of Intermediate 1, using a method analogous to that described in Intermediate 18), (300 mg), palladium (II) acetate (3.0 mg), XantPhos (8 mg), tetrahydro-2H-pyran-3-amine (113 mg), sodium carbonate (230 mg) and toluene (3 mL) were purged with CO then heated to 80° C. overnight. The solvent was evaporated and the residue was purified twice by column chromatography (normal phase, 10 g silica, Biotage SNAP cartridge KP-Sil, gradient 2% methanol in EtOAc then 1% methanol in EtOAc) to give the desired compound as a racemate (50 mg).

LCMS: m/z 402.19 [M+H]⁺.
¹H NMR (400 MHz, DMSO-d6): ppm 1.51-1.81 (m, 3H) 1.96 (br. s., 1H) 3.39 (d, J=7.0 Hz, 1H) 3.51-3.60 (m, 1H) 3.61-3.70 (m, 1H) 3.81 (dd, J=10.8, 2.9 Hz, 1H) 4.02 (dd, J=7.6, 3.7 Hz, 1H) 5.57 (s, 2H) 6.53 (dd, J=2.4, 1.8 Hz, 1H) 7.29 (dd, J=8.2, 4.6 Hz, 1H) 7.45 (d, J=8.9 Hz, 2H) 7.72 (d, J=1.8 Hz, 1H) 7.77-7.84 (m, 2H) 8.07-8.15 (m, 1H) 8.42-8.48 (m, 2H) 8.51 (dd, J=4.7, 1.4 Hz, 1H) 8.86 (d, J=8.2 Hz, 1H)

Example 50: 1-((4-(1H-Pyrazol-1-yl)benzyl)-N-cyclohexyl-1H-pyrrolo[3,2-b]pyridine-3-carboxamide To a mixture of 1-(4-(1H-pyrazol-1-yl)benzyl)-3-iodo-1H-pyrrolo[3,2-b]pyridine (made by alkylation of Intermediate 1, using a method analogous to that described in Intermediate 18), (200 mg), palladium (II) acetate (2.0 mg), XantPhos (5 mg), cyclohexylamine (74 mg), sodium carbonate (160 mg) and toluene (2 mL) were purged with CO then heated to 85° C. overnight. The reaction mixture was diluted with EtOAc, washed with water and the aqueous phase extracted with EtOAc. The combined organic extracts were dried (MgSO$_4$), filtered and evaporated under vacuum and the residue purified by column chromatography (normal phase, gradient 0% to 40% EtOAc in n-hexane) followed by prep. LCMS to give the pure desired compound (55 mg).
LCMS: m/z 400.40 [M+H]$^+$.
$^1$H NMR (400 MHz, DMSO-d$_6$) ppm 1.21-1.47 (m, 5H) 1.56 (br. s., 1H) 1.70 (br. s., 2H) 1.90 (d, J=9.8 Hz, 2H) 3.89 (d, J=8.2 Hz, 1H) 5.56 (s, 2H) 6.49-6.56 (m, 1H) 7.28 (dd, J=8.4, 4.7 Hz, 1H) 7.45 (d, J=8.9 Hz, 2H) 7.72 (d, J=1.5 Hz, 1H) 7.80 (d, J=8.6 Hz, 2H) 8.10 (dd, J=8.2, 1.2 Hz, 1H) 8.44 (s, 1H) 8.45-8.47 (m, 1H) 8.50 (dd, J=4.7, 1.4 Hz, 1H) 8.73 (d, J=8.2 Hz, 1H)

Example 51: 1-(4-(1H-Pyrazol-1-yl)benzyl)-N-(4,4-difluorocyclohexyl)-1H-pyrrolo[3,2-b]pyridine-3-carboxamide A mixture of 1-(4-(1H-pyrazol-1-yl)benzyl)-3-iodo-1H-pyrrolo[3,2-b]pyridine (made by alkylation of Intermediate 1, using a method analogous to that described in Intermediate 18), (200 mg), palladium (II) acetate (3 mg), XantPhos (6 mg), 4,4-difluorocyclohexanamine hydrochloride (129 mg), sodium carbonate (159 mg) and toluene (2 mL) was purged with CO then heated to 85° C. overnight. The reaction mixture was diluted with EtOAc, washed with water and the aqueous phase extracted with EtOAc. The combined organic extracts were dried (MgSO$_4$), filtered and evaporated under vacuum and the residue was purified by column chromatography (normal phase, gradient 0% to 50% EtOAc in n-hexane) followed by prep. LCMS to give the pure desired compound (50 mg).
LCMS: m/z 436.36 [M+H]$^+$.
$^1$H NMR (400 MHz, DMSO-d$_6$) ppm 1.61 (br. s., 2H) 1.96-2.12 (m, 6H) 4.09 (br. s., 1H) 5.57 (s, 2H) 6.50-6.56 (m, 1H) 7.29 (dd, J=8.6 4.6 Hz, 1H) 7.45 (d, J=8.6 Hz, 2H) 7.73 (d, J=1.5 Hz, 1H) 7.80 (d, J=8.6 Hz, 2H) 8.12 (d; J=8.2 Hz, 1H) 8.41-8.55 (m, 3H) 8.80 (d, J=7.6 Hz, 1H)

Example 52: (S)-1-(4-(1H-Pyrazol-1-yl)benzyl)-N-(piperidin-3-yl)-1H-pyrrolo[3,2-b]pyridine-3-carboxamide To a solution of (S)-tert-butyl 3-(1-(4-(1H-pyrazol-1-yl)benzyl)-1H-pyrrolo[3,2-b]pyridine-3-carboxamido)piperidine-1-carboxylate[1] (300 mg) in 1,4-dioxane (6 mL) stirred at 0° C. was added HCl (4M in 1,4-dioxane, 3 mL). The reaction mixture was allowed to warm to rt stirred for 3 hours at which point TLC indicated completion. The reaction mixture was concentrated in vacuo and partitioned between CHCl$_3$ and sat NaHCO$_3$. Layers were separated and the aqueous phase was extracted with CHCl$_3$. Combined organic phases were reduced in vacuo. The residue was purified by flash chromatography, eluting with 2% MeOH/DCM) to give an impure product, which was triturated with diethyl ether, followed by pentane to give the desired product (185 mg).
LCMS: m/z 401.10 [M+H]$^+$.
$^1$H NMR (400 MHz, DMSO-d$_6$) ppm 1.34-1.56 (m, 2H) 1.65 (d, J=6.1 Hz, 1H) 1.86 (br. s., 1H) 2.57 (br. s., 2H) 2.75 (d, J=13.1 Hz, 1H) 3.01 (d, J=11.9 Hz, 1H) 3.76-4.02 (m, 1H) 5.56 (s, 2H) 6.52 (dd, J=2.4, 1.8 Hz, 1H) 7.27 (dd, J=8.2, 4.6 Hz, 1H) 7.44 (d, J=8.9 Hz, 2H) 7.71 (d, J=1.5 Hz, 1H) 7.79 (d, J=8.6 Hz, 2H) 8.09 (dd, J=8.6, 1.2 Hz, 1H) 8.36-8.54 (m, 3H) 8.78 (d, J=7.6 Hz, 1H)

[1](S)-tert-butyl 3-(1-(4-(1H-pyrazol-1-yl)benzyl)-1H-pyrrolo[3,2-b]pyridine-3-carboxamido)piperidine-1-carboxylate was prepared using a method analogous to that used for Example 18, by a palladium-catalysed aminocarbonylation of 1-(4-(1H-pyrazol-1-yl)benzyl)-3-iodo-1H-pyrrolo[3,2-b]pyridine, substituting (trans-2-aminocyclohexyl)methanol with (S)-tert-butyl 3-aminopiperidine-1-carboxylate. 1-(4-(1H-pyrazol-1-yl)benzyl)-3-iodo-1H-pyrrolo[3,2-b]pyridine was prepared using a method analogous to that used for Intermediate 18, alkylating Intermediate 1 with 1-(4-(bromomethyl)phenyl)-1H-pyrazole).

Example 53: (R)-1-(4-(1H-Pyrazol-1-yl)benzyl)-N-(piperidin-3-yl)-1H-pyrrolo[3,2-b]pyridine-3-carboxamide To a solution of (R)-tert-butyl 3-(1-(4-(1H-pyrazol-1-yl)benzyl)-1H-pyrrolo[3,2-b]pyridine-3-carboxamido)piperidine-1-carboxylate[2] (300 mg) in 1,4-dioxane (6 mL) stirred at 0° C. was added HCl (4M in 1,4-dioxane, 3 mL). The reaction mixture was allowed to warm to rt stirred for 3 hours at which point TLC indicated completion. The reaction mixture was concentrated in vacuo and triturated with diethyl ether. The residue was purified by flash chromatography, eluting with 2% MeOH/DCM) to give an impure product, which was triturated with EtOAc, followed by diethyl ether to give the desired product (180 mg).
LCMS: m/z 401.10 [M+H]$^+$.
$^1$H NMR (400 MHz, DMSO-d$_6$) ppm 1.52 (br. s., 2H) 1.70 (br. s., 1H) 1.90 (br. s., 1H) 2.50-2.63 (m, 2H) 2.82 (br. s., 1H) 3.09 (d, J=12.2 Hz, 1H) 3.99 (br. s., 1H) 5.57 (s, 2H) 6.53 (dd, J=2.6, 1.7 Hz, 1H) 7.19-7.33 (m, 1H) 7.45 (m, J=8.9 Hz, 2H) 7.73 (d, J=1.5 Hz, 1H) 7.80 (m, J=8.6 Hz, 2H) 8.11 (dd, J=8.4, 1.4 Hz, 1H) 8.38-8.54 (m, 3H) 8.79 (d, J=7.9 Hz, 1H).

[2](R)-tert-butyl 3-(1-(4-(1H-pyrazol-1-yl)benzyl)-1H-pyrrolo[3,2-b]pyridine-3-carboxamido)piperidine-1-carboxylate was made using a method analogous to that used to prepare (S)-tert-butyl 3-(1-(4-(1H-pyrazol-1-yl)benzyl)-1H-pyrrolo[3,2-b]pyridine-3-carboxamido)piperidine-1-carboxylate referred to in Example 52.

Example 54: (S)-1-(4-(1H-Pyrazol-1-yl)benzyl)-N-(1-methylpiperidin-3-yl)-1H-pyrrolo[3,2-b]pyridine-3-carboxamide A mixture of (S)-1-(4-(1H-pyrazol-1-yl)benzyl)-N-(piperidin-3-yl)-1H-pyrrolo[3,2-b]pyridine-3-carboxamide, (Example 52), (130 mg), dichloroethane (3 mL) and formaldehyde (37% solution in water, 30 mg) was stirred at rt for 30 min before addition of sodium tri-acetoxyborohydride (270 mg). The reaction was stirred at rt for 3 hours, at which point, TLC indicated completion. The reaction was diluted with sat. NaHCO$_3$ and extracted 2× with EtOAc. The combined organic layers were dried over Na$_2$SO$_4$, filtered and reduced in vacuo. The residue was purified by flash chromatography, eluting with 1% MeOH/DCM with 0.1% TEA added to give an impure product, which was triturated with diethyl ether and EtOAc to give the desired product (57 mg)

LCMS: m/z 415.11 [M+H]$^+$.

$^1$H NMR (400 MHz, DMSO-d$_6$) ppm 1.41 (br. s., 1H) 1.57 (br. s., 1H) 1.75 (d, J=17.1 Hz, 2H) 2.25 (br. s., 6H) 2.65-2.79 (m, 1H) 4.10 (br. s., 1H) 5.56 (s, 2H) 6.43-6.55 (m, 1H) 7.27 (dd, 4.7 Hz, 1H). 7.44 (m, J=8.6 Hz, 2H) 7.71 (d, J=1.2 Hz, 1H) 7.79 (m, J=8.6 Hz, 2H) 8.10 (dd, J=8.2, 1.2 Hz, 1H) 8.40-8.51 (m, 3H) 8.81 (d, J=7.6 Hz, 1H)

Example 55: (R)-1-(4-(1H-Pyrazol-1-yl)benzyl)-N-(1-methylpiperidin-3-yl)-1H-pyrrolo[3,2-b]pyridine-3-carboxamide A mixture of (R)-1-(4-(1H-pyrazol-1-yl)benzyl)-N-(piperidin-3-yl)-1H-pyrrolo[3,2-b]pyridine-3-carboxamide, (Example 53), (130 mg), dichloroethane (3 mL) and formaldehyde (37% solution in water, 30 mg) was stirred at rt for 30 min before addition of sodium tri-acetoxyborohydride (270 mg). The reaction was stirred at rt for 3 hours, at which point, TLC indicated completion. The reaction was diluted with sat. NaHCO$_3$ and extracted 2× with EtOAc. The combined organic layers were dried over Na$_2$SO$_4$, filtered and reduced in vacuo. The residue was purified by flash chromatography, eluting with 2% MeOH/DCM with 0.1% TEA added to give an impure product, which was triturated with diethyl ether and EtOAc to give the desired product (60 mg)

LCMS: m/z 415.11 [M+H]$^+$.

$^1$H NMR (400 MHz, DMSO-d$_6$) ppm 1.39 (br. s., 1H) 1.55 (br. s., 1H) 1.75 (br. s., 2H) 2.20 (br. s., 6H) 2.77 (br. s., 1H) 4.08 (br. s., 1H) 5.56 (s, 2H) 6.52 (dd, J=2.6, 1.7 Hz, 1H) 7.27 (dd, J=8.4, 4.7 Hz, 1H) 7.44 (d, J=8.9 Hz, 2H) 7.71 (d, J=1.2 Hz, 1H) 7.79 (d, J=8.6 Hz, 2H) 8.10 (dd, J=8.4, 1.4 Hz, 1H) 8.40-8.58 (m, 3H) 8.81 (d, J=6.4 Hz, 1H)

Example 56: 1-(4-Bromobenzyl)-N-((1S,2S)-2-hydroxycyclohexyl)-1H-pyrrolo[3,2-b]pyridine-3-carboxamide To a mixture of N-((1S,2S)-2-hydroxycyclohexyl)-1H-pyrrolo[3,2-b]pyridine-3-carboxamide (Intermediate 4) (750 mg) and cesium carbonate (1.131 g) in DMF (10 mL) stirred at rt under nitrogen was added 1-bromo-4-(bromomethyl)benzene (795 mg) and the reaction mixture stirred for 2 h. The reaction was then diluted with EtOAc, washed with water (3×), brine, dried (MgSO$_4$), filtered and evaporated under vacuum. The residue was purified by column chromatography (normal phase, 25 g, Biotage SNAP cartridge KP-Sil, 25 mL per min, gradient 0% to 100% EtOAc in n-hexane, followed by 0-10% MeOH in EtOAc) to afford the title compound (900 mg).

LCMS: m/z 428.53 [M+H]$^+$.

$^1$H NMR (400 MHz, CDCl$_3$) ppm 1.21-1.47 (m, 3H) 1.53 (qd, J=12.2, 3.2 Hz, 1H) 1.77 (d, J=3.2 Hz, 2H) 2.11 (d, J=11.1 Hz, 2H) 3.55 (t, J=9.5 Hz, 1H) 3.81-3.94 (m, 1H) 5.27 (s, 2H) 6.99 (d, J=8.2 Hz, 2H) 7.14 (dd, J=8.3, 4.6 Hz, 1H) 7.43 (d, J=8.3 Hz, 2H) 7.55 (d, J=8.2 Hz, 1H) 8.04 (s, 1H) 8.48 (d, J=4.5 Hz, 1H) 9.01 (d, J=6.5 Hz, 1H)

Example 57: N-((1S,2S)-2-Hydroxycyclohexyl)-1-(4-(1-methyl-1H-pyrazol-4-yl)benzyl)-1H-pyrrolo[3,2-b]pyridine-3-carboxamide A mixture of 3-iodo-1-(4-(1-methyl-1H-pyrazol-4-yl) benzyl)-1H-pyrrolo[3,2-b]pyridine (made by alkylation of Intermediate 1, using a method analogous to that described in Intermediate 18), (200 mg), palladium (II) acetate (3 mg), XantPhos (7 mg), (1S,2S)-2-aminocyclohexanol hydrochloride (226 mg), sodium carbonate (200 mg) and toluene (5 mL) were purged with CO then heated to 80° C. overnight. The reaction mixture was filtered and the filtrate was reduced in vacuo. The residue was purified by column chromatography to give the desired compound (55 mg).

LCMS: m/z 430.30 [M+H]$^+$.

$^1$H NMR (400 MHz, DMSO-d6): ppm 1.10-1.39 (m, 4H) 1.55-1.70 (m, 2H) 1.81-2.05 (m, 2H) 3.35-3.45 (m, 1H) 3.68-3.78 (m, 1H) 3.84 (s, 3H) 4.81 (d, J=5.2 H, 1H) 5.50 (s, 2H) 7.24-7.34 (m, 3H) 7.51 (d, J=8.0 Hz, 2H) 7.81 (s, 1H) 8.06-8.14 (m, 2H) 8.41 (s, 1H) 8.49 (dd, J=4.8, 1.2 Hz, 1H) 8.75 (d, J=7.6 Hz, 1H)

Example 58: 7-Chloro-N-((1S,2S)-2-hydroxycyclohexyl)-1-(4-methoxybenzyl)-1H-pyrrolo[3,2-b]pyridine-3-carboxamide A mixture of 7-chloro-N-((1S,2S)-2-hydroxycyclohexyl)-1H-pyrrolo[3,2-b]pyridine-3-carboxamide (Intermediate 17), (160 mg), 1-(bromomethyl)-4-methoxybenzene (110 mg) and cesium carbonate (408 mg) in DMF (3 mL) was stirred at rt overnight. The crude product was diluted with MeOH and purified by column chromatography followed by prep. LCMS to give the desired compound (86 mg).

LCMS: m/z 414.20 [M+H]$^+$.

$^1$H NMR (400 MHz, CDCl$_3$) ppm 0.99-1.61 (m, 4H) 1.79 (d, J=9.2 Hz, 2H) 2.10-2.24 (m, 2H) 3.55 (td, J=9.9, 4.5 Hz, 1H) 3.80 (s, 3H) 3.83-3.95 (m, 1H) 5.66 (s, 2H) 6.86 (d, J=8.4 Hz, 2H) 7.07 (d, J=8.4 Hz, 2H) 7.18 (d, J=5.0 Hz, 1H) 8.06 (s, 1H) 8.35 (d, J=5.1 Hz, 1H) 9.04 (d, J=6.4 Hz, 1H)

Example 59: 1-((6-Chloropyridin-3-yl)methyl)-N-((1S,2S)-2-hydroxycyclohexyl)-7-methyl-1H-pyrrolo[3,2-b]pyridine-3-carboxamide A mixture of N-((1S,2S)-2-hydroxycyclohexyl)-7-methyl-1H-pyrrolo[3,2-b]pyridine-3-carboxamide (Intermediate 13), (150 mg), 2-chloro-5-(chloromethyl)pyridine (89 mg) and cesium carbonate (411 mg) in DMF (4.9 mL) was stirred at rt overnight. The reaction mixture was filtered and the filtrate was reduced in vacuo. The residue was purified by column chromatography to give the desired compound (167 mg).

LCMS: m/z 399.57 [M+H]$^+$.

$^1$H NMR (400 MHz, CDCl$_3$) ppm 1.20-1.58 (m, 4 II) 1.70-1.82 (m, 2H) 2.00-2.16 (m, 2H) 2.46 (s, 3H) 3.55 (td, J=9.8, 4.3 Hz, 1H) 3.84-4.00 (m, 1H) 5.45-5.59 (m, 2H) 6.88 (d, J=4.8 Hz, 1H) 7.03-7.13 (m, 1H) 7.19 (d, J=8.2 Hz, 1H) 8.11 (d, J=12.4 Hz, 2H) 8.33 (d, J=4.8 Hz, 1H) 9.26 (d, J=7.0 Hz, 1H)

Example 60: 1-(4-Chlorobenzyl)-N-((1S,2S)-2-hydroxycyclohexyl)-7-methyl-1H-pyrrolo[3,2-b]pyridine-3-carboxamide A mixture of N-((1S,2S)-2-hydroxycyclohexyl)-7-methyl-1H-pyrrolo[3,2-b]pyridine-3-carboxamide (Intermediate 13), (150 mg), 1-(bromomethyl)-4-chlorobenzene (113 mg) and cesium carbonate (411 mg) in DMF (4.9 mL) was stirred at rt overnight. The reaction mixture was filtered and the filtrate was reduced in vacuo. The residue was purified by column chromatography to give the desired compound (107 mg).

LCMS: m/z 398.56 [M+H]$^+$.

¹H NMR (400 MHz, CDCl₃) ppm 1.23-1.83 (m, 6H) 2.13 (d, J=8.1 Hz, 2H) 2.56 (s, 3H) 3.70 (br. s., 1H) 3.87 (br. s., 1H) 5.52-5.63 (m, 2H) 6.89 (d, J=8.2 Hz, 2H) 7.20-7.36 (m, 3H) 8.42 (br. s., 1H) 9.27 (d, J=5.9 Hz, 1H)

Example 61: 7-Chloro-N-((1S,2S)-2-hydroxycyclohexyl)-1-((5-methylpyridin-2-yl)methyl)-1H-pyrrolo[3,2-b]pyridine-3-carboxamide A mixture of 7-chloro-N-((1S,2S)-2-hydroxycyclohexyl)-1H-pyrrolo[3,2-b]pyridine-3-carboxamide (Intermediate 17), (270 mg), 2-(chloromethyl)-5-methylpyridine hydrochloride (180 mg) and cesium carbonate (689 mg) in DMF (3 mL) was stirred at rt overnight. The crude product was purified by prep. LCMS then azeotroped with DCM to remove the residual AcOH to give the desired compound (141 mg).

LCMS: m/z 399.20 [M+H]⁺.

¹H NMR (400 MHz, CDCl₃) ppm 1.04-1.67 (m, 4H) 1.79 (d, J=9.2 Hz, 2H) 1.97-2.21 (m, 2H) 2.32 (s, 3H) 3.56 (td, J=9.9, 4.5 Hz, 1H) 3.79-4.00 (m, 1H) 5.61-5.98 (m, 2H) 6.69 (d, J=8.0 Hz, 1H) 7.17 (d, J=5.1 Hz, 1H) 7.41 (d, J=7.7 Hz, 1H) 8.14 (s, 1H) 8.35 (d, J=5.1 Hz, 1H) 8.41 (s, 1H) 9.04 (d, J=6.5 Hz, 1H)

Example 62: 7-Chloro-N-((1S,2S)-2-hydroxycyclohexyl)-1-((6-methylpyridin-3-yl)methyl)-1H-pyrrolo[3,2-b]pyridine-3-carboxamide A mixture of 7-chloro-N-((1S,2S)-2-hydroxycyclohexyl)-1H-pyrrolo[3,2-b]pyridine-3-carboxamide (Intermediate 17), (250 mg), 5-(chloromethyl)-2-methylpyridine hydrochloride (167 mg) and cesium carbonate (638 mg) in DMF (3 mL) was stirred at rt overnight. The crude product was diluted with EtOAc (60 mL) and washed with water (2×20 mL) and brine (20 mL). The combined aqueous layers were extracted with EtOAc (20 mL) and the combined organic layers were dried over MgSO₄, filtered and evaporated in vacuo. The residue was purified by column chromatography to give the desired compound (191 mg).

LCMS: m/z 399.24 [M+H]⁺.

¹H NMR (400 MHz, CDCl₃) ppm 1.01-1.64 (m, 4H) 1.79 (d, J=9.4 Hz, 2H) 2.06-2.19 (m, 2H) 2.55 (s, 3H) 3.55 (td, J=9.9, 4.5 Hz, 1H) 3.82-3.96 (m, 1H) 4.24 (br. s., 1H) 5.71 (s, 2H) 7.11 (d, J=8.1 Hz, 1H) 7.19 (d, J=5.3 Hz, 1H) 7.23 (dd, J=8.0, 2.1 Hz, 1H) 8.09 (s, 1H) 8.36 (d, J=5.1 Hz, 1H) 8.40 (d, J=1.6 Hz, 1H) 9.01 (d, J=6.4 Hz, 1H)

Example 63: N-((1S,2S)-2-Hydroxycyclohexyl)-7-methyl-1-(4-methylbenzyl)-1H-pyrrolo[3,2-b]pyridine-3-carboxamide A mixture of N-((1S,2S)-2-hydroxycyclohexyl)-7-methyl-1H-pyrrolo[3,2-b]pyridine-3-carboxamide (Intermediate 13), (110 mg), 1-(chloromethyl)-4-methylbenzene (37 μl) and cesium carbonate (302 mg) in DMF (3.6 mL) was stirred at rt overnight. The reaction mixture was filtered and the filtrate was reduced in vacuo. The residue was purified by column chromatography to give the desired compound (103 mg).

LCMS: m/z 378.65 [M+H]⁺.

¹H NMR (400 MHz, CDCl₃) ppm 1.22-1.64 (m, 4H) 1.78 (br. s., 2H) 2.07-2.19 (m, 2H) 2.31 (s, 3H) 2.51 (s, 3H) 3.57 (td, J=9.8, 4.3 Hz, 1H) 3.83-3.96 (m, 1H) 4.69 (br. s., 1H) 5.49 (s, 2H) 6.78-6.91 (m, 3H) 7.10 (d, J=7.8 Hz, 2H) 8.00 (s, 1H) 8.32 (d, J=4.7 Hz, 1H) 9.28 (d, J=6.1 Hz, 1H)

Example 64: N-((1S,2S)-2-Hydroxycyclohexyl)-7-methyl-1-((5-methylpyridin-2-yl)methyl)-1H-pyrrolo[3,2-b]pyridine-3-carboxamide A mixture of N-((1S,2S)-2-hydroxycyclohexyl)-7-methyl-1H-pyrrolo[3,2-b]pyridine-3-carboxamide (Intermediate 13), (110 mg), 2-(chloromethyl)-5-methylpyridine hydrochloride (72 mg) and cesium carbonate (302 mg) in DMF (3.6 mL) was stirred at rt overnight. The reaction mixture was filtered and the filtrate was reduced in vacuo. The residue was purified by column chromatography to give the desired compound (142 mg).

LCMS: m/z 379.63 [M+H]⁺.

¹H NMR (400 MHz, CDCl₃) ppm 1.20-1.87 (m, 6H) 2.15 (d, J=11.5 Hz, 2H) 2.32 (s, 3H) 2.53 (s, 3H) 3.60 (d, J=3.3 Hz, 1H) 3.83-3.98 (m, 1H) 5.56-5.69 (m, 2H) 6.56 (d, J=6.2 Hz, 1H) 6.92 (d, J=3.9 Hz, 1H) 7.39 (d, J=7.7 Hz, 1H) 8.35 (d, J=4.7 Hz, 1H) 8.42 (s, 1H) 9.28 (d, J=6.4 Hz, 1H)

Example 65: 1-(3-Fluorobenzyl)-N-((1S,2S)-2-hydroxycyclohexyl)-7-methyl-1H-pyrrolo[3,2-b]pyridine-3-carboxamide A mixture of N-((1S,2S)-2-hydroxycyclohexyl)-7-methyl-1H-pyrrolo[3,2-b]pyridine-3-carboxamide (Intermediate 13), (110 mg), 1-(bromomethyl)-3-fluorobenzene (76 mg) and cesium carbonate (302 mg) in DMF (3.6 mL) was stirred at rt overnight. The reaction mixture was filtered and the filtrate was reduced in vacuo. The residue was purified by column chromatography to give the desired compound (127 mg).

LCMS: m/z 382.62 [M+H]⁺.

¹H NMR (400 MHz, CDCl₃) ppm 1.22-1.62 (m, 4H) 1.78 (d, J=2.9 Hz, 2H) 2.06-2.19 (m, 2H) 2.48 (s, 3H) 3.57 (td, J=9.8, 4.5 Hz, 1H) 3.82-3.97 (m, 1H) 4.60 (br. s., 1H) 5.53 (s, 2H) 6.62 (d, J=9.4 Hz, 1H) 6.70 (d, J=7.7 Hz, 1H) 6.89 (d, J=4.8 Hz, 1H) 6.93-7.02 (m, 1H) 7.22-7.33 (m, 1H) 8.01 (s, 1H) 8.33 (d, J=4.8 Hz, 1H) 9.26 (d, J=6.4 Hz, 1H)

Example 66: N-((1S,2S)-2-Hydroxycyclohexyl)-1-(4-methoxy-3-methylbenzyl)-7-methyl-1H-pyrrolo[3,2-b]pyridine-3-carboxamide A mixture of N-((1S,2S)-2-hydroxycyclohexyl)-7-methyl-1H-pyrrolo[3,2-b]pyridine-3-carboxamide (Intermediate 13), (110 mg), 4-(chloromethyl)-1-methoxy-2-methylbenzene (69 mg) and cesium carbonate (302 mg) in DMF (3.6 mL) was stirred at rt overnight. The reaction mixture was filtered and the filtrate was reduced in vacuo. The residue was purified by column chromatography to give the desired compound (126 mg).

LCMS: m/z 408.65 [M+H]⁺.

¹H NMR (400 MHz, CDCl₃) ppm 1.17-1.63 (m, 4H) 1.76 (br. s., 2H) 2.06-2.18 (m, 5H) 2.54 (s, 3H) 3.56 (td, J=9.8, 4.5 Hz, 1H) 3.78 (s, 3H) 3.81-3.94 (m, 1H) 4.75 (br. s., 1H) 5.40 (s, 2H) 6.65-6.81 (m, 3H) 6.86 (d, J=4.8 Hz, 1H) 7.96 (s, 1H) 8.30 (d, J=4.8 Hz, 1H) 9.27 (d, J=6.4 Hz, 1H)

Example 67: N-((1S,2S)-2-Hydroxycyclohexyl)-1-((6-methoxypyridin-3-yl)methyl)-7-methyl-1H-pyrrolo[3,2-b]pyridine-3-carboxamide A mixture of N-((1S,2S)-2-hydroxycyclohexyl)-7-methyl-1H-pyrrolo[3,2-b]pyridine-3-carboxamide (Intermediate 13), (120 mg), 5-(chloromethyl)-2-methoxypyridine (69 mg) and cesium carbonate (329 mg) in DMF (3.9 mL) was stirred at rt overnight. A further 20 mg 5-(chloromethyl)-2-methoxypyridine was added and stirred for 2 days. A further 100 mg 5-(chloromethyl)-2-methoxypyridine was added and stirred for 24 h. Water (20 mL) was added and the reaction mixture was extracted with EtOAc (3×20 mL). The combined organic layers were washed with brine (20 mL) and dried over MgSO$_4$, filtered and evaporated in vacuo. The residue was purified by column chromatography to give the desired compound (131 mg).

LCMS: m/z 395.49 [M+H]$^+$.

$^1$H NMR (400 MHz, CDCl$_3$) ppm 1.15-1.52 ppm (m, 4H) 1.71 (d, J=9.9 Hz, 2H) 2.05 (t, J=9.0 Hz, 2H) 2.50 (s, 3H) 3.16 (br. s., 1H) 3.49 (td, J=9.7, 4.3 Hz, 1H) 3.71-3.84 (m, 1H) 3.83 (s, 3H) 5.43 (s, 2H) 6.62 (d, J=8.6 Hz, 1H) 6.84 (d, J=4.8 Hz, 1H) 7.10 (dd, J=8.6, 2.1 Hz, 1H) 7.79 (d, J=1.8 Hz, 1H) 7.95 (s, 1H) 8.25 (d, J=4.6 Hz, 1H) 9.24 (d, J=7.0 Hz, 1H)

Example 68: 7-Chloro-N-((1S,2S)-2-hydroxycyclohexyl)-1-((6-methoxypyridin-3-yl)methyl)-1H-pyrrolo[3,2-b]pyridine-3-carboxamide A mixture of 7-chloro-N-((1S,2S)-2-hydroxycyclohexyl)-1H-pyrrolo[3,2-b]pyridine-3-carboxamide (Intermediate 17), (160 mg), 5-(chloromethyl)-2-methoxypyridine (94 mg) and cesium carbonate (408 mg) in DMF (3 mL) was stirred at rt overnight. The crude product was purified by prep. LCMS then azeotroped with DCM to remove the residual AcOH to give the desired compound (111 mg).

LCMS: m/z 415.21 [M+H]$^+$.

$^1$H NMR (400 MHz, CDCl$_3$) ppm 1.05-1.64 (m, 4H) 1.79 (d, J=9.5 Hz, 2H) 2.02-2.28 (m, 2H) 3.56 (td, J=9.9, 4.5 Hz, 1H) 3.70-4.09 (m, 1H) 3.93 (s, 3H) 5.67 (s, 2H) 6.72 (d, J=8.6 Hz, 1H) 7.21 (d, J=5.1 Hz, 1H) 7.34 (dd, J=8.6, 2.3 Hz, 1H) 8.04 (s, 1H) 8.11 (s, 1H) 8.37 (d, J=5.1 Hz, 1H) 9.02 (d, J=6.5 Hz, 1H)

Example 69: 7-Chloro-N-((1S,2S)-2-hydroxycyclohexyl)-1-((2-methoxypyridin-4-yl)methyl)-1H-pyrrolo[3,2-b]pyridine-3-carboxamide A mixture of 7-chloro-N-((1S,2S)-2-hydroxycyclohexyl)-1H-pyrrolo[3,2-b]pyridine-3-carboxamide (Intermediate 17), (160 mg), 5-(chloromethyl)-2-methoxypyridine (94 mg) and cesium carbonate (408 mg) in DMF (3 mL) was stirred at rt overnight. The crude product was purified by prep. LCMS then azeotroped with DCM to remove the residual AcOH to give the desired compound (116 mg).

LCMS: m/z 415.21 [M+H]$^+$.

$^1$H NMR (400 MHz, CDCl$_3$) ppm 1.12-1.64 (m, 4H) 1.80 (d, J=9.3 Hz, 2H) 2.01-2.17 (m, 2H) 3.58 (td, J=9.9, 4.3 Hz, 1H) 3.79-4.03 (m, 1H) 3.91 (s, 3H) 5.67 (s, 2H) 6.28 (s, 1H) 6.55 (d, J=4.9 Hz, 1H) 7.19 (d, J=5.1 Hz, 1H) 7.98-8.22 (m, 2H) 8.38 (d, J=5.3 Hz, 1H) 9.03 (d, J=6.6 Hz, 1H)

Example 70: 7-Chloro-1-((6-cyanopyridin-3-yl)methyl)-N-((1S,2S)-2-hydroxycyclohexyl)-1H-pyrrolo[3,2-b]pyridine-3-carboxamide A mixture of 7-chloro-N-((1S,2S)-2-hydroxycyclohexyl)-1H-pyrrolo[3,2-b]pyridine-3-carboxamide (Intermediate 17), (150 mg), 5-(bromomethyl)picolinonitrile (111 mg) and cesium carbonate (383 mg) in DMF (3 mL) was stirred at rt overnight. The crude product was purified by prep. LCMS then azeotroped with DCM to remove the residual AcOH to give the desired compound (125 mg).

LCMS: m/z 410.19 [M+H]$^+$.

$^1$H NMR (400 MHz, CDCl$_3$) ppm 1.17-1.64 (m, 4H) 1.80 (d, J=9.7 Hz, 2H) 2.02-2.26 (m, 2H) 3.57 (td, J=9.8, 4.5 Hz, 1H) 3.82-4.04 (m, 1H) 5.83 (s, 2H) 7.21 (d, J=5.0 Hz, 1H) 7.37 (dd, J=8.0, 1.5 Hz, 1H) 7.64 (d, J=8.1 Hz, 1H) 8.17 (s, 1H) 8.41 (d, J=4.9 Hz, 1H) 8.56 (s, 1H) 9.00 (d, J=6.6 Hz, 1H)

Example 71: N-((1S,2S)-2-Hydroxycyclohexyl)-1-((2-methoxypyridin-4-yl)methyl)-7-methyl-1H-pyrrolo[3,2-b]pyridine-3-carboxamide A mixture of N-((1S,2S)-2-hydroxycyclohexyl)-7-methyl-1H-pyrrolo[3,2-b]pyridine-3-carboxamide (Intermediate 13), (110 mg), 4-(chloromethyl)-2-methoxypyridine (63 mg) and cesium carbonate (302 mg) in DMF (3.6 mL) was stirred at rt overnight. The reaction mixture was filtered and the filtrate was reduced in vacuo. The residue was purified by column chromatography to give the desired compound (63 mg).

LCMS: m/z 395.68 [M+H]$^+$.

$^1$H NMR (400 MHz, CDCl$_3$) ppm 1.29-1.62 (m, 4H) 1.70-1.95 (m, 2H) 2.08-2.21 (m, 2H) 2.47 (s, 3H) 3.57 (td, J=9.8, 4.5 Hz, 1H) 3.84-3.94 (m, 1H) 3.89 (s, 3H) 5.48 (s, 2H) 6.19 (s, 1H) 6.46 (d, J=5.4 Hz, 1H) 6.90 (d, J=4.7 Hz, 1H) 8.01 (s, 1H) 8.09 (d, J=5.4 Hz, 1H) 8.34 (d, J=4.7 Hz, 1H) 9.24 (d, J=6.4 Hz, 1H)

Example 72: 7-Chloro-N-((1S,2S)-2-hydroxycyclohexyl)-1-((1-methyl-1H-pyrazol-4-yl)methyl)-1H-pyrrolo[3,2-b]pyridine-3-carboxamide A mixture of 7-chloro-N-((1S,2S)-2-hydroxycyclohexyl)-1H-pyrrolo[3,2-b]pyridine-3-carboxamide (Intermediate 17), (150 mg), 4-(chloromethyl)-1-methyl-1H-pyrazole hydrochloride (94 mg) and cesium carbonate (383 mg) in DMF (3 mL) was stirred at rt weekend. The crude product was purified by prep. LCMS then azeotroped with DCM to remove the residual AcOH to give the desired compound (101 mg).

LCMS: m/z 388.18 [M+H]$^+$.

$^1$H NMR (400 MHz, CDCl$_3$) ppm 1.19-1.62 (m, 4H) 1.79 (d, J=9.5 Hz, 2H) 2.11 (d, J=8.2 Hz, 2H) 3.55 (td, J=9.9, 4.5 Hz, 1H) 3.73-4.02 (m, 1H) 3.87 (s, 3H) 5.60 (s, 2H) 7.21 (d, J=5.1 Hz, 1H) 7.30 (s, 1H) 7.46 (s, 1H) 8.12 (s, 1H) 8.35 (d, J=5.3 Hz, 1H) 9.02 (d, J=6.2 Hz, 1H)

Example 73: N-((1S,2S)-2-Hydroxycyclohexyl)-7-methyl-1-((1-methyl-1H-pyrazol-4-yl)methyl)-1H-pyrrolo[3,2-b]pyridine-3-carboxamide A mixture of N-((1S,2S)-2-hydroxycyclohexyl)-7-methyl-1H-pyrrolo[3,2-b]pyridine-3-carboxamide (Intermediate 13), (110 mg), 4-(chloromethyl)-1-methyl-1H-pyrazole (53 mg) and cesium carbonate (302 mg) in DMF (3.6 mL) was stirred at rt overnight. The reaction mixture was filtered and the filtrate was reduced in vacuo. The residue was purified by column chromatography to give the desired compound (59 mg).

LCMS: m/z 368.67 [M+H]$^+$.

$^1$H NMR (400 MHz, CDCl$_3$) ppm 1.16-1.56 (m, 4H) 1.66 (br. s., 2H) 1.92-2.10 (m, 2H) 2.56 (s, 3H) 3.49 (td, J=9.8, 4.3 Hz, 1H) 3.75 (s, 3H) 3.79-3.93 (m, 1H) 5.27 (s, 2H) 6.82 (d, J=4.7 Hz, 1H) 7.09 (s, 1H) 7.17-7.22 (m, 1H) 8.00 (s, 1H) 8.24 (d, J=4.9 Hz, 1H) 9.15 (d, J=7.1 Hz, 1H)

Example 74: 7-Chloro-N-((1S,2S)-2-hydroxycyclohexyl)-1-((4-methylthiazol-2-yl)methyl)-1H-pyrrolo[3,2-b]pyridine-3-carboxamide A mixture of 7-chloro-N-((1S,2S)-2-hydroxycyclohexyl)-1H-pyrrolo[3,2-b]pyridine-3-carboxamide (Intermediate 17), (150 mg), 2-(bromomethyl)-4-methylthiazole (118 mg) and cesium carbonate (383 mg) in DMF (3 mL) was stirred at rt overnight. The crude product was purified by prep. LCMS to give the desired compound (125 mg).
LCMS: m/z 405.57 [M+H]$^+$.
$^1$H NMR (400 MHz, DMSO-d$_6$) ppm 1.20-1.40 (m, 4H) 1.55-1.74 (m, 2H) 1.89 (d, J=10.3 Hz, 1H) 2.04 (d, J=10.3 Hz, 1H) 2.35 (s, 3H) 3.34-3.46 (m, 1H) 3.72 (d, J=8.3 Hz, 1H) 4.78 (d, J=5.1 Hz, 1H) 6.04 (s, 2H) 7.35-7.42 (m, 2H) 8.40-8.50 (m, 2H) 8.74 (d, J=7.6 Hz, 1H)

Example 75: 7-Chloro-N-((1S,2S)-2-hydroxycyclohexyl)-1-((5-methylthiazol-2-yl)methyl)-1H-pyrrolo[3,2-b]pyridine-3-carboxamide A mixture of 7-chloro-N-((1S,2S)-2-hydroxycyclohexyl)-1H-pyrrolo[3,2-b]pyridine-3-carboxamide (Intermediate 17), (150 mg), 2-(bromomethyl)-5-methylthiazole (118 mg) and cesium carbonate (383 mg) in DMF (3 mL) was stirred at rt overnight. The crude product was purified by prep. LCMS to give the desired compound (113 mg).
LCMS: m/z 405.57 [M+H]$^+$.
$^1$H NMR (400 MHz, DMSO-d$_6$) ppm 1.18-1.39 (m, 4H) 1.52-1.74 (m, 2H) 1.89 (d, J=10.0 Hz, 1H) 2.04 (d, J=9.3 Hz, 1H) 2.35 (s, 3H) 3.33-3.46 (m, 1H) 3.72 (d, J=8.3 Hz, 1H) 4.78 (d, J=5.3 Hz, 1H) 6.04 (s, 2H) 7.32-7.44 (m, 2H) 8.43 (d, J=5.1 Hz, 1H) 8.46 (s, 1H) 8.74 (d, J=7.6 Hz, 1H)

Example 76: N-((1S,2S)-2-Hydroxycyclohexyl)-1-((2-methylpyridin-4-yl)methyl)-1H-pyrrolo[3,2-b]pyridine-3-carboxamide A mixture of N-((1S,2S)-2-hydroxycyclohexyl)-1H-pyrrolo[3,2-b]pyridine-3-carboxamide (Intermediate 4), (70 mg), 2-methyl-4-(bromomethyl)pyridine (50 mg) and cesium carbonate (220 mg) in DMF (2 mL) was stirred at rt overnight. The reaction mixture was filtered thought Celite and concentrated in vacuo. The residue was triturated with small amount of MeOH to afford the desired compound (19 mg).
LCMS: m/z 365.23 [M+H]$^+$.
$^1$H NMR (400 MHz, DMSO-d$_6$) ppm 1.20-1.37 (m, 4H) 1.57-1.67 (m, 2H) 1.82-1.91 (m, 1H) 2.02 (d, J=10.2 Hz, 1H) 2.38 (s, 3H) 3.39 (d, J=4.3 Hz, 1H) 3.71 (d, J=8.4 Hz, 1H) 4.79 (d, J=3.9 Hz, 1H) 5.53 (s, 2H) 6.92 (d, J=4.7 Hz, 1H) 7.05 (s, 1H) 7.25 (dd, J=8.4, 4.7 Hz, 1H) 7.97 (d, J=8.2 Hz, 1H) 8.34 (d, J=5.1 Hz, 1H) 8.38 (s, 1H) 8.48 (d, J=4.5 Hz, 1H) 8.74 (d, J=7.6 Hz, 1H)

Example 77: N-((1S,2S)-2-Hydroxycyclohexyl)-1-(pyridin-4-ylmethyl)-1H-pyrrolo[3,2-b]pyridine-3-carboxamide A mixture of N-((1S,2S)-2-hydroxycyclohexyl)-1H-pyrrolo[3,2-b]pyridine-3-carboxamide (Intermediate 4), (70 mg), 4-(chloromethyl)pyridine hydrochloride (44 mg) and cesium carbonate (220 mg) in DMF (2 mL) was stirred at rt overnight. The reaction mixture was filtered thought Celite and concentrated in vacuo. The residue was triturated with small amount of MeOH to afford the desired compound (26 mg).
LCMS: m/z 351.17 [M+H]$^+$.
$^1$H NMR (400 MHz, DMSO-d$_6$) ppm 1.19-1.37 (m, 4H) 1.56-1.68 (m, 2H) 1.87 (d, J=7.8 Hz, 1H) 2.02 (d, J=9.6 Hz, 1H) 3.40 (br. s., 1H) 3.71 (d, J=8.0 Hz, 1H) 4.79 (d, J=5.1 Hz, 1H) 5.59 (s, 2H) 7.13 (d, J=5.5 Hz, 2H) 7.25 (dd, J=8.2, 4.7 Hz, 1H) 7.98 (d, J=8.2 Hz, 1H) 8.40 (s, 1H) 8.48 (d, J=4.5 Hz, 3H) 8.75 (d, J=7.6 Hz, 1H)

Example 78: 7-Chloro-N-((1S,2S)-2-hydroxycyclohexyl)-1-((2-methylpyridin-4-yl)methyl)-1H-pyrrolo[3,2-b]pyridine-3-carboxamide A mixture of 7-chloro-N-((1S,2S)-2-hydroxycyclohexyl)-1H-pyrrolo[3,2-b]pyridine-3-carboxamide (Intermediate 17), (150 mg), 2-methyl-4-(bromomethyl)pyridine (95 mg) and cesium carbonate (416 mg) in DMF (3 mL) was stirred at rt overnight. The reaction mixture was filtered thought Celite and concentrated in vacuo. The residue was triturated with small amount of MeOH to afford the desired compound (87 mg).
LCMS: m/z 399.20 [M+H]$^+$.
$^1$H NMR (400 MHz, DMSO-d$_6$) ppm 1.28 (d, J=6.8 Hz, 4H) 1.55-1.69 (m, 2H) 1.86 (br. s., 1H) 2.03 (d, J=9.8 Hz, 1H) 2.37 (s, 3H) 3.36-3.46 (m, 1H) 3.71 (d, J=8.0 Hz, 1H) 4.80 (d, J=4.5 Hz, 1H) 5.79 (s, 2H) 6.70 (d, J=4.7 Hz, 1H) 6.85 (s, 1H) 7.35 (d, J=5.1 Hz, 1H) 8.33 (d, J=5.1 Hz, 1H) 8.42 (d, J=5.1 Hz, 1H) 8.48 (s, 1H) 8.76 (d, J=7.4 Hz, 1H)

Example 79: 7-Chloro-N-((1S,2S)-2-hydroxycyclohexyl)-1-(pyridin-4-ylmethyl)-1H-pyrrolo[3,2-b]pyridine-3-carboxamide A mixture of 7-chloro-N-((1S,2S)-2-hydroxycyclohexyl)-1H-pyrrolo[3,2-b]pyridine-3-carboxamide (Intermediate 17), (150 mg), 4-(chloromethyl)pyridine hydrochloride (84 mg) and cesium carbonate (416 mg) in DMF (3 mL) was stirred at rt overnight. The reaction was incomplete by LC-MS, so an additional 4-(chloromethyl)pyridine hydrochloride (84 mg) and cesium carbonate (416 mg) were added and the reaction was stirred at rt 2 d. The reaction mixture was filtered thought Celite and concentrated in vacuo. The residue was triturated with small amount of MeOH to afford the desired compound (10 mg).
LCMS: m/z 385.18 [M+H]$^+$.
$^1$H NMR (400 MHz, DMSO-d$_6$) ppm 1.28 (br. s., 4H) 1.65 (br. s., 2H) 1.87 (br. s., 1H) 2.04 (br. s., 1H) 3.39 (br. s., 1H) 3.62-3.80 (m, 1H) 4.79 (br. s., 1H) 5.84 (br. s., 2H) 6.93 (d, J=3.1 Hz, 2H) 7.35 (d, J=4.3 Hz, 1H) 8.30-8.58 (m, 4H) 8.76 (d, J=6.8 Hz, 1H)

Example 80: 7-Chloro-N-((1S,2S)-2-hydroxycyclohexyl)-1-((4-methylpyridin-2-yl)methyl)-1H-pyrrolo[3,2-b]pyridine-3-carboxamide A mixture of 7-chloro-N-((1S,2S)-2-hydroxycyclohexyl)-1H-pyrrolo[3,2-b]pyridine-3-carboxamide (Intermediate 17), (160 mg), 2-(chloromethyl)-4-methylpyridine hydrochloride (107 mg) and cesium carbonate (408 mg) in DMF (42 uL) was stirred at rt overnight. The crude product was purified by prep. LCMS then azeotroped with DCM to remove the residual AcOH to give the desired compound (123 mg).
LCMS: m/z 399.64 [M+H]$^+$.
$^1$H NMR (400 MHz, CDCl$_3$) ppm 0.84-2.02 (m, 6H) 2.11-2.21 (m, 2H) 2.27 (s, 3H) 3.57 (td, J=9.9, 4.4 Hz, 1H) 3.77-4.00 (m, 1H) 4.01-4.70 (m, 1H) 5.63-5.99 (m, 2H) 6.59

(s, 1H) 7.05 (d, J=4.7 Hz, 1H) 7.18 (d, J=5.1 Hz, 1H) 8.14 (s, 1H) 8.37 (d, J=5.1 Hz, 1 H) 8.44 (d, J=5.0 Hz, 1H) 9.06 (d, J=6.6 Hz, 1H)

Example 81: 1-((5-Chloropyridin-2-yl)methyl)-N-((1S,2S)-2-hydroxycyclohexyl)-7-methyl-1H-pyrrolo[3,2-b]pyridine-3-carboxamide A mixture of N-((1S,2S)-2-hydroxycyclohexyl)-7-methyl-1H-pyrrolo[3,2-b]pyridine-3-carboxamide (Intermediate 13), (110 mg), 5-chloro-2-(chloromethyl)pyridine (65 mg), sodium iodide (1 mg) and cesium carbonate (302 mg) in DMF (3.6 mL) was stirred at 40° C. overnight. The reaction mixture was diluted with EtOAc and filtered and the filtrate was reduced in vacuo. The residue was purified by column chromatography to give the desired compound (13 mg).

LCMS: m/z 399.62 [M+H]$^+$.

$^1$H NMR (400 MHz, CDCl$_3$) ppm 1.23-1.65 (m, 4H) 1.70-1.92 (m, 2H) 2.09-2.29 (m, 2H) 2.49 (s, 3H) 3.57 (td, J=9.8, 4.5 Hz, 1H) 3.76-4.03 (m, 1H) 5.53-5.71 (m, 2H) 6.59 (d, J=8.3 Hz, 1H) 6.90 (d, J=4.9 Hz, 1H) 7.54 (dd, J=8.4, 2.3 Hz, 1H) 8.06 (s, 1H) 8.33 (d, J=4.7 Hz, 1H) 8.54 (d, J=2.2 Hz, 1H) 9.25 (d, J=6.6 Hz, 1H)

Example 82: 1-(4-Fluorobenzyl)-N-(trans-3-hydroxytetrahydro-2H-pyran-4-yl)-7-methyl-1H-pyrrolo[3,2-b]pyridine-3-carboxamide To a solution of tert-butyl 3-((trans-3-hydroxytetrahydro-2H-pyran-4-yl)carbamoyl)-7-methyl-1H-pyrrolo[3,2-b]pyridine-1-carboxylate (Intermediate 74), (90 mg)), in DCM (5 mL) stirred at rt under nitrogen was added TFA (5 mL) and the reaction was stirred at rt for 1.5 h. The reaction was concentrated under vacuum and the residue was dissolved in MeOH (5 mL) and loaded onto an SCX cartridge, washing with MeOH (5 CV) and eluting with 2M NH3/MeOH (10 CV). The ammonia-containing fractions were combined and reduced in vacuo. The residue was dissolved in DMF (2.4 mL) and the resultant solution was stirred at rt under nitrogen. To this solution was added 1-(bromomethyl)-4-fluorobenzene (45.3 mg) and Cs$_2$CO$_3$ (180 mg) and the reaction was stirred at rt under nitrogen overnight. The solid was filtered and the filtrate was concentrated under reduced pressure and purified by column chromatography (normal phase, Biotage SNAP cartridge KP-Sil, gradient 20% to 100% EtOAc in n-hexane, followed by 0-10% Methanol in EtOAc). The major band to elute was then subjected to chiral chromatographic separation using preparative IE column (i.d. 20 mm; length 250 mm) and 97% DCM, 3% EtOH (v/v) as eluent, injection volume: 1500 microL, flow rate: 18.0 mL/min, oven temperature: 30° C., which afforded the two major eluting peaks.

The first eluting peak afforded 1-(4-fluorobenzyl)-N-(trans-3-hydroxytetrahydro-2H-pyran-4-yl)-7-methyl-1H-pyrrolo[3,2-b]pyridine-3-carboxamide, a single enantiomer of trans relative stereochemistry but unknown absolute configuration, (33 mg).

Specific optical rotation [α]$_D$: +37.8 (25° C., MeOH)
LCMS: m/z 384.58 [M+H]$^+$.

$^1$H NMR (400 MHz, CDCl$_3$) ppm 1.86-1.98 (m, 1H) 2.11 (m, 1H) 2.53 (s, 3H) 3.25 (dd, J=11.3, 9.8 Hz, 1H) 3.50 (td, J=11.9, 2.2 Hz, 1H) 3.70 (td, J=9.4, 4.9 Hz, 1H) 3.98-4.07 (m, 2H) 4.12 (dd, J=11.5, 4.9 Hz, 1H) 5.54 (s, 2H) 6.91-7.05 (m, 5H) 8.06 (br. s., 1H) 8.36 (d, J=4.9 Hz, 1H) 9.43 (d, J=5.6 Hz, 1H)

Example 83: 1-(4-Methoxybenzyl)-N-(trans-3-hydroxytetrahydro-2H-pyran-4-yl)-7-methyl-1H-pyrrolo[3,2-b]pyridine-3-carboxamide To a solution of tert-butyl 3-((trans-3-hydroxytetrahydro-2H-pyran-4-yl)carbamoyl)-7-methyl-1H-pyrrolo[3,2-b]pyridine-1-carboxylate (Intermediate 74), (72 mg) in DCM (5 mL) stirred at rt under nitrogen was added TFA (5 mL) and the reaction was stirred at rt for 1.5 h. The reaction was concentrated under vacuum and the residue was dissolved in MeOH (5 mL) and loaded onto an SCX cartridge, washing with MeOH (5 CV) and eluting with 2M NH3/MeOH (10 CV). The ammonia-containing fractions were combined and concentrated under vacuum. The residue was dissolved in DMF (1.9 mL) and the resultant solution was stirred at rt under nitrogen. To this solution was added 1-(bromomethyl)-4-methoxybenzene (39 mg) and Cs$_2$CO$_3$ (144 mg) and the reaction was stirred at rt under nitrogen overnight. The solid was filtered and the filtrate was concentrated under vacuum. The residue was purified by column chromatography (normal phase, Biotage SNAP cartridge KP-Sil, gradient 20% to 100% EtOAc in n-hexane, followed by 0-10% Methanol in EtOAc). Chiral chromatographic separation of the major eluting peak using preparative IE column (i.d. 20 mm; length 250 mm) and 96% DCM, 4% EtOH (v/v) as eluent, injection volume: 1500 microL, flow rate: 18.0 mL/min, oven temperature: 30 C, afforded the two major eluting peaks.

The first eluting peak afforded 1-(4-methoxybenzyl)-N-(trans-3-hydroxytetrahydro-2H-pyran-4-yl)-7-methyl-1H-pyrrolo[3,2-b]pyridine-3-carboxamide, a single enantiomer of trans relative stereochemistry but unknown absolute configuration, (10 mg).

Specific optical rotation [α]$_D$: +37.4 (25° C., MeOH)
LCMS: m/z 396.62 [M+H]$^+$.

$^1$H NMR (400 MHz, CDCl$_3$) ppm 1.93 (d, J=9.1 Hz, 1H) 2.10-2.14 (m, 1H) 2.56-2.61 (m, 3H) 3.25 (t, J=10.6 Hz, 1H) 3.49 (t, J=11.6 Hz, 1H) 3.73 (br. s., 1H) 3.76 (br. s., 1H) 3.79 (s, 3H) 3.99-4.06 (m, 2H) 4.12 (dd, J=11.2, 4.7 Hz, 1H) 5.52 (s, 2H) 6.85 (d, J=8.8 Hz, 2H) 6.91 (d, J=8.5 Hz, 2H) 6.96 (br. s., 1H) 8.04 (br. s., 1H) 8.37 (br. S., 1H) 9.44 (br. s., 1H)

Example 84: 1-(3-Fluoro-4-methoxybenzyl)-N-(trans-3-hydroxytetrahydro-2H-pyran-4-yl)-7-methyl-1H-pyrrolo[3,2-b]pyridine-3-carboxamide To a solution of tert-butyl 3-((trans-3-hydroxytetrahydro-2H-pyran-4-yl)carbamoyl)-7-methyl-1H-pyrrolo[3,2-b]pyridine-1-carboxylate (Intermediate 74), (72 mg)), in DCM (5 mL) stirred at rt under nitrogen was added TFA (5 mL) and the reaction was stirred at rt for 1.5 h. The reaction was concentrated under vacuum and the residue was dissolved in MeOH (5 mL) and loaded onto an SCX cartridge, washing with MeOH (5 CV) and eluting with 2M NH3/MeOH (10 CV). The ammonia-containing fractions were combined and reduced in vacuo. The residue was dissolved in DMF (1.9 mL) and the resultant solution was stirred at rt under nitrogen. To this solution was added 4-(bromomethyl)-2-fluoro-1-methoxybenzene (42.0 mg,) and Cs$_2$CO$_3$ (144 mg) and the reaction was stirred at rt under nitrogen overnight. The solid was filtered and the filtrate was concentrated under reduced pressure and purified by column chromatography (normal phase, Biotage SNAP cartridge KP-Sil, gradient 20% to 100% EtOAc in n-hexane, followed by 0-10% Methanol in EtOAc). The major peak to elute was subjected to chiral chromatographic separation using preparative IE column (i.d. 20 mm; length 250 mm) and 97% DCM, 3%

EtOH (v/v) as eluent, injection volume: 1500 microL, flow rate: 18.0 mL/min, oven temperature: 30° C., which afforded the two major eluting peaks.

The first eluting peak afforded 1-(3-fluoro-4-methoxybenzyl)-N-(trans-3-hydroxytetrahydro-2H-pyran-4-yl)-7-methyl-1H-pyrrolo[3,2-b]pyridine-3-carboxamide, a single enantiomer of trans relative stereochemistry but unknown absolute configuration, (19 mg).

Specific optical rotation $[\alpha]_D$: +31.5 (25° C., MeOH)
LCMS: m/z 414.59 $[M+H]^+$.
$^1$H NMR (400 MHz, CDCl$_3$): ppm 1.93 (td, J=12.4, 4.7 Hz, 1H) 2.08-2.16 (m, 1H) 2.54 (s, 3H) 3.25 (dd, J=11.1, 10.2 Hz, 1H) 3.49 (td, J=11.8, 2.1 Hz, 1H) 3.70 (td, J=9.4, 4.9 Hz, 1H) 3.86-3.88 (m, 3H) 3.96-4.06 (m, 2H) 4.11 (dd, J=11.6, 5.3 Hz, 1H) 5.48 (s, 2H) 6.64 (d, J=8.6 Hz, 1H) 6.71 (d, J=11.7 Hz, 1H) 6.89 (d, J=11.7 Hz, 1H) 6.93 (d, J=8.6 Hz, 1H) 8.05 (br. s., 1H) 8.36 (d, J=4.9 Hz, 1H) 9.42 (d, J=5.6 Hz, 1H)

Example 85: N-(trans-3-Hydroxytetrahydro-2H-pyran-4-yl)-1-((2-methoxypyridin-4-yl)methyl)-7-methyl-1H-pyrrolo[3,2-b]pyridine-3-carboxamide To a solution of tert-butyl 3-((trans-3-hydroxytetrahydro-2H-pyran-4-yl)carbamoyl)-7-methyl-1H-pyrrolo[3,2-b]pyridine-1-carboxylate (Intermediate 74), (74 mg) in DCM (5 mL) stirred at rt under nitrogen was added TFA (5 mL) and the reaction was stirred at rt for 1.5 h. The reaction was concentrated under vacuum and the residue was dissolved in MeOH (5 mL) and loaded onto an SCX cartridge, washing with MeOH (5 CV) and eluting with 2M NH3/MeOH (10 CV). The ammonia-containing fractions were combined and concentrated under vacuum. The residue was dissolved in DMF (1.9 mL) and the resultant solution was stirred at rt under nitrogen. To this solution was added 4-(chloromethyl)-2-methoxypyridine (31 mg) and Cs$_2$CO$_3$ (148 mg) and the reaction was stirred at rt under nitrogen overnight. The solid was filtered and the filtrate was concentrated under vacuum and purified by column chromatography (normal phase, Biotage SNAP cartridge KP-Sil, gradient 0% to 100% EtOAc in n-hexane, followed by 0-10% Methanol in EtOAc). Chiral chromatographic separation using preparative IE column (i.d. 20 mm; length 250 mm) and 98% DCM, 2% EtOH (v/v) as eluent, injection volume: 1500 microL, flow rate: 18.0 mL/min, oven temperature: 30° C., afforded the two major eluting peaks.

The first eluting peak afforded N-(trans-3-hydroxytetrahydro-2H-pyran-4-yl)-1-((2-methoxypyridin-4-yl)methyl)-7-methyl-1H-pyrrolo[3,2-b]pyridine-3-carboxamide, a single enantiomer of trans relative stereochemistry but unknown absolute configuration, (25 mg).

LCMS: m/z 397.58 $[M+H]^+$.
Specific optical rotation $[\alpha]_D$: +38.0 (25° C., MeOH)
$^1$H NMR (400 MHz, CDCl$_3$) ppm 1.92 (qd, J=12.2, 4.4 Hz, 1H) 2.11-2.15 (m, 1H) 2.50-2.54 (m, 3H) 3.26 (t, J=10.6 Hz, 1H) 3.48-3.53 (m, 1H) 3.71-3.77 (m, 1H) 3.90 (s, 3H) 4.00-4.06 (m, 2H) 4.12 (dd, J=11.3, 4.8 Hz, 1H) 5.53 (s, 2H) 6.20 (s, 1H) 6.49 (d, J=5.3 Hz, 1H) 6.95-7.00 (m, 1H) 8.12 (d, J=5.3 Hz, 1H) 8.40 (d, J=4.4 Hz, 1H) 9.40 (d, J=4.7 Hz, 1H)

Example 86: 7-Chloro-1-(3-fluorobenzyl)-N-(trans-3-hydroxytetrahydro-2H-pyran-4-yl)-1H-pyrrolo[3,2-b]pyridine-3-carboxamide To a solution of tert-butyl 7-chloro-3-((trans-3-hydroxytetrahydro-2H-pyran-4-yl)carbamoyl)-1H-pyrrolo[3,2-b]pyridine-1-carboxylate (Intermediate 75), (112 mg) in DCM (5 mL) stirred at rt under nitrogen was added TFA (5 mL) and the reaction was stirred at rt for 1.5 h. The reaction was concentrated under vacuum and the residue was dissolved in MeOH (5 mL) and loaded onto an SCX cartridge, washing with MeOH (5 CV) and eluting with 2M NH3/MeOH (10 CV). The ammonia-containing fractions were combined and reduced in vacuo. The residue was dissolved in DMF (2.74 mL) and the resultant solution was stirred at rt under nitrogen. To this solution was added 1-(chloromethyl)-3-fluorobenzene (38.9 mg) and Cs$_2$CO$_3$ (212 mg) and the reaction was stirred at rt under nitrogen overnight. The solid was filtered and the filtrate was concentrated under vacuum and purified by column chromatography (normal phase, Biotage SNAP cartridge KP-Sil, gradient 20% to 100% EtOAc in n-hexane, followed by 0-10% Methanol in EtOAc). Chiral chromatographic separation of the major eluting peak using preparative IE column (i.d. 20 mm; length 250 mm) and 97% DCM, 3% EtOH (v/v) as eluent, injection volume: 1500 microL, flow rate: 18.0 mL/min, oven temperature: 30° C., afforded the two major eluting peaks.

The first eluting peak afforded 7-chloro-1-(3-fluorobenzyl)-N-(trans-3-hydroxytetrahydro-2H-pyran-4-yl)-1H-pyrrolo[3,2-b]pyridine-3-carboxamide, a single enantiomer of trans relative stereochemistry but unknown absolute configuration, (18 mg). Specific optical rotation $[\alpha]_D$: +39.2 (25° C., MeOH)

LCMS: m/z 404.53 $[M+H]^+$.
$^1$H NMR (400 MHz, CDCl$_3$) ppm 1.83-1.95 (m, 1H) 2.09 (m, 1H) 3.24 (dd, J=11.4, 9.9 Hz, 1H) 3.48 (td, J=11.9, 2.2 Hz, 1H) 3.70 (td, J=9.5, 5.0 Hz, 1H) 3.95-4.05 (m, 2H) 4.10 (dd, J=11.6, 4.8 Hz, 1H) 5.72 (s, 2H) 6.73-6.79 (m, 1H) 6.85 (d, J=7.6 Hz, 1H) 7.00 (td, J=8.4, 2.0 Hz, 1H) 7.23 (d, J=5.4 Hz, 1H) 7.30 (td, J=8.0, 5.9 Hz, 1H) 8.18 (s, 1H) 8.42 (d, J=5.4 Hz, 1H) 9.16 (d, J=5.9 Hz, 1H)

Example 87: 7-Chloro-1-(4-methoxybenzyl)-N-(trans-3-hydroxytetrahydro-2H-pyran-4-yl)-1H-pyrrolo[3,2-b]pyridine-3-carboxamide To a solution of tert-butyl 7-chloro-3-((trans-3-hydroxytetrahydro-2H-pyran-4-yl)carbamoyl)-1H-pyrrolo[3,2-b]pyridine-1-carboxylate (Intermediate 75), (100 mg) in DCM (5 mL) stirred at rt under nitrogen was added TFA (5 mL) and the reaction was stirred at rt for 1.5 h. The reaction was concentrated under vacuum and the residue was dissolved in MeOH (5 mL) and loaded onto an SCX cartridge, washing with MeOH (5 CV) and eluting with 2M NH3/MeOH (10 CV). The ammonia-containing fractions were combined and reduced in vacuo. The residue was dissolved in DMF (2.45 mL) and the resultant solution was stirred at rt under nitrogen. To this solution was added 1-(chloromethyl)-4-methoxybenzene (39.6 mg) and Cs$_2$CO$_3$ (189 mg) and the reaction was stirred at rt under nitrogen overnight. The solid was filtered and the filtrate was concentrated under vacuum and purified by column chromatography (normal phase, Biotage SNAP cartridge KP-Sil, gradient 20% to 100% EtOAc in n-hexane, followed by 0-10% Methanol in EtOAc). Chiral chromatographic separation of the major eluting peak using preparative IE column (i.d. 20 mm; length 250 mm) and 97% DCM, 3% EtOH (v/v) as eluent, injection volume: 1500 microL, flow rate: 18.0 mL/min, oven temperature: 30° C., afforded the two major eluting peaks.

The first eluting peak afforded 7-chloro-1-(4-methoxybenzyl)-N-(trans-3-hydroxytetrahydro-2H-pyran-4-yl)-1H- pyrrolo[3,2-b]pyridine-3-carboxamide, a single enantiomer of trans relative stereochemistry but unknown absolute configuration, (17 mg). Specific optical rotation [α]$_D$: +38.3 (25° C., MeOH)

LCMS: m/z 416.54 [M+H]$^+$.

$^1$H NMR (400 MHz, CDCl$_3$) ppm 1.83-1.96 (m, 1H) 2.09 (m, 1H) 3.24 (dd, J=11.3, 9.8 Hz, 1H) 3.49 (td, J=11.9, 2.5 Hz, 1H) 3.69 (td, J=9.5, 5.0 Hz, 1H) 3.79-3.81 (m, 3H) 3.95-4.05 (m, 2H) 4.11 (dd, J=11.5, 4.9 Hz, 1H) 5.67 (s, 2H) 6.85-6.90 (m, 2H) 7.08 (s, 1H) 7.10 (d, J=7.7 Hz, 1H) 7.23 (d, J=7.7 Hz, 1H) 8.12 (s, 1H) 8.38 (d, J=5.4 Hz, 1H) 9.18 (d, J=5.6 Hz, 1H)

Example 88: 7-Chloro-1-(4-fluorobenzyl)-N-((3R,4S)-3-hydroxytetrahydro-2H-pyran-4-yl)-1H-pyrrolo[3,2-b]pyridine-3-carboxamide A mixture of 7-chloro-N-((3R,4S)-3-hydroxytetrahydro-2H-pyran-4-yl)-1H-pyrrolo[3,2-b]pyridine-3-carboxamide (Intermediate 78), (70 mg), 4-fluorobenzyl bromide (49 mg) and cesium carbonate (193 mg) in DMF (3 mL) was stirred at rt overnight. The reaction mixture was filtered thought Celite and concentrated in vacuo. The residue was triturated with small amount of MeOH to afford the desired compound (71 mg).

LCMS: m/z 404.11 [M+H]$^+$.

$^1$H NMR (400 MHz, DMSO-d$_6$) ppm 1.61 (d, J=10.9 Hz, 1H) 1.80-1.95 (m, 1H) 3.42 (t, J=10.5 Hz, 1H) 3.51 (d, J=11.9 Hz, 1H) 3.64 (br. s., 1H) 3.68-3.83 (m, 2H) 4.14 (br. s., 1H) 5.13 (br. s., 1H) 5.77 (s, 2H) 7.04-7.17 (m, 4H) 7.35 (d, J=5.1 Hz, 1H) 8.41 (d, J=5.1 Hz, 1H) 8.50 (s, 1H) 8.97 (d, J=8.0 Hz, 1H)

Example 89: 7-Chloro-1-(4-fluorobenzyl)-N-((3S,4R)-3-hydroxytetrahydro-2H-pyran-4-yl)-1H-pyrrolo[3,2-b]pyridine-3-carboxamide A mixture of 7-chloro-N-((3S,4R)-3-hydroxytetrahydro-2H-pyran-4-yl)-1H-pyrrolo[3,2-b]pyridine-3-carboxamide (Intermediate 80), (77 mg), 4-fluorobenzyl bromide (54 mg) and cesium carbonate (212 mg) in DMF (3 mL) was stirred at rt overnight. The reaction mixture was filtered thought Celite and concentrated in vacuo. The residue was triturated with small amount of MeOH to afford the desired compound (57 mg).

LCMS: m/z 404.15 [M+H]$^+$.

$^1$H NMR (400 MHz, DMSO-d$_6$) ppm 1.61 (d, J=11.3 Hz, 1H) 1.87 (d, J=8.4 Hz, 1H) 3.38-3.47 (m, 1H) 3.51 (d, J=11.3 Hz, 1H) 3.64 (br. s., 1H) 3.68-3.82 (m, 2H) 4.14 (br. s., 1H) 5.15 (br. s., 1H) 5.77 (br. s., 2H) 7.04-7.18 (m, 4H) 7.35 (d, J=4.5 Hz, 1H) 8.41 (d, J=4.7 Hz, 1H) 8.50 (br. s., 1H) 8.97 (d, J=8.0 Hz, 1H)

Examples 90-105

The following Examples 90-105 were prepared by methods according or analogous to those described herein above;

Example 90

N-((1S,2S)-2-hydroxycyclohexyl)-1-(4-(trifluoromethyl)benzyl)-1H-pyrrolo[3,2-b]pyridine-3-carboxamide; LCMS: m/z 418.1 [M+H]$^+$.

Example 91

1-(4-fluoro-3-methoxybenzyl)-N-((1S,2S)-2-hydroxycyclohexyl)-1H-pyrrolo[3,2-b]pyridine-3-carboxamide; LCMS: m/z 398.23 [M+H]$^+$.

Example 92

1-(2-fluoro-4-methoxybenzyl)-N-((1S,2S)-2-hydroxycyclohexyl)-1H-pyrrolo[3,2-b]pyridine-3-carboxamide; LCMS: m/z 398.1 [M+H]$^+$.

Example 93

N-((1S,2S)-2-hydroxycyclohexyl)-1-(4-methoxybenzyl)-1H-pyrrolo[3,2-b]pyridine-3-carboxamide; LCMS: m/z 380.18 [M+H]$^+$.

Example 94

1-(3,4-difluorobenzyl)-N-((1S,2S)-2-hydroxycyclohexyl)-1H-pyrrolo[3,2-b]pyridine-3-carboxamide; LCMS: m/z 486.59 [M+H]$^+$.

Example 95

N-((1S,2S)-2-hydroxycyclohexyl)-1-(3-(trifluoromethyl)benzyl)-1H-pyrrolo[3,2-b]pyridine-3-carboxamide; LCMS: m/z 418.60 [M+H]$^+$.

Example 96

N-((1S,2S)-2-hydroxycyclohexyl)-1-(3-methylbenzyl)-1H-pyrrolo[3,2-b]pyridine-3-carboxamide; LCMS: m/z 364.65 [M+H]$^+$.

Example 97

1-(2-fluoro-4-methylbenzyl)-N-((1S,2S)-2-hydroxycyclohexyl)-1H-pyrrolo[3,2-b]pyridine-3-carboxamide; LCMS: m/z 382.60 [M+H]$^+$.

Example 98

1-(2,5-difluorobenzyl)-N-((1S,2S)-2-hydroxycyclohexyl)-7-methyl-1H-pyrrolo[3,2-b]pyridine-3-carboxamide; LCMS: m/z 400.60 [M+H]$^+$.

Example 99

7-chloro-N-((1S,2S)-2-hydroxycyclohexyl)-1-(4-(trifluoromethoxy)benzyl)-1H-pyrrolo[3,2-b]pyridine-3-carboxamide; LCMS: m/z 468.57 [M+H]$^+$.

Example 100

N-((1S,2S)-2-hydroxycyclohexyl)-7-methyl-1-(4-(trifluoromethoxy)benzyl)-1H-pyrrolo[3,2-b]pyridine-3-carboxamide; LCMS: m/z 448.64 [M+H]$^+$.

Example 101

1-(3,5-difluorobenzyl)-N-((1S,2S)-2-hydroxycyclohexyl)-7-methyl-1H-pyrrolo[3,2-b]pyridine-3-carboxamide; LCMS: m/z 400.62 [M+H]$^+$.

Examples 102

1-(2-fluoro-3-methoxybenzyl)-N-((1S,2S)-2-hydroxycyclohexyl)-1H-pyrrolo[3,2-b]pyridine-3-carboxamide; LCMS: m/z 398.66 [M+H]$^+$.

Example 103

N-((1S,2S)-2-hydroxycyclohexyl)-1-(4-methoxy-3-methylbenzyl)-1H-pyrrolo[3,2-b]pyridine-3-carboxamide; LCMS: m/z 394.69.15 [M+H]$^+$.

Examples 104

1-(2,3-difluorobenzyl)-N-((1S,2S)-2-hydroxycyclohexyl)-7-methoxy-1H-pyrrolo[3,2-b]pyridine-3-carboxamide; LCMS: m/z 416.65 [M+H]$^+$.

Example 105

N-((1S,2S)-2-hydroxycyclohexyl)-7-methoxy-1-(4-methoxybenzyl)-1H-pyrrolo[3,2-b]pyridine-3-carboxamide; LCMS: m/z 410.70 [M+H]$^+$.

The chemical structures of Examples 1-105 are depicted in Table 1

TABLE 1

| Example | Structure |
|---|---|
| 1 | 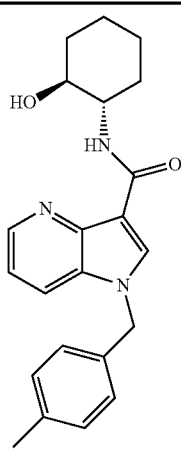 |
| 2 | 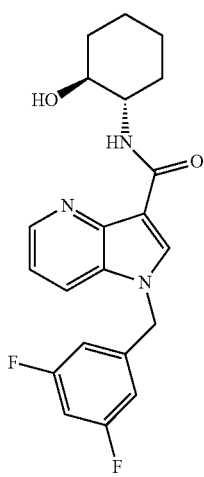 [SMILES: O=C(N[C@H]1CCCC[C@@H]1O)c1cn(Cc2cc(F)cc(F)c2)c2cccnc12] |
| 3 | 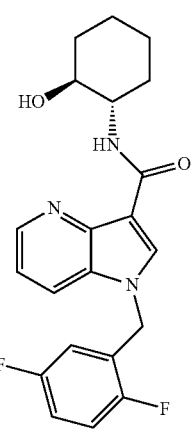 |
| 4 | 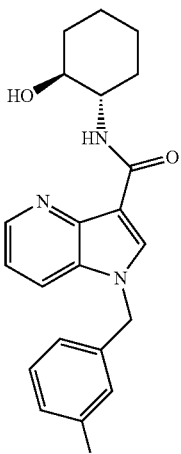 |
| 5 | 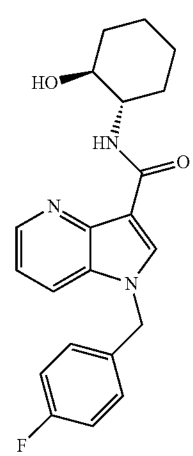 [SMILES: O=C(N[C@H]1CCCC[C@@H]1O)c1cn(Cc2ccc(F)cc2)c2cccnc12] |

TABLE 1-continued
| Example | Structure |
|---|---|
| 6 | 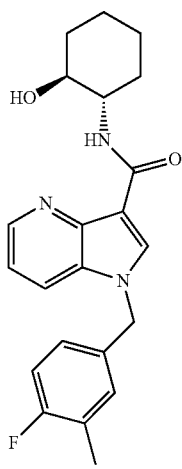 [SMILES: Cc1cc(Cn2cc(C(=O)N[C@H]3CCCC[C@@H]3O)c3ncccc32)ccc1F] |
| 7 | 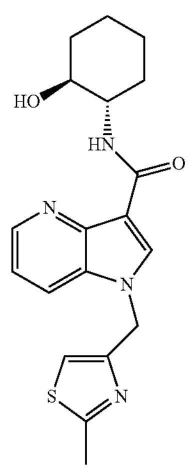 [SMILES: Cc1nc(Cn2cc(C(=O)N[C@H]3CCCC[C@@H]3O)c3ncccc32)cs1] |
| 8 | 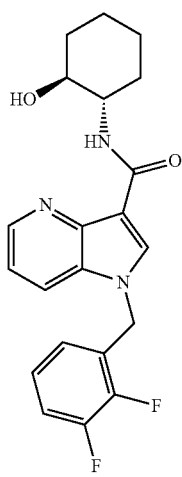 [SMILES: O=C(N[C@H]1CCCC[C@@H]1O)c1cn(Cc2cccc(F)c2F)c2cccnc12] |
| 9 | 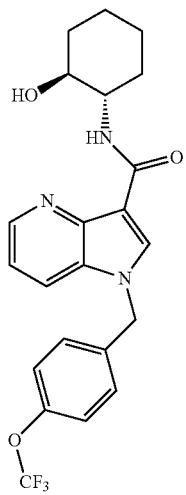 [SMILES: O=C(N[C@H]1CCCC[C@@H]1O)c1cn(Cc2ccc(OC(F)(F)F)cc2)c2cccnc12] |
| 10 | 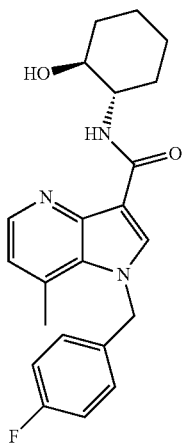 [SMILES: Cc1ccnc2c(C(=O)N[C@H]3CCCC[C@@H]3O)cn(Cc3ccc(F)cc3)c12] |
| 11 | 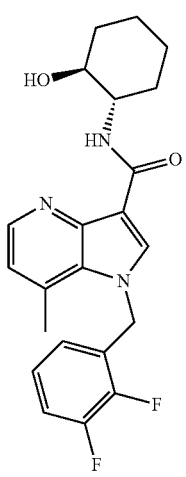 [SMILES: Cc1ccnc2c(C(=O)N[C@H]3CCCC[C@@H]3O)cn(Cc3cccc(F)c3F)c12] |

TABLE 1-continued
| Example | Structure |
|---|---|
| 12 | 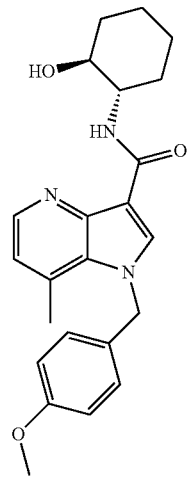 [SMILES: COc1ccc(Cn2cc(C(=O)N[C@H]3CCCC[C@@H]3O)c3nccc(C)c32)cc1] |
| 13 | 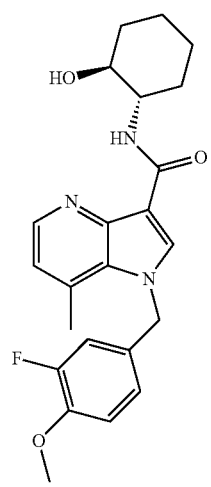 [SMILES: COc1ccc(Cn2cc(C(=O)N[C@H]3CCCC[C@@H]3O)c3nccc(C)c32)cc1F] |
| 14 | 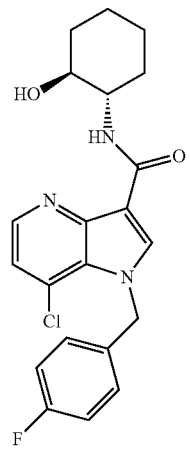 [SMILES: O=C(N[C@H]1CCCC[C@@H]1O)c1cn(Cc2ccc(F)cc2)c2c(Cl)ccnc12] |
| 15 | 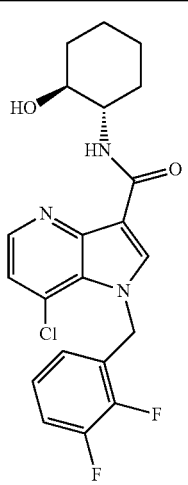 |
| 16 | 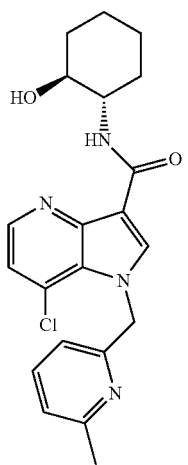 [SMILES: Cc1cccc(Cn2cc(C(=O)N[C@H]3CCCC[C@@H]3O)c3nccc(Cl)c32)n1] |
| 17 | 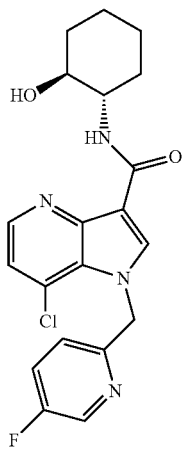 [SMILES: O=C(N[C@H]1CCCC[C@@H]1O)c1cn(Cc2ccc(F)cn2)c2c(Cl)ccnc12] |

TABLE 1-continued
| Example | Structure |
|---|---|
| 18 | 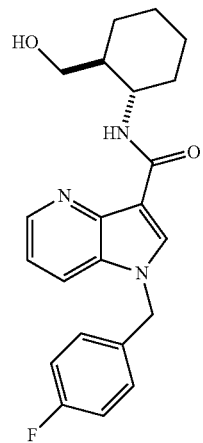 |
| 19 | 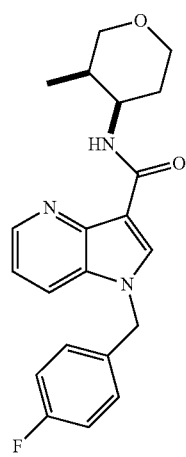 |
| 20 | 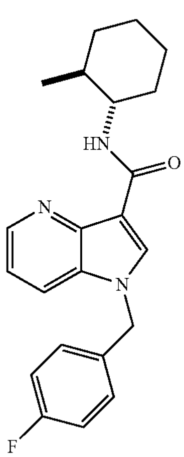 |
| 21 | 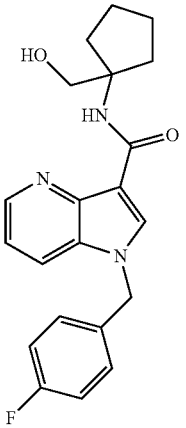 [SMILES: O=C(NC1(CO)CCCC1)c1cn(Cc2ccc(F)cc2)c2cccnc12] |
| 22 | 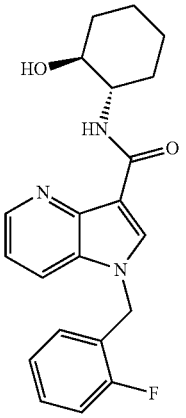 [SMILES: O=C(N[C@H]1CCCC[C@@H]1O)c1cn(Cc2ccccc2F)c2cccnc12] |
| 23 | 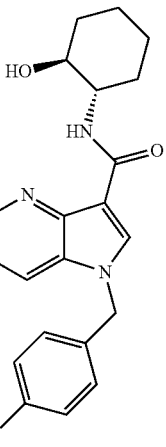 |

TABLE 1-continued
| Example | Structure |
|---|---|
| 24 | 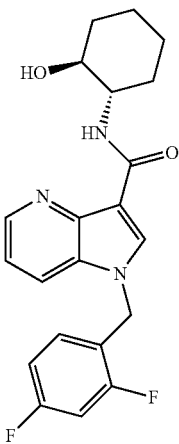 [SMILES: O=C(N[C@H]1CCCC[C@@H]1O)c1cn(Cc2ccc(F)cc2F)c2cccnc12] |
| 25 | 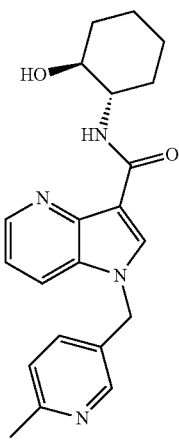 [SMILES: Cc1ccc(Cn2cc(C(=O)N[C@H]3CCCC[C@@H]3O)c3ncccc32)cn1] |
| 26 | 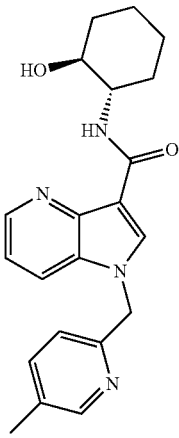 [SMILES: Cc1ccc(Cn2cc(C(=O)N[C@H]3CCCC[C@@H]3O)c3ncccc32)nc1] |
| 27 | 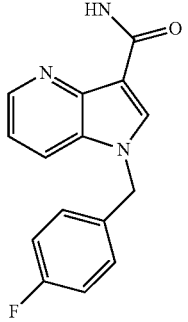 |
| 28 |  |
| 29 | 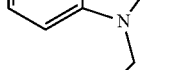 |

TABLE 1-continued
| Example | Structure |
|---|---|
| 30 | 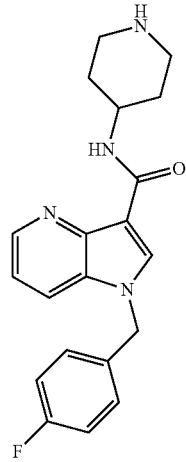 [SMILES: O=C(NC1CCNCC1)c1cn(Cc2ccc(F)cc2)c2cccnc12] |
| 31 | 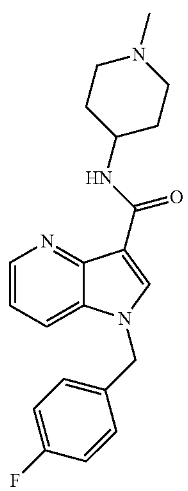 [SMILES: CN1CCC(NC(=O)c2cn(Cc3ccc(F)cc3)c3cccnc23)CC1] |
| 32 | 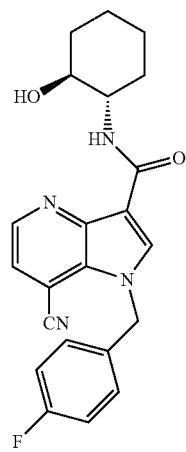 [SMILES: N#Cc1ccnc2c(C(=O)N[C@H]3CCCC[C@@H]3O)cn(Cc3ccc(F)cc3)c12] |
| 33 | 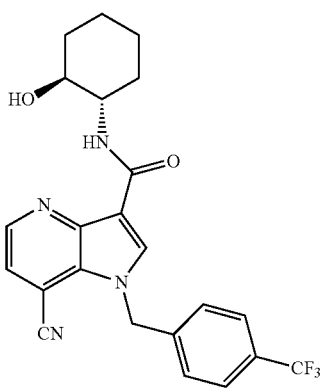 [SMILES: N#Cc1ccnc2c(C(=O)N[C@H]3CCCC[C@@H]3O)cn(Cc3ccc(C(F)(F)F)cc3)c12] |
| 34 | 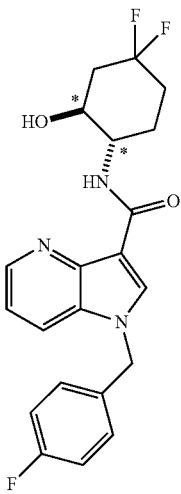 |
| 35 | 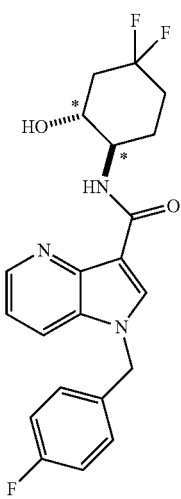 |

TABLE 1-continued
| Example | Structure |
|---|---|
| 36 | 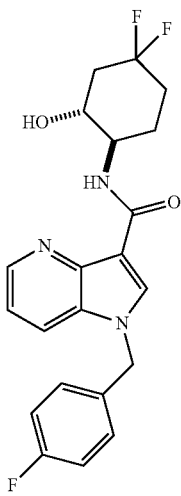 |
| 37 | 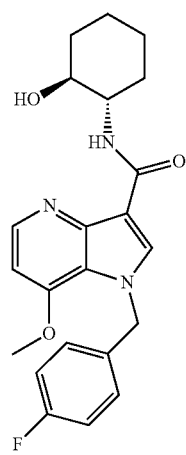 [SMILES: COc1ccnc2c(C(=O)N[C@H]3CCCC[C@@H]3O)cn(Cc3ccc(F)cc3)c12] |
| 38 | 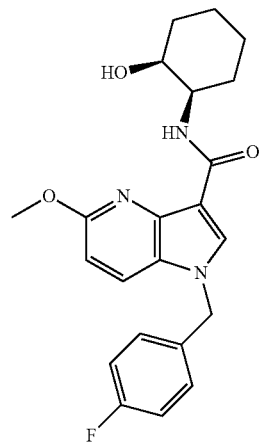 [SMILES: COc1ccc2c(n1)c(C(=O)N[C@@H]1CCCC[C@@H]1O)cn2Cc1ccc(F)cc1] |
| 39 | 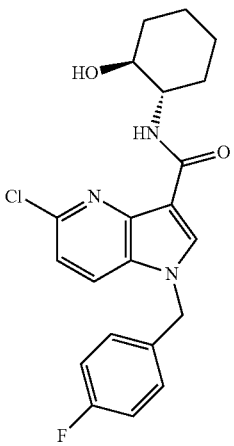 [SMILES: O=C(N[C@H]1CCCC[C@@H]1O)c1cn(Cc2ccc(F)cc2)c2ccc(Cl)nc12] |
| 40 | 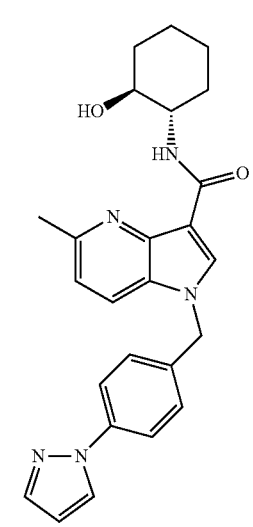 [SMILES: Cc1ccc2c(n1)c(C(=O)N[C@H]1CCCC[C@@H]1O)cn2Cc1ccc(-n2cccn2)cc1] |
| 41 | 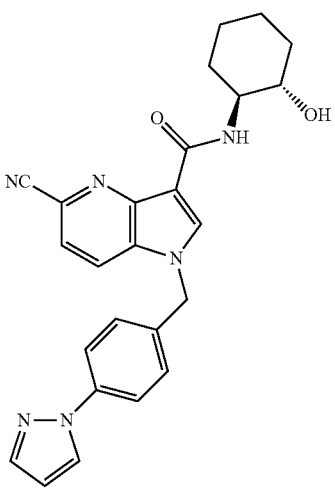 [SMILES: N#Cc1ccc2c(n1)c(C(=O)N[C@H]1CCCC[C@@H]1O)cn2Cc1ccc(-n2cccn2)cc1] |

TABLE 1-continued
| Example | Structure |
|---|---|
| 42 | 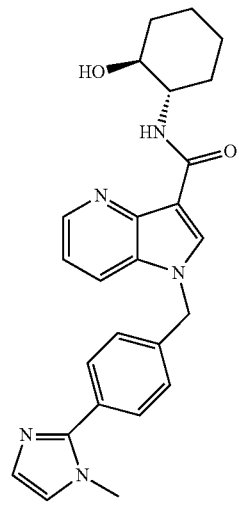 [SMILES: Cn1ccnc1-c1ccc(Cn2cc(C(=O)N[C@H]3CCCC[C@@H]3O)c3ncccc32)cc1] |
| 43 | 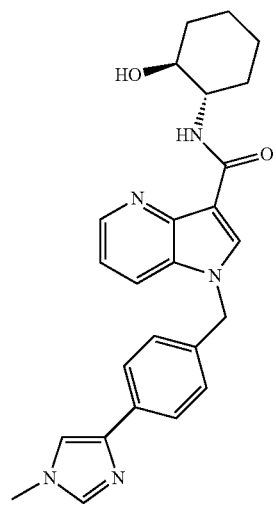 [SMILES: Cn1cnc(-c2ccc(Cn3cc(C(=O)N[C@H]4CCCC[C@@H]4O)c4ncccc43)cc2)c1] |
| 44 | 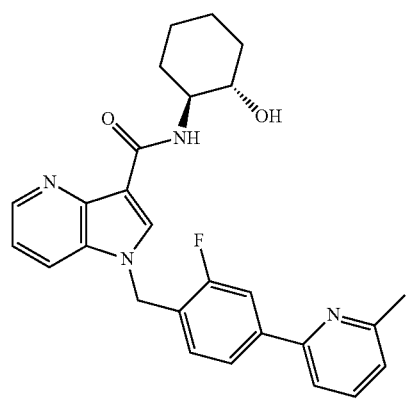 [SMILES: Cc1cccc(-c2ccc(Cn3cc(C(=O)N[C@H]4CCCC[C@@H]4O)c4ncccc43)c(F)c2)n1] |
| 45 | 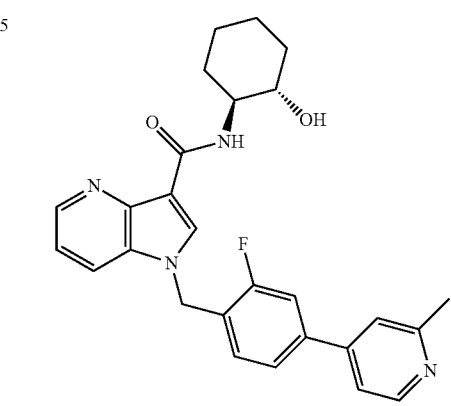 |
| 46 | 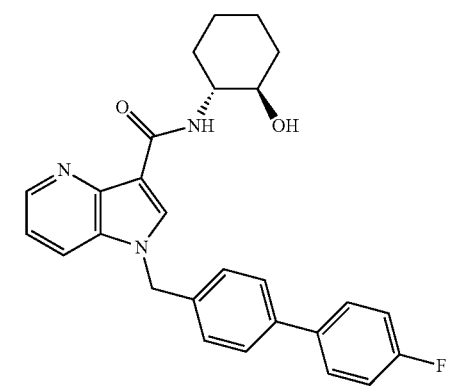 [SMILES: O=C(N[C@@H]1CCCC[C@H]1O)c1cn(Cc2ccc(-c3ccc(F)cc3)cc2)c2cccnc12] |
| 47 | 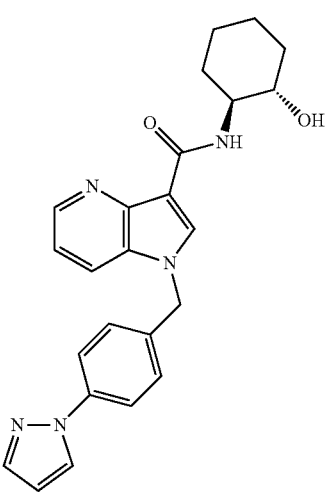 [SMILES: O=C(N[C@H]1CCCC[C@@H]1O)c1cn(Cc2ccc(-n3cccn3)cc2)c2cccnc12] |

TABLE 1-continued

| Example | Structure |
|---|---|
| 48 | 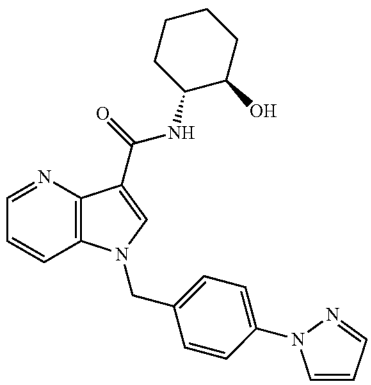 [SMILES: O=C(N[C@@H]1CCCC[C@H]1O)c1cn(Cc2ccc(-n3cccn3)cc2)c2cccnc12] |
| 49 | 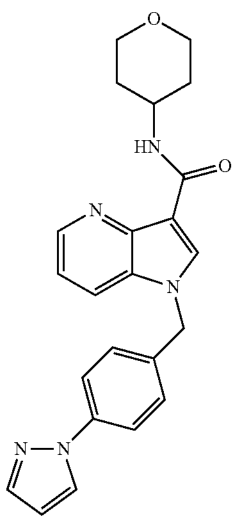 [SMILES: O=C(NC1CCOCC1)c1cn(Cc2ccc(-n3cccn3)cc2)c2cccnc12] |
| 50 | 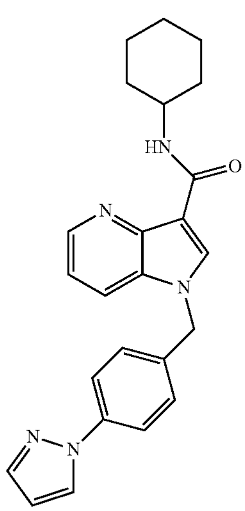 [SMILES: O=C(NC1CCCCC1)c1cn(Cc2ccc(-n3cccn3)cc2)c2cccnc12] |
| 51 | |
| 52 | |
| 53 | |

TABLE 1-continued
| Example | Structure |
|---|---|
| 54 | 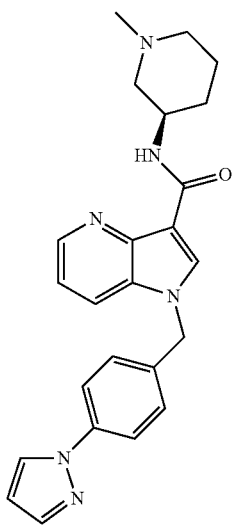 [SMILES: CN1CCC[C@@H](NC(=O)c2cn(Cc3ccc(-n4cccn4)cc3)c3cccnc23)C1] |
| 55 | 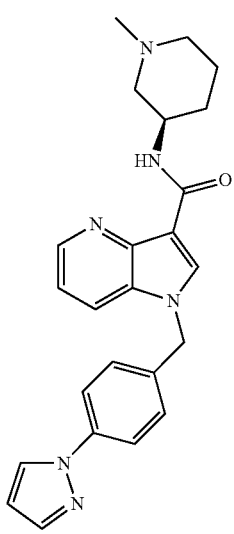 [SMILES: CN1CCC[C@@H](NC(=O)c2cn(Cc3ccc(-n4cccn4)cc3)c3cccnc23)C1] |
| 56 | 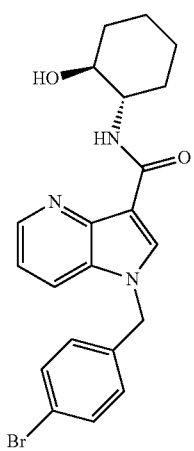 |
| 57 | 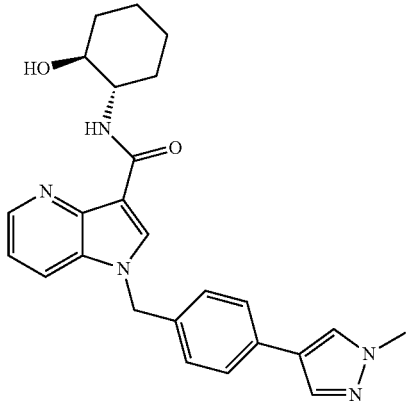 [SMILES: Cn1cc(-c2ccc(Cn3cc(C(=O)N[C@H]4CCCC[C@@H]4O)c4ncccc43)cc2)cn1] |
| 58 | 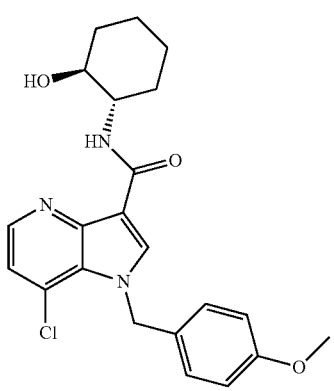 [SMILES: COc1ccc(Cn2cc(C(=O)N[C@H]3CCCC[C@@H]3O)c3nccc(Cl)c32)cc1] |
| 59 | 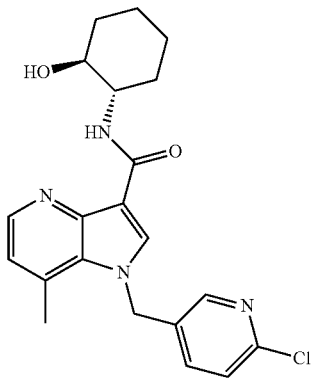 [SMILES: Cc1ccnc2c(C(=O)N[C@H]3CCCC[C@@H]3O)cn(Cc3ccc(Cl)nc3)c12] |
| 60 | 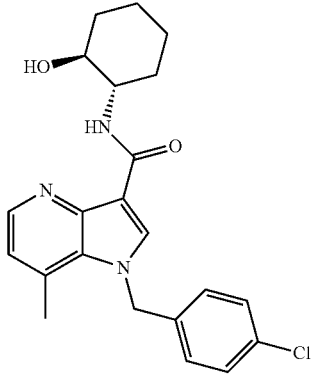 [SMILES: Cc1ccnc2c(C(=O)N[C@H]3CCCC[C@@H]3O)cn(Cc3ccc(Cl)cc3)c12] |

TABLE 1-continued
| Example | Structure |
|---|---|
| 61 | 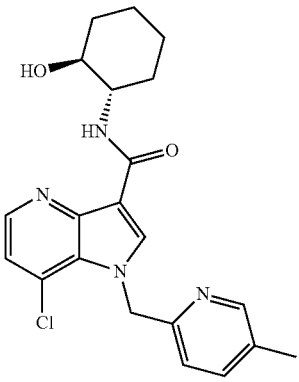 [SMILES: Cc1ccc(Cn2cc(C(=O)N[C@H]3CCCC[C@@H]3O)c3nccc(Cl)c32)nc1] |
| 62 | 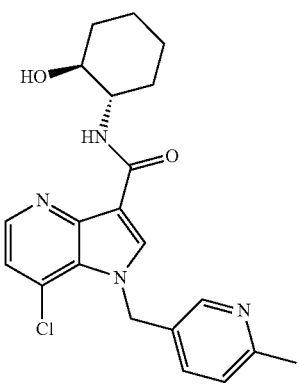 [SMILES: Cc1ccc(Cn2cc(C(=O)N[C@H]3CCCC[C@@H]3O)c3nccc(Cl)c32)cn1] |
| 63 | 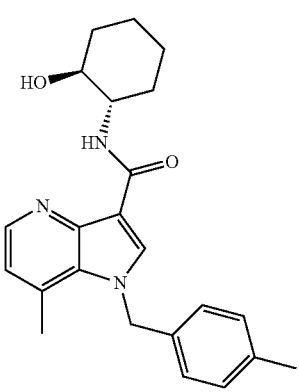 [SMILES: Cc1ccc(Cn2cc(C(=O)N[C@H]3CCCC[C@@H]3O)c3nccc(C)c32)cc1] |
| 64 | 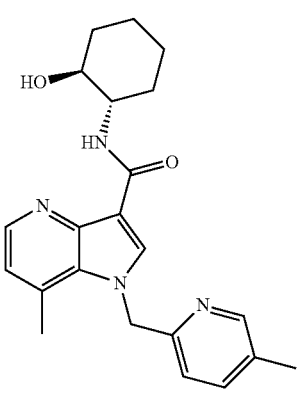 |
TABLE 1-continued
| Example | Structure |
|---|---|
| 65 | 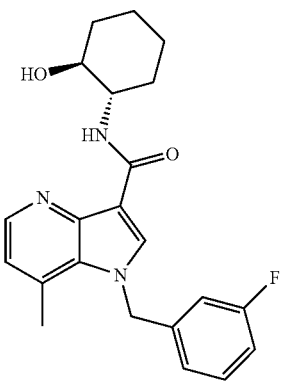 [SMILES: Cc1ccnc2c(C(=O)N[C@H]3CCCC[C@@H]3O)cn(Cc3cccc(F)c3)c12] |
| 66 | 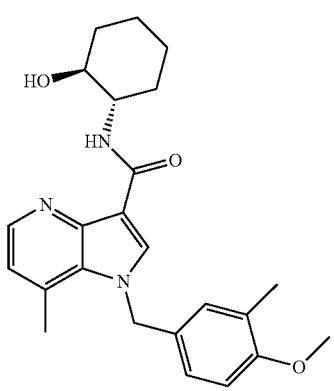 [SMILES: COc1ccc(Cn2cc(C(=O)N[C@H]3CCCC[C@@H]3O)c3nccc(C)c32)cc1C] |
| 67 | 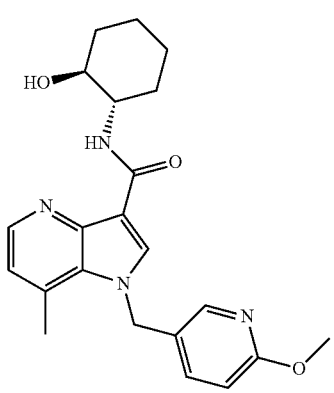 [SMILES: COc1ccc(Cn2cc(C(=O)N[C@H]3CCCC[C@@H]3O)c3nccc(C)c32)cn1] |
| 68 | 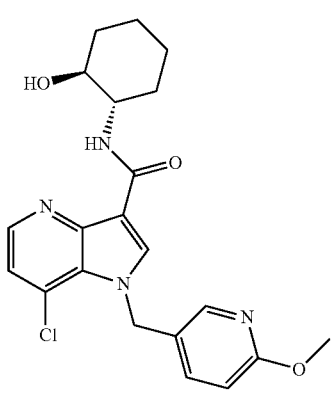 |

TABLE 1-continued
| Example | Structure |
|---------|-----------|
| 69 | 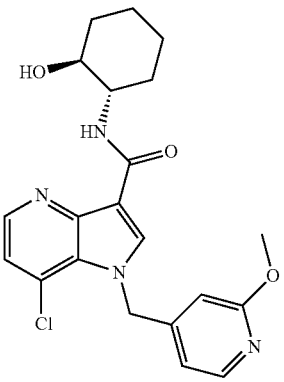 [SMILES: COc1cc(Cn2cc(C(=O)N[C@H]3CCCC[C@@H]3O)c3nccc(Cl)c32)ccn1] |
| 70 | 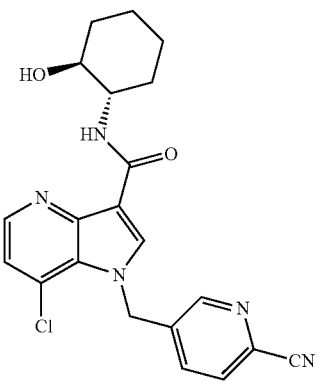 [SMILES: N#Cc1ccc(Cn2cc(C(=O)N[C@H]3CCCC[C@@H]3O)c3nccc(Cl)c32)cn1] |
| 71 | 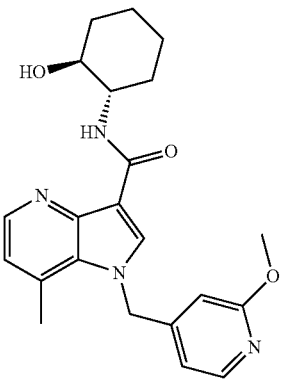 [SMILES: COc1cc(Cn2cc(C(=O)N[C@H]3CCCC[C@@H]3O)c3nccc(C)c32)ccn1] |
| 72 | 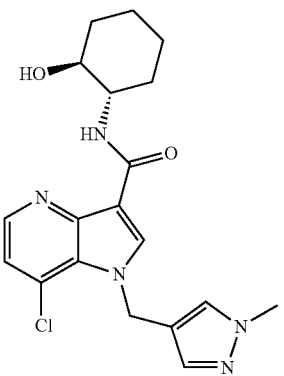 [SMILES: Cc1ccnc2c(C(=O)N[C@H]3CCCC[C@@H]3O)cn(Cc3cnn(C)c3)c12] |
TABLE 1-continued
| Example | Structure |
|---------|-----------|
| 73 | 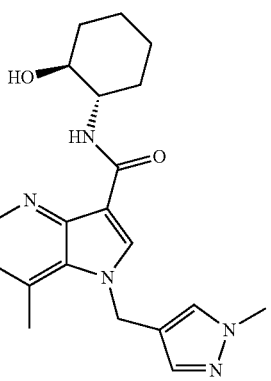 |
| 74 | 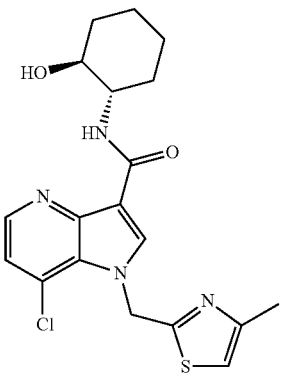 [SMILES: Cc1csc(Cn2cc(C(=O)N[C@H]3CCCC[C@@H]3O)c3nccc(Cl)c32)n1] |
| 75 | 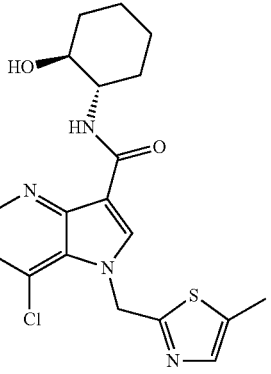 |
| 76 | 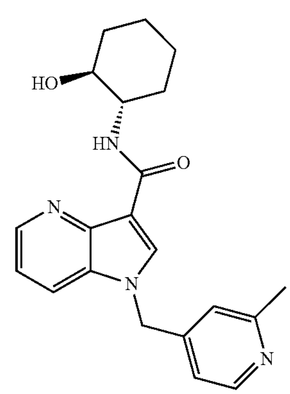 [SMILES: Cc1cc(Cn2cc(C(=O)N[C@H]3CCCC[C@@H]3O)c3ncccc32)ccn1] |

TABLE 1-continued
| Example | Structure |
|---|---|
| 77 | 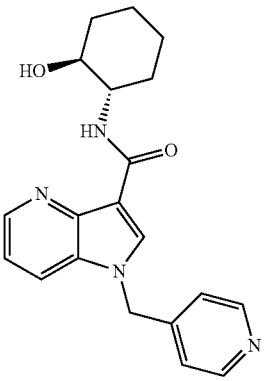 [SMILES: O=C(N[C@H]1CCCC[C@@H]1O)c1cn(Cc2ccncc2)c2cccnc12] |
| 78 | 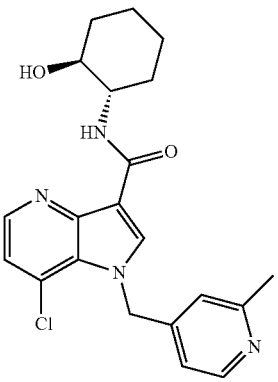 [SMILES: Cc1cc(Cn2cc(C(=O)N[C@H]3CCCC[C@@H]3O)c3nccc(Cl)c32)ccn1] |
| 79 | 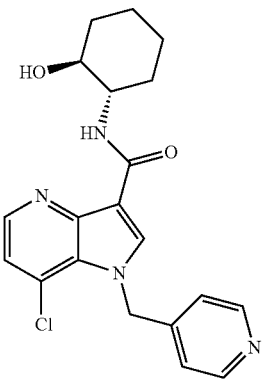 [SMILES: O=C(N[C@H]1CCCC[C@@H]1O)c1cn(Cc2ccncc2)c2c(Cl)ccnc12] |
| 80 | 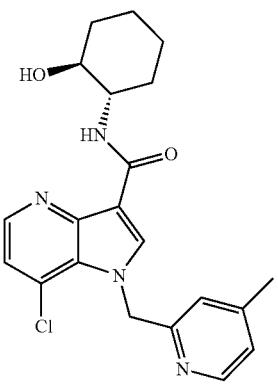 [SMILES: Cc1ccnc(Cn2cc(C(=O)N[C@H]3CCCC[C@@H]3O)c3nccc(Cl)c32)c1] |
| 81 | 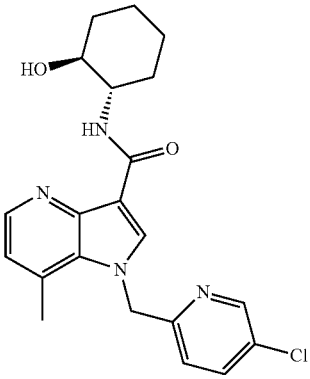 [SMILES: Cc1ccnc2c(C(=O)N[C@H]3CCCC[C@@H]3O)cn(Cc3ccc(Cl)cn3)c12] |
| 82 | 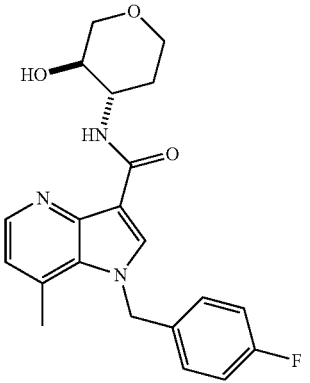 |
| 83 | 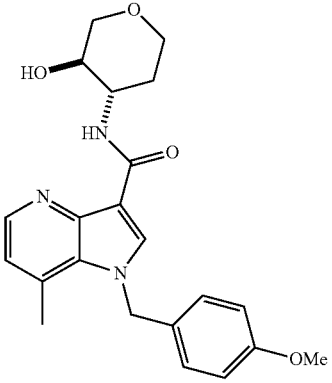 |
| 84 | 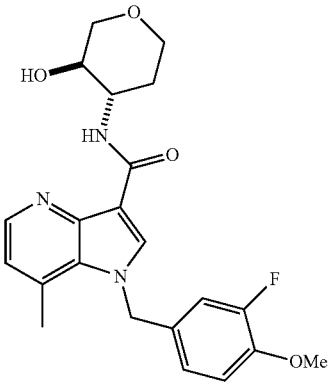 |

TABLE 1-continued

| Example | Structure |
|---|---|
| 85 | (3-hydroxytetrahydropyran-4-yl)amide of 7-methyl-1-[(2-methoxypyridin-4-yl)methyl]-1H-pyrrolo[3,2-b]pyridine-3-carboxamide |
| 86 | (3-hydroxytetrahydropyran-4-yl)amide of 7-methyl-1-(3-fluorobenzyl)-1H-pyrrolo[3,2-b]pyridine-3-carboxamide |
| 87 | (3-hydroxytetrahydropyran-4-yl)amide of 7-chloro-1-(4-methoxybenzyl)-1H-pyrrolo[3,2-b]pyridine-3-carboxamide |
| 88 | (3-hydroxytetrahydropyran-4-yl)amide of 7-chloro-1-(4-fluorobenzyl)-1H-pyrrolo[3,2-b]pyridine-3-carboxamide |
| 89 | (3-hydroxytetrahydropyran-4-yl)amide of 7-chloro-1-(4-fluorobenzyl)-1H-pyrrolo[3,2-b]pyridine-3-carboxamide |
| 90 | (2-hydroxycyclohexyl)amide of 1-(4-trifluoromethylbenzyl)-1H-pyrrolo[3,2-b]pyridine-3-carboxamide |
| 91 | (2-hydroxycyclohexyl)amide of 1-(3-methoxy-4-fluorobenzyl)-1H-pyrrolo[3,2-b]pyridine-3-carboxamide |
| 92 | (2-hydroxycyclohexyl)amide of 1-(2-fluoro-4-methoxybenzyl)-1H-pyrrolo[3,2-b]pyridine-3-carboxamide |

TABLE 1-continued
| Example | Structure |
|---|---|
| 93 | 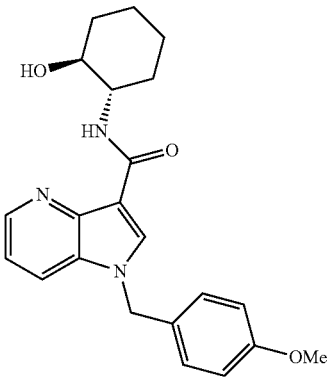 [SMILES: COc1ccc(Cn2cc(C(=O)N[C@H]3CCCC[C@@H]3O)c3ncccc32)cc1] |
| 94 | 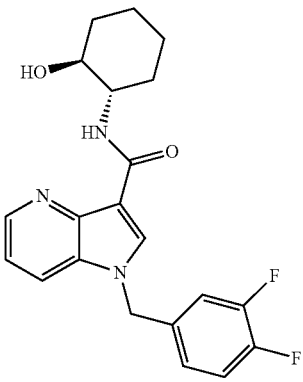 [SMILES: O=C(N[C@H]1CCCC[C@@H]1O)c1cn(Cc2ccc(F)c(F)c2)c2cccnc12] |
| 95 | 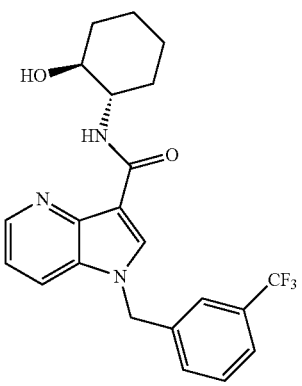 [SMILES: O=C(N[C@H]1CCCC[C@@H]1O)c1cn(Cc2cccc(C(F)(F)F)c2)c2cccnc12] |
| 96 | 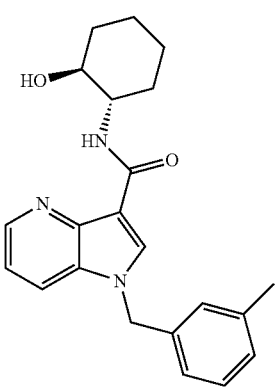 [SMILES: Cc1cccc(Cn2cc(C(=O)N[C@H]3CCCC[C@@H]3O)c3ncccc32)c1] |
| 97 | 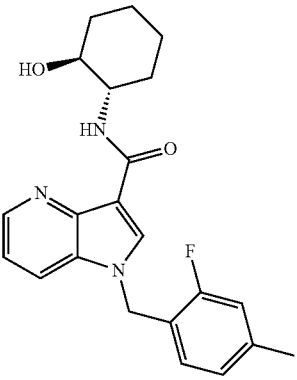 [SMILES: Cc1ccc(Cn2cc(C(=O)N[C@H]3CCCC[C@@H]3O)c3ncccc32)c(F)c1] |
| 98 | 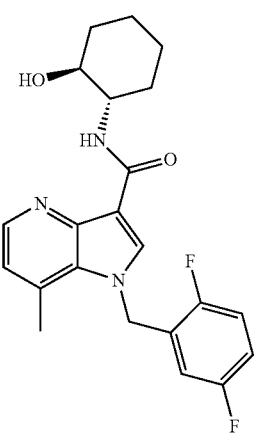 [SMILES: Cc1ccnc2c(C(=O)N[C@H]3CCCC[C@@H]3O)cn(Cc3cc(F)ccc3F)c12] |
| 99 | 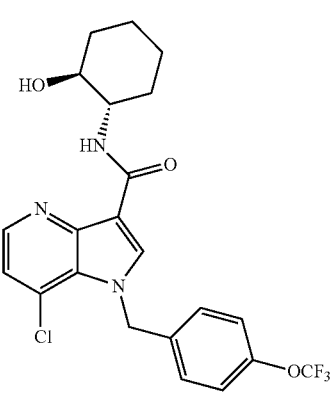 [SMILES: O=C(N[C@H]1CCCC[C@@H]1O)c1cn(Cc2ccc(OC(F)(F)F)cc2)c2c(Cl)ccnc12] |
| 100 | 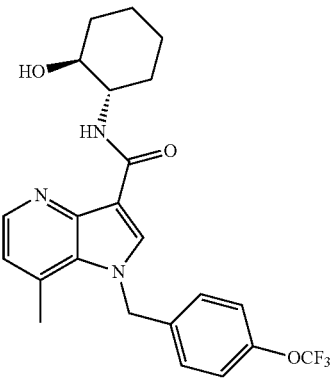 [SMILES: Cc1ccnc2c(C(=O)N[C@H]3CCCC[C@@H]3O)cn(Cc3ccc(OC(F)(F)F)cc3)c12] |

TABLE 1-continued

| Example | Structure |
|---|---|
| 101 | 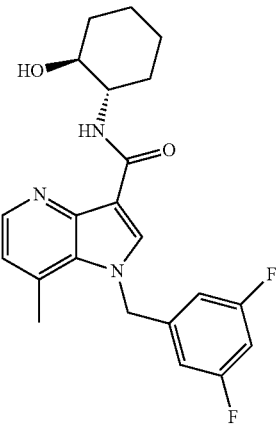 [SMILES: Cc1ccnc2c(C(=O)N[C@H]3CCCC[C@@H]3O)cn(Cc3cc(F)cc(F)c3)c12] |
| 102 | 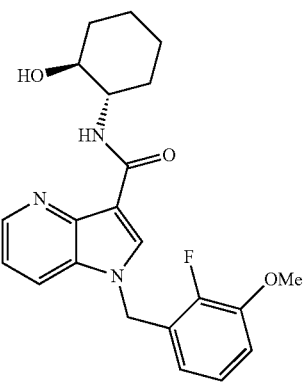 [SMILES: COc1cccc(Cn2cc(C(=O)N[C@H]3CCCC[C@@H]3O)c3ncccc32)c1F] |
| 103 | 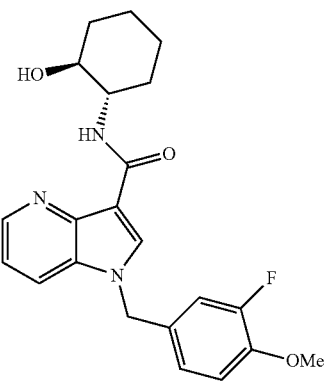 [SMILES: COc1ccc(Cn2cc(C(=O)N[C@H]3CCCC[C@@H]3O)c3ncccc32)cc1F] |
| 104 | 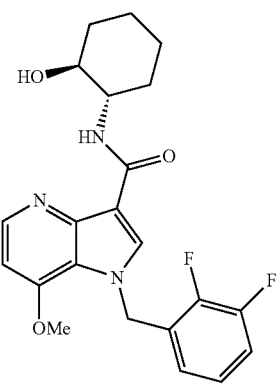 [SMILES: COc1ccnc2c(C(=O)N[C@H]3CCCC[C@@H]3O)cn(Cc3cccc(F)c3F)c12] |

TABLE 1-continued

| Example | Structure |
|---|---|
| 105 | 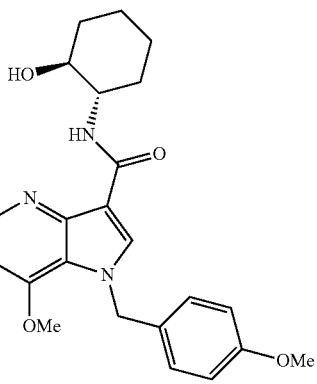 |

Biological Data In Vitro Analysis

In Vitro Cellular Assay

Baby hamster kidney cells stably expressing human or rat mAChR M1 to M5 were utilised for primary and selectivity profiling activities. mAChR M2 and M4 cell lines also stably expressed the chimeric Gαqi5 G-protein.

Human mAChR M1, M3, M5 and rat M1 cells were grown in low glucose Dulbecco's Modified Eagle's Medium (DMEM) medium plus heat inactivated 10% fetal bovine serum (HI FBS) and 500 µg/ml hygromycin B[1]. Human mAChR M2 and M4 cells were maintained as above with[2] the addition of 500 µg/ml G418 to the media. Cells were maintained in culture at 37° C./5% $CO_2$ and passaged twice weekly by treatment with 0.05% Trypsin/EDTA detachment solution, centrifugation (200 g, 5 min) and re-suspension in fresh media. Following cell expansion, cells were cryopreserved at −80° C. by treatment with 0.05% Trypsin/EDTA detachment solution, centrifugation (200 g, 5 min) and re-suspension of the pellet in freezing media (90% HI FBS/10% DMSO[3]) at 15E6 cells/ml[4].

Prior to assaying, cells were prepared by thawing at 37° C. in a water bath, centrifugation (200 g, 5 min) and re-suspension of the pellet in fresh media. 15000 cells per well were seeded in black, clear bottomed 384-well Greiner Bio-One plates in plating medium (DMEM/10% HI FBS) and incubated overnight at 37 C/5% $CO_2$.

On the day of the assay, media was removed from each well and replaced with 50 µl[5] assay buffer (HBSS with 20 mM HEPES and 2.5 mM Probenecid) containing the calcium indicator, Calcium 4 (Molecular Devices). Cells were then incubated at 37° C./5% $CO_2$ for 30 min and at room temperature.

Compound preparation was carried out by generation of 11-point, 1 in 3 serial dilution concentration response curves in 100% DMSO. Compound was then diluted 1 in 65[6] with assay buffer (HBSS with 20 mM HEPES and 2.5 mM Probenecid) prior to the addition of 10 ul[7] to the cells using a Tetra fluorometric imaging plate reader (Molecular Devices)[8]. Compound driven increases in intracellular calcium flux was measured as an increase in fluorescence ($494_{Ex}$, $516_{Em}$)[9]. Agonist $pEC_{50}$ values for each compound were determined and agonist Emax values were generated in relation to the maximum effect obtained by carbachol (100%).

Following agonist data acquisition, cells were then incubated for a further 30 min at room temperature before either an $EC_{20}$ concentration (to measure positive allosteric modulator activity) or an $EC_{80}$ concentration (to measure antagonism) of carbachol was added using a fluorometric imaging plate reader. Positive allosteric modulator $pEC_{50}$ values and antagonist $pIC_{50}$ values for each compound were then determined. PAM Emax values were generated following normalisation between the $EC_{20}$ base line fluorescence (0%) and maximal carbachol effect (100%). Antagonist Emax values were generated following normalisation between the $EC_{80}$ fluorescence (0%) and baseline $EC_0$ (DMSO) response (100%). Data analysis was carried out using a 4 parameter logistic nonlinear regression model with the XLFIT (IDBS) excel add-in[10].

[1-10]Examples 76-80 and 82-89 were tested in a slightly modified procedure. The points of modification and the alternate reagents, concentrations or equipment employed in these examples were: [1]200 µg/ml hygromycin B; [2]G418 not added; [3]CELLBANKER 1; [4]10E6; [5]40 µl; [6]1 in 99; [7]20 µl; [8]FDSS6000 (Hamamatsu Photonics); [9]($480_{Ex}$, $540_{Em}$); [10]Spotfire (TIBCO).

As measured by the above in vitro assay, compound Examples 1 to 105 are positive allosteric modulators of mAChR M1 displaying the pEC50 values for positive allosteric modulation given in Table 2.

TABLE 2

| Example | $pEC_{50}$ |
|---|---|
| 1 | 7.0 |
| 2 | 6.7 |
| 3 | 6.8 |
| 4 | 6.8 |
| 5 | 6.9 |
| 6 | 6.7 |
| 7 | 5.9 |
| 8 | 6.5 |
| 9 | 6.6 |
| 10 | 7.7 |
| 11 | 6.9 |
| 12 | 7.7 |
| 13 | 7.9 |
| 14 | 7.3 |
| 15 | 7.0 |
| 16 | 6.5 |
| 17 | 6.9 |
| 18 | 6.1 |
| 19 | 6.0 |
| 20 | 6.1 |
| 21 | 5.7 |
| 22 | 6.5 |
| 23 | 6.6 |
| 24 | 6.5 |
| 25 | 6.2 |
| 26 | 6.1 |
| 27 | 6.1 |
| 28 | 6.6 |
| 29 | 5.8 |
| 30 | 6.5 |
| 31 | 6.5 |
| 32 | 6.7 |
| 33 | 7.0 |
| 34 | 6.9 |
| 35 | 6.1 |
| 36 | 6.3 |
| 37 | 6.7 |
| 38 | 5.8 |
| 39 | 6.0 |
| 40 | 6.5 |
| 41 | 6.5 |
| 42 | 7.0 |
| 43 | 8.0 |
| 44 | 6.9 |
| 45 | 7.5 |
| 46 | 6.5 |
| 47 | 7.6 |
| 48 | 6.7 |
| 49 | 5.6 |
| 50 | 6.4 |
| 51 | 6.3 |
| 52 | 6.7 |
| 53 | 6.2 |
| 54 | 7.5 |
| 55 | 6.7 |
| 56 | 6.5 |
| 57 | 7.6 |
| 58 | 7.7 |
| 59 | 7.4 |
| 60 | 7.8 |
| 61 | 7.0 |
| 62 | 7.4 |
| 63 | 7.6 |
| 64 | 7.2 |
| 65 | 7.7 |
| 66 | 7.9 |
| 67 | 7.5 |
| 68 | 7.7 |
| 69 | 8.0 |
| 70 | 7.0 |
| 71 | 7.9 |
| 72 | 7.8 |
| 73 | 7.9 |
| 74 | 6.7 |
| 75 | 6.6 |
| 76 | 6.4 |
| 77 | 6.3 |
| 78 | 7.8 |
| 79 | 7.4 |
| 80 | 7.1 |
| 81 | 7.2 |
| 82 | 7.8 |
| 83 | 8.0 |
| 84 | 7.9 |
| 85 | 7.3 |
| 86 | 7.6 |
| 87 | 7.9 |
| 88 | 6.4 |
| 89 | 6.6 |
| 90 | 6.6 |
| 91 | 6.3 |
| 92 | 6.4 |
| 93 | 6.9 |
| 94 | 6.6 |
| 95 | 6.1 |
| 96 | 6.7 |
| 97 | 6.9 |
| 98 | 7.0 |
| 99 | 6.7 |
| 100 | 6.8 |
| 101 | 7.0 |
| 102 | 6.4 |
| 103 | 6.8 |
| 104 | 6.3 |
| 105 | 6.7 |

Certain compounds were tested in PAM, NAM and agonist modes against mAChR M2, M3, M4 and M5. All examples tested in these assays demonstrated selectivity for mAChR M1. For example, compound examples 5, 6, 8, 10, 11, 12, 13, 34 and 47 were shown to have $pIC_{50}$ or $pEC_{50}$ values<5.0 against mAChR M2, M3, M4 and M5.

Biological Data—In Vivo Analysis
Novel Object Recognition Test

The Novel Object Recognition test (NOR) is based on the greater spontaneous exploration of a novel object, compared with a familiar object, observed in rodents (Behav. Brain Res., 1988, 31(1), 47-59). The test is considered a model of recognition memory and does not involve appetitive or aversive reinforcement. Therefore, it is considered to be analogous to recognition memory tests used in human clinical testing. Male Lister Hooded rats were assessed for object recognition in a test apparatus comprising of a perspex test arena housed within a sound attenuating chamber. Video images of behaviour were captured by digital camera and recorded to a computer. Rats were habituated to the test arena on four occasions prior to testing. Habituation sessions replicated the test day sequence exactly with the exception of object presentation. On test days, each rat was placed into the test arena and 3 minutes later the rat was presented with two identical objects (plastic shapes). The time spent actively exploring the objects during a 3-minute test period (T1) was recorded. Following T1 rats were returned to home cages. After 24 hours each rat was again placed in the test arena and 3 minutes later was presented with one of the now familiar objects and a novel object, and again the time spent actively exploring the objects during a 3-minute test period (T2) was recorded. The presentation order and position of objects (left/right) was randomised within groups to prevent bias from order or place preference. Objects were cleaned with 70% ethanol solution between trials to remove any olfactory/taste cues. Compounds were administered by oral gavage at an appropriate pre-treatment time prior to T1 and T2 (n=12) at dosage ranges between 0.03 and 3 mg/kg. In some experiments the 5-HT6 receptor antagonist N-(3,5-dichloro-2-methoxyphenyl)-4-methoxy-3-(piperazin-1-yl)benzenesulfonamide (CAS 402713-80-8) (10 mg/kg p.o.; 4 h pre-treatment time) was included as a positive control. Vehicle controls (1% methylcellulose in water) were included for comparison in each study. Results are expressed as the d2 index (difference in time spent exploring novel and familiar objects/total object exploration in T2).

Results for Compound Examples 5, 6, 8, 10, 11, 12, 13, 34 and 47 are given in Table 3, which shows d2 index values (mean±SEM) for each dose administered.

utes after the test compound administration, scopolamine hydrobromide dissolved in a saline was intraperitoneally administered at a 0.7 mg/kg dose, so as to induce cognitive impairment. After another 30 minutes, each rat was acclimated in the test device for 3 minutes, and thereafter, two blocks in the same shape were put in the test device as acquisition trial, and exploring time for each block was measured for 5 minutes. Two hours after the acquisition trial, the rat was acclimated in the test device for 3 minutes, and thereafter, the same block as those used in the acquisition trial and a new block in a different shape were put in the cage for retention trial. The exploring time for each block was measured for 3 minutes, and a ratio of the exploring time for the newly used block to the sum of the exploring times for the respective blocks was calculated as a discrimination index (novel object exploration time/total object exploration time in retention trial×100). The thus obtained discrimination indexes were compared among a group of rats to which a vehicle alone was administered (vehicle group), a group of rats to which scopolamine alone was administered (scopolamine alone group) and a group of rats to which both the test compound and scopolamine were administered, so as to evaluate the action of the test compound on the novel object recognition function (cognitive function) of the rats.

Each discrimination index was shown as an average and a standard error. The statistical significance between the vehicle group and the scopolamine alone group was analyzed by the independent t-test. The statistical significance between the scopolamine alone group and each sample group was analyzed by one-way analysis of variance and then by Dunnett's multiple comparison test. The signifi-

TABLE 3

| Ex. | Vehicle (1% MCW p.o.) [mean ± SEM] | Dose 1 (mg/kg p.o.) [mean ± SEM] | Dose 2 (mg/kg p.o.) [mean ± SEM] | Dose 3 (mg/kg p.o.) [mean ± SEM] | CAS 402713-80-8 (10 mg/kg p.o.) [mean ± SEM] |
|---|---|---|---|---|---|
| 5 |  | 0.03 | 0.1 | 0.3 | nt |
|  | [0.00 ± 0.03] | [0.04 ± 0.06] | [0.20 ± 0.05]** | [0.28 ± 0.05]*** |  |
| 6 |  | 0.3 | 1 | 3 | nt |
|  | [0.04 ± 0.04] | [0.11 ± 0.09] | [0.27 ± 0.08]* | [0.36 ± 0.09]** |  |
| 8 |  | 0.03 | 0.1 | 0.3 | [0.34 ± 0.05]*** |
|  | [0.05 ± 0.04] | [0.00 ± 0.07] | [0.09 ± 0.06] | [0.34 ± 0.06]*** |  |
| 10 |  | 0.03 | 0.1 | 0.3 | nt |
|  | [−0.03 ± 0.04] | [0.18 ± 0.10] | [0.18 ± 0.09] | [0.30 ± 0.08]** |  |
| 11 |  | 0.3 | 1 | 3 | — |
|  | [0.08 ± 0.05] | [0.24 ± 0.06] | [0.24 ± 0.07] | [0.31 ± 0.06]** | [0.34 ± 0.04]** |
| 12 |  | 0.3 | 1 | 3 | — |
|  | [0.04 ± 0.05] | [0.13 ± 0.06] | [0.30 ± 0.05]*** | [0.33 ± 0.06]*** | [0.28 ± 0.07]*** |
| 13 |  | 0.3 | 1 | 3 | — |
|  | [0.07 ± 0.04] | [0.09 ± 0.05] | [0.13 ± 0.07] | [0.25 ± 0.09]* | [0.34 ± 0.05]** |
| 34 |  | 0.1 | 0.3 | 1 | — |
|  | [0.04 ± 0.05] | [0.08 ± 0.08] | [0.24 ± 0.05]* | [0.23 ± 0.06]* | [0.27 ± 0.08]* |
| 47 |  | 0.1 | 0.3 | 1 | — |
|  | [−0.02 ± 0.04] | [0.11 ± 0.09] | [0.10 ± 0.05] | [0.32 ± 0.07]*** | [0.33 ± 0.08]*** |

SEM = standard error of the mean;
MCW = methylcellulose in water;
p.o. = per os;
nt = not tested;
*P < 0.05, P < 0.01, *P < 0.001 compared to vehicle (ANOVA followed by LSD post-hoc planned comparisons).

Novel Object Recognition Test in Scopolamine-Induced Cognitive Deficit Condition For 2 days before starting the test, 6-week old male Long-Evans rats were acclimated to experimental operations such as administration and a test device (that is, a black or gray plastic cage with a width of 40 cm, a depth of 30 cm and a height of 45 cm). Each test compound was dissolved in a 0.5% methylcellulose in water to be orally administered at dosage ranges between 0.01 and 0.1 mg/kg. Thirty mincance level was set to 5% on both sides. If the discrimination index was significantly lower in the scopolamine alone group than in the vehicle group, it was determined that the cognitive impairment was sufficiently induced, and hence, the test compound was evaluated in the corresponding group. The analysis was carried out by using Prism 6 for Windows, ver. 6.02. Results for Compound Example 5 are given in Table 4, which shows the discrimination index for each dose administered.

TABLE 4

| Group | Saline/ Vehicle | Scopolamine/ Vehicle | Scopolamine/ 0.01 mg/kg p.o. | Scopolamine/ 0.03 mg/kg p.o. | Scopolamine/ 0.1 mg/kg p.o. |
| --- | --- | --- | --- | --- | --- |
| N | 10 | 9 | 11 | 11 | 10 |
| [mean ± SEM] | [74.4 ± 2.1] | [52.2 ± 4.3]*** | [50.5 ± 4.3] | [61.7 ± 2.5] | [72.9 ± 2.6]### |

SEM = standard error of the mean;
p.o. = per os;
***P < 0.001 compared to vehicle group (unpaired t test)
P < 0.001 compared to scopolamine alone group (one-way analysis of variance followed by Dunnett multiple comparison test).

Morris Water Maze Test in Ibotenic Acid-Induced Learning Disability Model

Ibotenic acid at 5 μg/0.5 μL was injected into both basal nuclei of 8-week old male Crlj: WI rats, and a Morris water maze test was performed 10-14 days after ibotenic acid injection. It has been reported that rats in which basal forebrain was lesioned by ibotenic acid injection show learning disability in the Morris water maze test. (Pharmacopsychiat, 1999, 32, 242-247). The test is considered a model of spatial learning and memory. Therefore, it is considered to be comparable to spatial learning and memory tests used in human clinical testing.

Learning trials were performed twice a day at an interval of 3 hours for 4 days (8 times in total), and probe trials were performed once the day after completion of the learning trials. Each test compound was dissolved in a 0.5% methylcellulose in water and orally administered 1 hour before the first trial on each day of the learning trials and 1 hour before the trial on the day of the probe trials.

A colorless clear acrylic platform (diameter: about 12 cm, height: about 30 cm) and a gray vinyl chloride circular pool (diameter: about 148 cm, height: about 44 cm), which was filled with water (temperature: 17-18° C.) up to a height of about 32 cm so that the platform was fully immersed in water, were used as the test device. Four quadrants were prepared at the bottom of the pool, and the platform was set at the center of 1 of the 4 quadrants (about 37 cm from the center of the pool). A light bulb was placed near the quadrant with the platform as a spatial cue.

In learning trials, the animal was put into water and goal latency and swimming distance to reach the platform were measured (measurement time: 90 seconds at the longest) by a video image behavioral analysis device (Etho Vision XT, Noldus Information Technology Inc.). When an animal reached the platform within 90 seconds and stayed on the platform for 30 seconds, it was judged that the animal recognized the position of the platform, and the measurement was finished. When an animal failed to reach the platform within 90 seconds, the goal latency for that animal was recorded as 90 seconds. Any animal which failed to reach the platform within 90 seconds was placed on the platform for 30 seconds after the measurement and returned to the cage. When an animal reached the platform and went into the water again, it was judged that the animal failed to recognize the position of the platform, and the measurement was continued.

In probe trials, the platform was removed from the pool. The animal was put into water, and the swimming time in the quadrant where the platform had been located in the learning trials and the frequency of entry into the platform area where the platform had been located in the learning trials were measured by Etho Vision XT.

Each value was shown as an average and a standard error (n=10). The statistical significance between a control group and a vehicle group was analyzed by the independent t-test. The statistical significance between the vehicle group and each sample group was analyzed by one-way analysis of variance and then by Dunnett's multiple comparison test. The significance level was set to 5% on both sides. If the values were significantly higher or lower in the vehicle group than in the control group, it was determined that the cognitive impairment was sufficiently induced, and hence, the test compound was evaluated in the corresponding group. The analysis was carried out by using SAS system (SAS Institute Japan Ltd.). Results for Compound Example 5 are given in Table 5.

TABLE 5

| | Group | Control[1] [mean ± SEM] | Vehicle[2] [mean ± SEM] | 0.1 mg/kg p.o.[3] [mean ± SEM] | 0.3 mg/kg p.o.[3] [mean ± SEM] |
| --- | --- | --- | --- | --- | --- |
| Goal latency (sec.) | Trial 1 | [82.63 ± 4.51] | [90 ± 0.00] | [90 ± 0.00] | [90 ± 0.00] |
| | Trial 2 | [72.85 ± 8.29] | [90 ± 0.00] | [90 ± 0.00] | [89.47 ± 0.53] |
| | Trial 3 | [56.39 ± 10.63] | [90 ± 0.00]** | [78.81 ± 8.1] | [75.08 ± 7.99] |
| | Trial 4 | [59.98 ± 10.14] | [90 ± 0.00]** | [79.59 ± 7.36] | [60.53 ± 12.15]# |
| | Trial 5 | [31.47 ± 10.1] | [90 ± 0.00]** | [83.06 ± 4.7] | [53.99 ± 10.18]## |
| | Trial 6 | [22.7 ± 6.25] | [90 ± 0.00]** | [66.13 ± 12.22] | [33.09 ± 9.78]## |
| | Trial 7 | [19.89 ± 6.73] | [90 ± 0.00]** | [76.97 ± 8.11] | [50.1 ± 10.02]## |
| | Trial 8 | [13.38 ± 4.13] | [90 ± 0.00]** | [67.24 ± 10.13] | [38.02 ± 10.74]## |
| Swimming distance (cm) | Trial 1 | [2294.57 ± 175.61] | [2164.75 ± 92.56] | [2152.96 ± 91.73] | [2400.75 ± 122.49] |
| | Trial 2 | [2254.05 ± 236.92] | [2163.93 ± 170.94] | [2353.99 ± 145.71] | [2533.19 ± 86.87] |
| | Trial 3 | [1815.75 ± 297.48] | [2421.72 ± 155.56] | [1884.79 ± 174.8] | [1945.42 ± 189.94] |
| | Trial 4 | [1551.88 ± 243.76] | [2129.56 ± 238.64] | [1822.32 ± 206.29] | [1592.82 ± 308.21] |
| | Trial 5 | [961.27 ± 258.64] | [2333.29 ± 189.64]** | [1918.78 ± 132.12] | [1417.94 ± 229.44]## |
| | Trial 6 | [663.17 ± 160.79] | [2148.48 ± 153.69]** | [1464.97 ± 308.91] | [876.2 ± 203.14]## |
| | Trial 7 | [603.49 ± 134.79] | [2290.57 ± 207.2]** | [1839.16 ± 221.78] | [1329.27 ± 236.21]## |
| | Trial 8 | [428.85 ± 107.74] | [2053.14 ± 190.71]** | [1492.52 ± 260.05] | [1020.57 ± 253.94]## |

TABLE 5-continued

| Group | | Control[1] [mean ± SEM] | Vehicle[2] [mean ± SEM] | 0.1 mg/kg p.o.[3] [mean ± SEM] | 0.3 mg/kg p.o.[3] [mean ± SEM] |
|---|---|---|---|---|---|
| Swimming time in 4th quadrant (sec.) | 0-30 sec. | [8.84 ± 1.53] | [5.21 ± 0.76]* | [8.90 ± 1.02]# | [7.19 ± 1.11] |
| | 30-60 sec. | [9.54 ± 1.27] | [4.67 ± 1.02]** | [9.41 ± 1.80]# | [8.48 ± 1.25] |
| | 60-90 sec. | [9.41 ± 1.33] | [5.60 ± 0.76]* | [7.74 ± 0.85] | [7.49 ± 1.37] |
| | Total | [27.79 ± 3.42] | [15.48 ± 2.15]** | [26.05 ± 2.03]## | [23.16 ± 2.97] |
| Frequency of entry into platform area | | [4.2 ± 0.6] | [0.0 ± 0.0]** | [0.9 ± 0.3] | [1.7 ± 0.5]## |

SEM = standard error of the mean;
p.o. = per os;
*$P < 0.05$, **$P < 0.01$ compared to control group (unpaired t test).
$P < 0.05$, ##$P < 0.01$ compared to vehicle group (one-way analysis of variance followed by Dunnett multiple comparison test).
[1]Control group animals were placed under anaesthetic (without ibotenic acid injection) and then administered vehicle prior to testing
[2]Vehicle group animals received an ibotenic acid injection under anaesthetic and then administered vehicle prior to testing
[3]Sample group animals received an ibotenic acid injection under anaesthetic and then administered test compound prior to testing

The invention claimed is:
1. A compound, or a pharmaceutically acceptable salt thereof, which is:
   1-(4-fluorobenzyl)-N-((1S,2S)-2-hydroxycyclohexyl)-7-methyl-1H-pyrrolo[3,2-b]pyridine-3-carboxamide;
   1-(2,3-difluorobenzyl)-N-((1S,2S)-2-hydroxycyclohexyl)-7-methyl-1H-pyrrolo[3,2-b]pyridine-3-carboxamide;
   N-((1S,2S)-2-hydroxycyclohexyl)-1-(4-methoxybenzyl)-7-methyl-1H-pyrrolo[3,2-b]pyridine-3-carboxamide;
   1-(3-fluoro-4-methoxybenzyl)-N-((1S,2S)-2-hydroxycyclohexyl)-7-methyl-1H-pyrrolo[3,2-b]pyridine-3-carboxamide;
   7-chloro-1-(4-fluorobenzyl)-N(1S,2S)-2-hydroxycyclohexyl)-1H-pyrrolo[3,2-b]pyridine-3-carboxamide;
   7-chloro-1-(2,3-difluorobenzyl)-N-((1S,2S)-2-hydroxycyclohexyl)-1H-pyrrolo[3,2-b]pyridine-3-carboxamide;
   7-chloro-N-((1S,2S)-2-hydroxycyclohexyl)-1-((6-methylpyridin-2-yl)methyl)-1H-pyrrolo[3,2-b]pyridine-3-carboxamide;
   7-chloro-1-((5-fluoropyridin-2-yl)methyl)-N-((1S,2S)-2-hydroxycyclohexyl)-1H-pyrrolo[3,2-b]pyridine-3-carboxamide;
   7-cyano-1-(4-fluorobenzyl)-N-((1S,2S)-2-hydroxycyclohexyl)-1H-pyrrolo[3,2-b]pyridine-3-carboxamide;
   7-cyano-N-((1S,2S)-2-hydroxycyclohexyl)-1-(4-(trifluoromethyl)benzyl)-1H-pyrrolo[3,2-b]pyridine-3-carboxamide;
   1-(4-fluorobenzyl)-N-((1S,2S)-2-hydroxycyclohexyl)-7-methoxy-1H-pyrrolo[3,2-b]pyridine-3-carboxamide;
   7-chloro-N-((1S,2S)-2-hydroxycyclohexyl)-1-(4-methoxybenzyl)-1H-pyrrolo[3,2-b]pyridine-3-carboxamide;
   1-((6-chloropyridin-3-yl)methyl)-N-((1S,2S)-2-hydroxycyclohexyl)-7-methyl-1H-pyrrolo[3,2-b]pyridine-3-carboxamide;
   1-(4-chlorobenzyl)-N-((1S,2S)-2-hydroxycyclohexyl)-7-methyl-1H-pyrrolo [3,2-b]pyridine-3-carboxamide;
   7-chloro-N-((1S,2S)-2-hydroxycyclohexyl)-1-((5-methylpyridin-2-yl)methyl)-1H-pyrrolo[3,2-b]pyridine-3-carboxamide;
   7-chloro-N-((1S,2S)-2-hydroxycyclohexyl)-1-((6-methylpyridin-3-yl)methyl)-1H-pyrrolo[3,2-b]pyridine-3-carboxamide;
   N-((1S,2S)-2-hydroxycyclohexyl)-7-methyl-1-(4-methylbenzyl)-1H-pyrrolo[3,2-b]pyridine-3-carboxamide;
   N-((1S,2S)-2-hydroxycyclohexyl)-7-methyl-1-((5-methylpyridin-2-yl)methyl)-1H-pyrrolo[3,2-b]pyridine-3-carboxamide;
   1-(3-fluorobenzyl)-N-((1S,2S)-2-hydroxycyclohexyl)-7-methyl-1H-pyrrolo[3,2-b]pyridine-3-carboxamide;
   N-((1S,2S)-2-hydroxycyclohexyl)-1-(4-methoxy-3-methylbenzyl)-7-methyl-1H-pyrrolo[3,2-b]pyridine-3-carboxamide;
   N-((1S,2S)-2-hydroxycyclohexyl)-1-((6-methoxypyridin-3-yl)methyl)-7-methyl-1H-pyrrolo[3,2-b]pyridine-3-carboxamide;
   7-chloro-N-((1S,2S)-2-hydroxycyclohexyl)-1-((6-methoxypyridin-3-yl)methyl)-1H-pyrrolo[3,2-b]pyridine-3-carboxamide;
   7-chloro-N-((1S,2S)-2-hydroxycyclohexyl)-1-((2-methoxypyridin-4-yl)methyl)-1H-pyrrolo[3,2-b]pyridine-3-carboxamide;
   7-chloro-1-((6-cyanopyridin-3-yl)methyl)-N-((1S,2S)-2-hydroxycyclohexyl)-1H-pyrrolo[3,2-b]pyridine-3-carboxamide;
   N-((1S,2S)-2-hydroxycyclohexyl)-1-((2-methoxypyridin-4-yl)methyl)-7-methyl-1H-pyrrolo[3,2-b]pyridine-3-carboxamide;
   7-chloro-N-((1S,2S)-2-hydroxycyclohexyl)-1-((1-methyl-1H-pyrazol-4-yl)methyl)-1H-pyrrolo[3,2-b]pyridine-3-carboxamide;
   N-((1S,2S)-2-hydroxycyclohexyl)-7-methyl-1-((1-methyl-1H-pyrazol-4-yl)methyl)-1H-pyrrolo[3,2-b]pyridine-3-carboxamide;
   7-chloro-N-((1S,2S)-2-hydroxycyclohexyl)-1-((4-methylthiazol-2-yl)methyl)-1H-pyrrolo[3,2-b]pyridine-3-carboxamide;
   7-chloro-N-((1S,2S)-2-hydroxycyclohexyl)-1-((5-methylthiazol-2-yl)methyl)-1H-pyrrolo[3,2-b]pyridine-3-carboxamide;
   7-chloro-N-((1S,2S)-2-hydroxycyclohexyl)-1-((2-methylpyridin-4-yl)methyl)-1H-pyrrolo[3,2-b]pyridine-3-carboxamide;
   7-chloro-N-((1S,2S)-2-hydroxycyclohexyl)-1-(pyridin-4-ylmethyl)-1H-pyrrolo[3,2-b]pyridine-3-carboxamide;
   7-chloro-N-((1S,2S)-2-hydroxycyclohexyl)-1-((4-methylpyridin-2-yl)methyl)-1H-pyrrolo[3,2-b]pyridine-3-carboxamide;
   1-((5-chloropyridin-2-yl)methyl)-N-((1S,2S)-2-hydroxycyclohexyl)-7-methyl-1H-pyrrolo[3,2-b]pyridine-3-carboxamide;
   1-(4-fluorobenzyl)-N-(trans-3-hydroxytetrahydro-2H-pyran-4-yl)-7-methyl-1H-pyrrolo[3,2-b]pyridine-3-carboxamide;

1-(4-methoxybenzyl)-N-(trans-3-hydroxytetrahydro-2H-pyran-4-yl)-7-methyl-1H-pyrrolo[3,2-b]pyridine-3-carboxamide;

1-(3-fluoro-4-methoxybenzyl)-N-(trans-3-hydroxytetrahydro-2H-pyran-4-yl)-7-methyl-1H-pyrrolo[3,2-b]pyridine-3-carboxamide;

N-(trans-3-hydroxytetrahydro-2H-pyran-4-yl)-1-((2-methoxypyridin-4-yl)methyl)-7-methyl-1H-pyrrolo[3,2-b]pyridine-3-carboxamide;

7-chloro-1-(3-fluorobenzyl)-N-(trans-3-hydroxytetrahydro-2H-pyran-4-yl)-1H-pyrrolo[3,2-b]pyridine-3-carboxamide;

7-chloro-1-(4-methoxybenzyl)-N-(trans-3-hydroxytetrahydro-2H-pyran-4-yl)-1H-pyrrolo[3,2-b]pyridine-3-carboxamide;

7-chloro-1-(4-fluorobenzyl)-N-((3R,4S)-3-hydroxytetrahydro-2H-pyran-4-yl)-1H-pyrrolo[3,2-b]pyridine-3-carboxamide; or 7-chloro-1-(4-fluorobenzyl)-N-((3 S,4R)-3-hydroxytetrahydro-2H-pyran-4-yl)-1H-pyrrolo[3,2-b]pyridine-3-carboxamide.

2. The compound according to claim 1, or a pharmaceutically acceptable salt thereof, which is 1-(4-fluorobenzyl)-N-((1S,2S)-2-hydroxycyclohexyl)-7-methyl-1H-pyrrolo[3,2-b]pyridine-3-carboxamide.

3. The compound according to claim 1, or a pharmaceutically acceptable salt thereof, which is 1-(2,3-difluorobenzyl)-N-((1S,2S)-2-hydroxycyclohexyl)-7-methyl-1H-pyrrolo[3,2-b]pyridine-3-carboxamide.

4. The compound according to claim 1, or a pharmaceutically acceptable salt thereof, which is N-((1S,2S)-2-hydroxycyclohexyl)-1-(4-methoxybenzyl)-7-methyl-1H-pyrrolo[3,2-b]pyridine-3-carboxamide.

5. The compound according to claim 1, or a pharmaceutically acceptable salt thereof, which is 1-(3-fluoro-4-methoxybenzyl)-N-((1S,2S)-2-hydroxycyclohexyl)-7-methyl-1H-pyrrolo[3,2-b]pyridine-3-carboxamide.

6. A method for positive allosteric modulation of muscarinic receptor mAChR M1, comprising administering to a human subject in need thereof an effective amount of the compound according to claim 1, or a pharmaceutically acceptable salt thereof.

7. A method for symptomatic treatment of cognitive impairment in Alzheimer-type dementia (AD), comprising administering to a human subject in need thereof a therapeutically effective amount of the compound according to claim 1, or a pharmaceutically acceptable salt thereof.

8. A method for symptomatic treatment of cognitive impairment in dementia with Lewy bodies (DLB), comprising administering to a human subject in need thereof a therapeutically effective amount of the compound according to claim 1, or a pharmaceutically acceptable salt thereof.

9. A pharmaceutical composition comprising the compound according to claim 1, or a pharmaceutically acceptable salt thereof, as an active ingredient in association with a pharmaceutically acceptable carrier.

10. A compound according to claim 1, or a pharmaceutically acceptable salt thereof, which is: 1-(3-fluoro-4-methoxybenzyl)-N-(trans-3-hydroxytetrahydro-2H-pyran-4-yl)-7-methyl-1H-pyrrolo[3,2-b]pyridine-3-carboxamide.

11. A compound according to claim 1, or a pharmaceutically acceptable salt thereof, which is: N-(trans-3-hydroxytetrahydro-2H-pyran-4-yl)-1-((2-methoxypyridin-4-yl)methyl)-7-methyl-1H-pyrrolo[3,2-b]pyridine-3-carboxamide.

12. A compound according to claim 1, or a pharmaceutically acceptable salt thereof, which is: 7-chloro-1-(4-methoxybenzyl)-N-(trans-3-hydroxytetrahydro-2H-pyran-4-yl)-1H-pyrrolo[3,2-b]pyridine-3-carboxamide.

13. A compound according to claim 1, or a pharmaceutically acceptable salt thereof, which is: 1-(3-fluoro-4-methoxybenzyl)-N-((3R,4S)-3-hydroxytetrahydro-2H-pyran-4-yl)-7-methyl-1H-pyrrolo[3,2-b]pyridine-3-carboxamide.

14. A compound according to claim 1, or a pharmaceutically acceptable salt thereof, which is: N-((3R,4S)-3-hydroxytetrahydro-2H-pyran-4-yl)-1-((2-methoxypyridin-4-yl)methyl)-7-methyl-1H-pyrrolo[3,2-b]pyridine-3-carboxamide.

15. A compound according to claim 1, or a pharmaceutically acceptable salt thereof, which is: 7-chloro-1-(4-methoxybenzyl)-N-((3R,4S)-3-hydroxytetrahydro-2H-pyran-4-yl)-1H-pyrrolo[3,2-b]pyridine-3-carboxamide.

* * * * *

UNITED STATES PATENT AND TRADEMARK OFFICE
CERTIFICATE OF CORRECTION

PATENT NO.         : 9,926,312 B2                                        Page 1 of 1
APPLICATION NO.    : 15/025996
DATED              : March 27, 2018
INVENTOR(S)        : Andrew Payne et al.

It is certified that error appears in the above-identified patent and that said Letters Patent is hereby corrected as shown below:

In the Claims

<u>Column 145</u>
Claim 1, Line 33, delete "N(1S,2S)" and insert -- N-((1S,2S) --.
Claim 1, Line 59, delete "pyrrolo [3," and insert -- pyrrolo[3, --.

<u>Column 147</u>
Claim 1, Line 19, delete "(3 S,4R)" and insert -- ((3S,4R) --.

Signed and Sealed this
Second Day of October, 2018

Andrei Iancu
*Director of the United States Patent and Trademark Office*